(12) United States Patent
Diener et al.

(10) Patent No.: US 7,998,940 B2
(45) Date of Patent: *Aug. 16, 2011

(54) APTAMERS TO VON WILLEBRAND FACTOR AND THEIR USE AS THROMBOTIC DISEASE THERAPEUTICS

(75) Inventors: John L. Diener, Cambridge, MA (US); H. A. Daniel Lagasse, Somerville, MA (US); Claude Benedict, Cambridge, MA (US)

(73) Assignee: Archemix Corp., Cambridge, MA (US)

( * ) Notice: Subject to any disclaimer, the term of this patent is extended or adjusted under 35 U.S.C. 154(b) by 201 days.

This patent is subject to a terminal disclaimer.

(21) Appl. No.: 12/322,078

(22) Filed: Jan. 29, 2009

(65) Prior Publication Data

US 2009/0149643 A1 Jun. 11, 2009

Related U.S. Application Data

(63) Continuation of application No. 11/222,346, filed on Sep. 7, 2005, now Pat. No. 7,566,701.

(60) Provisional application No. 60/608,047, filed on Sep. 7, 2004, provisional application No. 60/661,950, filed on Mar. 11, 2005, provisional application No. 60/678,427, filed on May 6, 2005, provisional application No. 60/690,231, filed on Jun. 13, 2005.

(51) Int. Cl.
*A01N 43/04* (2006.01)
*C07H 21/02* (2006.01)
*C12P 19/34* (2006.01)
*C12Q 1/68* (2006.01)

(52) U.S. Cl. ............. 514/44; 435/6; 435/91.1; 536/23.1

(58) Field of Classification Search ............. 435/6, 91.1, 435/91.31, 455; 514/44; 536/23.1, 24.5
See application file for complete search history.

(56) References Cited

U.S. PATENT DOCUMENTS

| | | | |
|---|---|---|---|
| 3,710,795 A | 1/1973 | Higuchi et al. |
| 4,666,884 A | 5/1987 | Hawiger et al. |
| 4,683,195 A | 7/1987 | Mullis |
| 4,935,363 A | 6/1990 | Brown et al. |
| 4,959,309 A | 9/1990 | Dattagupta et al. |
| 5,043,429 A | 8/1991 | Zimmerman et al. |
| 5,070,010 A | 12/1991 | Hsu |
| 5,112,950 A | 5/1992 | Meulien et al. |
| 5,171,844 A | 12/1992 | Van Ooyen et al. |
| 5,180,583 A | 1/1993 | Hedner |
| 5,200,510 A | 4/1993 | Kumar et al. |
| 5,238,919 A | 8/1993 | Zimmerman et al. |
| 5,260,274 A | 11/1993 | Zimmerman et al. |
| 5,262,564 A | 11/1993 | Kun et al. |
| 5,270,163 A | 12/1993 | Gold et al. |
| 5,298,239 A | 3/1994 | Miller et al. |
| 5,317,097 A | 5/1994 | Miller et al. |
| 5,318,899 A | 6/1994 | Scarborough et al. |
| 5,321,127 A | 6/1994 | Handin |
| 5,336,667 A | 8/1994 | Kirby et al. |
| 5,338,671 A | 8/1994 | Scalice et al. |
| 5,340,727 A | 8/1994 | Ruggeri et al. |
| 5,364,771 A | 11/1994 | Lollar et al. |
| 5,366,869 A | 11/1994 | Goldstein |
| 5,459,015 A | 10/1995 | Janjic et al. |
| 5,460,950 A | 10/1995 | Barr et al. |
| 5,462,752 A | 10/1995 | Chao et al. |
| 5,475,096 A | 12/1995 | Gold et al. |
| 5,496,938 A | 3/1996 | Gold et al. |
| 5,503,978 A | 4/1996 | Schneider et al. |
| 5,532,255 A | 7/1996 | Raddatz et al. |
| 5,539,086 A | 7/1996 | Farb et al. |
| 5,567,588 A | 10/1996 | Gold et al. |
| 5,580,737 A | 12/1996 | Polisky et al. |
| 5,593,959 A | 1/1997 | Miller et al. |
| 5,597,711 A | 1/1997 | Zimmerman et al. |
| 5,614,531 A | 3/1997 | Juraszyk et al. |
| 5,624,817 A | 4/1997 | Miller et al. |
| 5,627,046 A | 5/1997 | Falcone et al. |
| 5,635,615 A | 6/1997 | Allen et al. |
| 5,637,459 A | 6/1997 | Burke et al. |
| 5,648,214 A | 7/1997 | Nieuwlandt et al. |
| 5,654,151 A | 8/1997 | Allen et al. |
| 5,660,985 A | 8/1997 | Pieken et al. |
| 5,663,060 A | 9/1997 | Lollar et al. |
| 5,668,264 A | 9/1997 | Janjic et al. |

(Continued)

FOREIGN PATENT DOCUMENTS

EP 0197592 B1 10/1986

(Continued)

OTHER PUBLICATIONS

Altschul et al., "Basic Local Alignment Search Tool", (1990) *J. Mol. Biol.* 215: 403-410.
Altschul et al., "Gapped BLAST and PSI-BLAST: A New Generation of Protein Database Search Programs", (1997) *Nuc. Acids Res.* 15: 3389-3402.
Andrake, "DNA polymerase of bacteriophage T4 is an autogenous translational repressor ", (1988) *Proc. Natl. Acad. Sci.* USA 85: 7942-7946.
Barabino et al , "Inhibition of Sickle Erythrocyte Adhesion to Immobilized Thrombospondin by von Willebrand Factor Under Dynamic Flow Conditions", (1997) *Blood* 89: 2560-2567.
Burmeister et al., "Direct in vitro Selection of a 2'-O-Methyl Aptamer to VEGF", (2005) *Chemistry and Biology* 12: 25-33.

(Continued)

*Primary Examiner* — Jane Zara
(74) *Attorney, Agent, or Firm* — Mintz Levin Cohn Ferris Glovsky and Popeo, P.C.; Ivor R. Elrifi

(57) ABSTRACT

The invention relates generally to the field of nucleic acids and more particularly to aptamers capable of binding to von Willebrand Factor useful as therapeutics in and diagnostics of thrombotic diseases and/or other diseases or disorders in which von Willebrand Factor mediated platelet aggregation has been implicated. The invention further relates to materials and methods for the administration of aptamers capable of binding to von Willebrand Factor.

19 Claims, 27 Drawing Sheets

U.S. PATENT DOCUMENTS

| | | | |
|---|---|---|---|
| 5,674,685 A | 10/1997 | Janjic et al. |
| 5,683,867 A | 11/1997 | Biesecker et al. |
| 5,686,566 A | 11/1997 | Scarborough et al. |
| 5,686,567 A | 11/1997 | Scarborough et al. |
| 5,686,568 A | 11/1997 | Scarborough et al. |
| 5,686,569 A | 11/1997 | Scarborough et al. |
| 5,686,570 A | 11/1997 | Scarborough et al. |
| 5,686,571 A | 11/1997 | Scarborough et al. |
| 5,688,912 A | 11/1997 | Dadd et al. |
| 5,698,687 A | 12/1997 | Eckstein et al. |
| 5,705,337 A | 1/1998 | Gold et al. |
| 5,707,796 A | 1/1998 | Gold et al. |
| 5,710,131 A | 1/1998 | Hemberger et al. |
| 5,723,323 A | 3/1998 | Kauffman et al. |
| 5,763,173 A | 6/1998 | Gold et al. |
| 5,763,177 A | 6/1998 | Gold et al. |
| 5,789,157 A | 8/1998 | Jensen et al. |
| 5,817,635 A | 10/1998 | Eckstein et al. |
| 5,827,516 A | 10/1998 | Urban et al. |
| 5,830,880 A | 11/1998 | Sedlacek et al. |
| 5,837,486 A | 11/1998 | Bodary et al. |
| 5,837,488 A | 11/1998 | Garfinkel et al. |
| 5,847,086 A | 12/1998 | Farb et al. |
| 5,849,536 A | 12/1998 | Garfinkel et al. |
| 5,849,702 A | 12/1998 | Garfinkel et al. |
| 5,854,005 A | 12/1998 | Coller |
| 5,854,403 A | 12/1998 | Fischer et al. |
| 5,856,126 A | 1/1999 | Fukuchi et al. |
| 5,861,254 A | 1/1999 | Schneider et al. |
| 5,866,113 A | 2/1999 | Hendriks et al. |
| 5,869,615 A | 2/1999 | Hourcade et al. |
| 5,880,265 A | 3/1999 | Fischer et al. |
| 5,900,476 A | 5/1999 | Ruggeri et al. |
| 5,928,892 A | 7/1999 | Hourcade et al. |
| 5,958,691 A | 9/1999 | Pieken et al. |
| 5,958,732 A | 9/1999 | Scarborough et al. |
| 5,965,425 A | 10/1999 | Barr et al. |
| 6,008,193 A | 12/1999 | Garfinkel et al. |
| 6,011,020 A | 1/2000 | Gold et al. |
| 6,013,443 A | 1/2000 | Heilig et al. |
| 6,020,130 A | 2/2000 | Gold et al. |
| 6,028,090 A | 2/2000 | Gante et al. |
| 6,033,856 A | 3/2000 | Koerner et al. |
| 6,037,329 A | 3/2000 | Baird et al. |
| 6,040,143 A | 3/2000 | Venta et al. |
| 6,051,698 A | 4/2000 | Janjic et al. |
| 6,068,838 A | 5/2000 | Furlan et al. |
| 6,074,832 A | 6/2000 | Venta et al. |
| 6,100,061 A | 8/2000 | Reiter et al. |
| 6,103,693 A | 8/2000 | Fisher et al. |
| 6,114,135 A | 9/2000 | Goldstein |
| 6,177,059 B1 | 1/2001 | Matsuda et al. |
| 6,207,816 B1 | 3/2001 | Gold et al. |
| 6,210,929 B1 | 4/2001 | Schlokat et al. |
| 6,221,623 B1 | 4/2001 | Smith-McCune et al. |
| 6,229,002 B1 | 5/2001 | Janjic et al. |
| 6,239,261 B1 | 5/2001 | Heimburger et al. |
| 6,255,554 B1 | 7/2001 | Lubon et al. |
| 6,280,731 B1 | 8/2001 | Nagano et al. |
| 6,320,029 B1 | 11/2001 | Miekka et al. |
| 6,346,614 B1 | 2/2002 | Metelev et al. |
| 6,358,732 B1 | 3/2002 | Sedlacek et al. |
| 6,410,237 B1 | 6/2002 | Brewer et al. |
| 6,451,976 B1 | 9/2002 | Lu et al. |
| 6,465,624 B1 | 10/2002 | Fischer et al. |
| 6,475,725 B1 | 11/2002 | Reiter et al. |
| 6,489,290 B2 | 12/2002 | Loscalzo et al. |
| 6,503,886 B1 | 1/2003 | Baird et al. |
| 6,518,482 B2 | 2/2003 | Lubon et al. |
| 6,521,594 B1 | 2/2003 | Pierschbacher et al. |
| 6,576,758 B1 | 6/2003 | Seifart et al. |
| 6,579,723 B1 | 6/2003 | Mitterer et al. |
| 6,656,731 B1 | 12/2003 | Eckstein et al. |
| RE38,431 E | 2/2004 | Miekka et al. |
| 6,686,179 B2 | 2/2004 | Fleer et al. |
| 6,737,405 B2 | 5/2004 | Roemisch et al. |
| 6,780,583 B1 | 8/2004 | Venta et al. |
| 6,793,920 B2 | 9/2004 | Nagano et al. |
| 7,566,701 B2 * | 7/2009 | Diener et al. ............. 514/44 R |
| 2004/0180360 A1 | 9/2004 | Epstein et al. |
| 2004/0197804 A1 | 10/2004 | Keefe et al. |
| 2005/0037394 A1 | 2/2005 | Keefe et al. |
| 2005/0136056 A1 | 6/2005 | Kageyama et al. |
| 2005/0192224 A1 | 9/2005 | Huizinga et al. |
| 2006/0057573 A1 | 3/2006 | Gold et al. |

FOREIGN PATENT DOCUMENTS

| | | |
|---|---|---|
| EP | 0592035 | 1/1996 |
| GB | 2 183 661 A | 6/1987 |
| WO | WO86/06096 | 10/1986 |
| WO | WO89/06694 | 7/1989 |
| WO | WO91/14436 | 10/1991 |
| WO | WO91/19813 | 12/1991 |
| WO | WO92/05285 | 4/1992 |
| WO | WO92/07065 | 4/1992 |
| WO | WO92/14842 | 9/1992 |
| WO | WO92/14843 | 9/1992 |
| WO | WO93/15199 | 8/1993 |
| WO | WO93/15200 | 8/1993 |
| WO | WO95/21853 | 8/1995 |
| WO | WO98/18480 | 5/1998 |
| WO | WO00/10601 | 3/2000 |
| WO | WO01/04269 | 1/2001 |
| WO | WO 02/26932 | 4/2002 |
| WO | WO 02/096926 | 12/2002 |
| WO | WO2004/015425 | 2/2004 |
| WO | WO2006/074947 | 7/2006 |

OTHER PUBLICATIONS

Carey et al., "Sequence-specific interaction of R17 coat protein with its ribonucleic acid binding site", (1983) *Biochem.* 22: 2601-2610.

Chelliserrykatil and Ellington, "Evolution of a T7 RNA Polymerase Variant That Transcribes 2'-O-Methyl RNA", (2004) *Nat. Biotech* 9: 1150-1160.

Chen et al., "Selection of high-affinity RNA ligands to reverse transcriptase. Inhibition of cDNA synthesis and RNase H activity", (1994) *Biochem.* 33: 8746-8756.

Cohen et al., "Interactions of hormonal steroids with nucleic acids: A specific requirement for guanine", (1969) *Proc. Natl. Acad. Sci.* USA 63: 458-464.

Cotton et al., "2'-O-methyl, 2'-O-ethyl oligoribonucleotides and phosphorothioate oligodeoxyribonucleotides as inhibitors of the in vitro U7 snRNP-dependent mRNA processing event", (1991) Nucleic Acids Res. 19: 2629-2635.

Davis et al., "Identifying consensus patterns and secondary structure in SELEX sequence sets", (1996) *Methods in Enzymology* 267: 302-314.

Dehouck et al., "Blood-brain barrier in vitro—rapid evaluation of strategies for achieving drug targeting to the central nervous system", (1996) Biol. Physiology of the Blood Brain Barrier, Couraud and Scherman eds., 23: 143-146.

Ellington and Szostak, "Abstracts of papers presented at the 1990 meeting on RNA Processing", (1990) Cold Spring Harbor, NY, p. 84.

Fitzwater et al., "A SELEX primer", (1996) *Methods in Enzymology* 267: 275-301.

Froehler et al., "Synthesis of DNA via Deoxynucleoside H-phosphonate Intermediates", (1986) *Nuc. Acids Res.* 14: 5399-5407.

Froehler et al., "Deoxynucleoside H-Phosphonate Diester Intermediates in the Synthesis of Internucleotide Phosphate Analogues", (1986) *Tet. Lett.* 27: 5575-5578.

Gath et al., "The blood-CSF barrier in vitro", Biol. and Physiology of the Blood Brain Barrier, (1996) Couraud and Scherman eds., 25: 153-158.

Gold et al., "Diversity of Oligonucleotide Functions", (1995) *Annu. Rev. Biochem.* 64: 763-797.

Gralnick et al., "A monomeric von Willebrand factor fragment, Leu-504-Ser-728, inhibits von Willebrand factor interaction with glycoprotein Ib-IX", (1992) *Proc. Natl. Acad. Sci.* 89: 488-94.

Gray et al., "Rapid Measurement of Modified Oligonucleotide Levels in Plasma Samples With A Fluorophore Specific for Single-Stranded DNA", (1997) *Antisense and Nucleic Acid Drug Development* 7(3): 133-140.

Greenwald et al., "Highly Water Soluble Taxol Derivatives: 7-Polyethylene Glycol Carbamates and Carbonates", (1995) *J. Org. Chem.* 60: 331-336.
Harris et al., "Effect of Pegylation on Pharmaceuticals", (2003) *Nature* 2: 214-221.
Harrison et al., "The PFA-100: A potential rapid screening tool for the assessment of platelet dysfunction", (2002) *Clin. Lab. Haem.* 24: 225-232.
Hirose et al., "Rapid Synthesis of Trideoxyribonucleotide Blocks", (1978) *Tet. Lett.* 28: 2449-2452.
Hobbs et al., "Polynucleotides containing 2'-amino-2'-deoxyribose and 2'-azido-2'-deoxyribose", (1973) *Biochemistry* 12: 5138-5145.
Huizinga et al., "Structures of glycoprotein 1b-alpha and its complex with von Willebrand factor A1 domain", (2002) *Science* 297: 1176-1179.
Hwang et al., "Inhibition of gene expression in human cells through small molecule-RNA interactions", (1999) *PNAS* 96(23):12997-13002.
Ikram et al., "An Experimental Model for the In-Vivo Study of Coronary Arterial Thrombosis", (1975) *Angiology* 26(4): 356-364.
Jackson and Schoenwaelder, "Antiplatelet Therapy: In Search of the Magic Bullet", (2003) *Nature Reviews* 2: 1-15.
Joyce and Inoue, "A novel technique for the rapid preparation of mutant RNAs", (1998) *Nuc. Acids Res.* 17: 711-722.
Joyce, "Amplification, mutation and selection of catalytic RNA", (1989) RNA: Catalysis, Splicing, Evolution, Amsterdam pp. 83-87.
Kacian et al., "A replicating RNA molecule suitable for a detailed analysis of extracellular evolution and replication", (1972) *Proc. Natl. Acad. Sci.* USA 69: 3038-3042.
Kadonaga et al., "Affinity purification of sequence-specific DNA binding proteins", (1986) *Proc. Natl. Acad. Sci.* USA 83: 5889-5893.
Kageyama et al., "Anti-thrombotic effects and bleeding risk of AJvW-2, a monoclonal antibody against human von Willebrand factor", (1997) *Br. J. Pharmacol.* 122: 165-171.
Kageyama et al., "Anti-Human von Willebrand Factor Monoclonal Antibody AJvW-2 Prevents Thrombus Deposition and Neointima Formation After Balloon Injury in Guinea Pigs", (2000) *Arterioscler. Thromb. Vasc. Biol.* 20: 2303-2308.
Kageyama et al., "Anti-Human vWF Monoclonal Antibody, AJvW-2 Fab, Inhibits Repetitive Coronary Artery Thrombosis without Bleeding Time Prolongation in Dogs", (2001) *Thromb. Res.* 101: 395-404.
Kageyama et al., "Effect of a humanized monoclonal antibody to von Willebrand factor in a canine model of coronary arterial thrombosis", (2002) *Eur. J. Pharmacol.* 443: 143-149.
Kageyama et al., "Pharmacokinetics and Pharmacodynamics of AJW200, a Humanized Monoclonal Antibody to von Willebrand Factor in Monkeys", (2002) *Arterioscler Thromb. Vasc.* Biol. pp. 187-192.
Kellogg et al., "Taqstart antibody™: 'Hot start' PCR facilitated by a neutralizing monoclonal antibody directed against taq DNA polymerase", (1994) *BioTechniques* 16(6): 1134-1137.
Kinzler and Vogelstein, "Whole genome PCR: Application to the identification of sequences bound by gene regulatory proteins", (1989) *Nuc. Acids Res.* 17: 3645-3653.
Kinzler and Vogelstein, "The *GLI* gene encodes a nuclear protein which binds specific sequences in the human genome", (1989) *Mol. Cell. Biol.* 10: 634-642.
Koppelman et al., "Requirements of von Willebrand Factor to Protect Factor VII From Inactivation by Activated Protein C", (1996) *Blood* 87: 2292-2300.
Kramer et al., "Evolution in vitro: Sequence and phenotype of a mutant RNA resistant to ethidium bromide", (1974) *J. Mol. Biol.* 89: 719-736.
Lestienne et al., "Inhibition of human leucocyte elastase by polynucleotides", (1983) *Biochimie* 65: 49-52.
Levisohn and Spiegelman, "The cloning of a self-replicating RNA molecule", (1968) *PNAS USA* 60: 866-872.
Levisohn and Spiegelman, "Further extracellular Darwinian experiments with replicating RNA molecules: diverse variants isolated under different selective conditions", (1969) *PNAS USA* 63: 805-811.
Ma and Ptashne, "A new class of yeast transcriptional activators", (1987) *Cell* 51: 113-119.

Maniatis et al., "Molecular Cloning: A Laboratory Manual", (1982) Cold Spring Harbor, NY p. 118.
Maniatis et al.,"Regulation of inducible and tissue-specific gene expression", (1987) *Science* 236: 1237-1245.
Mathews et al., "Incorporating chemical modification constraints into a dynamic programming algorithm for prediction of RNA secondary structure", (2004) *Proc. Nat. Acad. Sci.* 101: 7287-7292.
McGhie et al., "Abolition of Cyclic Flow Variations in Stenosed, Endothelium-Injured Coronary Arteries in Nonhuman Primates with a Peptide Fragment (VCL) Derived from Human Plasma von Willebrand Factor-Glycoprotein Ib Binding Domain", (1994) *Circulation* 90(6): 2976-2981.
McGinnis et al., "BLAST: at the core of a powerful and diverse set of sequence analysis tools", (2004) *Nuc. Acids Res.* 32: W20-W25.
Miele et al., "Autocatalytic replication of a recombinant RNA", (1983) *J. Mol. Biol.* 171: 281-295.
Mills et al., "An extracellular Darwinian experiment with a self-duplicating nucleic acid molecule", (1967) *Proc. Natl. Acad. Sci.* USA 58: 217-220.
Mills et al., "Complete nucleotide sequence of a replicating RNA molecule", (1973) *Science* 180: 916-927.
Min et al., "Search for the optimal sequence of the ribosome binding site by random oligonucleotide-directed mutagenisis", (1988) *Nuc. Acids Res.* 16: 5075-5088.
Muesing et al., "Nucleic acid structure and expression of the human AIDS/lymphadenopathy retrovirus", (1985) *Nature* 313: 450-458.
Oliphant and Struhl, "The use of random-sequence oligonucleotides for determining consensus sequences", (1987) *Methods in Enzymology* 155: 568-582.
Oliphant and Struhl, "Defining the consensus sequences of E. coli promoter elements by random selection", (1988) *Nuc. Acids Res.*16: 7673-7683.
Oliphant et al., "Cloning of random-sequence oligodeoxynucleotides", (1986) *Gene* 44: 177-183.
Oliphant et al., "Defining the sequence specificity of DNA-binding proteins by selecting binding sites from random-sequence oligonucleotides: analysis of yeast GCN4 protein", (1989) *Mol. Cell. Biol.* 9: 2944-2949.
Orgel, "Selection in vitro", (1979) *Proc. R. Soc. Lon.* B205: 435-442.
Ou et al., "DNA amplification for direct detection of HIV-1 in DNA of peripheral blood mononuclear cells", (1988) *Science* 239: 295-297.
Padilla et al., "A Y639F/H784A T7 RNA polymerase double mutant displays superior properties for synthesizing RNAs with non-canonical NTPs", (2002) *Nuc. Acids Res.* 30: e138 (4 pgs).
Padilla et al., "Efficient synthesis of nucleic acids heavily modified with non-canonical ribose 2'-groups using a mutant T7 RNA polymerase (RNAP)", (1999) *Nuc. Acids Res.* 27(6): 1561-1563.
Pietersz et al., "A 16-mer peptide (RQIKIWFQNRRMKWKK) from Antennapedia Preferentially Targets the Class I Pathway", (2001) *Vaccine* 19(11-12): 1397-1405.
Phillips and Scarborough, "Clinical Pharmacology of Eptifibatide", (1997) *Am. J. Cardiol.* 80(4A): 11B-20B.
Roberts et al., "Chemistry for peptide and protein PEGylation", (2002) *Advanced Drug Delivery Rev.* 54: 459-476.
Robertson and Joyce, "Selection in vitro of an RNA enzyme that specifically cleaves single-stranded DNA", (1990) *Nature* 344: 467-468.
Romaniuk et al., "RNA binding site of R17 coat protein", (1987) *Biochem.* 26: 1563-1568.
Rote et al., "Chimeric 7E3 Prevents Carotid Artery Thrombosis in Cynomolgus Monkeys", (1994) *Stroke* 25: 1223-1233.
Rothbard et al., "Conjugation of Arginine Oligomers to Cyclosporin A FacilitatesTopical Delivery and Inhibition of Inflammation", (2000) *Nat. Med.* 6(11): 1253-1257.
Rothbard et al. "Arginine-Rich Molecular Transporters for Drug Delivery: Role of Backbone Spacing in Cellular Uptake" (2002) *J. Med. Chem.* 45(17): 3612-3618.
Ruckman et al., "2'-Fluoropyrimidine RNA-based Aptamers to the 165-amino acid form of vascular endothelial growth factor (VEGF165): Inhibition of receptor binding and VEGF-induced vascular permeability through interactions requiring the exon 7-encoded domain", (1998) *J. Biol. Chem.* 273: 20556-20567-20695.

Saffhill et al., "In vitro selection of bacteriophage Qβ ribonucleic acid variants resistant to ethidium bromide", (1970) *J. Mol. Biol.* 51: 531-539.

Sambrook et al., "Molecular Cloning: A Laboratory Manual", (1989) Cold Spring Harbor, NY, pp. 8.9-8.10.

Singleton et al., "Dictionary of Microbiol. and Molecular Biology", Wiley & Sons, New York, NY, 2nd ed. p. 493 (1991).

Sood et al., "A rapid and convenient synthesis of poly-thymidylic acid by the modified triester approach", (1977) *Nuc. Acids Res.* 4: 2757-2765.

Sproat et al., "New synthetic routes to synthons suitable for 2'-O-allyloligoribonucleotide assembly", (1991) *Nuc. Acids Res.* 19: 733-738.

Szostak, J.W., "Structure and Activity of Ribozymes" in "Redesigning the Molecules of Life" (1988) Springer-Verlag Berline Heidelberg, pp. 87-113.

Tanchou et al., "Monoclonal antibody-mediated inhibition of RNA binding and annealing activities of HIV type 1 nucleocapsid protein", (1994) *Aids Research and Human Retroviruses* 10: 983-993.

Thiesen and Bach, "Target detection assay (TDA): A versatile procedure to determine DNA binding sites as demonstrated on SPI protein", (1990) *Nuc. Acids Res.* 18: 3203-3209.

Uhlenbeck et al., "Interaction of R17 coat protein with its RNA binding site for translational repression", (1983) *J. Biomolecular Structure and Dynamics* 1: 539-552.

Vanhoorelbeke et al , "Inhibition of Platelet Adhesion to Collagen as a New Target for Antithrombotic Drugs", (2003) *Cardio. Haema. Disorders* 3: 125-140.

Vanhoorelbeke et al., "The role of VWF-collagen interaction in acute platelet thrombus formation", (2003) *Drugs of the Future* 28(1): 61-67.

Varughese et al., "Structure and Function of the Von Willebrand Factor A1 Domain", (2002) *Current Protein and Peptide Science* 3: 301-312.

Vives et al., "A truncated HIV-1 Tat protein basic domain rapidly translocates through the plasma membrane and accumulates in the cell nucleus", (1997) *J. Biol. Chem.* 27: 16010-16017.

Watson et al., "Molecular Biology of the Gene", (1987) Benjamin/Cummings Publishing Co., Inc. California, pp. 267, 295, 323, 361, 394, 396, 397 and 405.

Wu et al , "Inhibition of the von Willebrand (VWF)-collagen interaction by an antihuman VWF monoclonal antibody results in abolition of in vivo arterial platelet thrombus formation in baboons", (2002) *Blood* 99(10): 3623-3628.

Yao et al., "Blockade of Platelet Membrane Glycoprotein Ib Receptors Delays Intracoronary Thrombogenesis, eEnhances Thrombolysis, and Delays Coronary Artery Reocclusion in Dogs", (1994) *Circulation* 89(6): 2822-2828.

White et al., "Developing aptamers into therapeutics", (2000) *J. Clin. Invest.* 106(8):929-934.

Rusconi et al., "RNA aptamers as reversible antagonists of coagulation factor Ixa", (2002) *Nature* 419:90-94.

Bonnefoy et al , "Inhibition of von Willebrand factor-GP1b/IX/V interactions as a straegy to prevent arterial thrombosis", (2003) *Exp. Rev. Cario. Ther., Future Drugs* 1(2):257-269.

Nimjee et al., "The potential of aptamers as anticoagulants", (2005) Trends Cardio Med. 15(1):41-45.

\* cited by examiner

Amino Acid Sequence of Human vWF domain A1

MGHHHHHHEPPLHDFYCSRLLDLVFLLDGSSRLSEAEFEVLKAFVVDMMEQLRISQK
WVRVAVVEYHDGSHAYIGLKDRKRPSELRRIASQVKYAGSQVASTSEVLKYTLFQIFSK
IDRPEASRIALLLMASQEPQRMSRNFVRYVQGLKKKKVIVIPVGIGPHANLKQIRLIEKQ
APENKAFVLSSVDELEQQRDEIVSYLCDLAPEAPPPT (SEQ. ID. No. 4)

Amino Acid Sequence of Human vWF domain A1

MRGSHHHHHHGSQEPGGLVVPPTDAPVSPTTLYVEDISEPPLHDFYCSRLLDLVFLLD
GSSRLSEAEFEVLKAFVVDMMERLRISQKWVRVAVVEYHDGSHAYIGLKDRKRPSELR
RIASQVKYAGSQVASTSEVLKYTLFQIFSKIDRPEASRIALLLMASQEPQRMSRNFVRY
VQGLKKKKVIVIPVGIGPHANLKQIRLIEKQAPENKAFVLSSVDELEQQRDEIVSYLCDLA
PEAPPPTLPP (SEQ. ID. NO.5)

Amino Acid Sequence of Rabbit vWF domain A1

MGHHHHHHEPPLHDFYWSNLMDLVFLLDGSAQLSEAEFGVLKAFVVSVMERLHISQK
RIRVAVVEYHDGSHSYISLKDRKRPSELRRIASQVKYAGGPVASTSEVLKYTLFHIFSNV
DRPEASRIALLLSASQETPRMVRNLVRYAQGLKKEKVIVIPVGIGPHVSLRQIHLIEKQA
PENKAFVLSGVDELEQRRDEIISYLCDLGPEAPVPT (SEQ. ID. NO. 6)

Fig. 3

Amino Acid Sequence of Full Length Human vWF

MIPARFAGVLLALALILPGTLCAEGTRGRSSTARCSLFGSDFVNTFDGSMYSFAGYCSYLLAGG
CQKRSFSIIGDFQNGKRVSLSVYLGEFFDIHLFVNGTVTQGDQRVSMPYASKGLYLETEAGYYK
LSGEAYGFVARIDGSGNFQVLLSDRYFNKTCGLCGNFNIFAEDDFMTQEGTLTSDPYDFANSW
ALSSGEQWCERASPPSSSCNISSGEMQKGLWEQCQLLKSTSVFARCHPLVDPEPFVALCEKT
LCECAGGLECACPALLEYARTCAQEGMVLYGWTDHSACSPVCPAGMEYRQCVSPCARTCQS
LHINEMCQERCVDGCSCPEGQLLDEGLCVESRECPCVHSGKRYPPGTSLSRDCNTCICRNSQ
WICSNEECPGECLVTGQSHFKSFDNRYFTFSGICQYLLARDCQDHSFSIVIETVQCADDRDAVC
TRSVTVRLPGLHNSLVKLKHGAGVAMDGQDIQLPLLKGDLRIQHTVTASVRLSYGEDLQMDWD
GRGRLLVKLSPVYAGKTCGLCGNYNGNQGDDFLTPSGLAEPRVEDFGNAWKLHGDCQDLQK
QHSDPCALNPRMTRFSEEACAVLTSPTFEACHRAVSPLPYLRNCRYDVCSCSDGRECLCGAL
ASYAAACAGRGVRVAWREPGRCELNCPKGQVYLQCGTPCNLTCRSLSYPDEECNEACLEGC
FCPPGLYMDERGDCVPKAQCPCYYDGEIFQPEDIFSDHHTMCYCEDGFMHCTMSGVPGSLLP
DAVLSSPLSHRSKRSLSCRPPMVKLVCPADNLRAEGLECTKTCQNYDLECMSMGCVSGCLCP
PGMVRHENRCVALERCPCFHQGKEYAPGETVKIGCNTCVCRDRKWNCTDHVCDATCSTIGM
AHYLTFDGLKYLFPGECQYVLVQDYCGSNPGTFRILVGNKGCSHPSVKCKKRVTILVEGGEIEL
FDGEVNVKRPMKDETHFEVVESGRYIILLLGKALSVVWDRHLSISVVLKQTYQEKVCGLCGNFD
GIQNNDLTSSNLQVEEDPVDFGNSWKVSSQCADTRKVPLDSSPATCHNNIMKQTMVDSSCRIL
TSDVFQDCNKLVDPEPYLDVCIYDTCSCESIGDCACFCDTIAAYAHVCAQHGKVVTWRTATLC
PQSCEERNLRENGYECEWRYNSCAPACQVTCQHPEPLACPVQCVEGCHAHCPPGKILDELL
QTCVDPEDCPVCEVAGRRFASGKKVTLNPSDPEHCQICHCDVVNLTCEACQEPGGLVVPPTD
APVSPTTLYVEDISEPPLHDFYCSRLLDLVFLLDGSSRLSEAEFEVLKAFVVDMMERLRISQKW
VRVAVVEYHDGSHAYIGLKDRKRPSELRRIASQVKYAGSQVASTSEVLKYTLFQIFSKIDRPEAS
RIALLLMASQEPQRMSRNFVRYVQGLKKKKVIVIPVGIGPHANLKQIRLIEKQAPENKAFVLSSV
DELEQQRDEIVSYLCDLAPEAPPPTLPPHMAQVTVGPGLLGVSTLGPKRNSMVLDVAFVLEGS
DKIGEADFNRSKEFMEEVIQRMDVGQDSIHVTVLQYSYMVTVEYPFSEAQSKGDILQRVREIRY
QGGNRTNTGLALRYLSDHSFLVSQGDREQAPNLVYMVTGNPASDEIKRLPGDIQVVPIGVGPN
ANVQELERIGWPNAPILIQDFETLPREAPDLVLQRCCSGEGLQIPTLSPAPDCSQPLDVILLLDG
SSSFPASYFDEMKSFAKAFISKANIGPRLTQVSVLQYGSITTIDVPWNVVPEKAHLLSLVDVMQR
EGGPSQIGDALGFAVRYLTSEMHGARPGASKAVVILVTDVSVDSVDAAADAARSNRVTVFPIGI
GDRYDAAQLRILAGPAGDSNVVKLQRIEDLPTMVTLGNSFLHKLCSGFVRICMDEDGNEKRPG
DVWTLPDQCHTVTCQPDGQTLLKSHRVNCDRGLRPSCPNSQSPVKVEETCGCRWTCPCVCT
GSSTRHIVTFDGQNFKLTGSCSYVLFQNKEQDLEVILHNGACSPGARQGCMKSIEVKHSALSV
ELHSDMEVTVNGRLVSVPYVGGNMEVNVYGAIMHEVRFNHLGHIFTFTPQNNEFQLQLSPKTF
ASKTYGLCGICDENGANDFMLRDGTVTTDWKTLVQEWTVQRPGQTCQPILEEQCLVPDSSHC
QVLLLPLFAECHKVLAPATFYAICQQDSCHQEQVCEVIASTAHLCRTNGVCVDWRTPDFCAMS
CPPSLVYNHCEHGCPRHCDGNVSSCGDHPSEGCFCPPDKVMLEGSCVPEEACTQCIGEDGV
QHQFLEAWVPDHQPCQICTCLSGRKVNCTTQPCPTAKAPTCGLCEVARLRQNADQCCPEYEC
VCDPVSCDLPPVPHCERGLQPTLTNPGECRPNFTCACRKEECKRVSPPSCPPHRLPTLRKTQ
CCDEYECACNCVNSTVSCPLGYLASTATNDCGCTTTTCLPDKVCVHRSTIYPVGQFWEEGCD
VCTCTDMEDAVMGLRVAQCSQKPCEDSCRSGFTYVLHEGECCGRCLPSACEVVTGSPRGDS
QSSWKSVGSQWASPENPCLINECVRVKEEVFIQQRNVSCPQLEVPVCPSGFQLSCKTSACCP
SCRCERMEACMLNGTVIGPGKTVMIDVCTTCRCMVQVGVISGFKLECRKTTCNPCPLGYKEEN
NTGECCGRCLPTACTIQLRGGQIMTLKRDETLQDGCDTHFCKVNERGEYFWEKRVTGCPPFD
EHKCLAEGGKIMKIPGTCCDTCEEPECNDITARLQYVKVGSCKSEVEVDIHYCQGKCASKAMY
SIDINDVQDQCSCCSPTRTEPMQVALHCTNGSVVYHEVLNAMECKCSPRKCSK
(SEQ. ID. No. 7)

Fig. 4 vWF DNA SELEX 2, FAMILY 1 SEQUENCE ALIGNMENT

```
                            10         20         30         40         50         60         70         80         90
                    ....|....|....|....|....|....|....|....|....|....|....|....|....|....|....|....|....|....|
AMX237.E9     1     CTACCTACGATCTGACT--AGCTC--CAGT-GTT--TTGTCTAAT--AAC-CGTG-CGG--TG-CCT--CCG-T--GA-GCT-TACTCTCATGTAGTTCC  7
AMX237.B11    1     CTACCTACGATCTGACT--AGCTC--CAGT-GTT--TTATCTAAT--AAC-CGTG-CGG--TG-CCT--CCG-T--GA-GCT-TACTCTCATGTAGTTCC  7
AMX237.A11    1     CTACCTACGATCTGACT--AGCTC--CAGT-GTT--TTATCCAAT--AAC-CGTG-CGG--TG-CCT--CCG-T--GA-GCT-TACTCTCATGTAGTTCC  7
AMX238.G5     1     CTACCTACGATCTGACT--AGCTC--CAGT-GTT--TTATTCAAT--AAC-CGTG-CGG--TG-CCT--CCG-T--GA-GCT-TACTCTCATGTAGTTCC  7
AMX238.D8     1     CTACCTACGATCTGACT--AGCTC--CAGT-GTT--TTATTCAAC--AAC-CGTG-CGG--TG-CCT--CCG-T--GA-GCT-TACTCTCATGTAGTTCC  7
AMX237.E2     1     CTACCTACGATCTGACT--AGCTC--CAGT-GTT--TTATCCAAT--AAC-CGTG-CGG--TG-CCT--CCG-T--GA-GCT-TACTCTCATGTAGTTCC  7
AMX237.H5     1     CTACCTACGATCTGACT--AGCTC--CAGT-GTT--TCATTTAAT--AAC-CGTG-CGG--TG-CCT--CCG-T--GA-GCT-TACTCTCATGTAGTTCC  7
AMX238.D5     1     CTACCTACGATCTGACT--AGCTC--CAGT-GTT--TTATTCAAT--AAC-CGTG-CGG--TG-TCT--CCG-T--GA-GCT-TACTCTCATGTAGTTCC  7
AMX237.A2     1     CTACCTACGATCTGACT--AGCTC--CAGT-GTT--TCATTCCAAT--AAC-CGTG-CGG--TG-CCT--CCG-T--GA-GCT-TACTCTCATGTAGTTCC  7
AMX238.D12    1     CTACCTACGATCTGACT--AGCTC--CAGT-GTT--TCATTCAAT--AAC-CGTG-CGG--TG-CCT--CCG-T--GA-GCT-TACTCTCATGTAGTTCC  7
AMX237.F6     1     CTACCTACGATCTGACT--AGCTC--CAGT-GTT--TTATTCAAT--AAC-CGTG-CGG--TG-CCT--CCG-T--GATGCT-TACTCTCATGTAGTTCC  8
AMX237.D11    1     CTACCTACGATCTGACT--AGCTC--CAGT-GTT--TTATATAAT--AAC-CGTG-CGG--TG-CCT--CCG-T--GATGCT-TACTCTCATGTAGTTCC  8
AMX237.B4     1     CTACCTACGATCTGACT--AGCTC--CAGT-GTT--TCATCCAAT--AAC-CGTG-CGG--TG-CTT--CCG-T--GA-GCT-TACTCTCATGTAGTTCC  7
AMX237.F8     1     CTACCTACGATCTGACT--AGCTC--CAGT-GTT--TTATCCAAT--AAC-CGTG-CGG--TG-CCT--CCG-T--GATGCT-TACTCTCATGTAGTTCC  8
AMX237.C7     1     CTACCTACGATCTGACT--AGCTC--CAGT-GTT--TTATTCAAT--AAC-CGTG-CGG--GG-CCT--CCG-T--GATGCT-TACTCTCATGTAGTTCC  8
AMX238.G6     1     CTACCTACGATCTGACT--AGCTC--CAGT-GTT--TTATTCAAT--AAC-CGTG-CGG--TG-CCT--CCG-T--GATGCT-TACTCTCATGTAGTTCC  8
AMX238.H5     1     CTACCTACGATCTGACT--AGCGTG-CAGT-GCC--TATTCTA---GGC-CGTG-CGG--TG-CCT--CCG-T--CAC-GCT-TACTCTCATGTAGTTCC  7
AMX237.C11    1     CTACCTACGATCTGACT--AGCGTG-CAGT-GCC--TATTCTA---GGC-CGTG-CGG--TG-CCT--CCG-T--CAT-GCT-TACTCTCATGTAGTTCC  7
AMX237.E7     1     CTACCTACGATCTGACT--AGCGTG-CAGT-GCC--TATTTTA---GGC-CGTG-CGG--TG-CCT--CCG-T--CAC-GCT-TACTCTCATGTAGTTCC  7
AMX238.G6     1     CTACCTACGATCTGACT--AGCGTG-CAGT-GCC--TATTCCA---GGC-CGTG-CGG--TG-CCT--CCG-T--CAC-GCT-TACTCTCATGTAGTTCC  7
AMX237.F2     1     CTACCTACGATCTGACT--AGCATG-CAGT-GCC--CATTCTA---GGC-CGTG-CGG--TG-CCT--CCG-T--CAT-GCT-TACTCTCATGTAGTTCC  7
AMX238.E9     1     CTACCTACGATCTGACT--AGCGTG-CAGT-GCC--CATCTTA---GGC-CGTG-CGG--TG-CCT--CCG-T--CAC-GCT-TACTCTCATGTAGTTCC  7
AMX238.F3     1     CTACCTACGATCTGACT--AGCGTG-CAGT-GCC--TATTTTA---GGT-CGTG-CGG--GG-CCT--CCG-T--CAC-GCT-TACTCTCATGTAGTTCC  7
AMX237.F10    1     CTACCTACGATCTGACT--AGCGTG-CAGT-GCC--CATTCCA---GGC-CGTG-CGG--TATCCT--CCG-T--CAC-GCT-TACTCTCATGTAGTTCC  8
AMX237.C5     1     CTACCTACGATCTGACT--AGCGTG-CAGT-GCC--TATCTCA---GGC-CGTG-CGG--TATCCT--CCG-T--CAC-GCT-TACTCTCATGTAGTTCC  8
AMX236.H2     1     CTACCTACGATCTGACT--AGCGTG-CAGT-GCC--TATCCCA---GGC-CGTG-CGG--TAGCCT--CCG-T--CAC-GCT-TACTCTCATGTAGTTCC  8
```

|  | ANIMAL 1001 ||| ANIMAL 1101 ||| ANIMAL 1102 |||
|---|---|---|---|---|---|---|---|---|---|
|  | CBT | BIPA | PFA-100 | CBT | BIPA | PFA-100 | CBT | BIPA | PFA-100 |
| Pre | 1 | 30 | 79 | 3 | 36 | 124 | 2 | 34 | 120 |
| 5 min | 3.2 | >> | >> | 6.8 | >> | >> | 4.8 | >> | >> |
| 6 hours | 1 |  | 119 | 1.3 |  | 107 | 2.3 |  | 163 |
| 10 hours | 2.4 |  | 99 | 3 |  | 107 | 3.5 |  | 155 |
| 24 hours | 2.3 | 47 | 92 | 2.3 | 51 | 106 | 1.8 | NA | NA |

>> = 100% INHIBITION

US 7,998,940 B2

APTAMERS TO VON WILLEBRAND FACTOR AND THEIR USE AS THROMBOTIC DISEASE THERAPEUTICS

REFERENCE TO RELATED APPLICATIONS

This non-provisional patent application is a continuation of U.S. patent application Ser. No. 11/222,346, filed Sep. 7, 2005, which claims the benefit of and priority under 35 U.S.C. §119(e) to the following provisional applications: U.S. Provisional Patent Application Ser. No. 60/608,047, filed Sep. 7, 2004, U.S. Provisional Patent Application Ser. No. 60/661, 950, filed Mar. 11, 2005, U.S. Provisional Patent Application Ser. No. 60/678,427, filed May 6, 2005, and U.S. Provisional Patent Application Ser. No. 60/690,231, filed Jun. 13, 2005; each of which is herein incorporated by reference in its entirety.

FIELD OF THE INVENTION

The invention relates generally to the field of nucleic acids and more particularly to aptamers capable of binding to von Willebrand Factor useful as therapeutics in and diagnostics of thrombotic diseases and/or other diseases or disorders in which von Willebrand Factor mediated platelet aggregation is implicated. The invention further relates to materials and methods for the administration of aptamers capable of binding to von Willebrand Factor.

BACKGROUND OF THE INVENTION

Aptamers are nucleic acid molecules having specific binding affinity to molecules through interactions other than classic Watson-Crick base pairing.

Aptamers, like peptides generated by phage display or monoclonal antibodies ("mAbs"), are capable of specifically binding to selected targets and modulating the target's activity or binding interactions, e.g., through binding aptamers may block their target's ability to function. Discovered by an in vitro selection process from pools of random sequence oligonucleotides, aptamers have been generated for over 130 proteins including growth factors, transcription factors, enzymes, immunoglobulins, and receptors. A typical aptamer is 10-15 kDa in size (20-45 nucleotides), binds its target with nanomolar to sub-nanomolar affinity, and discriminates against closely related targets (e.g., aptamers will typically not bind other proteins from the same gene family). A series of structural studies have shown that aptamers are capable of using the same types of binding interactions (e.g., hydrogen bonding, electrostatic complementarities, hydrophobic contacts, steric exclusion) that drive affinity and specificity in antibody-antigen complexes.

Aptamers have a number of desirable characteristics for use as therapeutics and diagnostics including high specificity and affinity, biological efficacy, and excellent pharmacokinetic properties. In addition, they offer specific competitive advantages over antibodies and other protein biologics, for example:

1) Speed and control. Aptamers are produced by an entirely in vitro process, allowing for the rapid generation of initial leads, including therapeutic leads. In vitro selection allows the specificity and affinity of the aptamer to be tightly controlled and allows the generation of leads, including leads against both toxic and non-immunogenic targets.

2) Toxicity and Immunogenicity. Aptamers as a class have demonstrated therapeutically acceptable toxicity and lack of immunogenicity. Whereas the efficacy of many monoclonal antibodies can be severely limited by immune response to antibodies themselves, it is extremely difficult to elicit antibodies to aptamers most likely because aptamers cannot be presented by T-cells via the MHC and the immune response is generally trained not to recognize nucleic acid fragments.

3) Administration. Whereas most currently approved antibody therapeutics are administered by intravenous infusion (typically over 2-4 hours), aptamers can be administered by subcutaneous injection (aptamer bioavailability via subcutaneous administration is >80% in monkey studies (Tucker et al., J. Chromatography B. 732: 203-212, 1999)). With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

4) Scalability and cost. Therapeutic aptamers are chemically synthesized and consequently can be readily scaled as needed to meet production demand. Whereas difficulties in scaling production are currently limiting the availability of some biologics and the capital cost of a large-scale protein production plant is enormous, a single large-scale oligonucleotide synthesizer can produce upwards of 100 kg/year and requires a relatively modest initial investment. The current cost of goods for aptamer synthesis at the kilogram scale is estimated at $500/g, comparable to that for highly optimized antibodies. Continuing improvements in process development are expected to lower the cost of goods to <$100/g in five years.

5) Stability. Therapeutic aptamers are chemically robust. They are intrinsically adapted to regain activity following exposure to factors such as heat and denaturants and can be stored for extended periods (>1 yr) at room temperature as lyophilized powders.

Thrombotic Disease

During normal, controlled hemostasis, platelets do not adhere to healthy vessels, rather platelets typically adhere to the subendothelium of injured vessels. Platelet adhesion triggers a series of platelet activation processes which ultimately results in thrombus formation and cessation of bleeding. The von Willebrand Factor ("vWF") is a mediator of platelet adhesion at sites of vascular damage. vWF is a large multi-subunit, multimeric soluble factor mainly produced by vascular endothelial cells. The von Willebrand Factor becomes immobilized on the blood vessel wall via interactions between von Willebrand Factor domain A3 and exposed collagen. Transient interactions of the platelet-receptor glycoprotein Ib ("hereinafter GPIb") and the A1 domain of the immobilized von Willebrand Factor facilitates the adhesion and activation of platelets at sites of vascular injury. E. G. Huizing a et al., Science, 297, 1176 (2002). Accordingly, the von Willebrand factor is pro-thrombotic, playing an important role during hemostasis in facilitating thrombus formation at sites of vascular injury.

Conversely, the von Willebrand Factor, by the same mechanism, also plays a key role in pathological conditions, such as cardiovascular diseases, involving platelet aggregation and thrombosis formation. Although antithrombotic therapies are currently available there is still a large unmet need for additional therapies. The American Heart Association estimates that more than 60 million people in the United States alone have one or more forms of cardiovascular disease, and that a high proportion of people with cardiovascular disease are at higher risk for arterial thrombosis. S. P. Jackson and S. M. Schoenwaelder, Nature Reviews, 2, 1-12 (2003).

A significant problem with presently available therapies is that improving efficacy reduces safety. S. P. Jackson and S. M. Schoenwaelder, Nature Reviews, 2, 1-12 (2003). Accordingly, it would be beneficial to treat or prevent thrombotic disease by preventing platelet aggregation in the vasculature while minimizing bleeding side effects. The present invention provides materials and methods to meet these and other needs.

BRIEF DESCRIPTION OF THE DRAWINGS

FIG. 3 is a table listing the amino acid sequences of the von Willebrand Factor domain A1 proteins used in the experiments of the invention.

FIG. 4 is a table listing the amino acid sequence of the full length human von Willebrand Factor protein used in the experiments of the invention.

FIG. 14 is an illustration depicting the sequence alignment for 26 aptamers of the vWF DNA SELEX™ 2 Family #1. The black line at the top of the alignment represents the proposed core nucleic acid binding sequence required to bind the von Willebrand Factor target.

FIG. 16 is a table depicting the nucleic acid sequences including any modifications of ARC1029 (SEQ ID NO 214), ARC1115 (SEQ ID NO 221), ARC1172 (SEQ ID NO 222), and ARC1194 (SEQ ID NO 223) to ARC1243 (SEQ ID NO 272).

FIG. 17 is a table depicting the nucleic acid sequences including any modifications of ARC1172 (SEQ ID NO 222), ARC1338 (SEQ ID NO 273) to ARC1348 (SEQ ID NO 283) and ARC1361 (SEQ ID NO 284) to ARC1381 (SEQ ID NO 304). A black block in this table indicates a deletion. An "s" preceding a nucleotide indicator (e.g. T or dA) indicates a phosphorothioate substitution in the phosphate backbone 5' to the indicated nucleotide.

FIG. 18 is a table depicting the nucleic acid sequences including any modifications of ARC1172 (SEQ ID NO 222), ARC1524 (SEQ ID NO 305) to ARC1535 (SEQ ID NO 316), ARC1546 (SEQ ID NO 317) and ARC1759 (SEQ ID NO 318). A black block in this table indicates a deletion.

SUMMARY OF THE INVENTION

Figure 1:
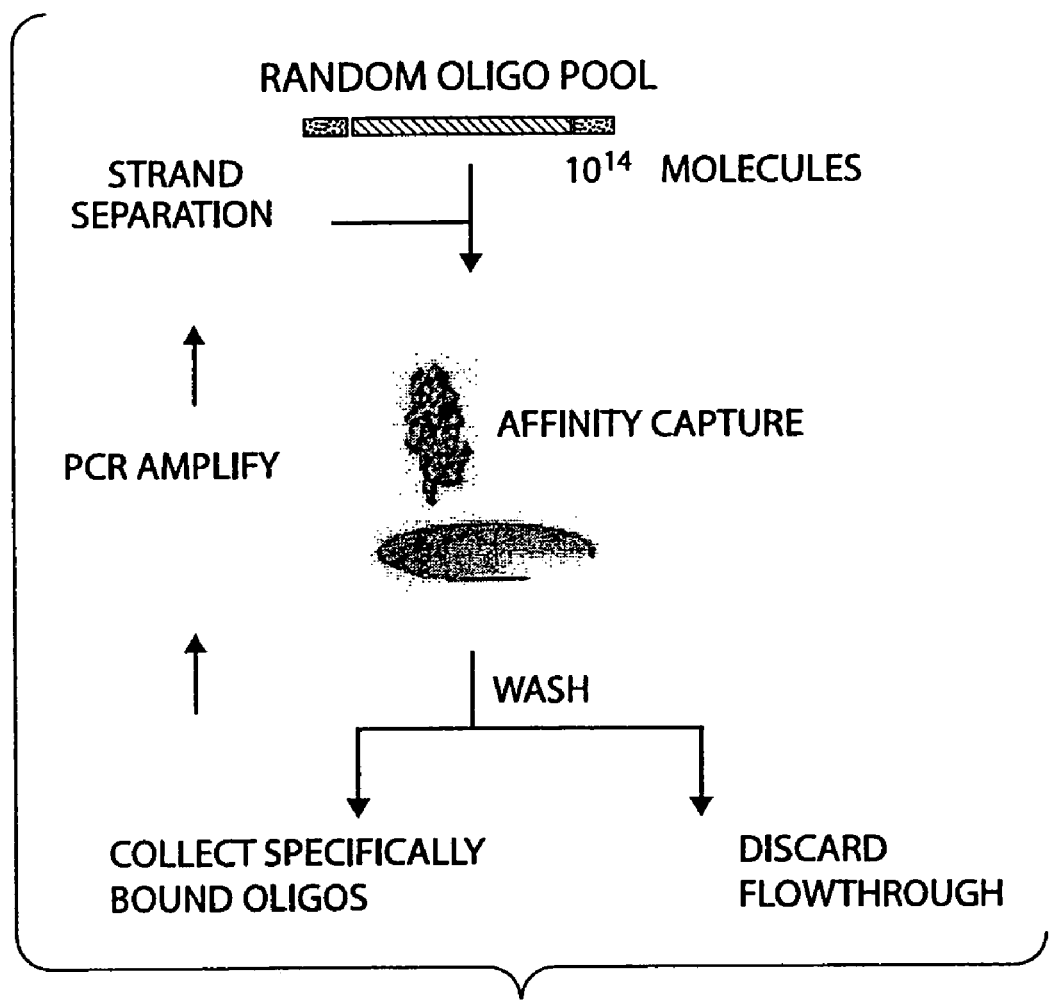
FIG. 1 is a schematic representation of the in vitro aptamer selection (SELEX™) process from pools of random sequence oligonucleotides.

The present invention provides materials and methods for the treatment of thrombotic disorders involving von Willebrand Factor mediated platelet aggregation.

The present invention provides aptamers that specifically bind to a von Willebrand Factor target. In some embodiments, the von Willebrand Factor target is human von Willebrand Factor. In some embodiments, the von Willebrand Factor target is a variant of human von Willebrand Factor that performs a biological function that is essentially the same as a function of human von Willebrand Factor. In some embodiments, the biological function of the von Willebrand Factor target or variant thereof is to mediate platelet aggregation. In some embodiments, the variant of the human von Willebrand Factor target has substantially the same structure and substantially the same ability to bind an aptamer of the invention as that of human von Willebrand Factor. In some embodiments, the vWF target is a non-human von Willebrand Factor. In some embodiments, the aptamer of the invention binds the von Willebrand Factor target or a variant thereof that comprises an amino acid sequence which is at least 75%, 80%, 90% or 95% identical to SEQ ID NO 7 (FIG. 4). In one embodiment, the von Willebrand Factor target comprises the amino acid sequence of SEQ ID NO 7.

The terms "sequence identity" or "% identity" in the context of two or more nucleic acid or protein sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters. Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad. Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel, F. M. et al., Current Protocols in Molecular Biology, pub. by Greene Publishing Assoc. and Wiley-Interscience (1987).

One example of an algorithm that is suitable for determining percent sequence identity is the algorithm used in the basic local alignment search tool (hereinafter "BLAST"), see, e.g. Altschul et al., J. Mol. Biol. 215: 403-410 (1990) and Altschul et al., Nucleic Acids Res., 15: 3389-3402 (1997). Software for performing BLAST analyses is publicly available through the National Center for Biotechnology Information (hereinafter "NCBI"). The default parameters used in determining sequence identity using the software available from NCBI, e.g., BLASTN (for nucleotide sequences) and BLASTP (for amino acid sequences) are described in McGinnis et al., Nucleic Acids Res., 32: W20-W25 (2004). In a preferred embodiment, percent identity is determined using the BLAST implemented algorithm of Altschul et al., and the default parameters of McGinnis et al., which herein may be referred to as BLAST percent identity.

In one embodiment, the vWF aptamer of the invention comprises a dissociation constant for human von Willebrand Factor or a variant thereof, of about 100 nM or less, preferably 50 nM or less, preferably 10 nM or less, preferably 5 nM or less, preferably 1 nM or less, and more preferably 500 pM or less. The dissociation constant may be determined by dot blot assay using a multi-point titration and fitting the equation $y=(max/(1+K/protein))+yint$ as described in Example 1, below.

The present invention also provides an aptamer that specifically binds to a von Willebrand Factor domain A1 target. In some embodiments, the von Willebrand Factor domain A1 target is a human von Willebrand Factor domain A1 target. In some embodiments, the human von Willebrand Factor domain A1 target is a variant of human von Willebrand Factor domain A1 that performs a biological function that is essentially the same as a function of human von Willebrand Factor domain A1. In some embodiments, the biological function of von Willebrand Factor domain A1 or a variant thereof is to bind to platelets. In some embodiments, the variant of human von Willebrand Factor domain target has substantially the same structure and substantially the same ability to bind said aptamer as that of human von Willebrand Factor domain A1. In other embodiments, the von Willebrand Factor domain A1 target is non-human von Willebrand Factor domain A1 target, e.g. a rabbit or non-human primate von Willebrand Factor domain A1 target.

In some embodiments, the von Willebrand Factor domain A1 target of the invention comprises an amino acid sequence which is at least 75%, 80%, 90% or 95% identical to any one of the sequences selected from the group consisting of: SEQ ID NOS 4 to 6. In a preferred embodiment, the von Willebrand Factor domain A1 target comprises any one of the amino acid sequences selected from the group consisting: of SEQ ID NOS 4 to 6.

In one embodiment, the vWF aptamer of the invention comprises a dissociation constant for human von Willebrand Factor domain A1 or a variant thereof, of about 100 nM or less, preferably 50 nM or less, preferably 10 nM or less, preferably 5 nM or less, preferably 1 nM or less, and more preferably 500 pM or less. In another embodiment, the aptamer of the invention comprises a dissociation constant for non-human von Willebrand Factor domain A1 or a variant thereof, of about 100 nM or less, preferably 50 nM or less, preferably 10 nM or less, preferably 5 nM or less, preferably 1 nM or less, and more preferably 500 pM or less. The dissociation constant may be determined by dot blot assay using a multi-point titration and fitting the equation y=(max/(1+K/protein))+yint as described in Example 1, below.

In some embodiments, the invention provides an aptamer that specifically binds to a von Willebrand Factor full length target. In some embodiments, the invention provides an aptamer that specifically binds to a von Willebrand Factor full length target and a von Willebrand Factor domain A1 target. In some embodiments, the von Willebrand Factor full length target is a human von Willebrand target or variant thereof. In other embodiments, the von Willebrand Factor full length target is a non-human von Willebrand target or variant thereof. In some embodiments, the von Willebrand Factor domain A1 target is a non-human von Willebrand Factor domain A1 target or variant thereof. In other embodiments, the von Willebrand Factor domain A1 target is a human von Willebrand Factor domain A1 target or variant thereof. In some embodiments, the von Willebrand Factor full length target or domain A1 target is selected from the group consisting of: a rabbit, guinea pig, monkey, dog, sheep, mouse and rat, von Willebrand Factor full length or domain A1 target. In some embodiments, the von Willebrand Factor full length target and von Willebrand Factor domain A1 target to which the aptamer of the invention specifically binds, are from different species.

The present invention provides aptamers against a von Willebrand Factor target that are ribonucleic acid or deoxyribonucleic acid or mixed ribonucleic acid and deoxyribonucleic acid. Aptamers of the invention may be single stranded ribonucleic acid or deoxyribonucleic acid or mixed ribonucleic acid and deoxyribonucleic acid. In some embodiments, the aptamer of the invention comprises at least one chemical modification. In some embodiments, the chemical modification is selected from the group consisting of: a chemical substitution at a sugar position; a chemical substitution at a phosphate position; and a chemical substitution at a base position, of the nucleic acid. In other embodiments, the chemical modification is selected from the group consisting of: incorporation of a modified nucleotide, 3' capping, conjugation to a high molecular weight, non-immunogenic compound, conjugation to a lipophilic compound, and incorporation of phosphorothioate into the phosphate back bone. In a preferred embodiment, the non-immunogenic, high molecular weight compound is polyalkylene glycol, more preferably polyethylene glycol.

In some embodiments of the present invention, an aptamer, e.g. a von Willebrand Factor aptamer, that binds specifically to a target wherein the aptamer comprises a nucleotide sequence having no more than four, no more than three, no more than two or no more than one phosphorothioate backbone modifications, and the aptamer has a binding affinity for the target wherein the binding affinity is increased relative to a second aptamer having the same nucleotide sequence but lacking phosphorothioate back bone modification is provided. In some embodiments, the target is a protein or peptide not having the known function of binding nucleic acid, particularly not have the known primary function of binding nucleic acid.

In some embodiments, the aptamer of the invention modulates a function of any one of the group consisting of: the von Willebrand Factor target, the von Willebrand Factor domain A1 target and a variant of either target. In some embodiments, the modulated function is platelet aggregation mediation. In some embodiments, the aptamer of the invention inhibits von Willebrand Factor mediated platelet aggregation in vivo. In other embodiments, the aptamer of the invention prevents binding of any one of the group consisting of: the von Willebrand Factor target, the von Willebrand Factor domain A1 target and a variant thereof, to a platelet. In other embodiments, the aptamer of the invention prevents binding of any one of the group consisting of: the von Willebrand Factor target, the von Willebrand Factor domain A1 target and a variant of either target, to a platelet receptor protein. In yet other embodiments, the aptamer of the invention prevents binding of any one of the group consisting of: the von Willebrand Factor target, the von Willebrand Factor domain A1 target and a variant of either target, to the platelet receptor protein GPIb. In some embodiments, the aptamer of the invention prevents vWF Factor mediated platelet aggregation while not significantly increasing bleeding time. In some embodiments, a non-significant increase in bleeding time is less than 15, minutes, preferably less than 10 minutes, more preferably less than 5 minutes, and in some embodiments, less than 3 minutes relative to the bleeding time of a subject not treated with the aptamer of the invention. In some embodiments the bleeding time is determined by cutaneous (or template) bleeding time.

In some embodiments, the aptamer of the invention has substantially the same ability to bind any one of the group consisting of: the von Willebrand Factor target, the von Willebrand Factor domain A1 target and a variant thereof, as that of an aptamer selected from the group consisting of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323). In other embodiments, the aptamer of the invention has substantially the same structure and substantially the same ability to bind of any one of the group consisting of: the von Willebrand Factor target, the von Willebrand Factor domain A1 target and a variant thereof, as that of an aptamer selected from the group of sequences consisting of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323). In yet other embodiments, the aptamer of the invention is selected from the group consisting of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323).

In a particular embodiment, the aptamer of the invention comprises the primary nucleic acid sequence of ARC1172 (SEQ ID NO 222) or ARC11115 (SEQ ID NO 221) or ARC1029 (SEQ ID NO 214) or SEQ ID NO 220 and does not comprise a 2'-O-Me substituted nucleotide at position 6 to 9, 20, 22, 24 to 27, 30 or 32 to 33. In another embodiment, the aptamer of the invention comprises the nucleic acid sequence of ARC1172 (SEQ ID NO 222) or ARC1115 (SEQ ID NO 221) or ARC1029 (SEQ ID NO 214) or SEQ ID NO 220 and comprises a 2'-O-Me substituted nucleotide at one or more positions, at 5 or more positions, at 10 or more positions, at 15 or more positions, or at 20 or more positions. In another embodiment, the aptamer of the invention comprises the nucleic acid sequence of ARC1172 (SEQ ID NO 222) or ARC1115 (SEQ ID NO 221) or ARC1029 (SEQ ID NO 214) or SEQ ID NO 220 and comprises a 2'-O-Me substituted nucleotide at all positions selected from the group consisting of: position 1 to 5, position 10 to 19, position 21, position 23, position 28 to 29, and position 34 to 41 wherein the position numbering starts at the 5' end of the nucleic acid sequence.

In a particular embodiment of the invention, an aptamer comprising a nucleotide sequence selected from the group consisting of: SEQ ID NO 95 to 97 and SEQ ID NO 217 to 219 wherein: Y=C or T/U, R=A or G, N=any nucleotide but in paired regions it assumes a Watson/Crick base pair; and X=1 to 4, is provided. In another embodiment, an aptamer of the invention is selected from the group consisting of: SEQ ID NO 217 and 220 wherein $N_x$-$N_x$-$N_x$-$N_x$-, or $N_{(3-10)}$ may be replaced with a PEG linker. In yet another embodiment, an aptamer of the invention is selected from the group consisting of SEQ ID NOs 325-327, where Y=C or T, R=A or G.

Figure 15A:
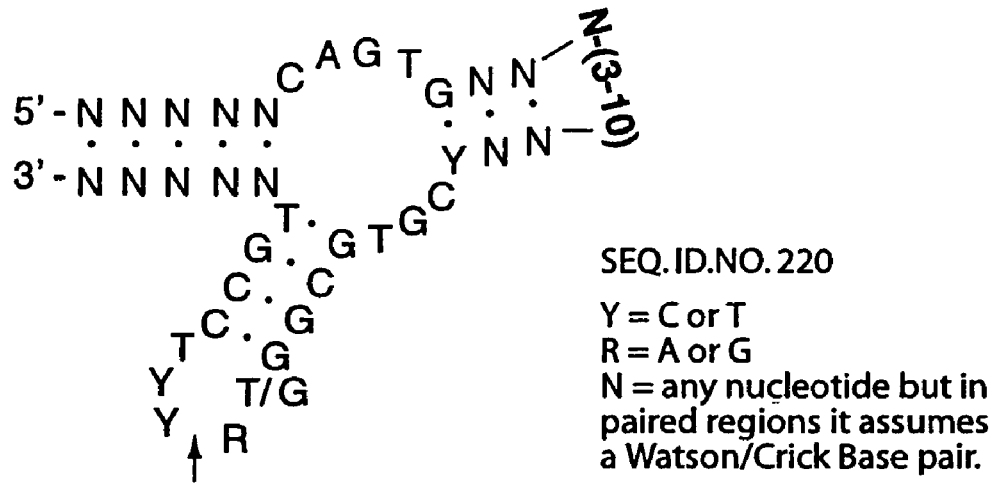
FIG. 15A is an illustration depicting the proposed secondary structure for SEQ ID NO 220.

In a particular embodiment, the aptamer that binds specifically to von Willebrand Factor comprises a three way helix junction secondary structure motif having the consensus sequence structure of SEQ ID NO 220 depicted in FIG. 15. In another particular embodiment, the aptamer having the three way helix junction comprises the consensus structure depicted in FIG. 19 A (ARC1368 (SEQ ID NO 291)). While in another embodiment, the aptamer having the three way helix junction comprises the consensus structure depicted in FIG. 19 B (ARC1534 (SEQ ID NO 315)).

Figure 10:
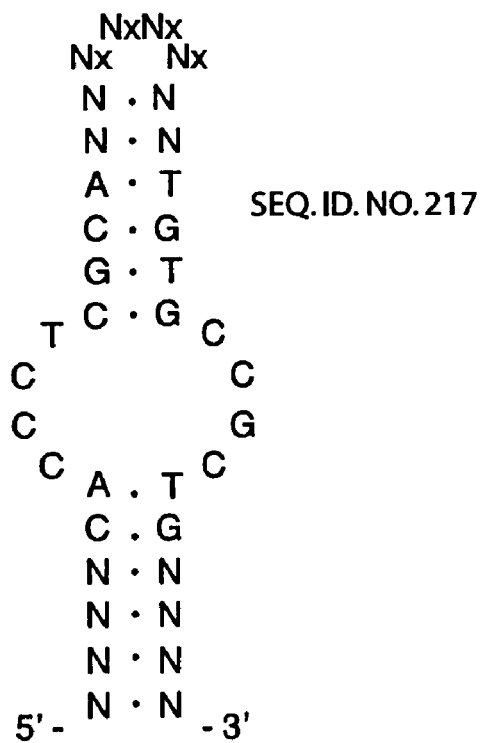
FIG. 10 is an illustration depicting the proposed secondary structure for the SEQ ID NO 217 wherein C=fC, T=fU, N=any nucleotide but in paired regions it assumes a Watson/Crick base pair, and X=1 to 4 nucleotides or Nx-Nx-Nx-Nx can be replaced with a PEG spacer.
Figure 11:
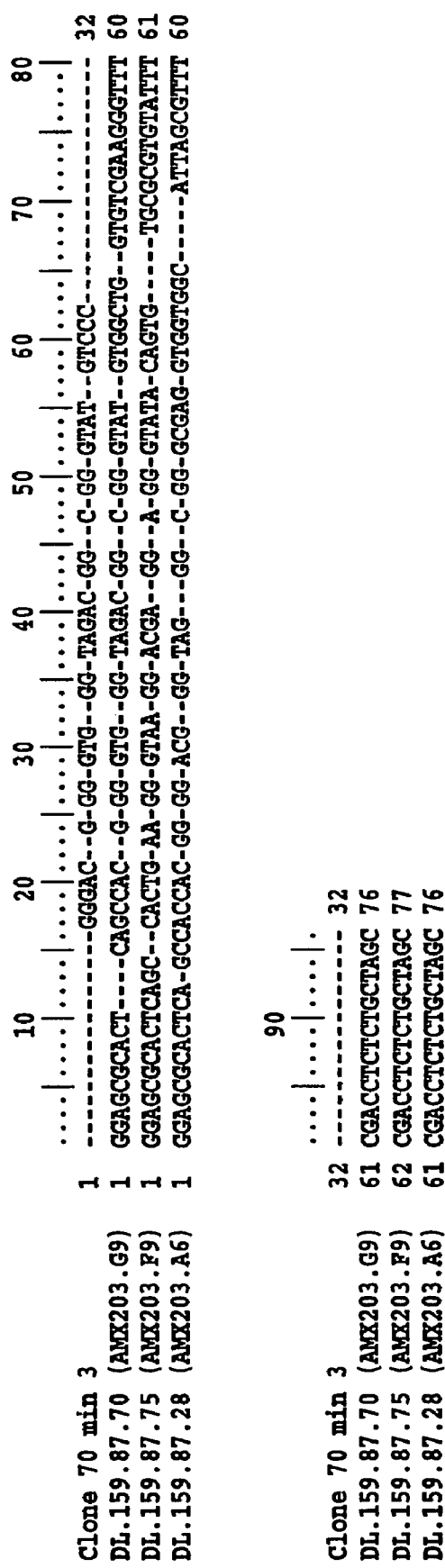
FIG. 11 is an illustration depicting the sequence alignment for three aptamers of the vWF rRdY SELEX™ Family #1.

In another embodiment, the aptamer that binds specifically to von Willebrand Factor comprises a stem-loop-stem-loop secondary structure motif having the consensus sequence structure of SEQ ID NO 217 depicted in FIG. 10. In another embodiment, the aptamer that specifically binds to von Willebrand Factor comprises the stem-loop-loop secondary structure motif having the consensus sequence structure of SEQ ID NO 218 depicted in FIG. 12. In another embodiment, the aptamer that binds specifically to von Willebrand Factor comprises a three way junction secondary structure motif with two helical stems and a stem-loop of SEQ ID NO 19 as depicted in FIG. 13. In some embodiments, the secondary structure motif of the aptamer of the invention is predicted by: RNAstructure, Version 4.1 (Mathews, D. H.; Disney, M. D.; Childs, J. L.; Schroeder, S. J.; Zuker, M.; and Turner, D. H., "Incorporating chemical modification constraints into a dynamic programming algorithm for prediction of RNA secondary structure," 2004. *Proceedings of the National Academy of Sciences, US*, 101, 7287-7292).

In a preferred embodiment, an aptamer that specifically binds to a human von Willebrand Factor target and to a non-human von Willebrand Factor target is provided.

In one embodiment, an aptamer comprising the following structure or a salt thereof is provided:

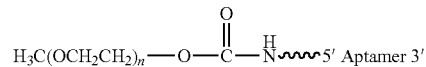

wherein: n is about 454 ethylene oxide units (PEG=20 kDa) $\sim\sim\sim\sim$ is a linker, and the aptamer is an anti-vWF aptamer of the invention. In a particular embodiment, the aptamer comprises the following nucleic acid sequence or fragment thereof: mGmCmGmUdGdCdAmGmUmGmCmCmU-mUmCmGmGmCdCmG-s-dTmGdCdGdGTmGmCd-CmUdCdCmGmUdCmAmCmGmC-3T (SEQ ID NO 291) wherein m refers to a 2'-OMe substitution, the "d" refers to a deoxy nucleotide, the "s" refers to a phosphorothioate substitution and "3T" refers to an inverted deoxy thymidine. In another embodiment, the aptamer comprises the following nucleic acid sequence or fragment thereof: dGdGdCdGdTdGdCdAdGdTdGdCd-CdTdTdCdGdGdCdCdGdTdGd-CdGdGdTdGdCdCdTdCdC dGdTdCdAdCdGdCdC-3T (SEQ ID NO 323) wherein "d" refers to a deoxy nucleotide and "3T" refers to an inverted deoxy thymidine. In some embodiments of this aspect of the invention the linker is an alkyl linker. In particular embodiments, the alkyl linker comprises 2 to 18 consecutive $CH_2$ groups. In preferred embodiments, the alkyl linker comprises 2 to 12 consecutive $CH_2$ groups. In particularly preferred embodiments the alkyl linker comprises 3 to 6 consecutive $CH_2$ groups.

In a particular embodiment, the aptamer of the invention comprises the following structure:

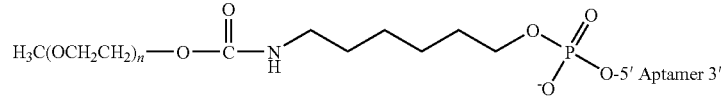

wherein: n is about 454 ethylene oxide units (PEG=20 kDa), and the aptamer nucleic acid sequence is an anti-vWF aptamer of the invention. In a particular embodiment, the aptamer comprises the following nucleic acid sequence or fragment thereof: mGmCmGmUdGdCdAmGmUmGmCm-CmUmUmCmGmGmCdCmG-s-dTmGdCdGdGTmGmCd-CmUdCdCmGmUdCmAmCmGmC-3T (SEQ ID NO 291) wherein m refers to a 2'-OMe substitution, the "d" refers to a deoxy nucleotide, the "s" refers to a phosphorothioate substitution and "3T" refers to an inverted deoxy thymidine. In another embodiment, the aptamer comprises the following nucleic acid sequence or fragment thereof: dGdGd-CdGdTdGdCdAdGdTdGdCdCdTdTd-CdGdGdCdCdGdTdGdCdGdGdTdGdCdCdTdCdC dGdT-dCdAdCdGdCdC-3T (SEQ ID NO 323) wherein "d" refers to a deoxy nucleotide and "3T" refers to an inverted deoxy thymidine.

In another embodiment, a salt of an aptamer of the invention is provided. In a particular embodiment, the following salt of an aptamer is provided:

N-(methoxy-polyethyleneglycol)-6-aminohexylyl-
(1→5')-2'-OMe-guanylyl-(3'→5')-2'-OMe-cytidylyl-
(3'→5')-2'-OMe-guanylyl-(3'→5')-2'-OMe-uracylyl-
(3'→5')-2'-deoxyguanylyl-(3'→5')-2'-deoxycytidylyl-
(3'→5')-2'-deoxyadenylyl-(3'→5')-2'-OMe-guanylyl-
(3'→5')-2'-OMe-uracylyl-(3'→5')-2'-OMe-guanylyl-
(3'→5')-2'-OMe-cytidylyl-(3'→5')-2'-OMe-cytidylyl-
(3'→5')-2'-OMe-uracylyl-(3'→5')-2'-OMe-uracylyl-(3'
5')-2'-OMe-cytidylyl-(3'→5')-2'-OMe-guanylyl-
(3'→5')-2'-OMe-guanylyl-(3'→5')-2'-OMe-cytidylyl-
(3'→5')-2'-deoxycytidylyl-(3'→5')-2'-OMe-P-thiogua-
nylyl-(3'→5')-2'-deoxythymidylyl-(3'→5')-2'-OMe-
guanylyl-(3'→5')-2'-deoxycytidylyl-(3'→5')-2'-
deoxyguanylyl-(3'→5')-2'-deoxyguanylyl-(3'→5')-2'-
deoxythymidylyl-(3'→5')-2'-OMe-guanylyl-(3'→5')-
2'-OMe-cytidylyl-(3'→5')-2'-deoxycytidylyl-(3'→5')-
2'-OMe-uracylyl-(3'→5')-2'-deoxycytidylyl-(3'→5')-
2'-deoxycytidylyl-(3'→5')-2'-OMe-guanylyl-(3'→5')-
2'-OMe-uracylyl-(3'→5')-2'-deoxycytidylyl-(3'→5')-
2'-OMe-adenylyl-(3'→5')-2'-OMe-cytidylyl-(3'→5')-
2'-OMe-guanylyl-(3'→5')-2'-OMe-cytidylyl-(3'→5')-
(3'→3')-2'-deoxythymidine, 40-sodium salt, wherein the methoxy polyethyleneglycol comprises a molecular weight of 20 kDa.

In yet another embodiment, a pharmaceutical composition comprising a therapeutically effective amount of any one of the aptamers of the invention or a salt thereof and a pharmaceutically acceptable carrier or diluent is provided. In a particular embodiment, the pharmaceutical composition of the invention comprises ARC1779. In a more particular embodiment the pharmaceutical composition comprises an aptamer having the following structure or a salt thereof:

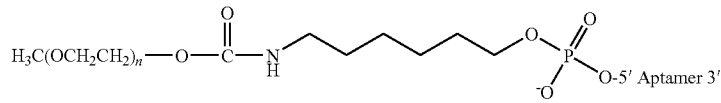

wherein: n is about 454 ethylene oxide units (PEG=20 kDa), and the aptamer comprises the following nucleic acid sequence or fragment thereof: mGmCmGmUdGdCdAmG-mUmGmCmCmUmUmCmGmGmCdCmG-s-dTmGd-CdGdGTmGmCdCmUdCdCmGmUdCmAmCmGmC-3T (SEQ ID NO 291) wherein m refers to a 2'-OMe substitution, the "d" refers to a deoxy nucleotide, the "s" refers to a phosphorothioate substitution and "3T" refers to an inverted deoxy thymidine.

The invention provides a method of treating, preventing or ameliorating a disease mediated by von Willebrand Factor, comprising administering an aptamer or a pharmaceutical composition of the invention to a vertebrate, preferably a mammal, more preferably a human. In some embodiments, the disease to be treated, prevented or ameliorated is selected from the group consisting of: essential thrombocytopenia, thrombotic thrombocopenic purpura ("TTP"), Type IIb von Willebrand's disease, pseudo von Willebrand disease, peripheral artery disease, e.g. peripheral arterial occlusive disease, unstable angina, angina pectoris, arterial thrombosis, atherosclerosis, myocardial infarction, acute coronary syndrome, atrial fibrillation, carotid stenosis, cerebral infarction, cerebral thrombosis, ischemic stroke, and transient cerebral ischemic attack. In some embodiments, the pharmaceutical composition of the invention is administered prior to/during and/or after dialysis, CABG surgery, percutaneous coronary intervention or heart valve replacement.

The length of the in vivo half life of the aptamer of the invention may vary depending on the disease to be treated, ameliorated and/or prevented. For example, in some embodiments in which chronic aptamer administration is desirable due to the characteristics of the disease to be treated, ameliorated and/or prevented, the aptamer of the invention may comprise a relatively long half life, e.g. a half life greater than five hours in humans.

In other embodiments, the aptamer of the invention comprises a desired functional half life or duration of effect. Functional half life or duration of effect is a function of both pharmacokinetic half life and pharmacodynamic activity of the aptamer. In some embodiments, the desired human functional half-life or duration of effect for an anti-vWF therapeutic aptamer is on the order of 1-5 hours for the proposed indications elective PCI and ACS. Aptamers with such kinetics represent a balance between the dual objectives of (1) minimizing total aptamer dose (achieved with longer half-life) and (2) allowing rapid normalization of platelet function following cessation of treatment (achieved with shorter half-life). In some embodiments, rapid normalization of platelet function is important as it allows clinicians the option of rapid intervention (e.g. CABG) should a patient fail to stabilize in response to treatment.

Accordingly, in some embodiments the aptamer for use in the methods of treatment and/or pharmaceutical compositions of the invention comprises a relatively short functional half life, e.g. a functional half life in humans of about 1 to 5 hours. In some embodiments, the functional half life in humans is at least 1 hour, at least 2 hours, at least 3 hours, at least 4 hours and not more than about 5 hours. In some embodiments, the functional half life or duration of effect is about the same as the distribution half life $T_{1/2\alpha}$ of the aptamer.

In some embodiments, the aptamer of the invention comprising the short functional half life in humans is for use in methods and compositions for the treatment, amelioration or prevention of diseases that potentially may require surgical intervention, such as acute coronary syndrome. In some embodiments, the aptamer of this aspect of the invention comprising a short functional half life in humans is conjugated to a PEG, e.g. a 5, 10 or 20 kDa PEG. In some embodiments, the aptamer of this aspect of the invention comprising a short half life in humans is ARC1779.

The invention also provides a diagnostic method comprising contacting an aptamer of the invention with a composition suspected of comprising von Willebrand Factor, von Willebrand Factor domain A1 or a variant thereof and detecting the presence or absence of von Willebrand Factor, von Willebrand Factor domain A1 or a variant thereof. In some embodiments, the diagnostic method is for use in vitro while in other embodiments, the diagnostic method is for use in vivo.

The invention also provides a method for identifying an aptamer that blocks a biological function in vivo comprising:
 a) preparing a candidate mixture of single-stranded nucleic acids;
 b) contacting the candidate mixture with both a full length protein target and a domain of the full length protein target;
 c) partitioning the nucleic acids having an increased affinity for the full length protein target or the protein target domain; and
 d) amplifying the increased affinity nucleic acids, in vitro, to yield a protein target specific enriched aptamer mixture.

In some embodiments, the identification method further comprises;
 e) contacting the target specific enriched aptamer mixture with the full length protein target;
 f) partitioning the nucleic acids having an increased affinity for the full length protein target; and
 g) amplifying the increased affinity nucleic acids, in vitro; to yield a target specific enriched aptamer mixture;
 h) contacting the target specific enriched aptamer mixture with the protein target domain;
 i) partitioning the nucleic acids having an increased affinity for the protein target domain; and
 j) amplifying the increased affinity nucleic acids, in vitro, to yield a protein target specific enriched aptamer mixture.

In some embodiments, the identification method further comprises selecting an aptamer that blocks a biological function of the full length protein target in vivo while in other embodiments, the method further comprises selecting an aptamer that blocks a biological function of the protein target domain in vivo. In some embodiments of the identification method of the invention, the full length protein target is from a first species and the protein target domain is from a second species. In further embodiments of the identification method of the invention, the method further comprises selecting an aptamer capable of binding to both protein targets of both the first and second species, preferably selecting an aptamer that blocks a biological function of the protein target in both the first and second species. In some embodiments of the identification method of the invention, the full length target protein target is von Willebrand Factor. In some embodiments of the identification method of the invention, the full length target protein target is von Willebrand Factor, wherein it is preferred that the selected aptamer blocks von Willebrand Factor mediated platelet aggregation. In some embodiments the protein target domain is von Willebrand Factor domain A1. The invention also provides an aptamer identified by the identification method of the invention.

In some embodiments, the invention also provides an aptamer that specifically binds to von Willebrand Factor comprising a primary nucleic acid sequence at least 80% identical, particularly at least 90% identical, and more particularly at least 95% identical to any one of the primary nucleic acid sequences selected from the group consisting of SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 to ARC1780 (SEQ ID NO 321) and ARC1884 (SEQ ID NO 322) to ARC1885 (SEQ ID NO 323). In some embodiments, the % sequence identity of the aptamers of the invention is BLAST sequence identity.

In another embodiment, the aptamer of the invention comprises a nucleic acid sequence having chemical modifications that including chemical modifications is at least 80% identical, particularly 90% identical, and more particularly at least 95% identical to any one of the nucleic acid sequences selected from the group consisting of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 to ARC1780 (SEQ ID NO 321) and ARC1884 (SEQ ID NO 322) to ARC1885 (SEQ ID NO 323).

In yet another embodiment, the invention provides an aptamer that upon binding a von Willebrand Factor target modulates a von Willebrand Factor function, preferably in vivo and comprises a sequence of 30 contiguous nucleotides that are identical to a sequence of 30 contiguous nucleotides comprised in any one of the sequences selected from the group of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 to ARC1780 (SEQ ID NO 321) and ARC1884 (SEQ ID NO 322) to ARC1885 (SEQ ID NO 323). In yet another embodiment, the aptamer of the invention upon binding a von Willebrand Factor target modulates a von Willebrand Factor function, preferably in vivo, and comprises 20 contiguous nucleotides that are identical to a sequence of 20 contiguous nucleotides in the unique sequence region of any one of the aptamer selected from the group of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 to ARC1780 (SEQ ID NO 321) and ARC1884 (SEQ ID NO 322) to ARC1885 (SEQ ID NO 323). In yet another embodiment, the aptamer of the invention upon binding a von Willebrand Factor target modulates a von Willebrand Factor function, preferably in vivo, and comprises 8 contiguous nucleotides that are identical to a sequence of 8 contiguous nucleotides in the unique sequence region of any one of the aptamer selected from the group of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 to ARC1780 (SEQ ID NO 321) and ARC1884 (SEQ ID NO 322) to ARC1885 (SEQ ID NO 323). In yet another embodiment, the aptamer of the invention upon binding a von Willebrand Factor target modulates a von Willebrand Factor function, preferably in vivo, and comprises 4 contiguous nucleotides that are identical to a sequence of 4 contiguous nucleotides in the unique sequence region of any one of the aptamer selected from the group of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115 (SEQ ID NO 221), ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635 (SEQ ID NO 319), ARC1759 (SEQ ID NO 318), ARC1779 to ARC1780 (SEQ ID NO 321) and ARC1884 (SEQ ID NO 322) to ARC1885 (SEQ ID NO 323).

DETAILED DESCRIPTION OF THE INVENTION

The details of one or more embodiments of the invention are set forth in the accompanying description below. Although any methods and materials similar or equivalent to those described herein can be used in the practice or testing of the present invention, the preferred methods and materials are now described. Other features, objects, and advantages of the invention will be apparent from the description. In the specification, the singular forms also include the plural unless the context clearly dictates otherwise. Unless defined otherwise, all technical and scientific terms used herein have the same meaning as commonly understood by one of ordinary skill in the art to which this invention belongs. In the case of conflict, the present Specification will control.

The Selex™ Method

A suitable method for generating an aptamer is with the process entitled "Systematic Evolution of Ligands by Exponential Enrichment" ("SELEX™") generally depicted in FIG. 1. The SELEX™ process is a method for the in vitro evolution of nucleic acid molecules with highly specific binding to target molecules and is described in, e.g., U.S. patent application Ser. No. 07/536,428, filed Jun. 11, 1990, now abandoned, U.S. Pat. No. 5,475,096 entitled "Nucleic Acid Ligands", and U.S. Pat. No. 5,270,163 (see also WO 91/19813) entitled "Nucleic Acid Ligands". Each SELEX™-identified nucleic acid ligand, i.e., each aptamer, is a specific ligand of a given target compound or molecule. The SELEX™ process is based on the unique insight that nucleic acids have sufficient capacity for forming a variety of two- and three-dimensional structures and sufficient chemical versatility available within their monomers to act as ligands (i.e., form specific binding pairs) with virtually any chemical compound, whether monomeric or polymeric. Molecules of any size or composition can serve as targets.

SELEX™ relies as a starting point upon a large library or pool of single stranded oligonucleotides comprising randomized sequences. The oligonucleotides can be modified or unmodified DNA, RNA, or DNA/RNA hybrids. In some examples, the pool comprises 100% random or partially random oligonucleotides. In other examples, the pool comprises random or partially random oligonucleotides containing at least one fixed sequence and/or conserved sequence incorporated within randomized sequence. In other examples, the pool comprises random or partially random oligonucleotides containing at least one fixed and/or conserved sequence at its 5' and/or 3' end which may comprise a sequence shared by all the molecules of the oligonucleotide pool. Fixed sequences are sequences common to oligonucleotides in the pool which are incorporated for a preselected purpose, such as CpG motifs described further below, hybridization sites for PCR primers, promoter sequences for RNA polymerases (e.g., T3, T4, T7, and SP6), restriction sites, or homopolymeric sequences, such as poly A or poly T tracts, catalytic cores, sites for selective binding to affinity columns, and other sequences to facilitate cloning and/or sequencing of an oligonucleotide of interest. Conserved sequences are sequences, other than the previously described fixed sequences, shared by a number of aptamers that bind to the same target.

The oligonucleotides of the pool preferably include a randomized sequence portion as well as fixed sequences necessary for efficient amplification. Typically the oligonucleotides of the starting pool contain fixed 5' and 3' terminal sequences which flank an internal region of 30-50 random nucleotides. The randomized nucleotides can be produced in a number of ways including chemical synthesis and size selection from randomly cleaved cellular nucleic acids. Sequence variation in test nucleic acids can also be introduced or increased by mutagenesis before or during the selection/amplification iterations.

The random sequence portion of the oligonucleotide can be of any length and can comprise ribonucleotides and/or deoxyribonucleotides and can include modified or non-natural nucleotides or nucleotide analogs. See, e.g., U.S. Pat. No. 5,958,691; U.S. Pat. No. 5,660,985; U.S. Pat. No. 5,958,691; U.S. Pat. No. 5,698,687; U.S. Pat. No. 5,817,635; U.S. Pat. No. 5,672,695, and PCT Publication WO 92/07065. Random oligonucleotides can be synthesized from phosphodiester-linked nucleotides using solid phase oligonucleotide synthesis techniques well known in the art. See, e.g., Froehler et al., Nucl. Acid Res. 14:5399-5467 (1986) and Froehler et al., Tet. Lett. 27:5575-5578 (1986). Random oligonucleotides can also be synthesized using solution phase methods such as triester synthesis methods. See, e.g., Sood et al., Nucl. Acid Res. 4:2557 (1977) and Hirose et al., Tet. Lett., 28:2449 (1978). Typical syntheses carried out on automated DNA synthesis equipment yield $10^{14}$-$10^{16}$ individual molecules, a number sufficient for most SELEX™ experiments. Sufficiently large regions of random sequence in the sequence design increases the likelihood that each synthesized molecule is likely to represent a unique sequence.

The starting library of oligonucleotides may be generated by automated chemical synthesis on a DNA synthesizer. To synthesize randomized sequences, mixtures of all four nucleotides are added at each nucleotide addition step during the synthesis process, allowing for random incorporation of nucleotides. As stated above, in one embodiment, random oligonucleotides comprise entirely random sequences; however, in other embodiments, random oligonucleotides can comprise stretches of nonrandom or partially random sequences. Partially random sequences can be created by adding the four nucleotides in different molar ratios at each addition step.

The starting library of oligonucleotides may be either RNA or DNA, or substituted RNA or DNA. In those instances where an RNA library is to be used as the starting library it is typically generated by synthesizing a DNA library, optionally PCR amplifying, then transcribing the DNA library in vitro using T7 RNA polymerase or modified T7 RNA polymerases, and purifying the transcribed library. The RNA or DNA library is then mixed with the target under conditions favorable for binding and subjected to step-wise iterations of binding, partitioning and amplification, using the same general selection scheme, to achieve virtually any desired criterion of binding affinity and selectivity. More specifically, starting with a mixture containing the starting pool of nucleic acids, the SELEX™ method includes steps of: (a) contacting the mixture with the target under conditions favorable for binding; (b) partitioning unbound nucleic acids from those nucleic acids which have bound specifically to target molecules; (c) dissociating the nucleic acid-target complexes; (d) amplifying the nucleic acids dissociated from the nucleic acid-target complexes to yield a ligand-enriched mixture of nucleic acids; and (e) reiterating the steps of binding, partitioning, dissociating and amplifying through as many cycles as desired to yield highly specific, high affinity nucleic acid ligands to the target molecule. In those instances where RNA aptamers are being selected, the SELEX™ method further comprises the steps of: (i) reverse transcribing the nucleic acids dissociated from the nucleic acid-target complexes before amplification in step (d); and (ii) transcribing the amplified nucleic acids from step (d) before restarting the process.

Within a nucleic acid mixture containing a large number of possible sequences and structures, there is a wide range of binding affinities for a given target. A nucleic acid mixture comprising, for example, a 20 nucleotide randomized segment can have $4^{20}$ candidate possibilities. Those which have the higher affinity (lower dissociation constants) for the target are most likely to bind to the target. After partitioning, dissociation and amplification, a second nucleic acid mixture is generated, enriched for the higher binding affinity candidates. Additional rounds of selection progressively favor the best ligands until the resulting nucleic acid mixture is predominantly composed of only one or a few sequences. These can then be cloned, sequenced and individually tested for binding affinity as pure ligands or aptamers.

Cycles of selection and amplification are repeated until a desired goal is achieved. In the most general case, selection/amplification is continued until no significant improvement in binding strength is achieved on repetition of the cycle. The method is typically used to sample approximately $10^{14}$ different nucleic acid species but may be used to sample as many as about $10^{18}$ different nucleic acid species. Generally, nucleic acid aptamer molecules are selected in a 5 to 20 cycle procedure. In one embodiment, heterogeneity is introduced only in the initial selection stages and does not occur throughout the replicating process.

In one embodiment of SELEX™, the selection process is so efficient at isolating those nucleic acid ligands that bind most strongly to the selected target, that only one cycle of selection and amplification is required. Such an efficient selection may occur, for example, in a chromatographic-type process wherein the ability of nucleic acids to associate with targets bound on a column operates in such a manner that the column is sufficiently able to allow separation and isolation of the highest affinity nucleic acid ligands.

In many cases, it is not necessarily desirable to perform the iterative steps of SELEX™ until a single nucleic acid ligand is identified. The target-specific nucleic acid ligand solution may include a family of nucleic acid structures or motifs that have a number of conserved sequences and a number of sequences which can be substituted or added without significantly affecting the affinity of the nucleic acid ligands to the target. By terminating the SELEX™ process prior to completion, it is possible to determine the sequence of a number of members of the nucleic acid ligand solution family.

A variety of nucleic acid primary, secondary and tertiary structures are known to exist. The structures or motifs that have been shown most commonly to be involved in non-Watson-Crick type interactions are referred to as hairpin loops, symmetric and asymmetric bulges, pseudoknots and myriad combinations of the same. Almost all known cases of such motifs suggest that they can be formed in a nucleic acid sequence of no more than 30 nucleotides. For this reason, it is often preferred that SELEX™ procedures with contiguous randomized segments be initiated with nucleic acid sequences containing a randomized segment of between about 20 to about 50 nucleotides, and of about 30 to about 40 nucleotides in some embodiments. In one example, the 5'-fixed:random:3'-fixed sequence comprises a random sequence of about 30 to about 50 nucleotides.

The core SELEX™ method has been modified to achieve a number of specific objectives. For example, U.S. Pat. No. 5,707,796 describes the use of SELEX™ in conjunction with gel electrophoresis to select nucleic acid molecules with specific structural characteristics, such as bent DNA. U.S. Pat. No. 5,763,177 describes SELEX™ based methods for selecting nucleic acid ligands containing photoreactive groups capable of binding and/or photocrosslinking to and/or photoinactivating a target molecule. U.S. Pat. No. 5,567,588 and U.S. Pat. No. 5,861,254 describe SELEX™ based methods which achieve highly efficient partitioning between oligonucleotides having high and low affinity for a target molecule. U.S. Pat. No. 5,496,938 describes methods for obtaining improved nucleic acid ligands after the SELEX™ process has been performed. U.S. Pat. No. 5,705,337 describes methods for covalently linking a ligand to its target.

SELEX™ can also be used to obtain nucleic acid ligands that bind to more than one site on the target molecule, and to obtain nucleic acid ligands that include non-nucleic acid species that bind to specific sites on the target. SELEX™ provides means for isolating and identifying nucleic acid ligands which bind to any envisionable target, including large and small biomolecules such as nucleic acid-binding proteins and proteins not known to bind nucleic acids as part of their biological function as well as cofactors and other small molecules. For example, U.S. Pat. No. 5,580,737 discloses nucleic acid sequences identified through SELEX™ which are capable of binding with high affinity to caffeine and the closely related analog, theophylline.

Counter-SELEX™ is a method for improving the specificity of nucleic acid ligands to a target molecule by eliminating nucleic acid ligand sequences with cross-reactivity to one or more non-target molecules. Counter-SELEX™ is comprised of the steps of: (a) preparing a candidate mixture of nucleic acids; (b) contacting the candidate mixture with the target, wherein nucleic acids having an increased affinity to the target relative to the candidate mixture may be partitioned from the remainder of the candidate mixture; (c) partitioning the increased affinity nucleic acids from the remainder of the candidate mixture; (d) dissociating the increased affinity nucleic acids from the target; (e) contacting the increased affinity nucleic acids with one or more non-target molecules such that nucleic acid ligands with specific affinity for the non-target molecule(s) are removed; and (f) amplifying the nucleic acids with specific affinity only to the target molecule to yield a mixture of nucleic acids enriched for nucleic acid sequences with a relatively higher affinity and specificity for binding to the target molecule. As described above for SELEX™ cycles of selection and amplification are repeated as necessary until a desired goal is achieved.

One potential problem encountered in the use of nucleic acids as therapeutics and vaccines is that oligonucleotides in their phosphodiester form may be quickly degraded in body fluids by intracellular and extracellular enzymes such as endonucleases and exonucleases before the desired effect is manifest. The SELEX™ method thus encompasses the identification of high-affinity nucleic acid ligands containing modified nucleotides conferring improved characteristics on the ligand, such as improved in vivo stability or improved delivery characteristics. Examples of such modifications include chemical substitutions at the sugar and/or phosphate and/or base positions. SELEX™-identified nucleic acid ligands containing modified nucleotides are described, e.g., in U.S. Pat. No. 5,660,985, which describes oligonucleotides containing nucleotide derivatives chemically modified at the 2' position of ribose, 5 position of pyrimidines, and 8 position of purines, U.S. Pat. No. 5,756,703 which describes oligonucleotides containing various 2'-modified pyrimidines, and U.S. Pat. No. 5,580,737 which describes highly specific nucleic acid ligands containing one or more nucleotides modified with 2'-amino (2'-$NH_2$), 2'-fluoro (2'-F), and/or 2'-OMe substituents.

Modifications of the nucleic acid ligands contemplated in this invention include, but are not limited to, those which provide other chemical groups that incorporate additional charge, polarizability, hydrophobicity, hydrogen bonding, electrostatic interaction, and fluxionality to the nucleic acid ligand bases or to the nucleic acid ligand as a whole. Modifications to generate oligonucleotide populations which are resistant to nucleases can also include one or more substitute internucleotide linkages, altered sugars, altered bases, or combinations thereof. Such modifications include, but are not limited to, 2'-position sugar modifications, 5-position pyrimidine modifications, 8-position purine modifications, modifications at exocyclic amines, substitution of 4-thiouridine, substitution of 5-bromo or 5-iodo-uracil, backbone modifications, phosphorothioate or alkyl phosphate modifications, methylations, and unusual base-pairing combinations such as the isobases isocytidine and isoguanidine. Modifications can also include 3' and 5' modifications such as capping.

In one embodiment, oligonucleotides are provided in which the P(O)O group is replaced by P(O)S ("thioate"), P(S)S ("dithioate"), P(O)$NR_2$ ("amidate"), P(O)R, P(O)OR', CO or $CH_2$ ("formacetal") or 3'-amine (—NH—$CH_2$—$CH_2$—), wherein each R or R' is independently H or substituted or unsubstituted alkyl. Linkage groups can be attached to adjacent nucleotides through an —O-, —N-, or —S-linkage. Not all linkages in the oligonucleotide are required to be identical. As used herein, the term phosphorothioate encompasses one or more non-bridging oxygen atoms in a phosphodiester bond replaced by one or more sulfur atoms In further embodiments, the oligonucleotides comprise modified sugar groups, for example, one or more of the hydroxyl groups is replaced with halogen, aliphatic groups, or functionalized as ethers or amines. In one embodiment, the 2'-position of the furanose residue is substituted by any of an O-methyl, O-alkyl, O-allyl, S-alkyl, S-allyl, or halo group. Methods of synthesis of 2'-modified sugars are described, e.g., in Sproat, et al., Nucl. Acid Res. 19:733-738 (1991); Cotten, et al., Nucl. Acid Res. 19:2629-2635 (1991); and Hobbs, et al., Biochemistry 12:5138-5145 (1973). Other modifications are known to one of ordinary skill in the art. Such modifications may be pre-SELEX™ process modifications or post-SELEX™ process modifications (modification of previously identified unmodified ligands) or may be made by incorporation into the SELEX™ process.

Pre-SELEX™ process modifications or those made by incorporation into the SELEX™ process yield nucleic acid ligands with both specificity for their SELEX™ target and improved stability, e.g., in vivo stability. Post-SELEX™ process modifications made to nucleic acid ligands may result in improved stability, e.g., in vivo stability without adversely affecting the binding capacity of the nucleic acid ligand.

The SELEX™ method encompasses combining selected oligonucleotides with other selected oligonucleotides and non-oligonucleotide functional units as described in U.S. Pat. No. 5,637,459 and U.S. Pat. No. 5,683,867. The SELEX™ method further encompasses combining selected nucleic acid ligands with lipophilic or non-immunogenic high molecular weight compounds in a diagnostic or therapeutic complex, as described, e.g., in U.S. Pat. No. 6,011,020, U.S. Pat. No. 6,051,698, and PCT Publication No. WO 98/18480. These patents and applications teach the combination of a broad array of shapes and other properties, with the efficient amplification and replication properties of oligonucleotides, and with the desirable properties of other molecules.

The identification of nucleic acid ligands to small, flexible peptides via the SELEX™ method has also been explored. Small peptides have flexible structures and usually exist in solution in an equilibrium of multiple conformers, and thus it was initially thought that binding affinities may be limited by the conformational entropy lost upon binding a flexible peptide. However, the feasibility of identifying nucleic acid ligands to small peptides in solution was demonstrated in U.S. Pat. No. 5,648,214 in which high affinity RNA nucleic acid ligands to substance P, an 11 amino acid peptide, were identified.

The aptamers with specificity and binding affinity to the target(s) of the present invention are typically selected by the SELEX™ process as described herein. As part of the SELEX™ process, the sequences selected to bind to the target are then optionally minimized to determine the minimal sequence having the desired binding affinity. The selected aptamer sequences and/or the minimized aptamer sequences are optionally optimized by performing random or directed mutagenesis of the sequence to increase binding affinity or alternatively to determine which positions in the sequence are essential for binding activity. For example, a "doped reselections" may be used to explore the sequence requirements within an aptamer. During doped reselection, selections are carried out with a synthetic, degenerate pool that has been designed based on a single sequence. The level of degeneracy usually varies from 70% to 85% wild type nucleotide. In general, neutral mutations are observed following doped reselection but in some cases sequence changes can result in improvements in affinity. Additionally, selections can be performed with sequences incorporating modified sequences to stabilize the aptamer molecules against degradation in vivo.

2'Modified SELEX™

In order for an aptamer to be suitable for use as a therapeutic, it is preferably inexpensive to synthesize, safe and stable in vivo. Wild-type RNA and DNA aptamers are typically not stable in vivo because of their susceptibility to degradation by nucleases. Resistance to nuclease degradation can be greatly increased, if desired, by the incorporation of modifying groups at the 2'-position.

2'-fluoro and 2'-amino groups have been successfully incorporated into oligonucleotide libraries from which aptamers have been subsequently selected. However, these modifications greatly increase the cost of synthesis of the resultant aptamer, and may introduce safety concerns in some cases because of the possibility that the modified nucleotides could be recycled into host DNA by degradation of the modified oligonucleotides and subsequent use of the nucleotides as substrates for DNA synthesis.

Aptamers that contain 2'-O-methyl ("2'-OMe") nucleotides, as provided in some embodiments herein, overcome many of these drawbacks. Oligonucleotides containing 2'-OMe nucleotides are nuclease-resistant and inexpensive to synthesize. Although 2'-OMe nucleotides are ubiquitous in biological systems, natural polymerases do not accept 2'-OMe NTPs as substrates under physiological conditions, thus there are no safety concerns over the recycling of 2'-OMe nucleotides into host DNA. The SELEX™ methods used to generate 2'-modified aptamers is described, e.g., in U.S. Provisional Patent Application Ser. No. 60/430,761, filed Dec. 3, 2002, U.S. Provisional Patent Application Ser. No. 60/487,474, filed Jul. 15, 2003, U.S. Provisional Patent Application Ser. No. 60/517,039, filed Nov. 4, 2003, U.S. patent application Ser. No. 10/729,581, filed Dec. 3, 2003, U.S. patent application Ser. No. 10/873,856 filed Jun. 21, 2004, entitled "Method for in vitro Selection of 2'-OMe Substituted Nucleic Acids", and U.S. Provisional Patent Application Ser. No. 60/696,295, filed Jun. 30, 2005, entitled "Improved Materials and Methods for the Generation of Fully 2'-Modified Containing Nucleic Acid Transcripts", each of which is herein incorporated by reference in its entirety.

The present invention includes aptamers that bind to and modulate the function of von Willebrand Factor which contain modified nucleotides (e.g., nucleotides which have a modification at the 2'position) to make the oligonucleotide more stable than the unmodified oligonucleotide to enzymatic and chemical degradation as well as thermal and physical degradation. Although there are several examples of 2'-OMe containing aptamers in the literature (see, e.g., Ruckman et al., J. Biol. Chem., 1998 273, 20556-20567-695) these were generated by the in vitro selection of libraries of modified transcripts in which the C and U residues were 2'-fluoro (2'-F) substituted and the A and G residues were 2'-OH. Once functional sequences were identified then each A and G residue was tested for tolerance to 2'-OMe substitution, and the aptamer was re-synthesized having all A and G residues which tolerated 2'-OMe substitution as 2'-OMe residues. Most of the A and G residues of aptamers generated in this two-step fashion tolerate substitution with 2'-OMe residues, although, on average, approximately 20% do not. Consequently, aptamers generated using this method tend to contain from two to four 2'-OH residues, and stability and cost of synthesis are compromised as a result. By incorporating modified nucleotides into the transcription reaction which generate stabilized oligonucleotides used in oligonucleotide libraries from which aptamers are selected and enriched by SELEX™ (and/or any of its variations and improvements, including those described herein), the methods of the present invention eliminate the need for stabilizing the selected aptamer oligonucleotides (e.g., by resynthesizing the aptamer oligonucleotides with modified nucleotides).

In one embodiment, the present invention provides aptamers comprising combinations of 2'-OH, 2'-F, 2'-deoxy, and 2'-OMe modifications of the ATP, GTP, CTP, TTP, and UTP nucleotides. In another embodiment, the present invention provides aptamers comprising combinations of 2'-OH, 2'-F, 2'-deoxy, 2'-OMe, 2'-NH$_2$, and 2'-methoxyethyl modifications of the ATP, GTP, CTP, TTP, and UTP nucleotides. In another embodiment, the present invention provides aptamers comprising $5^6$ combinations of 2'-OH, 2'-F, 2'-deoxy, 2'-OMe, 2'-NH$_2$, and 2'-methoxyethyl modifications of the ATP, GTP, CTP, TTP, and UTP nucleotides.

2'-modified aptamers of some embodiments of the invention are created using modified polymerases, e.g., a modified T7 polymerase, having a rate of incorporation of modified nucleotides having bulky substituents at the furanose 2' position that is higher than that of wild-type polymerases. For example, a single mutant T7 polymerase (Y639F) in which the tyrosine residue at position 639 has been changed to phenylalanine readily utilizes 2'deoxy, 2'amino-, and 2'fluoro-nucleotide triphosphates (NTPs) as substrates and has been widely used to synthesize modified RNAs for a variety of applications. However, this mutant T7 polymerase reportedly can not readily utilize (i.e., incorporate) NTPs with bulky 2'-substituents such as 2'-OMe or 2'-azido (2'-N$_3$) substituents. For incorporation of bulky 2' substituents, a double T7 polymerase mutant (Y639F/H784A) having the histidine at position 784 changed to an alanine residue in addition to the Y639F mutation has been described and has been used in limited circumstances to incorporate modified pyrimidine NTPs. See Padilla, R. and Sousa, R., Nucleic Acids Res., 2002, 30(24): 138. A Y639F/H784A/K378R mutant T7 RNA polymerase has been used in limited circumstances to incorporate modified purine and pyrimidine NTPs, e.g., 2'-OMe NPTs, but requires a spike of 2'-OH GTP for transcription. See Burmeister et. al., Chemistry and Biology, 2005, 12: 25-33. A single mutant T7 polymerase (H784A) having the histidine at position 784 changed to an alanine residue has also been described. Padilla et al., Nucleic Acids Research, 2002, 30: 138. In both the Y639F/H784A double mutant and H784A single mutant T7 polymerases, the change to a smaller amino acid residue such as alanine allows for the incorporation of bulkier nucleotide substrates, e.g., 2'-O methyl substituted nucleotides. See Chelliserry, K. and Ellington, A. D., Nature Biotech, 2004, 9:1155-60. Additional T7 RNA polymerase have been described with mutations in the active site of the T7 RNA polymerase which more readily incorporate bulky 2'-modified substrates, e.g. a single T7 mutant RNA polymerase having the tyrosine residue at position 639 changed to a leucine (Y639L). However activity is often sacrificed for increased substrate specificity conferred by such mutations, leading to low transcript yields. See Padilla R and Sousa, R., Nucleic Acids Res., 1999, 27(6): 1561.

Generally, it has been found that under the conditions disclosed herein, the Y693F single mutant can be used for the incorporation of all 2'-OMe substituted NTPs except GTP and the Y639F/H784A, Y639F/H784A/K378R, Y639L/H784A, and Y639L/H784A/K378R mutant T7 RNA polymerases can be used for the incorporation of all 2'-OMe substituted NTPs including GTP. It is expected that the H784A single mutant possesses properties similar to the Y639F and the Y639F/H784A mutants when used under the conditions disclosed herein. 2'-modified oligonucleotides may be synthesized entirely of modified nucleotides, or with a subset of modified nucleotides. All nucleotides may be modified, and all may contain the same modification. All nucleotides may be modified, but contain different modifications, e.g., all nucleotides containing the same base may have one type of modification, while nucleotides containing other bases may have different types of modification. All purine nucleotides may have one type of modification (or are unmodified), while all pyrimidine nucleotides have another, different type of modification (or are unmodified). In this way, transcripts, or libraries of transcripts are generated using any combination of modifications, including for example, ribonucleotides (2'-OH), deoxyribonucleotides (2'-deoxy), 2'-F, and 2'-OMe nucleotides. A transcription mixture containing 2'-OMe C and U and 2'-OH A and G is referred to as a "rRmY" mixture and aptamers selected therefrom are referred to as "rRmY" aptamers. A transcription mixture containing deoxy A and G and 2'-OMe U and C is referred to as a "dRmY" mixture and aptamers selected therefrom are referred to as "dRmY" aptamers. A transcription mixture containing 2'-OMe A, C, and U, and 2'-OH G is referred to as a "rGmH" mixture and aptamers selected therefrom are referred to as "rGmH" aptamers. A transcription mixture alternately containing 2'-OMe A, C, U and G and 2'-OMe A, U and C and 2'-F G is referred to as a "alternating mixture" and aptamers selected therefrom are referred to as "alternating mixture" aptamers. A transcription mixture containing 2'-OMe A, U, C, and G, where up to 10% of the G's are ribonucleotides is referred to as a "r/mGmH" mixture and aptamers selected therefrom are referred to as "r/mGmH" aptamers. A transcription mixture containing 2'-OMe A, U, and C, and 2'-F G is referred to as a "fGmH" mixture and aptamers selected therefrom are referred to as "fGmH" aptamers. A transcription mixture containing 2'-OMe A, U, and C, and deoxy G is referred to as a "dGmH" mixture and aptamers selected therefrom are referred to as "dGmH" aptamers. A transcription mixture containing deoxy A, and 2'-OMe C, G and U is referred to as a "dAmB" mixture and aptamers selected therefrom are referred to as "dAmB" aptamers, and a transcription mixture containing all 2'-OH nucleotides is referred to as a "rN" mixture and aptamers selected therefrom are referred to as "rN", "rRrY", or "RNA" aptamers. A transcription mixture containing 2'-OH adenosine triphosphate and guanosine triphosphate and deoxy cytidine triphosphate and thymidine triphosphate is referred to as a rRdY mixture and aptamers selected therefrom are referred to as "rRdY" aptamers. A "mRmY" aptamer is one containing only 2'-OMe nucleotides except for the starting nucleotide which is 2'-hydroxy.

A preferred embodiment includes any combination of 2'-OH, 2'-deoxy and 2'-OMe nucleotides. Another embodiment includes any combination of 2'-deoxy and 2'-OMe nucleotides. Yet another embodiment includes any combination of 2'-deoxy and 2'-OMe nucleotides in which the pyrimidines are 2'-OMe (such as dRmY, mRmY or dGmH).

Incorporation of modified nucleotides into the aptamers of the invention may be accomplished before (pre-) the selection process (e.g., a pre-SELEX™ process modification). Optionally, aptamers of the invention in which modified nucleotides have been incorporated by pre-SELEX™ process modification can be further modified by a post-SELEX™ modification process (i.e., a post-SELEX™ process modification after a pre-SELEX™ modification). Pre-SELEX™ process modifications yield modified nucleic acid ligands with specificity for the SELEX™ target and also improved in vivo stability. Post-SELEX™ process modifications, i.e., modification (e.g., truncation, deletion, substitution or additional nucleotide modifications of previously identified ligands having nucleotides incorporated by pre-SELEX™ process modification) can result in a further improvement of in vivo stability without adversely affecting the binding capacity of the nucleic acid ligand having nucleotides incorporated by pre-SELEX™ process modification.

To generate pools of 2'-modified (e.g., 2'-OMe) RNA transcripts in conditions under which a polymerase accepts 2'-modified NTPs the Y693F, Y693F/K378R, Y693F/H784A, Y693F/H784A/K378R, Y693L/H784A, Y693L/H784A/K378R Y639L, or the Y639L/K378Rmutant T7 RNA polymerases can be used. A preferred polymerase is the Y639L/H784A mutant T7 RNA polymerase. Another preferred polymerase is the Y639L/H784A/K378R mutant T7 RNA polymerase. Other T7 RNA polymerases, particularly those that exhibit a high tolerance for bulky 2'-substituents, may also be used in the present invention. When used in a template-directed polymerization using the conditions disclosed herein, the Y639L/H784A or the Y639L/H784A/K378R mutant T7 RNA polymerase can be used for the incorporation of all 2'-OMe NTPs, including GTP, with higher transcript yields than achieved by using the Y639F, Y639F/K378R, Y639F/H784A, Y639F/H784A/K378R, Y639L, or the Y639L/K378R mutant T7 RNA polymerases. The Y639L/H784A and Y639L/H784A/K378R mutant T7 RNA polymerases can be used with but does not require 2'-OH GTP to achieve high yields of 2'-modified, e.g., 2'-OMe containing oligonucleotides.

A number of factors have been determined to be important for the transcription conditions useful in the methods disclosed herein. For example, increases in the yields of modified transcript are observed when a leader sequence is incorporated into the 5' end of the DNA transcription template. The leader sequence is typically 6-15 nucleotides long, and may be composed of all purines, or a mixture of purine and pyrimidine nucleotides.

Transcription can be divided into two phases: the first phase is initiation, during which an NTP is added to the 3'-hydroxyl end of GTP (or another substituted guanosine) to yield a dinucleotide which is then extended by about 10-12 nucleotides; the second phase is elongation, during which transcription proceeds beyond the addition of the first about 10-12 nucleotides. It has been found that small amounts of 2'-OH GTP added to a transcription mixture containing an excess of 2'-OMe GTP are sufficient to enable the polymerase to initiate transcription using 2'-OH GTP, but once transcription enters the elongation phase the reduced discrimination between 2'-OMe and 2'-OH GTP, and the excess of 2'-OMe GTP over 2'-OH GTP allows the incorporation of principally the 2'-OMe GTP.

Another important factor in the incorporation of 2'-OMe substituted nucleotides into transcripts is the use of both divalent magnesium and manganese in the transcription mixture. Different combinations of concentrations of magnesium chloride and manganese chloride have been found to affect yields of 2'-O-methylated transcripts, the optimum concentration of the magnesium and manganese chloride being dependent on the concentration in the transcription reaction mixture of NTPs which complex divalent metal ions. To obtain the greatest yields of maximally 2'-O-methylated transcripts (i.e., all 2'-OMe A, C, and U and about 90% of G nucleotides), concentrations of approximately 5 mM magnesium chloride and 1.5 mM manganese chloride are preferred when each NTP is present at a concentration of 0.5 mM. When the concentration of each NTP is 1.0 mM, concentrations of approximately 6.5 mM magnesium chloride and 2.0 mM manganese chloride are preferred. When the concentration of each NTP is 2.0 mM, concentrations of approximately 9.5 mM magnesium chloride and 3.0 mM manganese chloride are preferred. In any case, departures from these concentrations of up to two-fold still give significant amounts of modified transcripts.

Priming transcription with GMP or guanosine, or another non-2'-OMe non-triphosphate is also important. This effect results from the specificity of the polymerase for the initiating nucleotide. As a result, the 5'-terminal nucleotide of any transcript generated in this fashion is likely to be 2'-OH G. The preferred concentration of GMP (or guanosine) is 0.5 mM and even more preferably 1 mM. It has also been found that including PEG, preferably PEG-8000, in the transcription reaction is useful to maximize incorporation of modified nucleotides.

For maximum incorporation of 2'-OMe ATP (100%), UTP (100%), CTP (100%) and GTP (~90%) ("r/mGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (6.5 mM where the concentration of each 2'-OMe NTP is 1.0 mM), MnCl$_2$ 1.5 mM (2.0 mM where the concentration of each 2'-OMe NTP is 1.0 mM), 2'-OMe NTP (each) 500 µM (more preferably, 1.0 mM), 2'-OH GTP 30 µM, 2'-OH GMP 500 µM, pH 7.5, Y639F/H784A T7 RNA Polymerase 200 nM, inorganic pyrophosphatase 5 units/ml, and an all-purine leader sequence of at least 8 nucleotides long. As used herein, one unit of the Y639F/H784A mutant T7 RNA polymerase (or any other mutant T7 RNA polymerase specified herein) is defined as the amount of enzyme required to incorporate 1 nmole of 2'-OMe NTPs into transcripts under the r/mGmH conditions. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe ATP, UTP and CTP ("rGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.5 mM where the concentration of each 2'-OMe NTP is 2.0 mM), MnCl$_2$ 1.5 mM (3.0 mM where the concentration of each 2'-OMe NTP is 2.0 mM), 2'-OMe NTP (each) 500 µM (more preferably, 2.0 mM), pH 7.5, Y639F T7 RNA Polymerase 200 nM, inorganic pyrophosphatase 5 units/ml, and an all-purine leader sequence of at least 8 nucleotides long.

For maximum incorporation of 2'-OMe ATP (100%), 2'-OMe UTP (100%), 2'-OMe CTP (100%) and 2'-OMe GTP (100%) ("mRmY") into transcripts the following conditions are preferred: HEPES buffer 200 mM, DTT 40 mM, spermidine 2 mM, PEG-8000 10% (w/v), Triton X-100 0.01% (w/v), MgCl$_2$ 8 mM, MnCl$_2$ 2.5 mM, 2'-OMe NTP (each) 1.5 mM, 2'-OH GMP 1 mM, pH 7.5, Y639L/H784A/K378R mutant T7 RNA Polymerase 200 nM, inorganic pyrophosphatase 5 units/ml, and a leader sequence that increases the transcription yield under the derived transcription conditions. In one embodiment, the leader sequence is an all purine leader sequence. In another embodiment, the leader sequence is a mixture of purines and pyrimidines. As used herein, one unit of inorganic pyrophosphatase is defined as the amount of enzyme that will liberate 1.0 mole of inorganic orthophosphate per minute at pH 7.2 and 25° C.

For maximum incorporation (100%) of 2'-OMe UTP and CTP ("rRmY") into transcripts the following conditions are preferred: HEPES buffer 200 mM, DTT 40 mM, spermidine 2 mM, PEG-8000 10% (w/v), Triton X-100 0.01% (w/v), MgCl$_2$ 5 mM (9.5 mM where the concentration of each 2'-OMe NTP is 2.0 mM), MnCl$_2$ 1.5 mM (3.0 mM where the concentration of each 2'-OMe NTP is 2.0 mM), 2'-OMe NTP (each) 500 µM (more preferably, 2.0 mM), pH 7.5, Y639F/H784A T7 RNA Polymerase 200 nM, inorganic pyrophosphatase 5 units/ml, and an all-purine leader sequence of at least 8 nucleotides long.

For maximum incorporation (100%) of deoxy ATP and GTP and 2'-OMe UTP and CTP ("dRmY") into transcripts the following conditions are preferred: HEPES buffer 200 mM, DTT 40 mM, spermine 2 mM, spermidine 2 mM, PEG-8000 10% (w/v), Triton X-100 0.01% (w/v), MgCl$_2$ 9.5 mM, MnCl$_2$ 3.0 mM, 2'-OMe NTP (each) 2.0 mM, pH 7.5, Y639F T7 RNA Polymerase 200 nM, inorganic pyrophosphatase 5 units/ml, and an all-purine leader sequence of at least 8 nucleotides long.

For maximum incorporation (100%) of 2'-OMe ATP, UTP and CTP and 2'-F GTP ("fGmH") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.5 mM, MnCl$_2$ 3.0 mM, 2'-OMe NTP (each) 2.0 mM, pH 7.5, Y639F T7 RNA Polymerase 200 nM, inorganic pyrophosphatase 5 units/ml, and an all-purine leader sequence of at least 8 nucleotides long.

For maximum incorporation (100%) of deoxy ATP and 2'-OMe UTP, GTP and CTP ("dAmB") into transcripts the following conditions are preferred: HEPES buffer 200 mM, DTT 40 mM, spermidine 2 mM, PEG-8000 10% (w/v), Triton X-100 0.01% (w/v), MgCl$_2$ 9.5 mM, MnCl$_2$ 3.0 mM, 2'-OMe NTP (each) 2.0 mM, pH 7.5, Y639F T7 RNA Polymerase 200 nM, inorganic pyrophosphatase 5 units/ml, and an all-purine leader sequence of at least 8 nucleotides long.

For each of the above (a) transcription is preferably performed at a temperature of from about 20° C. to about 50° C., preferably from about 30° C. to 45° C., and more preferably at about 37° C. for a period of at least two hours and (b) 50-300 nM of a double stranded DNA transcription template is used (200 nM template is used in round 1 to increase diversity (300 nM template is used in dRmY transcriptions)), and for subsequent rounds approximately 50 nM, a ¹/₁₀ dilution of an optimized PCR reaction, using conditions described herein, is used). The preferred DNA transcription templates are described below (where ARC254 and ARC256 transcribe under all 2'-OMe conditions and ARC255 transcribes under rRmY conditions).

SEQ ID NO: 1
5'-CATCGATGCTAGTCGTAACGATCCNNNNNNNNNNNNNNNNNNNNNNNN

NNNNNNNCGAGAACGTTCTCTCCTCTCCCTATAGTGAGTCGTATTA-3'

SEQ ID NO: 2
5'-CATGCATCGCGACTGACTAGCCGNNNNNNNNNNNNNNNNNNNNNNNN

NNNNNNGTAGAACGTTCTCTCCTCTCCCTATAGTGAGTCGTATTA-3'

-continued

SEQ ID NO: 3
5'-CATCGATCGATCGATCGACAGCGNNNNNNNNNNNNNNNNNNNNNNNN
NNNNNNGTAGAACGTTCTCTCCTCTCCCTATAGTGAGTCGTATTA-3'

Under rN transcription conditions of the present invention, the transcription reaction mixture comprises 2'-OH adenosine triphosphates (ATP), 2'-OH guanosine triphosphates (GTP), 2'-OH cytidine triphosphates (CTP), and 2'-OH uridine triphosphates (UTP). The modified oligonucleotides produced using the rN transcription mixtures of the present invention comprise substantially all 2'-OH adenosine, 2'-OH guanosine, 2'-OH cytidine, and 2'-OH uridine. In a preferred embodiment of rN transcription, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OH cytidine, and at least 80% of all uridine nucleotides are 2'-OH uridine. In a more preferred embodiment of rN transcription, the resulting modified oligonucleotides of the present invention comprise a sequence where at least 90% of all adenosine nucleotides are 2'-OH adenosine, at least 90% of all guanosine nucleotides are 2'-OH guanosine, at least 90% of all cytidine nucleotides are 2'-OH cytidine, and at least 90% of all uridine nucleotides are 2'-OH uridine. In a most preferred embodiment of rN transcription, the modified oligonucleotides of the present invention comprise a sequence where 100% of all adenosine nucleotides are 2'-OH adenosine, 100% of all guanosine nucleotides are 2'-OH guanosine, 100% of all cytidine nucleotides are 2'-OH cytidine, and 100% of all uridine nucleotides are 2'-OH uridine.

Under rRmY transcription conditions of the present invention, the transcription reaction mixture comprises 2'-OH adenosine triphosphates, 2'-OH guanosine triphosphates, 2'-OMe cytidine triphosphates, and 2'-OMe uridine triphosphates. The modified oligonucleotides produced using the rRmY transcription mixtures of the present invention comprise substantially all 2'-OH adenosine, 2'-OH guanosine, 2'-OMe cytidine and 2'-OMe uridine. In a preferred embodiment, the resulting modified oligonucleotides comprise a sequence where at least 80% of all adenosine nucleotides are 2'-OH adenosine, at least 80% of all guanosine nucleotides are 2'-OH guanosine, at least 80% of all cytidine nucleotides are 2'-OMe cytidine and at least 80% of all uridine nucleotides are 2'-OMe uridine. In a more preferred embodiment, the resulting modified oligonucleotides comprise a sequence where at least 90% of all adenosine nucleotides are 2'-OH adenosine, at least 90% of all guanosine nucleotides are 2'-OH guanosine, at least 90% of all cytidine nucleotides are 2'-OMe cytidine and at least 90% of all uridine nucleotides are 2'-OMe uridine In a most preferred embodiment, the resulting modified oligonucleotides comprise a sequence where 100% of all adenosine nucleotides are 2'-OH adenosine, 100% of all guanosine nucleotides are 2'-OH guanosine, 100% of all cytidine nucleotides are 2'-OMe cytidine and 100% of all uridine nucleotides are 2'-OMe uridine.

Under dRmY transcription conditions of the present invention, the transcription reaction mixture comprises 2'-deoxy adenosine triphosphates, 2'-deoxy guanosine triphosphates, 2'-O-methyl cytidine triphosphates, and 2'-O-methyl uridine triphosphates. The modified oligonucleotides produced using the dRmY transcription conditions of the present invention comprise substantially all 2'-deoxy adenosine, 2'-deoxy guanosine, 2'-O-methyl cytidine, and 2'-O-methyl uridine. In a preferred embodiment, the resulting modified oligonucleotides of the present invention comprise a sequence where at least 80% of all adenosine nucleotides are 2'-deoxy adenosine, at least 80% of all guanosine nucleotides are 2'-deoxy guanosine, at least 80% of all cytidine nucleotides are 2'-O-methyl cytidine, and at least 80% of all uridine nucleotides are 2'-O-methyl uridine. In a more preferred embodiment, the resulting modified oligonucleotides of the present invention comprise a sequence where at least 90% of all adenosine nucleotides are 2'-deoxy adenosine, at least 90% of all guanosine nucleotides are 2'-deoxy guanosine, at least 90% of all cytidine nucleotides are 2'-O-methyl cytidine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all guanosine nucleotides are 2'-deoxy guanosine, 100% of all cytidine nucleotides are 2'-O-methyl cytidine, and 100% of all uridine nucleotides are 2'-O-methyl uridine.

Under rGmH transcription conditions of the present invention, the transcription reaction mixture comprises 2'-OH guanosine triphosphates, 2'-O-methyl cytidine triphosphates, 2'-O-methyl uridine triphosphates, and 2'-O-methyl adenosine triphosphates. The modified oligonucleotides produced using the rGmH transcription mixtures of the present invention comprise substantially all 2'-OH guanosine, 2'-O-methyl cytidine, 2'-O-methyl uridine, and 2'-O-methyl adenosine. In a preferred embodiment, the resulting modified oligonucleotides comprise a sequence where at least 80% of all guanosine nucleotides are 2'-OH guanosine, at least 80% of all cytidine nucleotides are 2'-O-methyl cytidine, at least 80% of all uridine nucleotides are 2'-O-methyl uridine, and at least 80% of all adenosine nucleotides are 2'-O-methyl adenosine. In a more preferred embodiment, the resulting modified oligonucleotides comprise a sequence where at least 90% of all guanosine nucleotides are 2'-OH guanosine, at least 90% of all cytidine nucleotides are 2'-O-methyl cytidine, at least 90% of all uridine nucleotides are 2'-O-methyl uridine, and at least 90% of all adenosine nucleotides are 2'-O-methyl adenosine. In a most preferred embodiment, the resulting modified oligonucleotides comprise a sequence where 100% of all guanosine nucleotides are 2'-OH guanosine, 100% of all cytidine nucleotides are 2'-O-methyl cytidine, 100% of all uridine nucleotides are 2'-O-methyl uridine, and 100% of all adenosine nucleotides are 2'-O-methyl adenosine.

Under r/mGmH transcription conditions of the present invention, the transcription reaction mixture comprises 2'-O-methyl adenosine triphosphate, 2'-O-methyl cytidine triphosphate, 2'-O-methyl guanosine triphosphate, 2'-O-methyl uridine triphosphate and 2'-OH guanosine triphosphate. The resulting modified oligonucleotides produced using the r/mGmH transcription mixtures of the present invention comprise substantially all 2'-O-methyl adenosine, 2'-O-methyl cytidine, 2'-O-methyl guanosine, and 2'-O-methyl uridine, wherein the population of guanosine nucleotides has a maximum of about 10% 2'-OH guanosine. In a preferred embodiment, the resulting r/mGmH modified oligonucleotides of the present invention comprise a sequence where at least 80% of all adenosine nucleotides are 2'-O-methyl adenosine, at least 80% of all cytidine nucleotides are 2'-O-methyl cytidine, at least 80% of all guanosine nucleotides are 2'-O-methyl guanosine, at least 80% of all uridine nucleotides are 2'-O-methyl uridine, and no more than about 10% of all guanosine nucleotides are 2'-OH guanosine. In a more preferred embodiment, the resulting modified oligonucleotides comprise a sequence where at least 90% of all adenosine nucleotides are 2'-O-methyl adenosine, at least 90% of all cytidine nucleotides are 2'-O-methyl cytidine, at least 90% of all guanosine nucleotides are 2'-O-methyl guanosine, at least 90% of all uridine nucleotides are 2'-O-methyl uridine, and no more than about 10% of all guanosine nucleotides are 2'-OH guanosine. In a most preferred embodiment, the resulting modified oligonucleotides comprise a sequence where 100% of all adenosine nucleotides are 2'-O-methyl adenosine, 100% of all cytidine nucleotides are 2'-O-methyl cytidine, 90% of all guanosine nucleotides are 2'-O-methyl guanosine, and 100% of all uridine nucleotides are 2'-O-methyl uridine, and no more than about 10% of all guanosine nucleotides are 2'-OH guanosine.

Under mRmY transcription conditions of the present invention, the transcription mixture comprises only 2'-O-methyl adenosine triphosphate, 2'-O-methyl cytidine triphosphate, 2'-O-methyl guanosine triphosphate, 2'-O-methyl uridine triphosphate. The resulting modified oligonucleotides produced using the mRmY transcription mixture of the present invention comprise a sequence where 100% of all adenosine nucleotides are 2'-O-methyl adenosine, 100% of all cytidine nucleotides are 2'-O-methyl cytidine, 100% of all guanosine nucleotides are 2'-O-methyl guanosine, and 100% of all uridine nucleotides are 2'-O-methyl uridine.

Under fGmH transcription conditions of the present invention, the transcription reaction mixture comprises 2'-O-methyl adenosine triphosphates, 2'-O-methyl uridine triphosphates, 2'-O-methyl cytidine triphosphates, and 2'-F guanosine triphosphates. The modified oligonucleotides produced using the fGmH transcription conditions of the present invention comprise substantially all 2'-O-methyl adenosine, 2'-O-methyl uridine, 2'-O-methyl cytidine, and 2'-F guanosine. In a preferred embodiment, the resulting modified oligonucleotides comprise a sequence where at least 80% of all adenosine nucleotides are 2'-O-methyl adenosine, at least 80% of all uridine nucleotides are 2'-O-methyl uridine, at least 80% of all cytidine nucleotides are 2'-O-methyl cytidine, and at least 80% of all guanosine nucleotides are 2'-F guanosine. In a more preferred embodiment, the resulting modified oligonucleotides comprise a sequence where at least 90% of all adenosine nucleotides are 2'-O-methyl adenosine, at least 90% of all uridine nucleotides are 2'-O-methyl uridine, at least 90% of all cytidine nucleotides are 2'-O-methyl cytidine, and at least 90% of all guanosine nucleotides are 2'-F guanosine. In a most preferred embodiment, the resulting modified oligonucleotides comprise a sequence where 100% of all adenosine nucleotides are 2'-O-methyl adenosine, 100% of all uridine nucleotides are 2'-O-methyl uridine, 100% of all cytidine nucleotides are 2'-O-methyl cytidine, and 100% of all guanosine nucleotides are 2'-F guanosine.

Under dAmB transcription conditions of the present invention, the transcription reaction mixture comprises 2'-deoxy adenosine triphosphates, 2'-O-methyl cytidine triphosphates, 2'-O-methyl guanosine triphosphates, and 2'-O-methyl uridine triphosphates. The modified oligonucleotides produced using the dAmB transcription mixtures of the present invention comprise substantially all 2'-deoxy adenosine, 2'-O-methyl cytidine, 2'-O-methyl guanosine, and 2'-O-methyl uridine. In a preferred embodiment, the resulting modified oligonucleotides comprise a sequence where at least 80% of all adenosine nucleotides are 2'-deoxy adenosine, at least 80% of all cytidine nucleotides are 2'-O-methyl cytidine, at least 80% of all guanosine nucleotides are 2'-O-methyl guanosine, and at least 80% of all uridine nucleotides are 2'-O-methyl uridine. In a more preferred embodiment, the resulting modified oligonucleotides comprise a sequence where at least 90% of all adenosine nucleotides are 2'-deoxy adenosine, at least 90% of all cytidine nucleotides are 2'-O-methyl cytidine, at least 90% of all guanosine nucleotides are 2'-O-methyl guanosine, and at least 90% of all uridine nucleotides are 2'-O-methyl uridine. In a most preferred embodiment, the resulting modified oligonucleotides of the present invention comprise a sequence where 100% of all adenosine nucleotides are 2'-deoxy adenosine, 100% of all cytidine nucleotides are 2'-O-methyl cytidine, 100% of all guanosine nucleotides are 2'-O-methyl guanosine, and 100% of all uridine nucleotides are 2'-O-methyl uridine.

In each case, the transcription products can then be used for input into the SELEX™ process to identify aptamers and/or to determine a conserved sequences that has binding specificity to a given target. The resulting sequences are already partially stabilized, eliminating this step from the post-SELEX™ process to arrive at an optimized aptamer sequence and giving a more highly stabilized aptamer as a result. Another advantage of the 2'-OMe SELEX™ process is that the resulting sequences are likely to have fewer 2'-OH nucleotides required in the sequence, possibly none. To the extent 2'OH nucleotides remain they may be removed by performing post-SELEX™ modifications.

As described below, lower but still useful yields of transcripts fully incorporating 2' substituted nucleotides can be obtained under conditions other than the optimized conditions described above. For example, variations to the above transcription conditions include:

The HEPES buffer concentration can range from 0 to 1 M. The present invention also contemplates the use of other buffering agents having a pKa between 5 and 10 including, for example, Tris-hydroxymethyl-aminomethane.

The DTT concentration can range from 0 to 400 mM. The methods of the present invention also provide for the use of other reducing agents including, for example, mercaptoethanol.

The spermidine and/or spermine concentration can range from 0 to 20 mM.

The PEG-8000 concentration can range from 0 to 50% (w/v). The methods of the present invention also provide for the use of other hydrophilic polymer including, for example, other molecular weight PEG or other polyalkylene glycols.

The Triton X-100 concentration can range from 0 to 0.1% (w/v). The methods of the present invention also provide for the use of other non-ionic detergents including, for example, other detergents, including other Triton-X detergents.

The $MgCl_2$ concentration can range from 0.5 mM to 50 mM. The $MnCl_2$ concentration can range from 0.15 mM to 15 mM. Both $MgCl_2$ and $MnCl_2$ must be present within the ranges described and in a preferred embodiment are present in about a 10 to about 3 ratio of $MgCl_2$:$MnCl_2$, preferably, the ratio is about 3-5:1, more preferably, the ratio is about 3-4:1.

The 2'-OMe NTP concentration (each NTP) can range from 5 µM to 5 mM.

The 2'-OH GTP concentration can range from 0 µM to 300 µM.

The 2'-OH GMP concentration can range from 0 to 5 mM.

The pH can range from pH 6 to pH 9. The methods of the present invention can be practiced within the pH range of activity of most polymerases that incorporate modified nucleotides. In addition, the methods of the present invention provide for the optional use of chelating agents in the transcription reaction condition including, for example, EDTA, EGTA, and DTT.

Aptamer Medicinal Chemistry

Aptamer Medicinal Chemistry is an aptamer improvement technique in which sets of variant aptamers are chemically synthesized. These sets of variants typically differ from the parent aptamer by the introduction of a single substituent, and differ from each other by the location of this substituent. These variants are then compared to each other and to the parent. Improvements in characteristics may be profound enough that the inclusion of a single substituent may be all that is necessary to achieve a particular therapeutic criterion.

Alternatively the information gleaned from the set of single variants may be used to design further sets of variants in which more than one substituent is introduced simultaneously. In one design strategy, all of the single substituent variants are ranked, the top 4 are chosen and all possible double (6), triple (4) and quadruple (1) combinations of these 4 single substituent variants are synthesized and assayed. In a second design strategy, the best single substituent variant is considered to be the new parent and all possible double substituent variants that include this highest-ranked single substituent variant are synthesized and assayed. Other strategies may be used, and these strategies may be applied repeatedly such that the number of substituents is gradually increased while continuing to identify further-improved variants.

Aptamer Medicinal Chemistry may be used particularly as a method to explore the local, rather than the global, introduction of substituents. Because aptamers are discovered within libraries that are generated by transcription, any substituents that are introduced during the SELEX™ process must be introduced globally. For example, if it is desired to introduce phosphorothioate linkages between nucleotides then they can only be introduced at every A (or every G, C, T, U etc.) (globally substituted). Aptamers which require phosphorothioates at some As (or some G, C, T, U etc.) (locally substituted) but cannot tolerate it at other As cannot be readily discovered by this process.

The kinds of substituent that can be utilized by the Aptamer Medicinal Chemistry process are only limited by the ability to generate them as solid-phase synthesis reagents and introduce them into an oligomer synthesis scheme. The process is certainly not limited to nucleotides alone. Aptamer Medicinal Chemistry schemes may include substituents that introduce steric bulk, hydrophobicity, hydrophilicity, lipophilicity, lipophobicity, positive charge, negative charge, neutral charge, zwitterions, polarizability, nuclease-resistance, conformational rigidity, conformational flexibility, protein-binding characteristics, mass etc. Aptamer Medicinal Chemistry schemes may include base-modifications, sugar-modifications or phosphodiester linkage-modifications.

When considering the kinds of substituents that are likely to be beneficial within the context of a therapeutic aptamer, it may be desirable to introduce substitutions that fall into one or more of the following categories:

(1) Substituents already present in the body, e.g., 2'-deoxy, 2'-ribo, 2'-O-methyl purines or pyrimidines or 5-methyl cytosine.
(2) Substituents already part of an approved therapeutic, e.g., phosphorothioate-linked oligonucleotides.
(3) Substituents that hydrolyze or degrade to one of the above two categories, e.g., methylphosphonate-linked oligonucleotides.

The vWF aptamers of the invention include aptamers developed through aptamer medicinal chemistry as described herein.

von Willebrand Factor Specific Binding Aptamers

The materials of the present invention comprise a series of nucleic acid aptamers of 29 to 76 nucleotides in length which bind specifically to von Willebrand Factor. In one embodiment, materials of the present invention comprise a series of nucleic acid aptamers of 29 to 76 nucleotides in length which bind specifically to von Willebrand Factor and which functionally modulate, e.g., block, an activity of von Willebrand Factor in vivo and/or cell-based assays.

Aptamers specifically capable of binding and modulating full length von Willebrand Factor and/or von Willebrand Factor domain A1 are set forth herein. These aptamers provide a low-toxicity, safe, and effective modality of treating and/or preventing cardiovascular diseases or disorders. In one embodiment, the aptamers of the invention are used in a method to treat and/or prevent coronary artery diseases, including any one of the disorders selected from the group consisting of: arterial thrombosis and acute coronary syndromes such as unstable angina and myocardial infarction which are known to be caused by or otherwise associated with von Willebrand Factor mediated platelet aggregation. In particular embodiments, the aptamers of the invention are used in a method to treat and/or prevent coronary artery diseases, including any one of the disorders selected from the group consisting of: arterial thrombosis and acute coronary syndromes such as unstable angina and myocardial infarction which are known to be caused by or otherwise associated with von Willebrand Factor mediated platelet aggregation while minimizing bleeding side effects. In another embodiment, the aptamers of the invention are used in a method to treat and/or prevent peripheral vascular diseases which are known to be caused by or otherwise associated with von Willebrand Factor mediated platelet aggregation. In a particular embodiment, the aptamers of the invention are used in a method to treat and/or prevent peripheral vascular diseases which are known to be caused by or otherwise associated with von Willebrand Factor mediated platelet aggregation, preferably, while minimizing bleeding side effects. In another embodiment, the aptamers of the invention are used to treat and/or prevent cerebrovascular diseases, including any one of the disorders selected from the group consisting of: transient cerebral ischemic attack, stroke and carotid stenosis which are known to be caused by or otherwise associated with von Willebrand Factor mediated platelet aggregation, preferably, while minimizing bleeding side effects. Further, aptamers of the invention are useful to inhibit von Willebrand Factor mediated platelet aggregation in a subject prior to, during, and/or after a subject has undergone percutaneous coronary intervention including angioplasty, thrombolytic treatment or coronary bypass surgery. Aptamers of the invention are also useful for maintaining blood vessel patency in a subject prior to, during and/or after the subject has undergone coronary bypass surgery. The aptamers of the invention are also useful for treating a patient undergoing dialysis. The aptamers of the invention are also useful for inhibiting von Willebrand Factor mediated thrombosis in a subject, preferably while also minimizing bleeding side effects. The thrombosis to be treated and/or inhibited may be associated with an inflammatory response.

In one embodiment, the von Willebrand Factor specific binding aptamer for use in therapeutics and/or diagnostics is selected from the group consisting of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC11115 (SEQ ID NO 221), ARC172 (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635, ARC1759 (SEQ ID NO 318), ARC1779 (SEQ ID NO 320) to ARC1780 and ARC1884 (SEQ ID NO 322) to ARC1885 (SEQ ID NO 323).

In another embodiment, von Willebrand Factor specific binding aptamers for use as therapeutics and/or diagnostics include any one of the following sequences: SEQ ID NO 23, SEQ ID NO 44, SEQ ID NO 49, SEQ ID NOS 98-100, SEQ ID NO 106, SEQ ID NO 109, SEQ ID NOS 114 to 115, SEQ ID NO 118, SEQ ID NO 127, SEQ ID NO 134, SEQ ID NO 164, SEQ ID NO165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 208, and SEQ ID NOS 212 to 214. In some embodiments, von Willebrand Factor specific bind aptamers for use as therapeutics and/or diagnostics include any one of the following sequences: ARC1029 (SEQ ID NO 214), ARC115 (SEQ ID NO 221), ARC1172 (SEQ ID NO 222), ARC1346 (SEQ ID NO 281), ARC1361 (SEQ ID NO 284), ARC1368 (SEQ ID NO 291), ARC1635 (SEQ ID NO 319), ARC1759 (SEQ ID NO 318), ARC1779 (SEQ ID NO 320), ARC1780 (SEQ ID NO 321), ARC1884 (SEQ ID NO 322) to ARC1885 (SEQ ID NO 323).

Other aptamers of the invention that bind von Willebrand Factor are described below in Examples 1 and 2.

These aptamers may include modifications as described herein including, e.g., conjugation to lipophilic or high molecular weight compounds (e.g., PEG), incorporation of a capping moiety, incorporation of modified nucleotides, and phosphate back bone modification (including incorporation of phosphorothioate into the phosphate backbone).

In one embodiment of the invention an isolated, non-naturally occurring aptamer that binds to von Willebrand Factor is provided. In another embodiment, the aptamer of the invention modulates a function of von Willebrand Factor. In another embodiment, the aptamer of the invention inhibits a function of von Willebrand Factor while in another embodiment the aptamer stimulates a function of von Willebrand Factor. In another embodiment of the invention, the aptamer binds and/or modulates a function of a von Willebrand Factor variant. A von Willebrand Factor variant as used herein encompasses variants that perform essentially the same function as a von Willebrand Factor function, preferably comprises substantially the same structure and in some embodiments comprises at least 70% sequence identity, preferably at least 80% sequence identity, more preferably at least 90% sequence identity, and more preferably at least 95% sequence identity to the amino acid sequence of human von Willebrand Factor.

In another embodiment of the invention, the aptamer has substantially the same ability to bind von Willebrand Factor as that of an aptamer comprising any one of SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115, ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635, ARC1759 (SEQ ID NO 318), ARC1779 (SEQ ID NO 320) to ARC1780 and ARC1884 (SEQ ID NO 322) to ARC1885 (SEQ ID NO 323). In another embodiment of the invention, the aptamer has substantially the same structure and ability to bind von Willebrand Factor as that of an aptamer comprising any one of SEQ ID NOS 11 to 50, SEQ ID NOS 54 to 94, SEQ ID NOS 98 to 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115, ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635, ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323). In another embodiment, the aptamers of the invention comprise a sequence according to any one of SEQ ID NOS 11 to 50, SEQ ID NOS 54 to 94, SEQ ID NOS 98 to 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-213, ARC1115, ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635, ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323). In another embodiment, the aptamers of the invention comprise a sequence that is at least 80% identical, preferably at least 90% identical and in some embodiments at least 95% identical to a sequence according to any one of SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115, ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635, ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323). In another embodiment, the aptamers of the invention specifically bind von Willebrand Factor and comprise a sequence of 30 contiguous nucleotides that are identical to 30 contiguous nucleotides in any one of the aptamers selected from the group consisting of: SEQ ID NOS 11 to 50, SEQ ID NOS 54 to 94, SEQ ID NOS 98 to 164, SEQ ID NO 165, SEQ ID NO 169, SEQ ID NO 172, SEQ ID NO 174, SEQ ID NO 177, SEQ ID NO 180, SEQ ID NO 183, SEQ ID NO 186, SEQ ID NO 189, SEQ ID NO 192, SEQ ID NO 198, SEQ ID NO 201, SEQ ID NO 205, SEQ ID NO 208, SEQ ID NOS 212-214, ARC1115, ARC1172 (SEQ ID NO 222) (SEQ ID NO 222), ARC1194 (SEQ ID NO 223) to ARC1240 (SEQ ID NO 269), ARC1338 (SEQ ID NO 273) to ARC1346 (SEQ ID NO 281), ARC1361 (SEQ ID NO 284) to ARC1381 (SEQ ID NO 304), ARC1524 (SEQ ID NO 305), ARC1526 (SEQ ID NO 307) to ARC1535 (SEQ ID NO 316), ARC1546 (SEQ ID NO 317), ARC1635, ARC1759 (SEQ ID NO 318), ARC1779 (SEQ ID NO 320) to ARC1780 (SEQ ID NO 321) and ARC1884 (SEQ ID NO 322) to ARC1885 (SEQ ID NO 323). In another embodiment, the aptamers of the invention are used as an active ingredient in pharmaceutical compositions. In another embodiment, the aptamers of the invention or compositions comprising the aptamers of the invention are used to treat thrombotic disease such as cardiovascular disorders, including acute coronary syndrome; peripheral arterial disease; and cerebrovascular disorders, including stroke. In some embodiments, the aptamers of the invention or compositions comprising the aptamers of the invention are use to treat, prevent or ameliorate a disorder selected from the group consisting of: essential thrombocytopenia: thrombotic thrombocopenic purpura ("TTP"), Type IIb von Willebrand's disease, pseudo von Willebrand disease, peripheral artery disease, e.g. peripheral arterial occlusive disease, unstable angina, angina pectoris, arterial thrombosis, atherosclerosis, myocardial infarction, acute coronary syndrome, atrial fibrillation, carotid stenosis, cerebral infarction, cerebral thrombosis, ischemic stroke, and transient cerebral ischemic attack. In some embodiments, the pharmaceutical composition of the invention is administered prior to/during and/or after dialysis, CABG surgery, percutaneous coronary intervention or heart valve replacement.

In some embodiments, aptamer therapeutics of the present invention have great affinity and specificity to their targets while reducing the deleterious side effects from non-naturally occurring nucleotide substitutions if the aptamer therapeutics break down in the body of patients or subjects. In some embodiments, the therapeutic compositions containing the aptamer therapeutics of the present invention are free of or have a reduced amount of fluorinated nucleotides.

The aptamers of the present invention can be synthesized using any oligonucleotide synthesis techniques known in the art including solid phase oligonucleotide synthesis techniques (see, e.g., Froehler et al., Nucl. Acid Res. 14:5399-5467 (1986) and Froehler et al., Tet. Lett. 27:5575-5578 (1986)) and solution phase methods such as triester synthesis methods (see, e.g., Sood et al., Nucl. Acid Res. 4:2557 (1977) and Hirose et al., Tet. Lett, 28:2449 (1978)) both of which are well known in the art.

Pharmaceutical Compositions

The invention also includes pharmaceutical compositions containing aptamer molecules that bind to von Willebrand Factor. In some embodiments, the compositions are suitable for internal use and include an effective amount of a pharmacologically active compound of the invention, alone or in combination, with one or more pharmaceutically acceptable carriers. The compounds are especially useful in that they have very low, if any toxicity.

Compositions of the invention can be used to treat or prevent a pathology, such as a disease or disorder, or alleviate the symptoms of such disease or disorder in a patient. For example, compositions of the present invention can be used to treat or prevent a pathology associated with platelet aggregation. In some embodiments, the disease to be treated, prevented or ameliorated is selected from the group consisting of: essential thrombocytopenia: thrombotic thrombocopenic purpura ("TTP"), Type IIb von Willebrand's disease, pseudo von Willebrand disease, peripheral artery disease, e.g. peripheral arterial occlusive disease, unstable angina, angina pectoris, arterial thrombosis, atherosclerosis, myocardial infarction, acute coronary syndrome, atrial fibrillation, carotid stenosis, cerebral infarction, cerebral thrombosis, ischemic stroke, and transient cerebral ischemic attack. In some embodiments, the pharmaceutical composition of the invention is administered prior to, during and/or after dialysis, CABG surgery, percutaneous coronary intervention or heart valve replacement.

Compositions of the invention are useful for administration to a subject suffering from, or predisposed to, a disease or disorder which is related to or derived from a target to which the aptamers of the invention specifically bind.

Compositions of the invention can be used in a method for treating a patient or subject having a pathology. The method involves administering to the patient or subject an aptamer or a composition comprising aptamers that bind to von Willebrand Factor involved with the pathology, so that binding of the aptamer to the target alters the biological function of von Willebrand Factor, thereby treating the pathology.

The patient or subject having a pathology, i.e., the patient or subject treated by the methods of this invention can be a mammal, more particularly a vertebrate, or more particularly, a human.

In practice, the aptamers or their pharmaceutically acceptable salts, are administered in amounts which will be sufficient to exert their desired biological activity, e.g., preventing vWF dependent platelet aggregation.

One aspect of the invention comprises an aptamer composition of the invention in combination with other treatments for thrombotic related disorders. The aptamer composition of the invention may contain, for example, more than one aptamer, e.g. an anti-thrombin aptamer and an anti-vWF aptamer. In some examples, an aptamer composition of the invention, containing one or more aptamers of the invention, is administered in combination with another useful composition such as an anti-inflammatory agent, an immunosuppressant, an antiviral agent, or the like. In general, the currently available dosage forms of the known therapeutic agents for use in such combinations will be suitable.

"Combination therapy" (or "co-therapy") includes the administration of an aptamer composition of the invention and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

"Combination therapy" may, but generally is not, intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents.

Sequential or substantially simultaneous administration of each therapeutic agent can be effected by any appropriate route including, but not limited to, topical routes, oral routes, intravenous routes, intramuscular routes, and direct absorption through mucous membrane tissues. The therapeutic agents can be administered by the same route or by different routes. For example, a first therapeutic agent of the combination selected may be administered by injection while the other therapeutic agents of the combination may be administered topically.

Alternatively, for example, all therapeutic agents may be administered topically or all therapeutic agents may be administered by injection. The sequence in which the therapeutic agents are administered is not narrowly critical unless noted otherwise. "Combination therapy" also can embrace the administration of the therapeutic agents as described above in further combination with other biologically active ingredients. Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Therapeutic or pharmacological compositions of the present invention will generally comprise an effective amount of the active component(s) of the therapy, dissolved or dispersed in a pharmaceutically acceptable medium. Pharmaceutically acceptable media or carriers include any and all solvents, dispersion media, coatings, antibacterial and antifungal agents, isotonic and absorption delaying agents and the like. The use of such media and agents for pharmaceutical active substances is well known in the art. Supplementary active ingredients can also be incorporated into the therapeutic compositions of the present invention.

The preparation of pharmaceutical or pharmacological compositions will be known to those of skill in the art in light of the present disclosure. Typically, such compositions may be prepared as injectables, either as liquid solutions or suspensions; solid forms suitable for solution in, or suspension in, liquid prior to injection; as tablets or other solids for oral administration; as time release capsules; or in any other form currently used, including eye drops, creams, lotions, salves, inhalants and the like. The use of sterile formulations, such as saline-based washes, by surgeons, physicians or health care workers to treat a particular area in the operating field may also be particularly useful. Compositions may also be delivered via microdevice, microparticle or sponge.

Upon formulation, therapeutics will be administered in a manner compatible with the dosage formulation, and in such amount as is pharmacologically effective. The formulations are easily administered in a variety of dosage forms. In a preferred embodiment the aptamer of the invention is formulated as an injectable solution described above, but drug release capsules and the like can also be employed.

In this context, the quantity of active ingredient and volume of composition to be administered depends on the host animal to be treated. Precise amounts of active compound required for administration depend on the judgment of the practitioner and are peculiar to each individual.

A minimal volume of a composition required to disperse the active compounds is typically utilized. Suitable regimes for administration are also variable, but would be typified by initially administering the compound and monitoring the results and then giving further controlled doses at further intervals. The effects of administration of the anti-vWF aptamer of the invention could be monitored by measuring platelet aggregation formation such as measuring botrocetin induced platelet aggregation ("BIPA") and/or shear force induced hemostatic plug formation using the PFA-100 instrument as described in Example 3 below.

For instance, for oral administration in the form of a tablet or capsule (e.g., a gelatin capsule), the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, magnesium aluminum silicate, starch paste, gelatin, methylcellulose, sodium carboxymethylcellulose and/or polyvinylpyrrolidone, natural sugars such as glucose or beta-lactose, corn sweeteners, natural and synthetic gums such as acacia, tragacanth or sodium alginate, polyethylene glycol, waxes and the like. Lubricants used in these dosage forms include sodium oleate, sodium stearate, magnesium stearate, sodium benzoate, sodium acetate, sodium chloride, silica, talcum, stearic acid, its magnesium or calcium salt and/or polyethyleneglycol and the like. Disintegrators include, without limitation, starch, methyl cellulose, agar, bentonite, xanthan gum starches, agar, alginic acid or its sodium salt, or effervescent mixtures, and the like. Diluents, include, e.g., lactose, dextrose, sucrose, mannitol, sorbitol, cellulose and/or glycine.

Injectable compositions are preferably aqueous isotonic solutions or suspensions, and suppositories are advantageously prepared from fatty emulsions or suspensions. The compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. The compositions are prepared according to conventional mixing, granulating or coating methods, respectively, and typically contain about 0.1 to 75%, preferably about 1 to 50%, of the active ingredient.

The compounds of the invention can also be administered in such oral dosage forms as timed release and sustained release tablets or capsules, pills, powders, granules, elixirs, tinctures, suspensions, syrups and emulsions.

Liquid, particularly injectable compositions can, for example, be prepared by dissolving, dispersing, etc. The active compound is dissolved in or mixed with a pharmaceutically pure solvent such as, for example, water, saline, aqueous dextrose, glycerol, ethanol, and the like, to thereby form the injectable solution or suspension. Additionally, solid forms suitable for dissolving in liquid prior to injection can be formulated.

The compounds of the present invention can be administered in intravenous (both bolus and infusion), intraperitoneal, subcutaneous or intramuscular form, all using forms well known to those of ordinary skill in the pharmaceutical arts. Injectables can be prepared in conventional forms, either as liquid solutions or suspensions.

Parenteral injectable administration is generally used for subcutaneous, intramuscular or intravenous injections and infusions. Additionally, one approach for parenteral administration employs the implantation of a slow-release or sustained-released systems, which assures that a constant level of dosage is maintained, according to U.S. Pat. No. 3,710,795, incorporated herein by reference.

Furthermore, preferred compounds for the present invention can be administered in intranasal form via topical use of suitable intranasal vehicles, inhalants, or via transdermal routes, using those forms of transdermal skin patches well known to those of ordinary skill in that art. To be administered in the form of a transdermal delivery system, the dosage administration will, of course, be continuous rather than intermittent throughout the dosage regimen. Other preferred topical preparations include creams, ointments, lotions, aerosol sprays and gels, wherein the concentration of active ingredient would typically range from 0.01% to 15%, w/w or w/v.

For solid compositions, excipients include pharmaceutical grades of mannitol, lactose, starch, magnesium stearate, sodium saccharin, talcum, cellulose, glucose, sucrose, magnesium carbonate, and the like may be used. The active compound defined above, may be also formulated as suppositories using for example, polyalkylene glycols, for example, propylene glycol, as the carrier. In some embodiments, suppositories are advantageously prepared from fatty emulsions or suspensions.

The compounds of the present invention can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564. For example, the aptamer molecules described herein can be provided as a complex with a lipophilic compound or non-immunogenic, high molecular weight compound constructed using methods known in the art. Additionally, liposomes may bear aptamers on their surface for targeting and carrying cytotoxic agents internally to mediate cell killing. An example of nucleic-acid associated complexes is provided in U.S. Pat. No. 6,011,020.

The compounds of the present invention may also be coupled with soluble polymers as targetable drug carriers. Such polymers can include polyvinylpyrrolidone, pyran copolymer, polyhydroxypropyl-methacrylamide-phenol, polyhydroxyethylaspanamidephenol, or polyethyleneoxidepolylysine substituted with palmitoyl residues. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

If desired, the pharmaceutical composition to be administered may also contain minor amounts of non-toxic auxiliary substances such as wetting or emulsifying agents, pH buffering agents, and other substances such as for example, sodium acetate, and triethanolamine oleate.

The dosage regimen utilizing the aptamers is selected in accordance with a variety of factors including type, species, age, weight, sex and medical condition of the patient; the severity of the condition to be treated; the route of administration; the renal and hepatic function of the patient; and the particular aptamer or salt thereof employed. An ordinarily skilled physician or veterinarian can readily determine and prescribe the effective amount of the drug required to prevent, counter or arrest the progress of the condition.

Oral dosages of the present invention, when used for the indicated effects, will range between about 0.05 to 7500 mg/day orally. The compositions are preferably provided in the form of scored tablets containing 0.5, 1.0, 2.5, 5.0, 10.0, 15.0, 25.0, 50.0, 100.0, 250.0, 500.0 and 1000.0 mg of active ingredient. Infused dosages, intranasal dosages and transdermal dosages will range between 0.05 to 7500 mg/day. Subcutaneous, intravenous and intraperitoneal dosages will range between 0.05 to 3800 mg/day.

Compounds of the present invention may be administered in a single daily dose, or the total daily dosage may be administered in divided doses of two, three or four times daily.

Effective plasma levels of the compounds of the present invention range from 0.002 mg/mL to 50 mg/mL. In the dosages of the present invention, mass refers only to the molecular weight of the oligonucleotide portion of the aptamer, irrespective of the mass conferred by PEG conjugation.

Modulation of Pharmacokinetics and Biodistribution of Aptamer Therapeutics

It is important that the pharmacokinetic properties for all oligonucleotide-based therapeutics, including aptamers, be tailored to match the desired pharmaceutical application. While aptamers directed against extracellular targets do not suffer from difficulties associated with intracellular delivery (as is the case with antisense and RNAi-based therapeutics), such aptamers must still be able to be distributed to target organs and tissues, and remain in the body (unmodified) for a period of time consistent with the desired dosing regimen.

Thus, the present invention provides materials and methods to affect the pharmacokinetics of aptamer compositions, and, in particular, the ability to tune aptamer pharmacokinetics. The tunability of (i.e., the ability to modulate) aptamer pharmacokinetics is achieved through conjugation of modifying moieties (e.g., PEG polymers) to the aptamer and/or the incorporation of modified nucleotides (e.g., 2'-fluoro or 2'-O-methyl) to alter the chemical composition of the nucleic acid. The ability to tune aptamer pharmacokinetics is used in the improvement of existing therapeutic applications, or alternatively, in the development of new therapeutic applications. For example, in some therapeutic applications, e.g., in antineoplastic or acute care settings where rapid drug clearance or turn-off may be desired, it is desirable to decrease the residence times of aptamers in the circulation. Alternatively, in other therapeutic applications, e.g., maintenance therapies where systemic circulation of a therapeutic is desired, it may be desirable to increase the residence times of aptamers in circulation.

In addition, the tunability of aptamer pharmacokinetics is used to modify the biodistribution of an aptamer therapeutic in a subject. For example, in some therapeutic applications, it may be desirable to alter the biodistribution of an aptamer therapeutic in an effort to target a particular type of tissue or a specific organ (or set of organs). In these applications, the aptamer therapeutic preferentially accumulates in a specific tissue or organ(s). In other therapeutic applications, it may be desirable to target tissues displaying a cellular marker or a symptom associated with a given disease, cellular injury or other abnormal pathology, such that the aptamer therapeutic preferentially accumulates in the affected tissue. For example, as described in copending provisional application U.S. Ser. No. 60/550,790, filed on Mar. 5, 2004, and entitled "Controlled Modulation of the Pharmacokinetics and Biodistribution of Aptamer Therapeutics), PEGylation of an aptamer therapeutic (e.g., PEGylation with a 20 kDa PEG polymer) is used to target inflamed tissues, such that the PEGylated aptamer therapeutic preferentially accumulates in inflamed tissue.

To determine the pharmacokinetic and biodistribution profiles of aptamer therapeutics (e.g., aptamer conjugates or aptamers having altered chemistries, such as modified nucleotides) a variety of parameters are monitored. Such parameters include, for example, the half-life ($t_{1/2}$), the plasma clearance (CL), the volume of distribution (Vss), the area under the concentration-time curve (AUC), maximum observed serum or plasma concentration ($C_{max}$), and the mean residence time (MRT) of an aptamer composition. As used herein, the term "AUC" refers to the area under the plot of the plasma concentration of an aptamer therapeutic versus the time after aptamer administration. The AUC value is used to estimate the bioavailability (i.e., the percentage of administered aptamer therapeutic in the circulation after aptamer administration) and/or total clearance (CL) (i.e., the rate at which the aptamer therapeutic is removed from circulation) of a given aptamer therapeutic. The volume of distribution relates the plasma concentration of an aptamer therapeutic to the amount of aptamer present in the body. The larger the Vss, the more an aptamer is found outside of the plasma (i.e., the more extravasation).

The present invention provides materials and methods to modulate, in a controlled manner, the pharmacokinetics and biodistribution of stabilized aptamer compositions in vivo by conjugating an aptamer to a modulating moiety such as a small molecule, peptide, or polymer terminal group, or by incorporating modified nucleotides into an aptamer. As described herein, conjugation of a modifying moiety and/or altering nucleotide(s) chemical composition alter fundamental aspects of aptamer residence time in circulation and distribution to tissues.

In addition to clearance by nucleases, oligonucleotide therapeutics are subject to elimination via renal filtration. As such, a nuclease-resistant oligonucleotide administered intravenously typically exhibits an in vivo half-life of <10 min, unless filtration can be blocked. This can be accomplished by either facilitating rapid distribution out of the blood stream into tissues or by increasing the apparent molecular weight of the oligonucleotide above the effective size cut-off for the glomerulus. Conjugation of small therapeutics to a PEG polymer (PEGylation), described below, can dramatically lengthen residence times of aptamers in circulation, thereby decreasing dosing frequency and enhancing effectiveness against vascular targets.

Aptamers can be conjugated to a variety of modifying moieties, such as high molecular weight polymers, e.g., PEG; peptides, e.g., Tat (a 13-amino acid fragment of the HIV Tat protein (Vives, et al., (1997), J. Biol. Chem. 272(25): 16010-7)), Ant (a 16-amino acid sequence derived from the third helix of the Drosophila antennapedia homeotic protein (Pietersz, et al., (2001), Vaccine 19(11-12): 1397-405)) and $Arg_7$ (a short, positively charged cell-permeating peptides composed of polyarginine ($Arg_7$) (Rothbard, et al., (2000), Nat. Med. 6(11): 1253-7; Rothbard, J et al., (2002), J. Med. Chem. 45(17): 3612-8)); and small molecules, e.g., lipophilic compounds such as cholesterol. Among the various conjugates described herein, in vivo properties of aptamers are altered most profoundly by complexation with PEG groups. For example, complexation of a mixed 2' F. and 2'-OMe modified aptamer therapeutic with a 20 kDa PEG polymer hinders renal filtration and promotes aptamer distribution to both healthy and inflamed tissues. Furthermore, the 20 kDa PEG polymer-aptamer conjugate proves nearly as effective as a 40 kDa PEG polymer in preventing renal filtration of aptamers. While one effect of PEGylation is on aptamer clearance, the prolonged systemic exposure afforded by presence of the 20 kDa moiety also facilitates distribution of aptamer to tissues, particularly those of highly perfused organs and those at the site of inflammation. The aptamer-20 kDa PEG polymer conjugate directs aptamer distribution to the site of inflammation, such that the PEGylated aptamer preferentially accumulates in inflamed tissue. In some instances, the 20 kDa PEGylated aptamer conjugate is able to access the interior of cells, such as, for example, kidney cells.

Modified nucleotides can also be used to modulate the plasma clearance of aptamers. For example, an unconjugated aptamer which incorporates both 2'-F and 2'-OMe stabilizing chemistries, which is typical of current generation aptamers as it exhibits a high degree of nuclease stability in vitro and in vivo, displays rapid loss from plasma (i.e., rapid plasma clearance) and a rapid distribution into tissues, primarily into the kidney, when compared to unmodified aptamer.

Peg-Derivatized Nucleic Acids

As described above, derivatization of nucleic acids with high molecular weight non-immunogenic polymers has the potential to alter the pharmacokinetic and pharmacodynamic properties of nucleic acids making them more effective therapeutic agents. Favorable changes in activity can include increased resistance to degradation by nucleases, decreased filtration through the kidneys, decreased exposure to the immune system, and altered distribution of the therapeutic through the body.

The aptamer compositions of the invention may be derivatized with polyalkylene glycol (PAG) moieties. Examples of PAG-derivatized nucleic acids are found in United States patent application Ser. No. 10/718,833, filed on Nov. 21, 2003, which is herein incorporated by reference in its entirety. Typical polymers used in the invention include poly(ethylene glycol) (PEG), also known as poly(ethylene oxide) (PEO) and polypropylene glycol (including poly isopropylene glycol). Additionally, random or block copolymers of different alkylene oxides (e.g., ethylene oxide and propylene oxide) can be used in many applications. In its most common form, a polyalkylene glycol, such as PEG, is a linear polymer terminated at each end with hydroxyl groups: $HO-CH_2CH_2O-(CH_2CH_2O)_n-CH_2CH_2-OH$. This polymer, alpha-, omega-dihydroxylpoly(ethylene glycol), can also be represented as HO-PEG-OH, where it is understood that the -PEG-symbol represents the following structural unit: $-CH_2CH_2O-(CH_2CH_2O)_n-CH_2CH_2-$ where n typically ranges from about 4 to about 10,000.

As shown, the PEG molecule is di-functional and is sometimes referred to as "PEG diol." The terminal portions of the PEG molecule are relatively non-reactive hydroxyl moieties, the —OH groups, that can be activated, or converted to functional moieties, for attachment of the PEG to other compounds at reactive sites on the compound. Such activated PEG diols are referred to herein as bi-activated PEGs. For example, the terminal moieties of PEG diol have been functionalized as active carbonate ester for selective reaction with amino moieties by substitution of the relatively nonreactive hydroxyl moieties, —OH, with succinimidyl active ester moieties from N-hydroxy succinimide.

In many applications, it is desirable to cap the PEG molecule on one end with an essentially non-reactive moiety so that the PEG molecule is mono-functional (or mono-activated). In the case of protein therapeutics which generally display multiple reaction sites for activated PEGs, bi-functional activated PEGs lead to extensive cross-linking, yielding poorly functional aggregates. To generate mono-activated PEGs, one hydroxyl moiety on the terminus of the PEG diol molecule typically is substituted with non-reactive methoxy end moiety, $-OCH_3$. The other, un-capped terminus of the PEG molecule typically is converted to a reactive end moiety that can be activated for attachment at a reactive site on a surface or a molecule such as a protein.

PAGs are polymers which typically have the properties of solubility in water and in many organic solvents, lack of toxicity, and lack of immunogenicity. One use of PAGs is to covalently attach the polymer to insoluble molecules to make the resulting PAG-molecule "conjugate" soluble. For example, it has been shown that the water-insoluble drug paclitaxel, when coupled to PEG, becomes water-soluble. Greenwald, et al., *J. Org. Chem.*, 60:331-336 (1995). PAG conjugates are often used not only to enhance solubility and stability but also to prolong the blood circulation half-life of molecules.

Polyalkylated compounds of the invention are typically between 5 and 80 kDa in size however any size can be used, the choice dependent on the aptamer and application. Other PAG compounds of the invention are between 10 and 80 kDa in size. Still other PAG compounds of the invention are between 10 and 60 kDa in size. For example, a PAG polymer may be at least 10, 20, 30, 40, 50, 60, or 80 kDa in size. Such polymers can be linear or branched.

In contrast to biologically-expressed protein therapeutics, nucleic acid therapeutics are typically chemically synthesized from activated monomer nucleotides. PEG-nucleic acid conjugates may be prepared by incorporating the PEG using the same iterative monomer synthesis. For example, PEGs activated by conversion to a phosphoramidite form can be incorporated into solid-phase oligonucleotide synthesis. Alternatively, oligonucleotide synthesis can be completed with site-specific incorporation of a reactive PEG attachment site. Most commonly this has been accomplished by addition of a free primary amine at the 5'-terminus (incorporated using a modifier phosphoramidite in the last coupling step of solid phase synthesis). Using this approach, a reactive PEG (e.g., one which is activated so that it will react and form a bond with an amine) is combined with the purified oligonucleotide and the coupling reaction is carried out in solution.

The ability of PEG conjugation to alter the biodistribution of a therapeutic is related to a number of factors including the apparent size (e.g., as measured in terms of hydrodynamic radius) of the conjugate. Larger conjugates (>10 kDa) are known to more effectively block filtration via the kidney and to consequently increase the serum half-life of small macromolecules (e.g., peptides, antisense oligonucleotides). The ability of PEG conjugates to block filtration has been shown to increase with PEG size up to approximately 50 kDa (further increases have minimal beneficial effect as half life becomes defined by macrophage-mediated metabolism rather than elimination via the kidneys).

Production of high molecular weight PEGs (>10 kDa) can be difficult, inefficient, and expensive. As a route towards the synthesis of high molecular weight PEG-nucleic acid conjugates, previous work has been focused towards the generation of higher molecular weight activated PEGs. One method for generating such molecules involves the formation of a branched activated PEG in which two or more PEGs are attached to a central core carrying the activated group. The terminal portions of these higher molecular weight PEG molecules, i.e., the relatively non-reactive hydroxyl (—OH) moieties, can be activated, or converted to functional moieties, for attachment of one or more of the PEGs to other compounds at reactive sites on the compound. Branched activated PEGs will have more than two termini, and in cases where two or more termini have been activated, such activated higher molecular weight PEG molecules are referred to herein as, multi-activated PEGs. In some cases, not all termini in a branch PEG molecule are activated. In cases where any two termini of a branch PEG molecule are activated, such PEG molecules are referred to as bi-activated PEGs. In some cases where only one terminus in a branch PEG molecule is activated, such PEG molecules are referred to as mono-activated. As an example of this approach, activated PEG prepared by the attachment of two monomethoxy PEGs to a lysine core which is subsequently activated for reaction has been described (Harris et al., Nature, vol. 2: 214-221, 2003).

The present invention provides another cost effective route to the synthesis of high molecular weight PEG-nucleic acid (preferably, aptamer) conjugates including multiply PEGylated nucleic acids. The present invention also encompasses PEG-linked multimeric oligonucleotides, e.g., dimerized aptamers. The present invention also relates to high molecular weight compositions where a PEG stabilizing moiety is a linker which separates different portions of an aptamer, e.g., the PEG is conjugated within a single aptamer sequence, such that the linear arrangement of the high molecular weight aptamer composition is, e.g., nucleic acid -PEG-nucleic acid (-PEG-nucleic acid)$_n$ where n is greater than or equal to 1.

High molecular weight compositions of the invention include those having a molecular weight of at least 10 kDa. Compositions typically have a molecular weight between 10 and 80 kDa in size. High molecular weight compositions of the invention are at least 10, 20, 30, 40, 50, 60, or 80 kDa in size.

A stabilizing moiety is a molecule, or portion of a molecule, which improves pharmacokinetic and pharmacodynamic properties of the high molecular weight aptamer compositions of the invention. In some cases, a stabilizing moiety is a molecule or portion of a molecule which brings two or more aptamers, or aptamer domains, into proximity, or provides decreased overall rotational freedom of the high molecular weight aptamer compositions of the invention. A stabilizing moiety can be a polyalkylene glycol, such a polyethylene glycol, which can be linear or branched, a homopolymer or a heteropolymer. Other stabilizing moieties include polymers such as peptide nucleic acids (PNA). Oligonucleotides can also be stabilizing moieties; such oligonucleotides can include modified nucleotides, and/or modified linkages, such as phosphorothioates. A stabilizing moiety can be an integral part of an aptamer composition, i.e., it is covalently bonded to the aptamer.

Compositions of the invention include high molecular weight aptamer compositions in which two or more nucleic acid moieties are covalently conjugated to at least one polyalkylene glycol moiety. The polyalkylene glycol moieties serve as stabilizing moieties. In compositions where a polyalkylene glycol moiety is covalently bound at either end to an aptamer, such that the polyalkylene glycol joins the nucleic acid moieties together in one molecule, the polyalkylene glycol is said to be a linking moiety. In such compositions, the primary structure of the covalent molecule includes the linear arrangement nucleic acid-PAG-nucleic acid. One example is a composition having the primary structure nucleic acid-PEG-nucleic acid. Another example is a linear arrangement of: nucleic acid-PEG-nucleic acid-PEG-nucleic acid.

To produce the nucleic acid-PEG-nucleic acid conjugate, the nucleic acid is originally synthesized such that it bears a single reactive site (e.g., it is mono-activated). In a preferred embodiment, this reactive site is an amino group introduced at the 5'-terminus by addition of a modifier phosphoramidite as the last step in solid phase synthesis of the oligonucleotide. Following deprotection and purification of the modified oligonucleotide, it is reconstituted at high concentration in a solution that minimizes spontaneous hydrolysis of the activated PEG. In a preferred embodiment, the concentration of oligonucleotide is 1 mM and the reconstituted solution contains 200 mM NaHCO$_3$-buffer, pH 8.3. Synthesis of the conjugate is initiated by slow, step-wise addition of highly purified bi-functional PEG. In a preferred embodiment, the PEG diol is activated at both ends (bi-activated) by derivatization with succinimidyl propionate. Following reaction, the PEG-nucleic acid conjugate is purified by gel electrophoresis or liquid chromatography to separate fully-, partially-, and un-conjugated species. Multiple PAG molecules concatenated (e.g., as random or block copolymers) or smaller PAG chains can be linked to achieve various lengths (or molecular weights). Non-PAG linkers can be used between PAG chains of varying lengths.

The 2'-O-methyl, 2'-fluoro and other modified nucleotide modifications stabilize the aptamer against nucleases and increase its half life in vivo. The 3'-3'-dT cap also increases exonuclease resistance. See, e.g., U.S. Pat. Nos. 5,674,685; 5,668,264; 6,207,816; and 6,229,002, each of which is incorporated by reference herein in its entirety.

PAG-Derivatization of a Reactive Nucleic Acid

Figure 2:
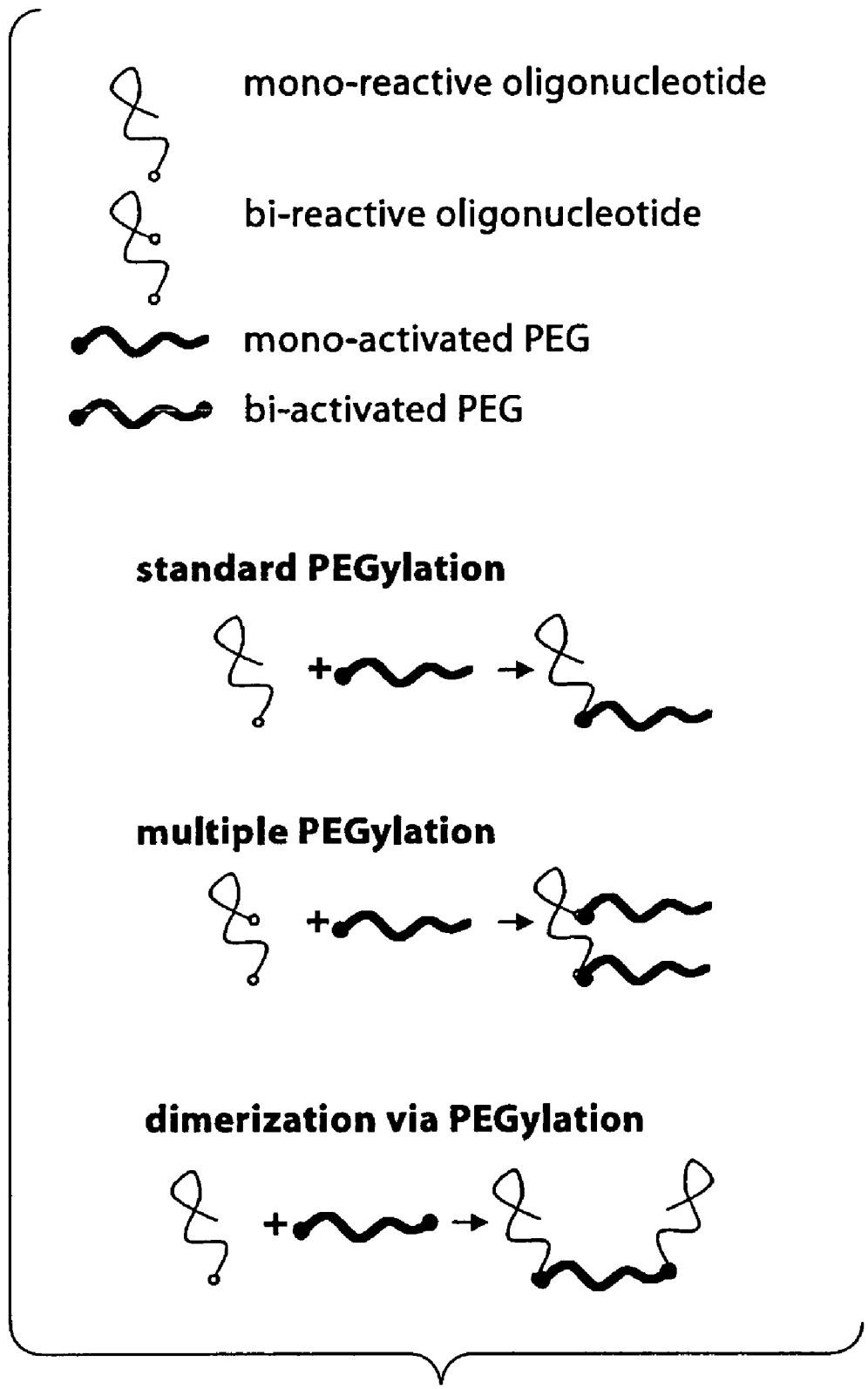
FIG. 2 is an illustration depicting various PEGylation strategies representing standard mono-PEGylation, multiple PEGylation, and oligomerization via PEGylation.

High molecular weight PAG-nucleic acid-PAG conjugates can be prepared by reaction of a mono-functional activated PEG with a nucleic acid containing more than one reactive site. In one embodiment, the nucleic acid is bi-reactive, or bi-activated, and contains two reactive sites: a 5'-amino group and a 3'-amino group introduced into the oligonucleotide through conventional phosphoramidite synthesis, for example: 3'-5'-di-PEGylation as illustrated in FIG. 2. In alternative embodiments, reactive sites can be introduced at internal positions, using for example, the 5-position of pyrimidines, the 8-position of purines, or the 2'-position of ribose as sites for attachment of primary amines. In such embodiments, the nucleic acid can have several activated or reactive sites and is said to be multiply activated. Following synthesis and purification, the modified oligonucleotide is combined with the mono-activated PEG under conditions that promote selective reaction with the oligonucleotide reactive sites while minimizing spontaneous hydrolysis. In the preferred embodiment, monomethoxy-PEG is activated with succinimidyl propionate and the coupled reaction is carried out at pH 8.3. To drive synthesis of the bi-substituted PEG, stoichiometric excess PEG is provided relative to the oligonucleotide. Following reaction, the PEG-nucleic acid conjugate is purified by gel electrophoresis or liquid chromatography to separate fully-, partially-, and un-conjugated species.

The linking domains can also have one or more polyalkylene glycol moieties attached thereto. Such PAGs can be of varying lengths and may be used in appropriate combinations to achieve the desired molecular weight of the composition.

The effect of a particular linker can be influenced by both its chemical composition and length. A linker that is too long, too short, or forms unfavorable steric and/or ionic interactions with the target will preclude the formation of complex between aptamer and target. A linker, which is longer than necessary to span the distance between nucleic acids, may reduce binding stability by diminishing the effective concentration of the ligand. Thus, it is often necessary to optimize linker compositions and lengths in order to maximize the affinity of an aptamer to a target.

All publications and patent documents cited herein are incorporated by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Example 1

Aptamer Selection and Sequences

Example 1A

Selection of rRfY vWF Domain A1 Aptamers

Selections were performed to identify aptamers that bind to human or rabbit vWF A1 domain using a nucleotide pool consisting of 2'-OH purine and 2'-F pyrimidine nucleotides (rRfY). The selection strategy yielded high affinity aptamers specific for human and rabbit vWF A1 domains which had been immobilized on a hydrophobic plate.

Pool Preparation

A DNA template with the sequence 5'-GGAGCGCACT-CAGCCAC NNNNNNNTTTCGACCTCTCTGCTAGC 3' (SEQ ID NO 8) was synthesized using an ABI EXPEDITE™ DNA synthesizer, and deprotected by standard methods. The series of N's in the DNA template (SEQ ID NO 8) can be any combination of nucleotides and gives rise to the unique sequence region of the resulting aptamers. The template was amplified with the primers 5'-TAATACGACTCACTATAG-GAGCGCACTCAGCCAC-3' (SEQ ID NO 9) and 5'-GCTAGCAGAGAGGTCGAAA-3' (SEQ ID NO 10) and then used as a template for in vitro transcription with T7 RNA polymerase (Y639F). Transcriptions were, typically, incubated at 37° C. overnight, using 40 mM Tris pH 8.0, 40 mM DTT, 1 mM spermidine-HCl, 0.002% TritonX-100, 4% (w/v) PEG-8000, 12 mM $MgCl_2$, 3 mM 2'-F-CTP, 3 mM 2'-F-UTP, 3 mM GTP, 3 mM ATP, 0.5× inorganic pyrophosphatase, and 1×T7 polymerase (Y639F), and approximately 0.5 μM template DNA.

Selection

For the human vWF A1 domain selection, the first ten rounds were initiated by immobilizing 24 pmoles of human vWF A1 domain (SEQ ID NO 4, FIG. 4) to the surface of a Nunc Maxisorp hydrophobic plate (Nunc Cat. #446612, Rochester, N.Y.) for 1 hour at room temperature in 100 μL of 1× Dulbecco's PBS (Gibco BRL Cat. #14040-133, Carlsbad, Calif.). For Rounds eleven and twelve, 12 pmoles of full length human vWF (SEQ ID NO 7, accession number VWHU, available from Calbiochem Cat. #681300, La Jolla, Calif.) were immobilized to the hydrophobic plate. For the rabbit vWF selection, each round was initiated by immobilizing 24 pmoles of rabbit vWF A1 domain (SEQ ID NO 6: accession number AAB51555, FIG. 3) under the same conditions as for human vWF A1 domain.

In all cases, after one hour of protein immobilization, the supernatant was removed and the wells were washed 4 times with 120 μL 1× Dulbecco's PBS. The protein-immobilized well was then blocked with 100 uL blocking buffer (1× Dulbecco's PBS with 1% BSA) for 1 hour at room temperature. In Round one, 333 pmoles of pool RNA ($2 \times 10^{14}$ unique molecules) were incubated in 100 μL 1× Dulbecco's PBS in the wells containing BSA-blocked immobilized protein target for 1 hour at room temperature. The supernatant was then removed and the wells were washed 4 times with 120 μL 1× Dulbecco's PBS. In later rounds, additional washes were added to increase the stringency of the positive selection step (see Tables 1 and 2). Starting at Round 2 and in all subsequent rounds, two negative selection steps were included before the positive selection step. First, the pool RNA was incubated for 1 hour at room temperature in an unblocked well to remove any plastic binding sequences from the pool. In the second negative selection step, the RNA was transferred to a BSA blocked well (not containing the protein target) for 1 hour at room temperature to remove any BSA binding sequences from the pool prior to the positive selection. Starting at Round 2 and in all subsequent rounds, 0.1 mg/mL tRNA and 0.1 mg/mL salmon sperm DNA were spiked into the positive selection reaction as non-specific competitors. In all cases, the pool RNA bound to the immobilized protein target was reverse transcribed directly in the selection plate with the addition of RT mix (Round 1: 100 uL; Round 2+: 50 uL; containing the 3'-primer according to SEQ ID NO 10 and Thermoscript RT (Invitrogen Cat. #11146-016, Carlsbad, Calif.) followed by incubation at 65° C. for 1 hour.

The resulting cDNA was used as a template for PCR (Round 1: 500 uL; Round 2+250 uL; containing the 5'-primer according to (SEQ ID NO 9), the 3'-primer according to (SEQ ID NO 10), and Taq polymerase (New England Biolabs Cat. #MO267L, Beverly, Mass.)). PCR reactions were done under the following conditions: a) denaturation step: 94° C. for 2 minutes; b) cycling steps: 94° C. for 30 seconds, 60° C. for 30 seconds, 72° C. for 1 minute; c) final extension step: 72° C. for 3 minutes. The cycles were repeated until sufficient PCR product was generated. The minimum number of cycles required to generate sufficient PCR product is reported in Tables 1 and 2 as the "PCR Threshold". The amplified pool template DNA was then isopropanol precipitated and half of the PCR product was used as template for the transcription of pool RNA for the next round of selection. The transcribed RNA pool was gel purified using a 10% polyacrylamide gel every third round. When not gel-purified, the transcribed RNA pool was desalted using two Centri-Spin 10 columns (Princeton Separations Cat. #CS-101, Adelphia, N.J.). In all cases, an equivalent of one-tenth of the total transcription product was carried forward as the starting pool for the subsequent round of selection.

TABLE 1

Human vWF A1 domain selection conditions using an rRfY pool

| Round | Target | Washes | PCR Threshold | Purification |
|---|---|---|---|---|
| 1 | 24 pmol hA1 | 4 × 120 uL | 16 | Desalt (2x) |
| 2 | 24 pmol hA1 | 4 × 120 uL | 18 | Desalt (2x) |
| 3 | 24 pmol hA1 | 4 × 120 uL | 16 | Gel purify |
| 4 | 24 pmol hA1 | 8 × 120 uL | 15 | Desalt (2x) |
| 5 | 24 pmol hA1 | 8 × 120 uL | 15 | Desalt (2x) |
| 6 | 24 pmol hA1 | 8 × 120 uL | 15 | Gel purify |
| 7 | 24 pmol hA1 | 8 × 120 uL | 12 | Desalt (2x) |
| 8 | 24 pmol hA1 | 8 × 120 uL | 12 | Desalt (2x) |
| 9 | 24 pmol hA1 | 8 × 120 uL | 10 | Gel purify |
| 10 | 24 pmol hA1 | 6 × 120 uL; 2 × 120 uL (15 min. each) | 10 | Desalt (2x) |
| 11 | 12 pmol full length vWF | 6 × 120 uL; 2 × 120 uL (15 min. each) | 20 | Desalt (2x) |
| 12 | 12 pmol full length vWF | 6 × 120 uL; 2 × 120 uL (15 min. each) | 15 | Gel purify |

TABLE 2

Rabbit vWF A1 domain selection conditions using an rRfY pool

| Round | Target | Washes | PCR Threshold | Purification |
|---|---|---|---|---|
| 1 | 24 pmol rA1 | 4 × 120 uL | 16 | Desalt (2x) |
| 2 | 24 pmol rA1 | 4 × 120 uL | 18 | Desalt (2x) |
| 3 | 24 pmol rA1 | 4 × 120 uL | 16 | Gel purify |
| 4 | 24 pmol rA1 | 8 × 120 uL | 15 | Desalt (2x) |
| 5 | 24 pmol rA1 | 8 × 120 uL | 15 | Desalt (2x) |
| 6 | 24 pmol rA1 | 8 × 120 uL | 15 | Gel purify |
| 7 | 24 pmol rA1 | 8 × 120 uL | 12 | Desalt (2x) |
| 8 | 24 pmol rA1 | 8 × 120 uL | 12 | Desalt (2x) |
| 9 | 24 pmol rA1 | 8 × 120 uL | 10 | Gel purify |
| 10 | 24 pmol rA1 | 6 × 120 uL; 2 × 120 uL (15 min. each) | 10 | Desalt (2x) |
| 11 | 24 pmol rA1 | 6 × 120 uL; 2 × 120 uL (15 min. each) | 10 | Desalt (2x) |
| 12 | 24 pmol rA1 | 6 × 120 uL; 2 × 120 uL (15 min. each) | 10 | Gel purify | vWF Domain A1 Binding Analysis

The selection progress was monitored using a sandwich filter binding assay. The 5'-$^{32}$P-labeled pool RNA (trace concentration) was incubated with either a no target protein control, 100 nM human vWF A1 domain (SEQ ID NO 4) or 100 nM rabbit vWF A1 domain (SEQ ID NO 6) in 1× Dulbecco's PBS containing 0.1 mg/mL tRNA, and 0.1 mg/mL salmon sperm DNA (in a final volume of 50 uL) for 30 minutes at room temperature and then applied to a nitrocellulose and nylon filter sandwich in a dot blot apparatus (Schleicher and Schuell, Keene, N.H.). The percentage of pool RNA bound to the nitrocellulose was calculated after Rounds 6, 9, and 12 with a three point screen (100 nM human vWF A1 domain, 100 nM rabbit vWF A1 domain, and a no-target control). Pool binding was compared to that of the naïve pool RNA (Round 0). The results of the rRfY pool binding analyses are found in Table 3.

TABLE 3 vWF A1 domain rRfY selection pool binding assays.

| Selection | Pool Round | 100 nM human A1 | 100 nM rabbit A1 | No Protein |
|---|---|---|---|---|
| Naïve Pool | Round 0 | 11.2% | 14.3% | 10.5% |
| Human vWF A1 | Round 6 | 16.0% | 16.9% | 13.8% |
| Rabbit vWF A1 | Round 6 | 15.2% | 17.9% | 14.7% |
| Human vWF A1 | Round 9 | 14.7% | 14.3% | 10.5% |
| Rabbit vWF A1 | Round 9 | 13.7% | 14.7% | 10.1% |
| Human vWF A1 | Round 12 | 31.8% | 33.1% | 13.2% |
| Rabbit vWF A1 | Round 12 | 24.1% | 17.7% | 10.3% |

When a significant positive ratio of binding of RNA in the presence of human or rabbit vWF A1 domain versus in the absence of protein was seen, the pools were cloned using the TOPO TA cloning kit (Invitrogen, Cat. #45-0641, Carlsbad, Calif.) according to the manufacturer's instructions. Round 9 and 12 pool templates were cloned and sequenced (125 total sequences), producing 48 unique clones. All unique clones were transcribed, desalted, 5-$^{32}$P end-labeled, and assayed in a 3-point dot blot screen (no protein target control, 100 nM human vWF A1 domain (SEQ ID NO 5, FIG. 3), or 100 nM rabbit vWF A1 domain (SEQ ID NO 6, FIG. 3). The data is presented in the third and fourth columns of Table 4 below as the ratio of the fraction of the aptamer bound to the nitrocellulose in the presence of the target protein to the fraction of aptamer bound in the absence of the target protein.

Based on this initial screen, $K_D$s were determined for 12 of the best vWF dependent binding sequences using the dot blot assay and are reported in column 5 of Table 4 below. For $K_D$ determination, aptamers transcripts were purified on 10% denaturing polyacrylamide gels, 5' end labeled with γ-$^{32}$P ATP. An 8 point titration of human vWF A1 domain (SEQ ID NO 5) was used in the dot blot assay (1 uM, 300 nM, 100 nM, 30 nM, 10 nM, 3 nM, 1 nM, 0 nM), and $K_D$ values were calculated by fitting the equation y=(max/(1+K/protein))+yint using KaleidaGraph (KaleidaGraph v. 3.51, Synergy Software) For all dot blot assays used to determine single clone $K_D$s in the Examples described herein, the target protein, e.g. human vWF A1 domain, is diluted with 1× Dulbecco's PBS buffer which includes 0.1 mg/mL BSA and incubated with labeled aptamer for 30 minutes at 24° C. prior to filtration and quantitation.

TABLE 4

Human and rabbit vWF A1 domain rRfY aptamer binding activity*

| Aptamer | Screen-Human/No Protein | Screen-Rabbit/No Protein | human A1 $K_D$ (nM) |
|---|---|---|---|
| (AMX201.B1) (SEQ ID NO 11) | ND | ND | 19 |
| (AMX198.G1)SEQ ID NO 12 | 1.89 | 1.90 | 45 |
| (AMX201.H3)SEQ ID NO 13 | 1.88 | 1.89 | 90 |
| (AMX201.B3)SEQ ID NO 14 | 1.69 | 1.64 | ND |
| (AMX201.G1)SEQ ID NO 15 | 2.14 | 2.20 | 190 |
| (AMX198.C6)SEQ ID NO 16 | 3.03 | 4.62 | 249 |
| (AMX201.B11)SEQ ID NO 17 | 1.55 | 1.52 | ND |
| (AMX201.D10)SEQ ID NO 18 | 1.59 | 1.52 | ND |
| (AMX198.C10)SEQ ID NO 19 | 1.40 | 3.39 | 555 |
| (AMX201.H4) SEQ ID NO 20 | 1.79 | 1.86 | ND |
| (AMX201.G9)SEQ ID NO 21 | 2.06 | 2.11 | 182 |
| (AMX201.H11)SEQ ID NO 22 | 1.75 | 1.40 | ND |
| (AMX201.C8)SEQ ID NO 23 | 2.47 | 1.50 | 0.2 |
| (AMX201.H1)SEQ ID NO 24 | 2.61 | 2.46 | 189 |
| (AMX198.E11)SEQ ID NO 25 | 1.03 | 2.37 | 1056 |
| (AMX198.A10)SEQ ID NO 26 | 1.26 | 5.74 | 1860 |
| (AMX201.D4)SEQ ID NO 27 | 2.23 | 2.46 | ND |
| (AMX201.D3)SEQ ID NO 28 | 1.76 | 1.52 | ND |
| (AMX201.A8)SEQ ID NO 29 | 1.82 | 1.51 | ND |
| (AMX198.E5)SEQ ID NO 30 | 1.60 | 1.56 | 172 |

*used human vWF A1 domain SEQ ID NO 5 for aptamer screen and aptamer $K_D$s
(ND = not done)

The nucleic acid sequences of the rRfY aptamers characterized in Table 4 above are given below. The unique sequence of each aptamer below begins at nucleotide 18, immediately following the sequence GGAGCGCACTCAGCCAC (SEQ ID NO 221), and runs until it meets the 3'fixed nucleic acid sequence TTTCGACCTCTCTGCTAGC (SEQ ID NO 222).

Unless noted otherwise, individual sequences listed below are represented in the 5' to 3' orientation and were selected under rRfY SELEX™ conditions wherein the purines (A and G) are 2'-OH (ribo) and the pyrimidines (U and C) are 2'-fluoro.

(AMX201.B1) SEQ ID NO 11
GGAGCGCACUCAGCCACAGAGCCCUGAGUGUAUGAUCGCCUAGAUCUAUC

GAUGCUUUUUCGACCUCUCUGCUAGC (AMX198.G1) SEQ ID NO 12
GGAGCGCACUCAGCCACAACACUAAUGGGGAAAGUUCAAGGAUUCUUGAC

CGGUGCGUUUCGACCUCUCUGCUAGC (AMX201.H3) SEQ ID NO 13
GGAGCGCACUCAGCCACUAACGGUUGAUCUCAGGACUAAAUAGUCAACAA

GGAUGCGUUUCGACCUCUCUGCUAGC (AMX201.B3) SEQ ID NO 14
GGAGCGCACUCAGCCACAGAGCCCUGAGUGUAUGAUCGCCGAGAUCUAUC

GAUGCUUUUUCGACCUCUCUGCUAGC (AMX201.G1) SEQ ID NO 15
GGAGCGCACUCAGCCACGCUCGGUGGGGAAAUUUUAGCCUAAUUGGCUAC

UUGUGCGUUUCGACCUCUCUGCUAGC (AMX198.C6) SEQ ID NO 16
GGAGCGCACUCAGCCACGGUGGUCAGUCAGUGAUAUGAUUAAGUUCAGCU

GUGGCUGUUUCGACCUCUCUGCUAGC (AMX201.B11) SEQ ID NO 17
GGAGCGCACUCAGCCACACCGAGGCUGGAUAUCUACGAGAGGAAGUGCUG

CUUGAAUUUCGACCUCUCUGCUAGC (AMX201.D10) SEQ ID NO 18
GGAGCGCACUCAGCCACACUGAGGCUGGAUAUCUACGAGAGGAAGUGCUG

CUUGGAUUUCGACCUCUCUGCUAGC (AMX198.C10) SEQ ID NO 19
GGAGCGCACUCAGCCACUGGUCCUUAGCUAGUUGUACUAGCGACGCGUUC

AGGUGGUUUCGACCUCUCUGCUAGC (AMX201.H4) SEQ ID NO 20
GGAGCGCACUCAGCCACUAACGGUUGAUCUCAGGACUAAAUAGUCAACAAG

GAUGCGUUUCGACCUCUCUGCUAGC (AMX201.G9) SEQ ID NO 21
GGAGCGCACUCAGCCACUAACGGCUGAUCUCAGGACUAAAUAGUCAACAA

GGAUGCGUUUCGACCUCUCUGCUAGC (AMX201.H11) SEQ ID NO 22
GGAGCGCACUCAGCCACCCUGUCGUCUUUUGGUAGUCAGCCAAAAGCUAG

UUGGUUGUUUCGACCUCUCUGCUAGC (AMX201.C8) (ARC840) SEQ ID NO 23
GGAGCGCACU CAGCCACCCUCGCAAG CAUUUUAAGAAUGA CUUGUGC

CGCUGCCUG UUUUCGACCUCUCUGCUAGC (AMX201.H1) SEQ ID NO 24
GGAGCGCACUCAGCCACUUUACGGUGAAAGUCUCUCGGGGUUCCGAGUUA

CGGUGCGUUUCGACCUCUCUGCUAGC (AMX198.E11) SEQ ID NO 25
GGAGCGCACUCAGCCACGGUAACAUUGUUUCCGGCGAUUCUUUGAACGCC

GUCGUGGUUUCGACCUCUCUGCUAGC (AMX198.A10) SEQ ID NO 26
GGAGCGCACUCAGCCACCAGUUAUGCUGGCUUUGGUCUUUGACUGUCUGA

GUGUUCGUUUCGACCUCUCUGCUAGC (AMX201.D4) SEQ ID NO 27
GGAGCGCACUCAGCCACUGGGGCUGAUCUCGCACGAUAGUUCGUGUCAAG

GAUGCGUUUCGACCUCUCUGCUAGC (AMX201.D3) SEQ ID NO 28
GGAGCGCACUCAGCCACGCCCACGUCAAAUUAUAGUCUACUUUGAUGUGC

CCGUGGUUUCGACCUCUCUGCUAGC (AMX201.A8) SEQ ID NO 29
GGAGCGCACUCAGCCACGCUGUACACUGAUGUUGUAACAUGUACCCCCUG

GCUGUUUCGACCUCUCUGCUAGC (AMX198.E5) SEQ ID NO 30
GGAGCGCACUCAGCCACUUCGACUUUCAUGUCUGAAGUCCCUGCAGUGCG

AGAGACGUUUCGACCUCUCUGCUAGC

While not wishing to be bound by any theory, based on the binding data presented in Table 4 above and the activity in cellular assays presented in Table 21 below for both the full length aptamers from this SELEX™ selection and the minimized aptamer sequences (see Example 2a below) the predicted generic secondary structure and predicted core nucleic acid sequence required for binding to the vWF target of all embodiments of the invention derived from this aptamer selection is depicted in FIG. 10 as SEQ ID NO 217 (RNAstructure, Version 4.1, Mathews, D. H.; Disney, M. D.; Childs, J. L.; Schroeder, S. J.; Zuker, M.; and Turner, D. H., "Incorporating chemical modification constraints into a dynamic programming algorithm for prediction of RNA secondary structure," 2004. *Proceedings of the National Academy of Sciences, US*, 101, 7287-7292). ARC840 (SEQ ID NO 23) is one example of an aptamer having the sequence depicted in FIG. 10 wherein the bold, underlined regions shown in the sequence listed above denote required bases.

Example 1B

Selection of rRdY vWF Domain A1 Aptamers

Selections were performed to identify aptamers that bind to (1) human vWF A1 domain, (2) rabbit vWF A1 domain, or (3) human and rabbit vWF A1 domains using a nucleotide pool consisting of 2'-OH purine and deoxy-pyrimidine nucleotides (rRdY). The selection strategy yielded high affinity aptamers specific for human and rabbit vWF A1 domains which had been immobilized on a hydrophobic plate.
Pool Preparation
A DNA template with the sequence 5'-GGAGCGCACTCAGCCAC NNNNNNNTTTCGACCTCTCTGCTAGC 3' (SEQ ID NO 8) was synthesized using an ABI EXPEDITE™ DNA synthesizer, and deprotected by standard methods. The series of N's in the DNA template (SEQ ID NO 8) can be any combination of nucleotides and gives rise to the unique sequence region of the resulting aptamers. The template was amplified with the primers 5'-TAATACGACTCACTATAG-GAGCGCACTCAGCCAC-3' (SEQ ID NO 9) and 5'-GCTAGCAGAGAGGTCGAAA-3' (SEQ ID NO 10) and then used as a template for in vitro transcription with T7 RNA polymerase (Y639F). Transcriptions were, typically, incubated at 37° C. overnight, using 40 mM Tris pH 8.0, 40 mM DTT, 1 mM spermidine-HCl, 0.002% Triton X-100, 4% (w/v) PEG-8000, 12 mM $MgCl_2$, 3 mM dCTP, 3 mM dTTP, 3 mM rGTP, 3 mM rATP, 0.5× inorganic pyrophosphatase, and 1×T7 polymerase (Y639F), and approximately 0.5 µM template DNA.
Selection
For the human vWF selection, the first ten rounds were initiated by immobilizing 24 pmoles of human vWF A1 domain (SEQ ID NO 4) to the surface of a Nunc Maxisorp hydrophobic plate (Nunc, Cat. #446612 Rochester, N.Y.) for 1 hour at room temperature in 100 µL of 1× Dulbecco's PBS (Gibco BRL Cat. #14040-133, Carlsbad, Calif.). For Rounds eleven and twelve, 12 pmoles of full length human vWF (SEQ ID NO 7, FIG. 4) were immobilized to the hydrophobic plate. For the rabbit vWF selection, each round was initiated by immobilizing 24 pmoles of rabbit vWF A1 domain (SEQ ID NO 6) under the same conditions. For the first two rounds of the human/rabbit alternating selection 12 pmoles of human vWF A1 domain (SEQ ID NO 4) and 12 pmoles of rabbit vWF A1 domain (SEQ ID NO 6) were immobilized to a hydrophobic plate as previously described. In the subsequent rounds of the alternating selection, the protein target was alternated each round between the human and rabbit vWF A1 domain (SEQ ID NOS 4 and 5, respectively), except in round 11, human full length vWF (SEQ ID NO 7) was used.

In all cases, after one hour of protein immobilization, the supernatant was removed and the wells were washed 4 times with 120 µL 1× Dulbecco's PBS. The protein-immobilized well was then blocked with 100 uL blocking buffer (1× Dulbecco's PBS with 1% BSA) for 1 hour at room temperature. In Round one, 333 pmoles of pool RNA ($2×10^{14}$ unique molecules) were incubated in 100 uL 1× Dulbecco's PBS in the wells containing BSA-blocked immobilized protein target for 1 hour at room temperature. The supernatant was then removed and the wells were washed 4 times with 120 µL 1× Dulbecco's PBS. In later rounds, additional washes were added to increase the stringency of the positive selection step (see Tables 5, 6, and 7). Starting at Round 2 and in all subsequent rounds, two negative selection steps were included before the positive selection step. First, the pool RNA was incubated for 1 hour at room temperature in an unblocked well to remove any plastic binding sequences from the pool. In the second negative selection step, the RNA was transferred to a BSA blocked well (not containing the protein target) for 1 hour at room temperature to remove any BSA binding sequences from the pool prior to the positive selection. Starting at Round 2 and in all subsequent rounds, 0.1 mg/mL tRNA and 0.1 mg/mL salmon sperm DNA were spiked into the positive selection reaction as non-specific competitors.

In all cases, the pool RNA bound to the immobilized protein target was reverse transcribed directly in the selection plate with the addition of RT mix (Round 1: 100 uL; Round 2+: 50 uL; containing the 3'-primer according to (SEQ ID NO 10) and Thermoscript RT (Invitrogen, Cat. #11146-016, Carlsbad, Calif.) followed by incubation at 65° C. for 1 hour. The resulting cDNA was used as a template for PCR (Round 1: 500 uL; Round 2+: 250 uL: containing the 5'-primer according to (SEQ ID NO 9), the 3'-primer according to (SEQ ID NO 10), and Taq polymerase (New England Biolabs, Cat. #MO267L, Beverly, Mass.)). PCR reactions were done under the following conditions: a) denaturation step: 94° C. for 2 minutes; b) cycling steps: 94° C. for 30 seconds, 60° C. for 30 seconds, 72° C. for 1 minute; c) final extension step: 72° C. for 3 minutes. The cycles were repeated until sufficient PCR product was generated. The minimum number of cycles required to generate sufficient PCR product is reported in Tables 5, 6 and 7 as the "PCR Threshold". The amplified pool template DNA was then isopropanol precipitated and half of the PCR product was used as template for the transcription of pool RNA for the next round of selection. The transcribed RNA pool was gel purified using a 10% polyacrylamide gel every two rounds. When not gel-purified, the transcribed pool was desalted using two Centri-Spin 10 columns (Princeton Separations Cat. #CS-101, Adelphia, N.J.). In all cases, an equivalent of one-tenth of the total transcription product was carried forward as the starting pool for the subsequent round of selection.

TABLE 5

Human vWF A1 domain selection conditions using an rRdY pool

| Round | Target | Washes | PCR Threshold | Purification |
|---|---|---|---|---|
| 1 | 24 pmol hA1 | 4 × 120 uL | 13 | Desalt (2x) |
| 2 | 24 pmol hA1 | 4 × 120 uL | 18 | Desalt (2x) |
| 3 | 24 pmol hA1 | 4 × 120 uL | 16 | Gel purify |
| 4 | 24 pmol hA1 | 8 × 120 uL | 15 | Desalt (2x) |
| 5 | 24 pmol hA1 | 8 × 120 uL | 15 | Desalt (2x) |
| 6 | 24 pmol hA1 | 8 × 120 uL | 15 | Gel purify |
| 7 | 24 pmol hA1 | 8 × 120 uL | 12 | Desalt (2x) |
| 8 | 24 pmol hA1 | 8 × 120 uL | 12 | Desalt (2x) |
| 9 | 24 pmol hA1 | 8 × 120 uL | 10 | Gel purify |
| 10 | 24 pmol hA1 | 6 × 120 uL; 2 × 120 uL (15 min. each) | 10 | Desalt (2x) |
| 11 | 12 pmol full length vWF | 6 × 120 uL; 2 × 120 uL (15 min. each) | 20 | Desalt (2x) |
| 12 | 12 pmol full length vWF | 6 × 120 uL; 2 × 120 uL (15 min. each) | 20 | Gel purify |

TABLE 6

Rabbit vWF A1 domain selection conditions using an rRdY pool

| Round | Target | Washes | PCR Threshold | Purification |
|---|---|---|---|---|
| 1 | 24 pmol rA1 | 4 × 120 uL | 13 | Desalt (2x) |
| 2 | 24 pmol rA1 | 4 × 120 uL | 18 | Desalt (2x) |
| 3 | 24 pmol rA1 | 4 × 120 uL | 10 | Gel purify |
| 4 | 24 pmol rA1 | 8 × 120 uL | 15 | Desalt (2x) |
| 5 | 24 pmol rA1 | 8 × 120 uL | 15 | Desalt (2x) |
| 6 | 24 pmol rA1 | 8 × 120 uL | 15 | Gel purify |
| 7 | 24 pmol rA1 | 8 × 120 uL | 15 | Desalt (2x) |
| 8 | 24 pmol rA1 | 8 × 120 uL | 12 | Desalt (2x) |
| 9 | 24 pmol rA1 | 8 × 120 uL | 10 | Gel purify |
| 10 | 24 pmol rA1 | 6 × 120 uL; 2 × 120 uL (15 min. each) | 10 | Desalt (2x) |
| 11 | 24 pmol rA1 | 6 × 120 uL; 2 × 120 uL (15 min. each) | 10 | Desalt (2x) |
| 12 | 24 pmol rA1 | 6 × 120 uL; 2 × 120 uL (15 min. each) | 10 | Gel purify |

TABLE 7

Human/rabbit vWF A1 domain alternating selection conditions using an rRdY pool

| Round | Target | Washes | PCR Threshold | Purification |
|---|---|---|---|---|
| 1 | 12 pmol hA1/ 12 pmol rA1 | 4 × 120 uL | 13 | Desalt (2x) |
| 2 | 12 pmol hA1/ 12 pmol rA1 | 4 × 120 uL | 18 | Desalt (2x) |
| 3 | 24 pmol hA1 | 4 × 120 uL | 16 | Gel purify |
| 4 | 24 pmol rA1 | 8 × 120 uL | 15 | Desalt (2x) |
| 5 | 24 pmol hA1 | 8 × 120 uL | 15 | Desalt (2x) |
| 6 | 24 pmol rA1 | 8 × 120 uL | 15 | Gel purify |
| 7 | 24 pmol hA1 | 8 × 120 uL | 12 | Desalt (2x) |
| 8 | 24 pmol rA1 | 8 × 120 uL | 12 | Desalt (2x) |
| 9 | 24 pmol hA1 | 8 × 120 uL | 10 | Gel purify |
| 10 | 24 pmol rA1 | 6 × 120 uL; 2 × 120 uL (15 min. each) | 10 | Desalt (2x) |
| 11 | 12 pmol full length vWF | 6 × 120 uL; 2 × 120 uL (15 min. each) | 20 | Desalt (2x) |
| 12 | 24 pmol rA1 | 6 × 120 uL; 2 × 120 uL (15 min. each) | 10 | Gel purify | vWF Binding Analysis

The selection progress was monitored using a sandwich filter binding assay. The 5'-$^{32}$P-labeled pool RNA (trace concentration) was incubated with either a no target protein control, 100 nM human vWF A1 domain or 100 nM rabbit vWF A1 domain, in 1× Dulbecco's PBS containing 0.1 mg/mL tRNA, and 0.1 mg/mL salmon sperm DNA (in a final volume of 50 uL) for 30 minutes at room temperature and then applied to a nitrocellulose and nylon filter sandwich in a dot blot apparatus (Schleicher and Schuell, Keene, N.H.). The percentage of pool RNA bound to the nitrocellulose was calculated after Rounds 6, 9, and 12 with a three point screen (100 nM human vWF A1 domain, 100 nM rabbit vWF A1 domain, and a no-target control). Pool binding was compared to that of the naïve pool RNA (Round 0). The results of the rRdY pool binding analyses are found in Table 8.

TABLE 8 vWF A1 domain rRdY selection pool binding assays.

| Selection | Pool Round | 100 nM hA1 | 100 nM rA1 | No Protein |
|---|---|---|---|---|
| Naïve Pool | Round 0 | 9.7% | 10.4% | 10.5% |
| Human vWF A1 | Round 6 | 19.6% | 19.7% | 15.3% |
| Rabbit vWF A1 | Round 6 | 14.3% | 14.4% | 12.3% |
| hA1/rA1 | Round 6 | 19.8% | 19.8% | 15.9% |
| Human vWF A1 | Round 9 | 23.8% | 24.3% | 15.6% |
| Rabbit vWF A1 | Round 9 | 24.4% | 24.0% | 16.6% |
| hA1/rA1 | Round 9 | 19.6% | 19.4% | 14.6% |
| Human vWF A1 | Round 12 | 25.8% | 23.0% | 17.0% |
| Rabbit vWF A1 | Round 12 | 20.7% | 20.5% | 13.8% |
| hA1/rA1 | Round 12 | 25.2% | 26.3% | 16.8% |

When a significant positive ratio of binding of RNA in the presence of human or rabbit vWF A1 domain (SEQ ID NOS 4 and 6, respectively) versus in the absence of protein was seen, the pools were cloned using the TOPO TA cloning kit (Invitrogen Cat. #45-0641, Carlsbad, Calif.) according to the manufacturer's instructions. Round 9 and 12 pool templates were cloned and sequenced (185 total sequences), producing 78 unique clones within 3 sequence families. All unique clones were transcribed, desalted, 5-$^{32}$P end-labeled, and assayed in a 3-point dot blot screen (no protein target control, 100 nM human vWF A1 domain (SEQ ID NO 5), or 100 nM rabbit vWF A1 domain (SEQ ID NO 6). The data are presented in the third and fourth columns of Table 9 below as the ratio of the fraction of the aptamer bound to the nitrocellulose in the presence of the target protein to the fraction of aptamer bound in the absence of the target protein. Of the three sequence families, members of Family #1 and #2 and two individual, non-family aptamers, bound to both human vWF domain A1 (SEQ ID NO 5) and rabbit vWF domain A1 (SEQ ID NO 6).

Based on this initial screen, $K_D$'S were determined for 16 of the best vWF dependent binding sequences using the dot blot assay. For $K_D$ determination, aptamers were purified on denaturing polyacrylamide gels and 5'-end labeled with $\gamma$-$^{32}$P ATP. A 6 point protein titration of human vWF A1 domain (SEQ ID NO 5) was used in the dot blot assay (333 nM, 100 nM, 33 nM, 10 nM, 3 nM, 0 nM) in 1×DPBS plus 0.1 mg/mL BSA at room temperature for 30 minutes. $K_D$ values were calculated by fitting the equation y=(max/(1+K/protein))+ yint using KaleidaGraph (KaleidaGraph v. 3.51, Synergy Software).

Results of protein binding characterization are tabulated in the final column of Table 9 below.

TABLE 9

Human and rabbit vWF A1 domain rRdY aptamer binding activity*

| # | Aptamer | Screen-Human/No Protein | Screen-Rabbit/No Protein | Human A1 $K_D$ (nM) |
|---|---|---|---|---|
| 1 | (AMX203.D6) SEQ ID NO 31 | 1.92 | 1.57 | 523 |
| 2 | (AMX205.H8) SEQ ID NO 32 | 2.04 | 2.84 | 788 |
| 3 | (AMX205.H11) SEQ ID NO 33 | 2.18 | 2.41 | 144 |
| 4 | (AMX205.A7) SEQ ID NO 34 | 1.24 | 1.37 | ND |
| 5 | (AMX205.D11) SEQ ID NO 35 | 2.22 | 2.07 | 124 |
| 6 | (AMX206.F9) SEQ ID NO 36 | 2.98 | 3.00 | 139 |
| 7 | (AMX206.H9) SEQ ID NO 37 | 1.98 | 2.31 | 109 |
| 8 | (AMX206.A10) SEQ ID NO 38 | 2.62 | 2.58 | 111 |
| 9 | (AMX205.F9) SEQ ID NO 39 | 2.22 | 2.47 | 145 |
| 10 | (AMX206.E7) SEQ ID NO 40 | 2.11 | 2.26 | 151 |
| 11 | (AMX206.D7) SEQ ID NO 41 | 2.19 | 2.08 | 187 |
| 12 | (AMX203.A6) SEQ ID NO 42 | 1.16 | 1.16 | ND |
| 13 | (AMX203.A1) SEQ ID NO 43 | 2.99 | 2.67 | 1148 |
| 14 | (AMX203.G9) SEQ ID NO 44 | 1.65 | 1.35 | 1.3 |
| 15 | (AMX205.H9) SEQ ID NO 45 | 2.36 | 3.14 | 178 |
| 16 | (AMX206.D8) SEQ ID NO 46 | 2.80 | 3.76 | 370 |
| 17 | (AMX203.F9) SEQ ID NO 47 | 1.45 | 1.29 | ND |
| 18 | (AMX205.G9) SEQ ID NO 48 | 1.30 | 1.73 | ND |
| 19 | (AMX205.F7) SEQ ID NO 49 | 3.13 | 2.37 | 1.5 |
| 20 | (AMX205.H10) SEQ ID NO 50 | 1.88 | 2.47 | 397 |

*used human vWF A1 domain (SEQ ID NO 5) for aptamer screen and aptamer $K_D$s
ND = not done The nucleic acid sequences of the rRdY aptamers characterized in Table 9 above are described below. The unique sequence of each aptamer below begins at nucleotide 18, immediately following the sequence GGAGCGCACT-CAGCCAC (SEQ ID NO 221), and runs until it meets the 3'fixed nucleic acid sequence TTTCGACCTCTCTGCTAGC (SEQ ID NO 222).

Unless noted otherwise, individual sequences listed below are represented in the 5' to 3' orientation and were selected under rRdY SELEX™ conditions wherein adenosine triphosphate and guanosine triphosphate are 2'-OH and cytidine triphosphate and thymidine triphosphate are deoxy.

vWF rRdY SELEX™ Family #1

The core target protein binding motifs for vWF rRdY Family #1 are shown in bold and underlined in the sequences below:

(AMX203.G9) (ARC842) SEQ ID NO 44
GGAGCGCACTCAGCCACGGGGTCGGTACACGGCGGGTATGTGGCT

G_GTGTCGAAGGGTTTCGACCTCTCTGCTAGC (AMX203.F9) SEQ ID NO 47
GGAGCGCACTCAGC CACTGAAGGGTAAGGACGACGAGGGTATACA

GTG_TGCGCGTGTATTTCGACCTCTCTGCTAGC (AMX203.A6) SEQ ID NO 42
GGAGCGCACTCA GCCACCACGCGGACGGGTAGGGCCGGCGAGGTG

GTGGC_ATTAGCGTTTCGACCTCTCTGCTAGC

Figure 12:
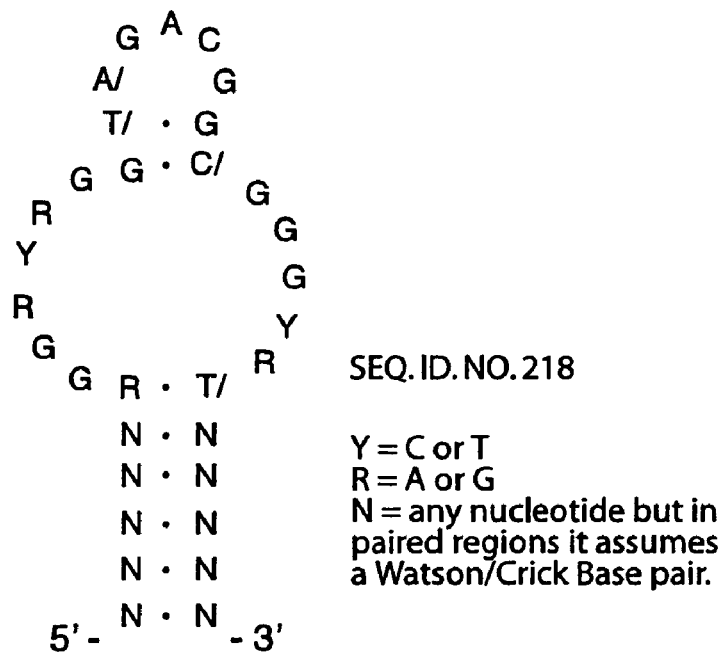
FIG. 12 is an illustration depicting the proposed secondary structure for SEQ ID NO 218.
Figure 13:
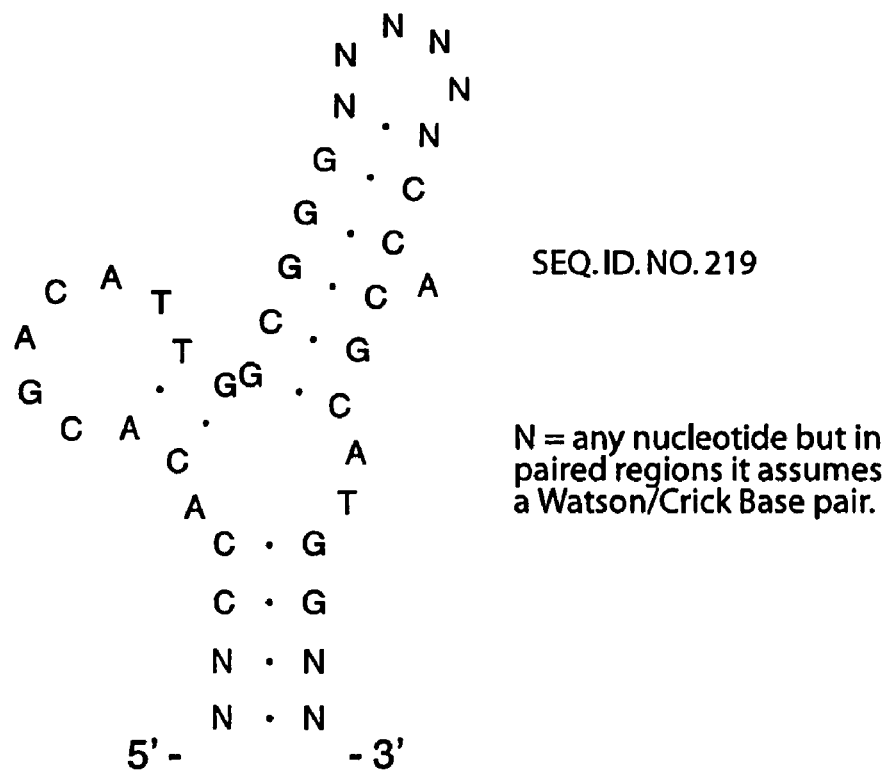
FIG. 13 is an illustration depicting the proposed secondary structure for SEQ ID NO 219.

The predicted secondary structure and core nucleic acid sequences required for binding to the vWF target of some embodiments of the invention is depicted in FIG. 12 as SEQ ID NO 218.

vWFrRdY SELEX™ Family #2

(AMX203.D6) SEQ ID NO 31
GGAGCGCACTCAGCCACAGTTCTGTCGGTGATGAATTAGCGCGAGAGCTG

TGGGACGTTTCGACCTCTCTGCTAGC (AMX205.H8), SEQ ID NO 32
GGAGCGCACTCAGCCACAAACGGACGGTGATGGATTAACGCGGGTTTATG

GCAAGGTTTCGACCTCTCTGCTAGC (AMX205.H11), SEQ ID NO 33
GGAGCGCACTCAGCCACGGCACGACGGTGATGGATTAGCGCGGTGTCGGT

GGTGTCATTTCGACCTCTCTGGTAGC (AMX205.D11), SEQ ID NO 35
GGAGCGCACTCAGCCACGGCACGACGGTGATGAATTAGCGCGGTGTCGGT

GGTGTCATTTCGACCTCTCTGCTAGC (AMX206.F9), SEQ ID NO 36
GGAGCGCACTCAGCCACGGAGCGTCGGTGATGGATTAGCGCGGCTCCGTG

GTACACATTTCGACCTCTCTGCTAGC (AMX206.H9), SEQ ID NO 37
GGAGCGCACTCAGCCACGGAGCGTCGGTGATGGATTAGCGCGGTTCCGTG

GTACACCTTTCGACCTCTCTGCTAGC (AMX206.A10), SEQ ID NO 38
GGAGCGCACTCAGCCACGGCATGACGGTGATGAATTAGCGCGGTGTCGGT

GGTGTCATTTCGACCTCTCTGCTAGC (AMX205.F9), SEQ ID NO 39
GGAGCGCACTCAGCCACGGAGCGTCGGTGATGGATTAGCGCGGCTCCGTG

GTACGCCTTTCGACCTCTCTGCTAGC

-continued (AMX206.E7), SEQ ID NO 40
GGAGCGCACTCAGCCACGGAGCGTCGGTGATGGATTAGCGCGGGTCCGTG

GTACACCTTTCGACCTCTCTGCTAGC (AMX206.D7), SEQ ID NO 41
GGAGCGCACTCAGCCACGGCACGACGGTGATGAATTAGCGCGGTGTCGGT

GGTGTTATTTCGACCTCTCTGCTAGC (AMX203.A 1), SEQ ID NO 43
GGAGCGCACTCAGCCACAGTTCTGTCGGTGATGAATTAGCGCGGGAGCTG

TGGGACGTTTCGACCTCTCTGCTAGC (AMX205.H9), SEQ ID NO 45
GGAGCGCACTCAGCCACGACGGTGATGGATTAGCGCGGTGGAGAAGATGC

GCTGTTGTTTCGACCTCTCTGCTAGC (AMX206.D8), SEQ ID NO 46
GGAGCGCACTCAGCCACGACGGTGATGGATTAGCGCGGTGGATCTTAACG

TGCGAGTTTCGACCTCTCTGCTAGC (AMX205.G9), SEQ ID NO 48
GGAGCGCACTCAGCCACAACTGGTTGTCGGTGATGGCATTAACGCGGACC

AGGCATGTTTCGACCTCTCTGCTAGC (AMX205.H10), SEQ ID NO 50
GGAGCGCACTCAGCCACTGTTGCCGACGGTGATGTATTAACGCGGGCAAC

GTTGGTGTTTCGACCTCTCTGCTAGC vWF rRdY SELEX™ Single sequences

The predicted core nucleic acid binding motif for SEQ ID NO 49 is shown in bold and underlined below:

(AMX205.F7) (ARC 841) SEQ ID NO 49
GGAGCGCACTCAGCCACACGACATTCGCGGGTTGTAATTACCACGCATGC

CTGTTTGTTTCGACCTCTCTGCTAGC (AMX205.A7), SEQ ID NO 34
GGAGCGCACTCAGCCACTCAAGGGGGTCGCGTGGGGACGAAGGGTTGCAG

TGTGTCGTTTCGACCTCTCTGCTAGC

The predicted core nucleic acid sequences and secondary structure required for binding to the vWF target of some embodiments of the invention is depicted in FIG. 13 as SEQ ID NO 219.

Example 1C

Selection #1 of DNA vWF Domain A1 Aptamers

Selections were performed to identify aptamers that bind to (1) human vWF A1 domain, (2) rabbit vWF A1 domain, or (3) human and rabbit vWF A1 domains, using a nucleotide pool consisting of deoxy-nucleotides (DNA). The selection strategy yielded high affinity aptamers specific for human and rabbit vWF A1 domains which had been immobilized on a hydrophobic plate.

Pool Preparation

A DNA template with the sequence 5'-CTACCTAC-GATCTGACTAGC NNNNNNNNGCTTACTCTCATG-TAGTTCC-3' (SEQ ID NO 51) (ARC 493) was synthesized using an ABI EXPEDITE™ DNA synthesizer, and deprotected by standard methods. The series of N's in the DNA template (SEQ ID NO 51) can be any combination of nucleotides and gives rise to the unique sequence region of the resulting aptamers. The template was PCR amplified with the primers (5'-CTACCTACGATCTGACTAGC-3') (SEQ ID NO 52) and (5'-AGGAACTACATGAGAGTAAGC(OH)-3') (SEQ ID NO 53) under standard conditions. The PCR product was subjected to alkaline hydrolysis (333 mM NaOH, 90° C., 15 min) followed by precipitation. The strands were separated on a 10% denaturing polyacrylamide gel and the single stranded DNA pool, which migrated with a lower mobility, was excised from the gel, passively eluted, and precipitated with isopropanol.

Selection

For the human vWF selection, the first ten rounds were initiated by immobilizing 24 pmoles of human vWF A1 domain (SEQ ID NO 4) to the surface of a Nunc Maxisorp hydrophobic plate (Nunc, Cat. #446612, Rochester, N.Y.) for 1 hour at room temperature in 100 µL of 1× Dulbecco's PBS (Gibco BRL, Cat. #14040-133, Carlsbad, Calif.). For Rounds eleven and twelve, 12 pmoles of full length human vWF (SEQ ID NO 7) were immobilized to the hydrophobic plate. For the rabbit vWF selection, each round was initiated by immobilizing 24 pmoles of rabbit vWF A1 (SEQ ID NO 6) domain under the same conditions. For the first two rounds of the human/rabbit alternating selection, 12 pmoles of human vWF A1 domain (SEQ ID NO 4) and 12 pmoles of rabbit vWF A1 domain (SEQ ID NO 6) were immobilized to a hydrophobic plate as previously described. In the subsequent rounds of the alternating selection, the protein target was alternated each round between human and rabbit vWF A1 domain, except in Round 11 human full length vWF (SEQ ID NO 7) was used.

In all cases, after one hour of protein immobilization, the supernatant was removed and the wells were washed 4 times with 120 µL 1× Dulbecco's PBS. The protein-immobilized well was then blocked with 100 uL blocking buffer (1× Dulbecco's PBS with 1% BSA) for 1 hour at room temperature. In Round one, 333 pmoles of pool DNA ($2\times10^{14}$ unique molecules) were incubated in 100 µL 1× Dulbecco's PBS in the wells containing BSA-blocked immobilized protein target for 1 hour at room temperature. The supernatant was then removed and the wells were washed 4 times with 120 µL 1× Dulbecco's PBS. In later rounds, additional washes were added to increase the stringency of the positive selection step (see Tables 10, 11, and 12). Starting at Round 2 and in all subsequent rounds, two negative selection steps were included before the positive selection step. First, the pool DNA was incubated for 1 hour at room temperature in an unblocked well to remove any plastic binding sequences from the pool. In the second negative selection step, the DNA was transferred to a BSA blocked well (not containing the protein target) for 1 hour at room temperature to remove any BSA binding sequences from the pool prior to the positive selection. Starting at Round 2 and in all subsequent rounds, 0.1 mg/mL tRNA and 0.1 mg/mL salmon sperm DNA were spiked into the positive selection reaction as non-specific competitors.

In all cases, the pool DNA bound to the immobilized protein target was eluted with 2×100 µL washes with elution buffer (preheated to 90° C., 7 M Urea, 100 mM NaOAc pH 5.3, 3 mM EDTA) for five minutes. Both elutions were pooled and precipitated by the addition of ethanol, then amplified in an initial PCR reaction (100 µL reactions including the 5'-primer according to SEQ ID NO 52, and the 3'-primer according to SEQ ID NO 53, and Taq polymerase (New England BioLabs, Cat. #M0267L, Beverly, Mass.). PCR reactions were done under the following conditions: a) denaturation step: 94° C. for 2 minutes; b) cycling steps: 94° C. for 30 seconds, 52° C. for 30 seconds, 72° C. for 1 minute; c) final extension step: 72° C. for 3 minutes. The cycles were repeated until sufficient PCR product was generated. The minimum number of cycles required to generate sufficient PCR product is reported in Tables 10, 11 and 12 as the "PCR Threshold". 10 µL of the PCR product was added to another 300 µL of PCR mix for a prep-scale PCR reaction. The prep-scale PCR product was ethanol precipitated and was subjected to alkaline hydrolysis (333 mM NaOH, 90° C., 15 min). The strands were separated on a 10% denaturing polyacrylamide gel and the single stranded DNA pool, which migrated with a lower mobility, was excised from the gel, passively eluted, and precipitated with isopropanol. In all cases, an equivalent of half of the total single stranded DNA product was carried forward as the starting pool for the subsequent round of selection.

TABLE 10

Human vWF A1 domain selection conditions using a DNA pool

| Round | Target | Washes | PCR Threshold | Purification |
|---|---|---|---|---|
| 1 | 24 pmol hA1 | 4 × 120 uL | 10 | Gel purify |
| 2 | 24 pmol hA1 | 4 × 120 uL | 15 | Gel purify |
| 3 | 24 pmol hA1 | 4 × 120 uL | 13 | Gel purify |
| 4 | 24 pmol hA1 | 8 × 120 uL | 15 | Gel purify |
| 5 | 24 pmol hA1 | 8 × 120 uL | 15 | Gel purify |
| 6 | 24 pmol hA1 | 8 × 120 uL | 20 | Gel purify |
| 7 | 24 pmol hA1 | 8 × 120 uL | 10 | Gel purify |
| 8 | 24 pmol hA1 | 8 × 120 uL | 10 | Gel purify |
| 9 | 24 pmol hA1 | 8 × 120 uL | 10 | Gel purify |
| 10 | 24 pmol hA1 | 6 × 120 uL; 2 × 120 uL (15 min. each) | 12 | Gel purify |
| 11 | 12 pmol full length vWF | 6 × 120 uL; 2 × 120 uL (15 min. each) | 18 | Gel purify |
| 12 | 12 pmol full length vWF | 6 × 120 uL; 2 × 120 uL (15 min. each) | 15 | Gel purify |

TABLE 11

Rabbit vWF A1 domain selection conditions using a DNA pool

| Round | Target | Washes | PCR Threshold | Purification |
|---|---|---|---|---|
| 1 | 24 pmol rA1 | 4 × 120 uL | 10 | Gel purify |
| 2 | 24 pmol rA1 | 4 × 120 uL | 13 | Gel purify |
| 3 | 24 pmol rA1 | 4 × 120 uL | 13 | Gel purify |
| 4 | 24 pmol rA1 | 8 × 120 uL | 15 | Gel purify |
| 5 | 24 pmol rA1 | 8 × 120 uL | 15 | Gel purify |
| 6 | 24 pmol rA1 | 8 × 120 uL | 20 | Gel purify |
| 7 | 24 pmol rA1 | 8 × 120 uL | 10 | Gel purify |
| 8 | 24 pmol rA1 | 8 × 120 uL | 10 | Gel purify |
| 9 | 24 pmol rA1 | 8 × 120 uL | 10 | Gel purify |
| 10 | 24 pmol rA1 | 6 × 120 uL; 2 × 120 uL (15 min. each) | 12 | Gel purify |
| 11 | 24 pmol rA1 | 6 × 120 uL; 2 × 120 uL (15 min. each) | 10 | Gel purify |
| 12 | 24 pmol rA1 | 6 × 120 uL; 2 × 120 uL (15 min. each) | 10 | Gel purify |

TABLE 12

Human/rabbit vWF A1 domain alternating selection conditions using a DNA pool

| Round | Target | Washes | PCR Threshold | Purification |
|---|---|---|---|---|
| 1 | 12 pmol hA1/ 12 pmol rA1 | 4 × 120 uL | 12 | Gel purify |
| 2 | 12 pmol hA1/ 12 pmol rA1 | 4 × 120 uL | 15 | Gel purify |
| 3 | 24 pmol hA1 | 4 × 120 uL | 10 | Gel purify |
| 4 | 24 pmol rA1 | 8 × 120 uL | 15 | Gel purify |
| 5 | 24 pmol hA1 | 8 × 120 uL | 15 | Gel purify |
| 6 | 24 pmol rA1 | 8 × 120 uL | 20 | Gel purify |
| 7 | 24 pmol hA1 | 8 × 120 uL | 12 | Gel purify |
| 8 | 24 pmol rA1 | 8 × 120 uL | 12 | Gel purify |
| 9 | 24 pmol hA1 | 8 × 120 uL | 12 | Gel purify |
| 10 | 24 pmol rA1 | 6 × 120 uL; 2 × 120 uL (15 min. each) | 12 | Gel purify |
| 11 | 12 pmol full length vWF | 6 × 120 uL; 2 × 120 uL (15 min. each) | 18 | Gel purify |
| 12 | 24 pmol rA1 | 6 × 120 uL; 2 × 120 uL (15 min. each) | 10 | Gel purify | vWF Binding Analysis

The selection progress was monitored using a sandwich filter binding assay. The 5'-$^{32}$P-labeled pool DNA (trace concentration) was incubated with either a no target protein control, 100 nM human vWF A1 domain (SEQ ID NO 4), or 100 nM rabbit vWF A1 domain (SEQ ID NO 6), in 1× Dulbecco's PBS containing 0.1 mg/mL tRNA, and 0.1 mg/mL salmon sperm DNA in a (final volume of 50 uL) for 30 minutes at room temperature and then applied to a nitrocellulose and nylon filter sandwich in a dot blot apparatus (Schleicher and Schuell, Keene, N.H.). The percentage of pool DNA bound to the nitrocellulose was calculated after Rounds 6, 9, and 12 with a three point screen (no protein target control, 100 nM human vWF A1 domain (SEQ ID NO 5), 100 nM rabbit vWF A1 domain (SEQ ID NO 6). Pool binding was compared to that of the naïve pool DNA (Round 0). The results of the DNA pool binding analyses are found in Table 13.

TABLE 13 vWF A1 domain DNA selection pool binding assays.

| Selection | Pool Round | 100 nM hA1 | 100 nM rA1 | No Protein |
|---|---|---|---|---|
| Naïve Pool | Round 0 | 30.1% | 35.4% | 29.4% |
| Human vWF A1 | Round 6 | 34.4% | 36.4% | NA |
| Rabbit vWF A1 | Round 6 | 37.9% | 36.8% | 35.6% |
| hA1/rA1 | Round 6 | 47.9% | 50.6% | 49.0% |
| Human vWF A1 | Round 9 | 30.4% | 43.7% | 19.1% |
| Rabbit vWF A1 | Round 9 | 15.9% | 35.0% | 6.6% |
| hA1/rA1 | Round 9 | 40.8% | 49.5% | 34.7% |
| Human vWF A1 | Round 12 | 36.7% | 45.9% | 33.0% |
| Rabbit vWF A1 | Round 12 | 23.7% | 38.7% | 13.4% |
| hA1/rA1 | Round 12 | 21.4% | 34.2% | 16.4% |

When a significant positive ratio of binding of DNA in the presence of human or rabbit vWF A1 domain versus in the absence of protein was seen, the pools were cloned using the TOPO TA cloning kit (Invitrogen, Carlsbad, Calif., Cat. #45-0641) according to the manufacturer's instructions. Round 9 and 12 pool templates were cloned and sequenced (243 total sequences), producing 106 unique clones within 8 sequence families, 41 of which bound to the vWF target and fell into the families described below.

All unique clones were assayed in a 3-point dot blot screen (no protein target control, 100 nM human vWF A1 domain (SEQ ID NO 5), or 100 nM rabbit vWF A1 domain (SEQ ID NO 6). The data are presented in the third and fourth columns of Table 14 below as the ratio of the fraction of the aptamer bound to the nitrocellulose in the presence of the target protein to the fraction of aptamer bound in the absence of the target protein.

Based on this initial screen, $K_D$'s were determined for 10 of the vWF dependent binding sequences. For $K_D$ determination, aptamers were 5' end labeled with $\gamma$-$^{32}$P ATP and a competition dot blot assay was used with a constant protein concentration of 100 nM and an 8 point cold competitor DNA titration (333 nM, 100 nM, 33 nM, 10 nM, 3 nM, 1 nM, 33 pM, 0 pM) in 1×DPBS plus 0.1 mg/mL BSA at room temperature for 30 minutes. $K_D$ values were calculated by fitting the equation y=(max/(1+K/protein))+yint using KaleidaGraph (KaleidaGraph v. 3.51, Synergy Software). Results of protein binding characterization are tabulated in Table 14.

TABLE 14

Human and rabbit vWF A1 domain DNA aptamer binding activity*

| # | Aptamer | Screen-Human/No Protein | Screen-Rabbit/No Protein | Human A1 $K_D$ (nM) |
|---|---|---|---|---|
| 1 | 1 (AMX199.B3) SEQ ID NO 54 | 1.76 | 1.99 | 30 |
| 2 | (AMX199.D11) SEQ ID NO 55 | 4.19 | 3.42 | 30 |
| 3 | (AMX200.G11) SEQ ID NO 56 | 1.73 | 1.28 | ND |
| 4 | (AMX200.D11) SEQ ID NO 57 | 3.34 | 2.04 | ND |
| 5 | (AMX200.D8) SEQ ID NO 58 | 2.86 | 1.61 | ND |
| 6 | (AMX200.C11) SEQ ID NO 59 | 6.00 | 3.64 | 26 |
| 7 | (AMX199.G10) SEQ ID NO 60 | 4.97 | 2.66 | 22 |
| 8 | (AMX199.F7) SEQ ID NO 61 | 5.47 | 5.00 | 22 |
| 9 | (AMX200.A7) SEQ ID NO 62 | 0.97 | 0.96 | ND |
| 10 | (AMX200.B9) SEQ ID NO 63 | 2.54 | 2.06 | ND |
| 11 | (AMX200.B1) SEQ ID NO 64 | 4.01 | 3.01 | ND |
| 12 | (AMX199.C2) SEQ ID NO 65 | 5.09 | 4.61 | 17 |
| 13 | (AMX200.B8) SEQ ID NO 66 | 4.13 | 3.13 | ND |
| 14 | (AMX200.F11) SEQ ID NO 67 | 3.83 | 3.25 | 34 |
| 15 | (AMX200.D1) SEQ ID NO 68 | 1.26 | 1.06 | ND |
| 16 | (AMX200.F9) SEQ ID NO 69 | 0.97 | 0.99 | ND |
| 17 | (AMX199.B7) SEQ ID NO 70 | 4.08 | 3.65 | 29 |
| 18 | (AMX200.D3) SEQ ID NO 71 | 2.68 | 2.41 | 36 |
| 19 | (AMX199.C4) SEQ ID NO 72 | 3.60 | 2.85 | 34 |
| 20 | (AMX200.E8) SEQ ID NO 73 | 1.04 | 1.03 | ND |
| 21 | (AMX199.F10) SEQ ID NO 74 | 1.17 | 1.24 | ND |
| 22 | (AMX199.F6) SEQ ID NO 75 | 1.37 | 1.30 | ND |
| 23 | (AMX199.G5) SEQ ID NO 76 | 1.41 | 1.34 | ND |
| 24 | (AMX199.F11) SEQ ID NO 77 | 1.44 | 1.35 | ND |
| 25 | (AMX199.H7) SEQ ID NO 78 | 1.32 | 1.14 | ND |
| 26 | (AMX199.A10) SEQ ID NO 79 | 1.25 | 1.29 | ND |
| 27 | (AMX199.G1) SEQ ID NO 80 | 1.19 | 1.26 | ND |
| 28 | (AMX199.F1) SEQ ID NO 81 | 1.32 | 1.36 | ND |
| 29 | (AMX199.G4) SEQ ID NO 82 | 1.19 | 1.11 | ND |
| 30 | (AMX200.A11) SEQ ID NO 83 | 1.49 | 1.19 | ND |
| 31 | DL.159.83.31 (AMX200.H8) SEQ ID NO 84 | 1.86 | 1.27 | ND |
| 32 | (AMX199.F8) SEQ ID NO 85 | 1.78 | 1.79 | ND |
| 33 | (AMX199.B6) SEQ ID NO 86 | 2.01 | 1.91 | ND |
| 34 | (AMX199.D8) SEQ ID NO 87 | 1.89 | 2.00 | ND |
| 35 | (AMX200.E10) SEQ ID NO 88 | 1.69 | 1.82 | ND |
| 36 | (AMX202.H10) SEQ ID NO 89 | 1.92 | 1.76 | ND |
| 37 | (AMX202.B8) SEQ ID NO 90 | 1.66 | 1.41 | ND |
| 38 | (AMX202.D6) SEQ ID NO 91 | 1.94 | 1.55 | ND |
| 39 | (AMX202.A3) SEQ ID NO 92 | 2.28 | 2.10 | ND |
| 40 | DL.159.83.98 (AMX202.A8) SEQ ID NO 93 | 1.27 | 1.27 | ND |
| 41 | (AMX202.F6) SEQ ID NO 94 | 1.49 | 1.46 | ND |

*used human vWF A1 domain (SEQ ID NO 5) for aptamer screen and aptamer $K_D$s
ND = not done The nucleic acid sequences of the DNA aptamers characterized in Table 14 above are described below, The unique sequence of each aptamer below begins at nucleotide 21, immediately following the sequence CTACCTACGATCTGACTAGC (SEQ ID NO 52), and runs until it meets the 3' fixed nucleic acid sequence GCTTACTCTCATGTAGTTCC (SEQ ID NO 223).

Unless noted otherwise, individual sequences listed below are represented in the 5' to 3' orientation and were selected under DNA SELEX™ wherein all of the nucleotides are deoxy.

DNA SELEX™ 1, Family #1

The predicted core nucleic acid binding sequence for DNA SELEX™ 1, Family #1 is shown in bold and underlined for aptamer AMX199.B3 (SEQ ID NO 54) and the consensus sequence (SEQ ID NO 95) below.

(AMX199.B3) SEQ ID NO 54
CTACCTACGATCTGACTAGCGGA ATGAGAATGCTGATGGATTGCTCAGG

TCTGCTGGCTGCTTACTCTCATGTAGTTCC (AMX200.C11) SEQ ID NO 59
CTACCTACGATCTGACTAGCGGAATGAGAGTGCTGATGGATTGCTCAGGT

CTGCTGGCTGCTTACTCTCATGTAGTTCC (AMX200.G11) SEQ ID NO 56
CTACCTACGATCTGACTAGCGGAACGAGAATGCTGATGGATTGCTCAGGT

CTGCTGGCTGCTTACTCTCATGTAGTTCC (AMX199.D11) SEQ ID NO 55
CTACCTACGATCTGACTAGCGGAATGAGAATGCTTGTGGATTGCTCAGGT

CTGCTGGCTGCTTACTCTCATGTAGTTCC (AMX200.D8) SEQ ID NO 58
CTACCTACGATCTGACTAGCGGAATGAGAATGTTGATGGATTGCTCAGGT

CTGCTGGCTGCTTACTCTCATGTAGTTCC (AMX200.D11) SEQ ID NO 57
CTACCTACGATCTGACTAGCGGAATAAGAATGCTGATGGATTGCTCAGGT

CTGCTGGCTGCTTACTCTCATGTAGTTCC (AMX199.F7) SEQ ID NO 61
CTACCTACGATCTGACTAGCGGAATGAGAGTGCTGGTGGATTGCTCAGGT

CTGCTGGCTGCTTACTCTCATGTAGTTCC (AMX200.A7) SEQ ID NO 62
CTACCTACGATCTGACTAGCGGAATGAGAATGCTGATGGATTGTTCAGGT

CTGCTGGCTGCTTACTCTCATGTAGTTCC (AMX202.D6) SEQ ID NO 91
CTACCTACGATCTGACTAGCGGAATGAGAAGGCTGATGGATTGCTCAGGT

CTGCTGGCTGCTTACTCTCATGTAGTTCC (AMX200.B1) SEQ ID NO 64
CTACCTACGATCTGACTAGCGGAATGAGAATGCTGATGGATTGCCCAGGT

CTGCTGGCTGCTTACTCTCATGTAGTTCC (AMX199.G10) SEQ ID NO 60
CTACCTACGATCTGACTAGCGGAATGAGAATGTTGGTGGATTGCTCAGGT

CTGCTGGCTGCTTACTCTCATGTAGTTCC (AMX200.B8) SEQ ID NO 66
CTACCTACGATCTGACTAGCGGAATGAGAATGCTGATGGATTGCACAGGT

CTGCTGGCTGCTTACTCTCATGTAGTTCC (AMX200.B9) SEQ ID NO 63
CTACCTACGATCTGACTAGCGGAATGAGAATGCTGATGGATTGCTCAGGT

CTGCTGACTGCTTACTCTCATGTAGTTCC (AMX202.B8) SEQ ID NO 90
CTACCTACGATCTGACTAGCGGAATGAGTATGCTGATGGATTGCTCAGGT

CTGCTGGCTGCTTACTCTCATGTAGTTCC (AMX202.H10) SEQ ID NO 89
CTACCTACGATCTGACTAGCGGAATGAGAAGGCTGGTGGATTGCTCAGGT

CTGCTGGCTGCTTACTCTCATGTAGTTCC (AMX200.F9) SEQ ID NO 69
CTACCTACGATCTGACTAGCGGAATGAGGATGCTGATGGATTGGTCAGGT

CTGCTGGCTGCTTACTCTCATGTAGTTCC (AMX202.A3) SEQ ID NO 92
CTACCTACGATCTGACTAGCGGAATGAGAGCGCTGATGGATTGCTCAGGT

CTGCTGGCTGCTTACTCTCATGTAGTTCC (AMX199.C2) SEQ ID NO 65
CTACCTACGATCTGACTAGCGGAATGAGAATGCTGGTGGATTGCCCAGGT

CTGCTGGCTGCTTACTCTCATGTAGTTCC (AMX200.F11) SEQ ID NO 67
CTACCTACGATCTGACTAGCGGAATGAGGATGCTGGTGGATTGCTCAGGT

CTGCTGGCTGCTTACTCTCATGTAGTTCC (AMX200.D1) SEQ ID NO 68
CTACCTACGATCTGACTAGCGGAATGAGAGTGCTGATGGATTGCTCAGGT

CTACTGGCTGCTTACTCTCATGTAGTTCC (AMX199.C4) SEQ ID NO 72
CTACCTACGATCTGACTAGCGGAATGAGGATGCTGATGGATTGCACAGGT

CTGCTGGCTGCTTACTCTCATGTAGTTCC (AMX200.D3) SEQ ID NO 71
CTACCTACGATCTGACTAGCGCAATGAGGATGCTGATGGATTGCTCAGGT

CTGCTGGCTGCTTACTCTCATGTAGTTCC (AMX199.B7) SEQ ID NO 70
CTACCTACGATCTGACTAGCGGGATGAGAGTGCTGGTGGATTGCTCAGGT

CTGCTGGCTGCTTACTCTCATGTAGTTCC (AMX200.E8) SEQ ID NO 73
CTACCTACGATCTGACTAGCGGAATGAGGATGCTGGTGGATTGCTCAGGT

CTGTTGGCTGCTTACTCTCATGTAGTTCC

The Consensus sequence for DNA SELEX™ 1, Family #1 is as follows:

SEQ ID NO 95
CTACCTACGATCTGACTAGCGGAATGAGRATGYTGRTGGATTGCHCAGGT

CTRYTGRCTGCTTACTCTCATGTAGTTCC

Where Y=C or T, R=A or G and H=A, C or T

DNA SELEX™ Family #2

(AMX199.F10) SEQ ID NO 74
CTACCTACGATCTGACTAGCGAAACACTAGGTTGGTTAGGATTGGTGTGT

TTCCGTTCTGCTTACTCTCATGTAGTTCC (AMX199.F6) SEQ ID NO 75
CTACCTACGATCTGACTAGCGAAACACTAGGTTGGTTAGGATTGGTGTGT

TCCCGCTCTGCTTACTCTCATGTAGTTCC (AMX199.H7) SEQ ID NO 78
CTACCTACGATCTGACTAGCGAAACACTAGGTTGGTTAGGTTTGGTGTGT

TTCCGCTTTGCTTACTCTCATGTAGTTCC (AMX199.G5) SEQ ID NO 76
CTACCTACGATCTGACTAGCGAAACACTAGGTTGGTTAGGATTGGTGTGT

TCCCGCCCTGCTTACTCTCATGTAGTTCC (AMX199.F11) SEQ ID NO 77
CTACCTACGATCTGACTAGCGAAACACTAGGTTGGTTAGGATTGGTGTGT

TTCTGCTCTGCTTACTCTCATGTAGTTCC (AMX199.A10) SEQ ID NO 79
CTACCTACGATCTGACTAGCGGAACACTAGGTTGGTTAGGATTGGTGTGT

TCCCGTTTTGCTTACTCTCATGTAGTTCC (AMX199.G1) SEQ ID NO 80
CTACCTACGATCTGACTAGCGAAACACTAGGTTGGTTAGGATTGGTGTGT

TCCCGCTTTGCTTACTCTCATGTAGTTCC (AMX199.G4) SEQ ID NO 82
CTACCTACGATCTGACTAGCGAAACACTAGGTTGGTTAGGGTTGGTGTGT

TCCCGCTTTGCTTACTCTCATGTAGTTCC

-continued (AMX199.F1) SEQ ID NO 81
CTACCTACGATCTGACTAGCGAAACACTAGGTTGGTTAGGATTGGTGTGT

TCCCGCTATGCTTACTCTCATGTAGTTCC

The consensus sequence for DNA SELEX™ Family #2 is as follows:

SEQ ID NO 96
CTACCTACGATCTGACTAGCGRAACACTAGGTTGGTTAGGRTTGGTGTGT

TYCYGYYHGCTTACTCTCATGTAGTTCC

Where Y=C or T, R=A or G and H=A, C or T
DNA SELEX™ 1 Family #3

(AMX199.B6) SEQ ID NO 86
CTACCTACGATCTGACTAGCAAGGGGATTGGCTCCGGGTCTGGCGTGCTT

GGTACCTCCGGCTTACTCTCATGTAGTTCC (AMX199.D8) SEQ ID NO 87
CTACCTACGATCTGACTAGCAAGGGGATTGGCTCCGGGTCTGGCGTGCTT

GGCATCTTCGGCTTACTCTCATGTAGTTCC (AMX199.F8) SEQ ID NO 85
CTACCTACGATCTGACTAGCAAGGGGATTGGCTCCGGGTCTGGCGTGCTT

GGCACCTCTGGCTTACTCTCATGTAGTTCC (AMX200.E10) SEQ ID NO 88
CTACCTACGATCTGACTAGCAAGGGGATTGGCTCCGGGTCTGGCGTGCTC

GGCACCTTTGGCTTACTCTCATGTAGTTCC (AMX202.F6) SEQ ID NO 94
CTACCTACGATCTGACTAGCAAGGGGATTGGCTCCGGGTCTGGCGTGCTC

GGCACCTTCGGCTTACTCTCATGTAGTTCC (AMX202.A8) SEQ ID NO 93
CTACCTACGATCTGACTAGCAAGGGGATTGGCTCCGGGTCTGGCGTGCTC

GGCACTTCCGGCTTACTCTCATGTAGTTCC

DNA SELEY™ 1, Family #4
(AMX200.A11) SEQ ID NO 83
CTACCTACGATCTGACTAGCTGAGTAGTTAGTAACTTTTTATTATGGTTT

GGTGGGTCTGGCTTACTCTCATGTAGTTCC (AMX200.H8) SEQ ID NO 84
CTACCTACGATCTGACTAGCTGAGTAGTCAGTAATTTTTTATTATGGTTT

GGTGGGCCTGGCTTACTCTCATGTAGTTCC

Example 1D

Selection #2 of DNA vWF Aptamers

A single set of DNA selections were done using full length human vWF and rabbit vWF domain A1 in a cross selection. While not wishing to be bound by any theory, our hypothesis is that such a selection should require successfully selected aptamers to bind to full length vWF, to bind to the A1 domain specifically and to cross react between human and rabbit proteins. The dominant sequence family from this second set of DNA selections binds to full length human vWF, rabbit vWF domain A1 and is functional in both the FACS and BIPA biological assays as described in Example 3 below.

Selections were performed to identify aptamers that bind to full length human vWF and rabbit vWF A1 domain, using a full length human vWF/rabbit vWF A1 domain alternating selection. This selection used a nucleotide pool consisting of deoxy-nucleotides (DNA). The selection strategy yielded high affinity aptamers specific for full length human vWF and rabbit vWF A1 domain which had been immobilized on a hydrophobic plate.

Pool Preparation

A DNA template with the sequence 5'-CTACCTAC-GATCTGACTAGC NNNNNGCTTACTCTCATGTAGT-TCC-3' (SEQ ID NO 51) (ARC 493) was synthesized using an ABI EXPEDITE™ DNA synthesizer, and deprotected by standard methods. The series of N's in the DNA template (SEQ ID NO 51) can be any combination of nucleotides and gives rise to the unique sequence region of the resulting aptamers. The template was PCR amplified with the primers (5'-CTACCTACGATCTGACTAGC-3') (SEQ ID NO 52) and (5'-AGGAACTACATGAGAGTAAGC(OH)-3') (SEQ ID NO 53) under standard conditions. The PCR product was subjected to alkaline hydrolysis (333 mM NaOH, 90° C., 15 min) followed by precipitation. The strands were separated on a 10% denaturing polyacrylamide gel and the single stranded DNA pool, which migrated with a lower mobility, was excised from the gel, passively eluted, and precipitated with isopropanol.

Selection

For the first three rounds of the full length human vWF/rabbit vWF A1 domain alternating selection, 24 pmoles of full length human vWF (SEQ ID NO 7) and 24 moles of rabbit vWF A1 domain (SEQ ID NO 6) were immobilized. In the subsequent rounds, the protein target was alternated each round between full length human vWF and rabbit vWF A1 domain. In all cases, after one hour of protein immobilization, the supernatant was removed and the wells were washed 4 times with 120 μL 1× Dulbecco's PBS. The protein-immobilized well was then blocked with 100 μL blocking buffer (1× Dulbecco's PBS with 1% BSA) for 1 hour at room temperature. In Round one, 333 pmoles of pool DNA ($2 \times 10^{14}$ unique molecules) were incubated in 100 μL 1× Dulbecco's PBS in the wells containing BSA-blocked immobilized protein target for 1 hour. The supernatant was then removed and the wells were washed 4 times with 120 μL 1× Dulbecco's PBS. In later rounds, additional washes were added to increase the stringency of the positive selection step (see Table 15). At Round 8, the selection was split to include a high salt wash condition as a possible means to increase the stringency of the SELEX™ (using 1× Dulbecco's PBS+400 mM NaCl) (see Table 15). Starting at Round 2 and in all subsequent rounds, two negative selection steps were included before the positive selection step. First, the pool DNA was incubated for 1 hour at room temperature in an unblocked well to remove any plastic binding sequences from the pool. In the second negative selection step, the DNA was transferred to a BSA blocked well (not containing the protein target) for 1 hour at room temperature to remove any BSA binding sequences from the pool prior to the positive selection. Starting at Round 2 and in all subsequent rounds, 0.1 mg/mL tRNA and 0.1 mg/mL salmon sperm DNA were spiked into the positive selection reaction as non-specific competitors.

In all cases, the pool DNA bound to the immobilized protein target was eluted with 2×100 μL washes with elution buffer (preheated to 90° C., 7 M Urea, 100 mM NaOAc pH 5.3, 3 mM EDTA) for five minutes. Both elutions were pooled and precipitated by the addition of ethanol, then amplified in an initial PCR reaction (100 μL reactions including the 5'-primer according to SEQ ID NO 52, the 3'-primer according to SEQ ID NO 53, and Taq polymerase, (New England BioLabs, Cat. #M0267L, Beverly, Mass.). PCR reactions were done under the following conditions: a) denaturation step: 94° C. for 2 minutes; b) cycling steps: 94° C. for 30 seconds, 52° C. for 30 seconds, 72° C. for 1 minute; c) final extension step: 72° C. for 3 minutes. The cycles were repeated until sufficient PCR product was generated. The minimum number of cycles required to generate sufficient PCR product is reported in Table 15 as the "PCR Threshold". 10 μL of the PCR product was added to another 300 L of PCR mix for a prep-scale PCR reaction. The prep-scale PCR product was ethanol precipitated and was subjected to alkaline hydrolysis (333 mM NaOH, 90° C., 15 min). The strands were separated on a 10% denaturing polyacrylamide gel and the single stranded DNA pool, which migrated with a lower mobility, was excised from the gel, passively eluted, and precipitated with isopropanol. In all cases, an equivalent of half of the total single stranded DNA product was carried forward as the starting pool for the subsequent round of selection.

TABLE 15

Full length human vWF/rabbit vWF A1 domain alternating selection conditions using a DNA pool

| Round | Target | Washes | | PCR Threshold | | Purification |
|---|---|---|---|---|---|---|
| 1 | 24 pmol full length human/ 24 pmol rA1 | 4 × 120 uL | | 15 | | Gel purify |
| 2 | 24 pmol full length human/ 24 pmol rA1 | 4 × 120 uL | | 13 | | Gel purify |
| 3 | 24 pmol full length human/ 24 pmol rA1 | 4 × 120 uL | | 10 | | Gel purify |
| 4 | 24 pmol full length human vWF | 4 × 120 uL | | 10 | | Gel purify |
| 5 | 24 pmol rA1 | 4 × 120 uL | | 10 | | Gel purify |
| 6 | 24 pmol full length human vWF | 8 × 120 uL | | 10 | | Gel purify |
| 7 | 24 pmol rA1 | 8 × 120 uL | | 10 | | Gel purify |
| | | Normal Wash | High Salt Wash | Normal Wash | High Salt Wash | |
| 8 | 24 pmol full length human vWF | 8 × 120 uL | 8 × 120 uL | 10 | 10 | Gel purify |
| 9 | 24 pmol rA1 | 8 × 120 uL | 8 × 120 uL | 10 | 13 | Gel purify |
| 10 | 24 pmol full length human vWF | 8 × 120 uL | 8 × 120 uL | 10 | 10 | Gel purify |
| 11 | 24 pmol rA1 | 8 × 120 uL | 8 × 120 uL | 10 | 10 | Gel purify |

TABLE 16 full length human vWF/rabbit vWF A1 domain DNA selection pool binding assays.

| Pool Selection | Round | full length human vWF | | rabbit vWF A1 domain | | No Protein |
|---|---|---|---|---|---|---|
| | | 30 nM | 100 nM | 30 nM | 100 nM | |
| Naïve Pool | Round 0 | 40.3% | 39.8% | 41.6% | 45.5% | 35.2% |
| Human vWF/rA1 | Round 7 | 59.4% | 66.9% | 58.9% | 68.3% | 39.9% |
| Naïve Pool | Round 0 | 53.0% | 55.1% | 53.9% | 56.9% | 52.6% |
| Human vWF/rA1 | Round 9 | 70.9% | 65.0% | 71.7% | 81.6% | 54.5% |
| Human vWF/rA1 High Salt Wash | Round 9 | 72.1% | 73.8% | 74.5% | 82.3% | 59.7% |

When a significant positive ratio of binding of DNA in the presence of human or rabbit vWF A1 domain versus in the absence of protein was seen, the pools were cloned using the TOPO TA cloning kit (Invitrogen Cat. #45-0641, Carlsbad, Calif.) according to the manufacturer's instructions. Round 7 and 11 pool templates were cloned and sequenced (218 total sequences), producing 146 unique clones within 12 sequence families of which sequences from six families show vWF target binding activity. All unique clones were assayed twice in a 3-point dot blot screen (no protein target control, 20 nM full length human vWF (Calbiochem Cat. #681300, La Jolla, Calif.), or 20 nM rabbit vWF A1 domain. The data is presented in the third and fourth columns of Table 17 below as the ratio of the fraction of the aptamer bound to the nitrocellulose in the presence of the target protein to the fraction of aptamer bound in the absence of the target protein.

Based on this initial screen, $K_D$s were determined for 3 of the vWF dependent binding sequences using the dot blot assay. For $K_D$ determination, aptamers were 5'end labeled with $\gamma$-$^{32}$P ATP and were tested for direct binding to full vWF Binding Analysis The selection progress was monitored using a sandwich filter binding assay. The 5'-$^{32}$P-labeled pool DNA (trace concentration) was incubated with either a no target protein control, 100 nM full length human vWF (Calbiochem Cat. #681300, La Jolla, Calif.), or 100 nM rabbit vWF A1 domain, in 1× Dulbecco's PBS containing 0.1 mg/mL tRNA, and 0.1 mg/mL salmon sperm DNA, and 0.1 mg/mL BSA in a (final volume of 50 uL) for 30 minutes at room temperature and then applied to a nitrocellulose and nylon filter sandwich in a dot blot apparatus (Schleicher and Schuell, Keene, N.H.). The percentage of pool DNA bound to the nitrocellulose was calculated after Rounds 7 and 9 by screening with a no protein target control, 30 nM/100 nM full length human vWF (Calbiochem Cat. #681300, La Jolla, Calif.), and 30 nM/100 nM rabbit vWF A1 domain (SEQ ID NO 6). Pool binding was compared to that of the naïve pool DNA (Round 0). The results of the DNA pool binding analyses are found in Table 16 below.

length human vWF and rabbit vWF A1 domain. A 12 point protein titration was used in the dot blot assay (300 nM, 100 nM, 30 nM, 10 nM, 3 nM, 1 nM, 300 pM, 100 pM, 30 pM, 10 pM, 3 pM, 0 pM) in 1×DPBS plus 0.1 mg/mL BSA at room temperature for 30 minutes. $K_D$ values were calculated by fitting the equation y=(max/(1+K/protein))+yint using KaleidaGraph (KaleidaGraph v. 3.51, Synergy Software). Results of protein binding characterization are tabulated in Table 17 below.

TABLE 17

Full length human vWF and rabbit vWF A1 domain DNA aptamer binding activity*

| # | Aptamer | Screen-Human/No Protein | Screen Rabbit/No Protein | full length human vWF $K_D$ (nM) | rabbit vWF A1 domain $K_D$ (nM) |
|---|---|---|---|---|---|
| 1 | AMX237.A11 (SEQ ID NO 98) | 2.66 | 2.38 | ND | ND |
| 2 | AMX237.A2 (SEQ ID NO 99) | 2.60 | 2.34 | ND | ND |
| 3 | AMX238.D12 (SEQ ID NO 100) | 2.40 | 2.19 | ND | ND |
| 4 | AMX237.H5 (SEQ ID NO 101) | 1.63 | 1.61 | ND | ND |
| 5 | AMX237.E2 (SEQ ID NO 102) | 1.61 | 1.61 | ND | ND |
| 6 | AMX237.B4 (SEQ ID NO 103) | 1.42 | 1.38 | ND | ND |
| 7 | AMX237.E9 (SEQ ID NO 104) | 2.13 | 2.06 | ND | ND |
| 8 | AMX237.D11 (SEQ ID NO 105) | 1.16 | 1.17 | ND | ND |
| 9 | AMX238.G5 (SEQ ID NO 106) | 3.06 | 2.68 | ND | ND |
| 10 | AMX237.C7 (SEQ ID NO 107) | 1.15 | 1.16 | ND | ND |
| 11 | AMX238.D5 (SEQ ID NO 108) | 1.46 | 1.40 | ND | ND |
| 12 | AMX237.B11 (SEQ ID NO 109) | 2.87 | 2.57 | ND | ND |
| 13 | AMX237.F6 (SEQ ID NO 110) | 1.20 | 1.21 | ND | ND |
| 14 | AMX238.D8 (SEQ ID NO 111) | 2.02 | 1.97 | ND | ND |
| 15 | AMX238.G6 (SEQ ID NO 112) | 1.25 | 1.22 | ND | ND |
| 16 | AMX236.F8 (SEQ ID NO 113) | 1.14 | 1.13 | ND | ND |
| 17 | AMX237.G6 (SEQ ID NO 114) | 3.80 | 3.63 | 0.20 | 47 |
| 18 | AMX238.E9 (SEQ ID NO 115) | 3.44 | 3.36 | 0.39 | 5.3 |
| 19 | AMX238.E7 (SEQ ID NO 116) | 3.02 | 2.83 | ND | ND |
| 20 | AMX238.F3 (SEQ ID NO 117) | 2.83 | 2.72 | ND | ND |
| 21 | AMX238.H5 (SEQ ID NO 118) | 3.75 | 3.46 | 0.33 | 6.0 |
| 22 | AMX237.C11 (SEQ ID NO 119) | 2.04 | 1.95 | ND | ND |
| 23 | AMX238.F2 (SEQ ID NO 120) | 2.84 | 2.76 | ND | ND |
| 24 | AMX237.F9 (SEQ ID NO 121) | 2.21 | 2.31 | ND | ND |
| 25 | AMX237.F12 (SEQ ID NO 122) | 1.95 | 2.08 | ND | ND |
| 26 | AMX237.C9 (SEQ ID NO 123) | 2.05 | 2.19 | ND | ND |
| 27 | AMX237.F10 (SEQ ID NO 124) | 2.90 | 2.90 | ND | ND |
| 28 | AMX236.H2 (SEQ ID NO 125) | 2.12 | 2.06 | ND | ND |
| 29 | AMX237.C5 (SEQ ID NO 126) | 2.55 | 2.36 | ND | ND |
| 30 | AMX236.A12 (SEQ ID NO 127) | 2.64 | 2.41 | ND | ND |
| 31 | AMX236.B8 (SEQ ID NO 128) | 1.66 | 1.88 | ND | ND |
| 32 | AMX236.A11 (SEQ ID NO 129) | 2.02 | 2.02 | ND | ND |
| 33 | AMX237.D5 (SEQ ID NO 130) | 1.41 | 1.48 | ND | ND |
| 34 | AMX236.E6 (SEQ ID NO 131) | 1.31 | 1.49 | ND | ND |
| 35 | AMX236.C12 (SEQ ID NO 132) | 1.99 | 2.24 | ND | ND |
| 36 | AMX237.H10 (SEQ ID NO 133) | 1.71 | 1.94 | ND | ND |
| 37 | AMX237.G7 (SEQ ID NO 134) | 2.68 | 2.54 | ND | ND |
| 38 | AMX237.H8 (SEQ ID NO 135) | 1.21 | 1.41 | ND | ND |
| 39 | AMX236.G4 (SEQ ID NO 136) | 1.70 | 1.72 | ND | ND |
| 40 | AMX236.C1 (SEQ ID NO 137) | 1.03 | 3.28 | ND | ND |
| 41 | AMX237.E10 (SEQ ID NO 138) | 1.12 | 6.04 | ND | ND |
| 42 | AMX238.F5 (SEQ ID NO 139) | 1.05 | 4.40 | ND | ND |
| 43 | AMX237.C1 (SEQ ID NO 140) | 0.76 | 3.47 | ND | ND |

TABLE 17-continued

Full length human vWF and rabbit vWF A1 domain DNA aptamer binding activity*

| # | Aptamer | Screen-Human/No Protein | Screen Rabbit/No Protein | full length human vWF $K_D$ (nM) | rabbit vWF A1 domain $K_D$ (nM) |
|---|---|---|---|---|---|
| 44 | AMX237.B12 (SEQ ID NO 141) | 1.13 | 4.67 | ND | ND |
| 45 | AMX238.A6 (SEQ ID NO 142) | 0.92 | 3.47 | ND | ND |
| 46 | AMX238.A11 (SEQ ID NO 143) | 0.85 | 4.54 | ND | ND |
| 47 | AMX236.C6 (SEQ ID NO 144) | 1.06 | 5.77 | ND | ND |
| 48 | AMX238.F6 (SEQ ID NO 145) | 1.18 | 5.36 | ND | ND |
| 49 | AMX236.E2 (SEQ ID NO 146) | 0.93 | 3.59 | ND | ND |
| 50 | AMX238.G4 (SEQ ID NO 147) | 1.09 | 1.39 | ND | ND |
| 51 | AMX238.H9 (SEQ ID NO 148) | 1.11 | 1.32 | ND | ND |
| 52 | AMX237.B1 (SEQ ID NO 149) | 2.00 | 2.10 | ND | ND |
| 53 | AMX238.A3 (SEQ ID NO 150) | 1.36 | 1.03 | ND | ND |
| 54 | AMX237.C4 (SEQ ID NO 151) | 0.97 | 1.31 | ND | ND |
| 55 | AMX237.E5 (SEQ ID NO 152) | 0.97 | 1.15 | ND | ND |
| 56 | AMX237.F1 (SEQ ID NO 153) | 0.98 | 1.22 | ND | ND |
| 57 | AMX237.F5 (SEQ ID NO 154) | 0.99 | 1.22 | ND | ND |
| 58 | AMX238.H11 (SEQ ID NO 155) | 0.98 | 1.14 | ND | ND |
| 59 | AMX237.G2 (SEQ ID NO 156) | 1.02 | 1.16 | ND | ND |
| 60 | AMX238.A12 (SEQ ID NO 157) | 1.23 | 0.99 | ND | ND |
| 61 | AMX236.C9 (SEQ ID NO 158) | 1.24 | 1.00 | ND | ND |
| 62 | AMX236.H1 (SEQ ID NO 159) | 1.10 | 1.14 | ND | ND |
| 63 | AMX236.F7 (SEQ ID NO 160) | 1.18 | 1.20 | ND | ND |
| 64 | AMX236.B3 (SEQ ID NO 161) | 1.54 | 1.41 | ND | ND |
| 65 | AMX238.D9 (SEQ ID NO 162) | 1.22 | 0.97 | ND | ND |
| 66 | AMX238.F7 (SEQ ID NO 163) | 1.20 | 1.88 | ND | ND |
| 67 | AMX236.G1 (SEQ ID NO 164) | 1.47 | 1.51 | ND | ND |

*used full length human vWF (SEQ ID NO 7) and rabbit vWF A1 domain (SEQ ID NO 6) for aptamer screen and aptamer $K_D$s
ND = not done The nucleic acid sequences of the DNA aptamers characterized in Table 17 above are described below. The unique sequence of each aptamer below begins at nucleotide 21, immediately following the sequence CTACCTACGATCTGACTAGC (SEQ ID NO 52), and runs until it meets the 3' fixed nucleic acid sequence GCTTACTCTCATGTAGTTCC (SEQ ID NO 223).

Unless noted otherwise, individual sequences listed below are represented in the 5' to 3' orientation and were selected under DNA SELEX™ wherein all of the nucleotides are deoxy.

vWF DNA SELEX™ 2, Family 1.1

Families 1.1 and 1.2 yielded the parent of ARC1029 (SEQ ID NO 214). The predicted core nucleic acid binding sequences to the target von Willebrand Factor are underlined and shown in bold for aptamers AMX237.E9 (SEQ ID NO 104) and AMX238.H5 (SEQ ID NO 118) below.

```
AMX237.E9 (SEQ ID NO 104)
CTACCTACGATCTGACTAGCTCCAGTGTTTTGTCTAATAACCGTGCGGTG
CCTCCGTGAGCTTACTCTCATGTAGTTCC

AMX237.B11 (SEQ ID NO 109)
CTACCTACGATCTGACTAGCTCCAGTGTTTTATCTAATAACCGTGCGGTG
CCTCCGTGAGCTTACTCTCATGTAGTTCC

AMX237.A11 (SEQ ID NO 98)
CTACCTACGATCTGACTAGCTCCAGTGTTTTATCCAATAACCGTGCGGTG
CCTCCGTGAGCTTACTCTCATGTAGTTCC

AMX238.G5 (SEQ ID NO 106)
CTACCTACGATCTGACTAGCTCCAGTGTTTTATTCAATAACCGTGCGGTG
CCTCCGTGAGCTTACTCTCATGTAGTTCC

AMX238.D8 (SEQ ID NO 111)
CTACCTACGATCTGACTAGCTCCAGTGTTTTATCCAACAACCGTGCGGTG
CCTCCGTGAGCTTACTCTCATGTAGTTCC

AMX237.E2 (SEQ ID NO 102)
CTACCTACGATCTGACTAGCTCCAGTGTTTCATC17AATAACCGTGCGGT
GCCTCCGTGAGCTTACTCTCATGTAGTTCC

AMX237.H5 (SEQ ID NO 101)
CTACCTACGATCTGACTAGCTCCAGTGTTTCATTTAATAACCGTGCGGTG
CCTCCGTGAGCTTACTCTCATGTAGTTCC
```

-continued

AMX238.D5 (SEQ ID NO 108)
CTACCTACGATCTGACTAGCTCCAGTGTTTTATTCAATAACCGTGCGGTG

TCTCCGTGAGCTTACTCTCATGTAGTTCC

AMX237.A2 (SEQ ID NO 99)
CTACCTACGATCTGACTAGCTCCAGTGTTTCATCCAATAACCGTGCGGTG

CCTCCGTGAGCTTACTCTCATGTAGTTCC

AMX238.D12 (SEQ ID NO 100)
CTACCTACGATCTGACTAGCTCCAGTGTTTCATTCAATAACCGTGCGGTG

CCTCCGTGAGCTTACTCTCATGTAGTTCC

AMX237.F6 (SEQ ID NO 110)
CTACCTACGATCTGACTAGCTCCAGTGTTTTATCTAATAACCGTGCGGTG

CCTCCGTGATGCTTACTCTCATGTAGTTCC

AMX237.D11 (SEQ ID NO 105)
CTACCTACGATCTGACTAGCTCCAGTGTTTTATATAATAACCGTGCGGTG

CCTCCGTGATGCTTACTCTCATGTAGTTCC

AMX237.B4 (SEQ ID NO 103)
CTACCTACGATCTGACTAGCTCCAGTGTTTCATCCAATAACCGTGCGGTG

CTTCCGTGAGCTTACTCTCATGTAGTTCC

AMX236.F8 (SEQ ID NO 113)
CTACCTACGATGTGACTAGCTCCAGTGTTTTATCCAATAACCGTGCGGTG

CCTCCGTGATGCTTACTCTCATGTAGTTCC

AMX237.C7 (SEQ ID NO 107)
CTACCTACGATCTGACTAGCTCCAGTGTTTTATTCAATAACCGTGCGGTG

CCTCCGTGATGC1TACTCTCATGTAGTTCC

AMX238.G6 (SEQ ID NO 112)
CTACCTACGATCTGACTAGCTCCAGTGTTTTATCCAATAACCGTGCGGGG

CCTCCGTGATGCTTACTCTCATGTAGTTCC vWF DNA SELEX ™ 2, Family # 1.2
AMX238.H5 (SEQ ID NO 118)
CTACCTACGATCTGACTAGCGTGCAGTGCCTATTCTAGCCCGTGCGGTGC

CTCCCTCACCCTTACTCTCATGTAGTTCC

AMX237.C11 (SEQ ID NO 119)
CTACCTACGATCTGACTAGCGTGCAGTGCCTATTCTAGGCCGTGCGGTGC

CTCCGTCATGCTTACTCTCATGTAGTTCC

AMX238.E7 (SEQ ID NO 116)
CTACCTACGATCTGACTAGCGTGCAGTGCCTATTTTAGGCCGTGCGGTGC

CTCCGTCACGCTTACTCTCATGTAGTTCC

AMX237.G6 (SEQ ID NO 114)
CTACCTACGATCTGACTAGCGTGCAGTGCCTATTCCAGGCCGTGCGGTGC

CTCCGTCACGCTTACTCTCATGTAGTTCC

AMX238.F2 (SEQ ID NO 120)
CTACCTACGATCTGACTAGCATGCAGTGCCCATTCTAGGCCGTGCGGTGC

CTCCGTCATGCTTACTCTCATGTAGTTCC

AMX238.E9 (SEQ ID NO 115)
CTACCTACGATCTGACTAGCGTGCAGTGCCCATCTTAGGCCGTGCGGTGC

CTCCGTCACGCTTACTCTCATGTAGTTCC

AMX238.F3 (SEQ ID NO 117)
CTACCTACGATCTGACTAGCGTGCAGTGCCTATTTTAGGTCGTGCGGGGC

CTCCGTCACGCTTACTCTCATGTAGTTCC

AMX237.F10 (SEQ ID NO 124)
CTACCTACGATCTGACTAGCGTGCAGTGCCCATTCCAGGCCGTGCGGTAT

CCTCCGTCACGCTTACTCTCATGTAGTTCC

AMX237.C5 (SEQ ID NO 126)
CTACCTACGATCTGACTAGCGTGCAGTGCCTATCTCAGGCCGTGCGGTAT

CCTCCGTCACGCTTACTCTCATGTAGTTCC

AMX236.H2 (SEQ ID NO 125)
CTACCTACGATCTGACTAGCGTGCAGTGCCTATCCCAGGCCGTGCGGTAG

CCTCCGTCACGCTTACTCTCATGTAGTTCC

The predicted secondary structure and core nucleic acid sequences required for binding to the vWF target of some embodiments of the invention comprised in Family #1 of this aptamer selection is depicted in FIG. 15 as SEQ ID NO 220.

vWF DNA SELEX™ 2, Binding Family #2

AMX237.C9 (SEQ ID NO 123)
CTACCTACGATCTGACTAGCTTGGTAGTGACTTTGTGGAGCTGCGGTTTG

GTCGACGTCAGCTTACTCTCATGTAGTTCC

AMX237.F12 (SEQ ID NO 122)
CTACCTACGATCTGACTAGCTTGGTAGCGATTTTGTGGAGCTGCGGTTTG

GTCGACGTCAGCTTACTCTCATGTAGTTCC

AMX237.F9 (SEQ ID NO 121)
CTACCTACGATCTGACTAGCTTGGTAGCGATTCTGTGGAGCTGCGGTTTG

GTCGACGTCAGCTTACTCTCATGTAGTTCC

AMX237.G7 (SEQ ID NO 134)
CTACCTACGATCTGACTAGCTTGGTAGCGACTTTGTGGAGCTGCGGTTTG

GTCGACGTCAGCTTACTCTCATGTAGTTCC

AMX236.A12 (SEQ ID NO 127)
CTACCTACGATCTGACTAGCTTGGTAGCGACTCTGTGGAGCTGCGGTTTG

GTCGACGTCAGCTTACTCTCATGTAGTTCC

AMX236.G4 (SEQ ID NO 136)
CTACCTACGATCTGACTAGCTTGGTAGCGACTTTGTGGAGATGCGGTTTG

GTTGACGTCAGCTTACTCTCATGTAGTTCC

AMX236.C12 (SEQ ID NO 132)
CTACCTACGATCTGACTAGCTTGGTAGCGACTCCGTGGAGCTGCGGTTTG

GTCGACGTCAGCTTACTCTCATGTAGTTCC

AMX236.A11 (SEQ ID NO 129)
CTACCTACGATCTGACTAGCTTGGTAGCGACTCTGTGGAGCTGCGGTCTG

GCCGACGTCAGCTTACTCTCATGTAGTTCC

AMX236.E6 (SEQ ID NO 131)
CTACCTACGATCTGACTAGCTTGGTAGCGACCCTGTGGAGCTGCGGTTTG

GTCGACGTCAGCTTACTCTCATGTAGTTCC

AMX236.B8 (SEQ ID NO 128)
CTACCTACGATCTGACTAGCTTGGTAGCGACTCTGTGGAGCTGCGGTCTG

GTCGACGTCAGCTTACTCTCATGTAGTTCC

AMX237.H8 (SEQ ID NO 135)
CTACCTACGATCTGACTAGCTTGGTAGCGACTTTGTGGAGCTGCGGTTTG

GTCGACATCAGCTTACTCTCATGTAGTTCC

```
AMX237.D5 (SEQ ID NO 130)
CTACCTACGATCTGACTAGCTTGGTAGCGACACTGTGGAGCTGCGGTTTG

GTTGACGTCAGCTTACTCTCATGTAGTTCC

AMX237.H10 (SEQ ID NO 133)
CTACCTACGATCTGACTAGCTTGGTAGCGACTCAGAGGAGCTGCGGTTTG

GTCGACGTCAGCTTACTCTCATGTAGTTCC

AMX237.B1 (SEQ ID NO 149)
CTACCTACGATCTGACTAGCTTGGTAGCGACACAGTGGAGCTGCGGTTTG

GTCGACGTCAGCTTACTCTCATGTAGTTCC
```

The consensus sequence for DNA SELEX™ 2 Family #2 is as follows:

```
SEQ ID NO 325
CTACCTACGATCTGACTAGCTTGGTAG Y GA Y (Y/A) Y (Y/A) G (T/A) GGAG (C/A) TGCGGT Y TGG YY GAC R TCAGCTTACTC

TCATGTAGTTCC
```

Where Y=C or T, R=A or G and (Y/A)=C, T or A, vWF DNA SELEX™ 2, Binding Family #3 This family is equivalent to vWF DNA SELEX™ 1, Family #1 described above in that the sequences in both families are more than 90% identical.

```
AMX238.A11 (SEQ ID NO 143)
CTACCTACGATCTGACTAGCGGAATGAGAGTGTTGGTGGATTGCTCAGGT

CTGCTGGCTGCTTACTCTCATGTAGTTCC

AMX237.C1 (SEQ ID NO 140)
CTACCTACGATCTGACTAGCGGAATGAGGATGCTGGTGGATTGCTCAGGT

CTGCTGGCTGCTTACTCTCATGTAGTTCC

AMX236.C6 (SEQ ID NO 144)
CTACCTACGATCTGACTAGCGGAATGAGAGTGCTGGTGGATTGCTCAGGT

CTGCTGGCTGCTTACTCTCATGTAGTTCC

AMX236.C1 (SEQ ID NO 137)
CTACCTACGATCTGACTAGCGGAATGAGAATGTTGGTGGATTGCTCAGGT

CTGCTGGCTGCTTACTCTCATGTAGTTCC

AMX237.E10 (SEQ ID NO 138)
CTACCTACGATCTGACTAGCGGAATGAGAATGGTGGTGGATTGCTCAGGT

CTGCTGGCTGCTTACTCTCATGTAGTTCC

AMX238.F6 (SEQ ID NO 145)
CTACCTACGATCTGACTAGCGGAATGAGTATGCTGGTGGATTGCTCAGGT

CTGCTGGCTGCTTACTCTCATGTAGTTCC

AMX236.E2 (SEQ ID NO 146)
CTACCTACGATCTGACTAGCGGAATGAGTATGGTGATGGATTGCTCAGGT

CTGCTGGCTGCTTACTCTCATGTAGTTCC

AMX237.B12 (SEQ ID NO 141)
CTACCTACGATCTGACTAGCGGAATGAGAATGCAGGTGGATTGCTCAGGT

CTGCTGGCTGCTTACTCTCATGTAGTTCC

AMX238.A6 (SEQ ID NO 142)
CTACCTACGATCTGACTAGCGGAATGAGAATGCAGATGGATTGCTCAGGT

CTGCTGGCTGCTTACTCTCATGTAGTTCC

AMX238.F5 (SEQ ID NO 139)
CTACCTACGATCTGACTAGCGGAATGAGAAGCTGGTGGATTGCTCAGGTC

TGCTGGCTGCTTACTCTCATGTAGTTCC
``` vWF DNA SELEX™ 2, Binding Family #4

```
AMX237.G2 (SEQ ID NO 156)
CTACCTACGATCTGACTAGCTTTCAGTCTTTCATATTTATAGGGTTTGGC

ATTGGGTCTGGCTTACTCTCATGTAGTTCC

AMX237.C4 (SEQ ID NO 151)
CTACCTACGATCTGACTAGCTTTCAGTCTTCCACATTTATAGGGTTTGGC

ATTGGGTCTGGCTTACTCTCATGTAGTTCC

AMX237.F5 (SEQ ID NO 154)
CTACCTACGATCTGACTAGCTTTTAGTCTTCCACATTTATAGGGTTTGGC

ATTGGGTCTGGCTTACTCTCATGTAGTTCC

AMX238.H11 (SEQ ID NO 155)
CTACCTACGATCTGACTAGCTTTCAGTCTTTCACATTTATAGGGTTTGGC

ATTGGGTCTGGCTTACTCTCATGTAGTTCC

AMX238.G4 (SEQ ID NO 147)
CTACCTACGATCTGACTAGCTTGTCGCACTTTTGGTTGGTCTGGTTGGTT

CTAAGTGCGCTTACTCTCATGTAGTTCC

AMX237.E5 (SEQ ID NO 152)
CTACCTACGATCTGACTAGCTTTCAGTGTTCTACATTTATAGGGTTTGGC

ATTGGGTCTGGCTTACTCTCATGTAGTTCC

AMX238.H9 (SEQ ID NO 148)
CTACCTACGATCTGACTAGCTTGTCGCACTTTTGGTTGGTCTGGTTGGTT

TTAAGTGCGCTTACTCTCATGTAGTTCC

AMX237.F1 (SEQ ID NO 153)
CTACCTACGATCTGACTAGCTTTCAGTCTTCCACGTTTATAGGGTTTGGC

ATTGGGTCTGGCTTACTCTCATGTAGTTCC
``` vWF DNA SELEX™ 2, Family #5

```
AMX236.G1 (SEQ ID NO 164)
CTACCTACGATCTGACTAGCCTCAGATTGACTCCGGCTGACTTGTTTTAA

TCTTCTGAGTGCTTACTCTCATGTAGTTCC

AMX236.B3 (SEQ ID NO 161)
CTACCTACGATCTGACTAGCCTTACCTATTCCCTTCTGCGGAATACGTCG

AGTACTATGCTTACTCTCATGTAGTTCC

AMX236.F7 (SEQ ID NO 160)
CTACCTACGATCTGACTAGCCCCCACTTATCGTGTACCTTATGATATGTC

GAATACTCTTGCTTACTCTCATGTAGTTCC

AMX236.H1 (SEQ ID NO 159)
CTACCTACGATCTGACTAGCCTCAGATTGACTCCGGCCGACTTGTTTTAA

TCTTCTGAGTGCTTACTCTCATGTAGTTCC
```

The consensus sequences for DNA SELEX™ 2 Family #5 are as follows:

```
SEQ ID NO 326
Family5.1 = SEQ ID NO 164 and SEQ ID NO 159
CTACCTACGATCTGACTAGCCTCAGATTGACTCCGGCYGACTTGTTTTAA

TCTTCTGAGTGCTTACTCTCATGTAGTTCC
```

Wherein Y=C or T

```
SEQ ID NO 327
Family5.2 = SEQ ID NO 161 & SEQ ID NO 160
CTACCTACGATCTGACTAGCC YY AC Y TAT Y (C/G) Y (C/G)

T (T/A) C Y (G/T) Y R (G/T) R ATA Y GTCGA R TACT (A/C) TGCTTACTCTCATGTAGTTCC
```

Where Y=C or T, R=A or G vWF DNA SELEX™ 2, Family #6

```
AMX238.A3 (SEQ ID NO 150)
CTACCTACGATCTGACTAGCTCAAAGTATTACTTATTGGCAATAAGTCGT

TTACTCTATAGCTTACTCTCATGTAGTTCC

AMX238.F7 (SEQ ID NO 163)
CTACCTACGATCTGACTAGCAAGGGGATTGGCTCCGGGTCTGGCGTGCTT

GGCATCTTTGGCTTACTCTCATGTAGTTCC

AMX236.C9 (SEQ ID NO 158)
CTACCTACGATCTGACTAGCCAGTTCTGGGAAAAATTATTTTTTATTTC

GATCGTATTTGCTTACTCTCATGTAGTTCC

AMX238.D9 (SEQ ID NO 162)
CTACCTACGATCTGACTAGCCAGTTCTGGGAAAAATCATTTTTTATTTCG

ATCGTATTTGCTTACTCTCATGTAGTTCC

AMX238.A12 (SEQ ID NO 157)
CTACCTACGATCTGACTAGCCAGTTCTGGGAAAAATTATTTTTTATTTC

GATCGTATATGCTTACTCTCATGTAGTTCC
```

Example 2

Composition and Sequence Optimization and Sequences

Example 2A

Truncation of rRfY vWF Aptamers

On the basis of the vWF binding analysis described in Example 1 above and the cell based assay data described in Example 3 below, aptamer ARC840 (AMX201.C8) (SEQ ID NO 23) was chosen from the rRfY selections for further characterization.

In order to identify the core structural elements required for vWF binding, the 3'-boundary of ARC840 (AMX201.C8) (SEQ ID NO 23) was determined. The full length RNA transcript was labeled at the 5'-end with γ-$^{32}$P ATP and T4 polynucleotide kinase. Radiolabeled ligands were subjected to partial alkaline hydrolysis and then selectively bound in solution to human von Willebrand Factor A1 domain (SEQ ID NO 5) at 500 nM before being passed through nitrocellulose filters. Both the retained and the not retained oligonucleotides were resolved separately on 8% denaturing polyacrylamide gels. The smallest oligonucleotide bound to vWF defined the 3'-boundary. On the basis of the boundary experiments as well as visual inspection of predicted folds, a panel of minimized sequences was designed. Folds of all the nucleic acid sequences of the invention were predicted using RNAstructure, Version 4.1 downloaded from the University of Rochester. RNAstructure is a Windows implementation of the Zuker algorithm for RNA secondary structure prediction based on free energy minimization (Mathews, D. H.; Disney, M. D.; Childs, J. L.; Schroeder, S. J.; Zuker, M.; and Turner, D. H., "Incorporating chemical modification constraints into a dynamic programming algorithm for prediction of RNA secondary structure," 2004. *Proceedings of the National Academy of sciences, US*, 101, 7287-7292). RNAstructure 4.1 uses the most current thermodynamic parameters from the Turner lab.

For the minimized rRfY aptamers, described below, the purines comprise a 2'-OH and the pyrimidines comprise a 2'-F modification, while, the templates and primers comprise unmodified deoxyribonucleotides.

For the minimized rRfY aptamer 5'-GGAGCGCACU-CAGCCACCCUCGCAAGCAUUUAA-GAAUGACUUGUGCCGCUGGCU G-3' (SEQ ID NO 165), the 5' PCR primer 5'-GATCGATCTAATACGACT-CACTATA-3' (SEQ ID NO 166) and 3' PCR primer 5'-CAGCCAGCGGCACAAGTC-3' (SEQ ID NO 167) were used to amplify template 5'-TCGATCTAATACGACTCAC-TATAGGAGCGCACTCAGCCACCCTCG-CAAGCATTTTAA GAATGACTTGTGCCGCTGGCTG-3' (SEQ ID NO 168).

For minimized aptamer 5'-GGACCACCCUCGCAAG-CAUUUUAAGAAUGACUUGUGCCGCUGGUCC-3' (SEQ ID NO 169), 5' PCR primer 5'-GATCGATCTAATAC-GACTCACTATA-3' (SEQ ID NO 166) and 3' PCR primer 5'-GGACCAGCGGCACAAGTC-3' (SEQ ID NO 170) were used to amplify template 5'-GATCGATCTAATACGACT-CACTATAGGACCACCCTCGCAAGCATTT-TAAGAATGACT TGTGCCGCTGGTCC-3' (SEQ ID NO171).

For minimized aptamer 5'-GGACCACCCUCGCAAG-CAUUGAGAAAUGACUUGUGCCGCUGGUCC-3' (SEQ ID NO 172), 5' PCR primer 5'-GATCGATCTAATACGACT-CACTATA-3' (SEQ ID NO 166) and 3' PCR primer 5'-GGACCAGCGGCACAAGTC-3' (SEQ ID NO 170) were used to amplify template 5'-GATCGATCTAATACGACT-CACTATAGGACCACCCTCGCAAGCAT-TGAGAAATGACTT GTGCCGCTGGTCC-3' (SEQ ID NO 173).

For minimized aptamer 5'-GGACCACCCUCGCAAC-GAGAGUUGUGCCGCUGGUCC-3' (SEQ ID NO 174), 5' PCR primer 5'-GATCGATCTAATACGACTCACTATA-3' (SEQ ID NO$_{166}$) and 3' PCR primer 5'-GGACCAGCGGCA-CAACTC-3' (SEQ ID NO 175) were used to amplify template 5'-GATCGATCTAATACGACTCACTATAG-GACCACCCTCGCAACGAGAGTTGTGCCGCTG GTCC-3' (SEQ ID NO 176).

All of the above minimized aptamer sequences were transcribed, gel-purified on 15% denaturing polyacrylamide gels, 5-$^{32}$P end-labeled with γ$^{32}$P ATP, and then desalted using two Centri-Spin 10 columns (Princeton Separations Cat. #CS-101, Adelphia, N.J.). These minimers were primarily characterized in the cellular assays described in Example 3 below.

Example 2B

Truncation of rRdY vWF Aptamers

On the basis of the vWF binding analysis described in Example 1 above and cell based assay data described in Example 3 below, aptamers AMX203.G9 (SEQ ID NO 44) and AMX205.F7 (SEQ ID NO 49), respectively, were identified for further characterization.

In order to identify the core structural elements required for vWF binding, the 3'-boundaries of aptamers AMX203.G9 (SEQ ID NO 44) and AMX205.F7 (SEQ ID NO 49) were determined. The full length RNA transcripts were labeled at the 5'-end with γ-$^{32}$P ATP and T4 polynucleotide kinase. Radiolabeled ligands were subjected to partial alkaline hydrolysis and then selectively bound in solution to human vWF A1 domain (SEQ ID NO 5) at 500 nM before being passed through nitrocellulose filters. Retained oligonucleotides were resolved on 8% denaturing polyacrylamide gels. The smallest oligonucleotide bound to vWF defined the 3'-boundary. On the basis of the boundary experiments as well as visual inspection of predicted folds using RNAstructure, Version 4.1, a panel of minimized sequences was designed.

For the minimized rRdY aptamers, described below, the purines are 2'-OH purines and the pyrimidines are deoxypyrimidines, while the templates and primers comprise unmodified deoxyribonucleotides. The following three minimized aptamer sequences were derived from DL.159.87.70 (SEQ ID NO 44):

For minimized aptamer sequence 5'-GGAGCGCACT-CAGCCACGGGGTGGGTAGACGGCGGG-TATGTGGCT-3' (SEQ ID NO 177), 5' PCR primer 5'-GATC-GATCTAATACGACTCACTATA-3' (SEQ ID NO 166) and 3' PCR primer 5'-AGCCACATACCCGCCGTC-3' (SEQ ID NO 178) were used to amplify template 5'-GATC-GATCTAATACGACTCACTATAGGAGCG-CACTCAGCCACGGGGTGGGTAGACG GCGGGTAT-GTGGCT-3' (SEQ ID NO 179).

For minimized aptamer sequence 5'-GGAGC-CACGGGGTGGGTAGACGGCGGGTATGTGGCTCC-3' (SEQ ID NO 180), 5' PCR primer 5'-GATCGATCTAATAC-GACTCACTATA-3' (SEQ ID NO 166) and 3' PCR primer 5'-GGAGCCACATACCCGCCG-3' (SEQ ID NO 181), were used to amplify template 5'-GATCGATCTAATACGACT-CACTATAGGAGCCACGGGGTGGGTA-GACGGCGGGTATG TGGCTCC-3' (SEQ ID NO 182).

For minimized aptamer sequence 5'-GG-GACGGGGTGGGTAGACGGCGGGTATGTCCC-3' (SEQ ID NO183), 5' PCR primer 5'-GATCGATCTAATACGACT-CACTATA-3' (SEQ ID NO 166) and 3' PCR primer 5'-GG-GACATACCCGCCG-3' (SEQ ID NO 184), were used to amplify template 5'-GATCGATCTAATACGACTCACTAT-AGGGACGGGGTGGGTAGACGGCGGGTATGTCC C-3' (SEQ ID NO 185).

The following seven minimized aptamer sequences were derived from the aptamer according to SEQ ID NO 49:

For minimized aptamer sequence 5'-GGAGCGCACT-CAGCCACACGACATTGGCGGGTTGTAAT-TACCACGCATGGCTG-3'(SEQ ID NO 186), 5' PCR primer 5'-GATCGATCTAATACGACTCACTATA-3' (SEQ ID NO 166) and 3' PCR primer 5'-CAGCCATGCGTGGTAATT-3' (SEQ ID NO 187), were used to amplify template 5'-GATC-GATCTAATACGACTCACTATAGGAGCG-CACTCAGCCACACGACATTGGCGGG TTGTAATTAC-CACGCATGGCTG-3' (SEQ ID NO 188).

For minimized aptamer sequence 5'-GGAGCCACACGA-CATTGGCGGGTTGTAATTACCACGCATGGCTCC-3' (SEQ ID NO 189), 5' PCR primer 5'-GATCGATCTAATAC-GACTCACTATA-3' (SEQ ID NO 166) and 3' PCR primer 5'-GGAGCCATGCGTGG-3' (SEQ ID NO190), were used to amplify template 5'-GATCGATCTAATACGACTCACTAT-AGGAGCCACACGACATTGGCGGGTTGTAATTAC CACGCATGGCTCC-3' (SEQ ID NO191).

For minimized aptamer sequence 5'-GGAGCCACACGA-CATTGGCGGGCGAGAGCCACGCATGGCTCC-3' (SEQ ID NO 192), 5' PCR primer b 5'-GATCGATCTAATAC-GACTCACTATA-3' (SEQ ID NO 166) and 3' PCR primer 5'-GGAGCCATGCGTGG-3' (SEQ ID NO190), were used to amplify template 5'-GATCGATCTAATACGACTCACTAT-AGGAGCCACACGACATTGGCGGGCGAGAGCCA CGCATGGCTCC-3' (SEQ ID NO 193).

For minimized aptamer sequence 5'-GGAGCCACACGA-CATTGGCGAGAGCCACGCATGGCTCC-3' (SEQ ID NO 194), 5' PCR primer 5'-GATCGATCTAATACGACTCAC-TATA-3' (SEQ ID NO 166) and 3' PCR primer 5'-GGAGC-CATGCGTGG-3' (SEQ ID NO 190), were used to amplify template 5'-GATCGATCTAATACGACTCACTATAG-GAGCCACACGACATTGGCGAGAGCCACGCA TGGCTCC-3' (SEQ ID NO 195).

For minimized aptamer sequence 5'-GGAGCCACAC-GAGAGTGGCGGGTTGTAATTACCACGCATGGCTCC-3' (SEQ ID NO 196), 5' PCR primer 5'-GATC-GATCTAATACGACTCACTATA-3' (SEQ ID NO 166) and 3' PCR primer 5'-GGAGCCATGCGTGG-3' (SEQ ID NO 190), were used to amplify template 5'-GATCGATCTAATAC-GACTCACTATAGGAGCCACACGAGAGTG-GCGGGTTGTAATTA CCACGCATGGCTCC-3' (SEQ ID NO 197).

For minimized aptamer sequence 5'-GGCCACACGA-CATTGGCGGGCGAGAGCCACGCATGGCC-3' (SEQ ID NO 198), 5' PCR primer 5'-GATCGATCTAATACGACT-CACTATA-3' (SEQ ID NO 166) and 3' PCR primer 5'-GGC-CATGCGTGGCTCTC-3' (SEQ ID NO 199), were used to amplify template 5'-GATCGATCTAATACGACTCACTAT-AGGCCACACGACATTGGCGGGCGAGAGCCACG CATGGCC-3' (SEQ ID NO 200).

For minimized aptamer sequence 5'-GGAGCCACACGA-CATTGGCGCGAGAGCGCATGGCTCC-3' (SEQ ID NO 201), 5' PCR primer 5'-GATCGATCTAATACGACTCAC-TATA-3' (SEQ ID NO 166) and 3' PCR primer 5'-GGAGC-CATGCGCTCTCG-3' (SEQ ID NO 202), were used to amplify template 5'-GATCGATCTAATACGACTCACTAT-AGGAGCCACACGACATTGGCGCGAGAGCGCAT GGCTCC-3' (SEQ ID NO 203).

rRdY vWF Minimer Binding

All minimer sequences were transcribed, gel-purified on 15% denaturing polyacrylamide gels, 5-$^{32}$ end-labeled with γ$^{32}$P ATP, and then desalted using two Centri-Spin 10 columns (Princeton Separations Cat. #CS-101, Adelphia, N.J.). For $K_D$ determination, minimer transcripts were tested for direct binding to full length human vWF (SEQ ID NO 7), human vWF A1 domain (SEQ ID NO 5), and rabbit vWF A1 domain (SEQ ID NO 6) using an 8 point protein titration from 0-300 nM (3 fold dilutions) in 1× Dulbecco's PBS containing 0.1 mg/mL BSA (in a final volume of 50 uL) for 30 minutes at room temperature and then applied to a nitrocellulose and nylon filter sandwich in a dot blot apparatus (Schleicher and Schuell, Keene, N.H.). $K_D$ values were calculated by fitting the equation y=(max/(1+K/protein))+yint using Kaleida-Graph (KaleidaGraph v. 3.51, Synergy Software). Results of protein binding characterization are tabulated in Table 18.

TABLE 18 rRdY aptamer minimer binding data, only aptamers that showed potent activity in cellular assays had their binding affinity measured. (ND = not done)

| # | Minimer | Full length human vWF $K_D$ (nM) | Human vWF A1 domain $K_D$ (nM) | Rabbit vWF A1 domain $K_D$ (nM) |
|---|---|---|---|---|
| 1 | SEQ ID NO 177 | ND | ND | ND |
| 2 | SEQ ID NO 180 | 1 | 11 | 14 |
| 3 | SEQ ID NO 183 | 10 ± 5 | ND | 14 ± 7 |
| 4 | SEQ ID NO 186 | ND | ND | ND |
| 5 | SEQ ID NO 189 | 1 | ND | ND |
| 6 | SEQ ID NO 192 | 2 ± 0.2 | 4 ± 1 | 8 ± 1 |
| 7 | SEQ ID NO 194 |  | ND |  |
| 8 | SEQ ID NO 196 | ND | ND | ND |
| 9 | SEQ ID NO 198 | 3 ± 0.6 | 5 ± 2 | 11 ± 2 |
| 10 | SEQ ID NO 201 | ND | ND | ND |

Example 2C

Truncation of DNA SELEX™ #1 vWF Aptamer

On the basis of the vWF binding analysis described in Example 1 above, as well as visual inspection of predicted folds, a panel of minimized sequences was designed for the best class of binders from Family #1. In this case all of the binders from Family #1 are structurally related and fell into one of four mutually exclusive folds (predicted by RNAStructure 4.1) as determined by the base-pairing constraints put on the 5'- and 3'-ends of the molecules. We synthesized and tested each of the four predicted folds. The sequence for each of the synthesized minimized DNA aptamers is as follows:

```
SEQ ID NO 204
5'-CCAGCGGAATGAGAATGCTGATGGATTGCTCAGGTCTGCTGG -3'

ARC 845 (SEQ ID NO 205)
5' ATGAGAGTGCTGGTGGATTGCTCAGGTCTGCTGGCTGCTTACTCTCA T -3'

SEQ ID NO 206
5'-CGATCTGACTAGCGGAATGAGAATGCTGGTGGATCG -3'

SEQ ID NO 207
5'-GATCTGACTAGCGCAATGAGGATGCdTGATGGATTGCTCAGGTC -3'
```

All minimer DNA sequences were chemically synthesized, 5-$^{32}$P end-labeled with γ-$^{32}$P ATP, and then desalted using two Centri-Spin 10 columns (Princeton Separations, Cat. #CS-101, Adelphia, N.J.). For $K_D$ determination, minimers were tested for binding to human vWF A1 domain (SEQ ID NO 5) using a competition dot blot assay with a constant protein concentration of 10 nM and a 12 point cold competitor DNA titration (3 uM, 1 uM, 333 nM, 100 nM, 33 nM, 10 nM, 3.3 nM, 1 nM, 333 pM, 100 pM, 33.3 pM, 0 pM) in 1×Dulbecco's PBS containing 0.1 mg/mL BSA (final volume of 50 uL) for 30 minutes at room temperature. $K_D$ values were calculated by fitting the equation y=(max/(1+K/protein))+yint using KaleidaGraph (KaleidaGraph v. 3.51, Synergy Software). Results of protein binding characterization are tabulated in Table 19 below. As shown, only ARC845 of the minimized constructs retained the ability to bind to either human or rabbit vWF A1 domain

TABLE 19

DNA 1 Minimer Binding Data (ND = Not Done)

| # | Minimer | Full length human vWF $K_D$ (nM) | Human vWF A1 domain $K_D$ (nM) | Rabbit vWF A1 domain $K_D$ (nM) |
|---|---|---|---|---|
| 1 | ARC845 = SEQ ID NO 205 | No binding | 10 | 56 |
| 2 | SEQ ID NO 204 | ND | No binding | No binding |
| 3 | SEQ ID NO 206 | ND | No binding | ND |
| 4 | SEQ ID NO 207 | ND | No binding | ND |

Based on these binding results, ARC 845 (SEQ ID NO 205) represents the core nucleic acid binding sequence of the DNA SELEX™ 1, Family 1 aptamers.

Example 2D

DNA vWF Alternating Selection Aptamer Minimization

On the basis of the vWF binding analysis described in Example 1 above and cell based assay data described in Example 3 below as well as visual inspection of predicted folds for aptamers AMX237.B11 (SEQ ID NO 109) and AMX236.A12 (SEQ ID NO 127), a series of minimized sequences were designed. Additionally, based on the observation that aptamers AMX237.G6 (SEQ ID NO 114), AMX238.E9 (SEQ ID NO 115), and AMX238.H5 (SEQ ID NO 118) appeared to be slightly more potent in cellular assays, a series of minimized sequences ARC1027-1031 (SEQ ID NOS 212-216) were synthesized. The minimized sequences according to SEQ ID NO 208 and SEQ ID NO 209 represent two mutually exclusive folds predicted from the full length aptamer AMX237.B11 (SEQ ID NO 109).

The nucleic acid sequences for above-described minimized DNA aptamers are as follows:

```
(SEQ ID NO 208)
5'- GGACGATCTGACTAGCTCCAGTGTTTTATCTAATAACCGTCC -3'

(SEQ ID NO 209)
5'- GGAGCTCCAGTGTTTTATCTAATAACCGTGCGGTGCCTCCGTGAGC TCC -3'

(SEQ ID NO 210)
5'- GGAGCTGCGGTTTGGTCGACGTCAGCTCC -3'

(SEQ ID NO 211)
5'- GGTAGCGACTCTGTGGAGCTGCGGTTTGG -3'

ARC1027 (SEQ ID NO 212)
5'-GGCGTGCAGTGCCTATTCTAGGCCGTGCGGTGCCTCCGTCACGCC-3T -3'

ARC1028 (SEQ ID NO 213)
5'-dGCGTGCAGTGCCT-[PEG]-AGGCCGTGCGGTGCCTCCGTCACGC C-3T -3'

ARC1029 (SEQ ID NO 214)
5'-GGCGTGCAGTGCC-[PEG]-GGCCGTGCGGTGCCTCCGTCACGCC-3T -3'

ARC1030 (SEQ ID NO 215)
5'-GGCGTGCAGTGCCTATTCTAGGCCGTGCGG-[PEG]-CCGTCACGC C-3T -3'

ARC1031 (SEQ ID NO 216)
5'-GGCGTGCAGTGCCT-[PEG]-AGGCCGTGCGG-[PEG]-CCGTCACG CC-3T -3'
```

All of the above minimized aptamer sequences were chemically synthesized, gel-purified on 15% denaturing polyacrylamide gels and then desalted using two Centri-Spin 10 columns (Princeton Separations Cat. #CS-101, Adelphia, N.J.) using standard methods and techniques. The minimized sequences were characterized in cellular assays as described in Example 3 below.

Figure 5:
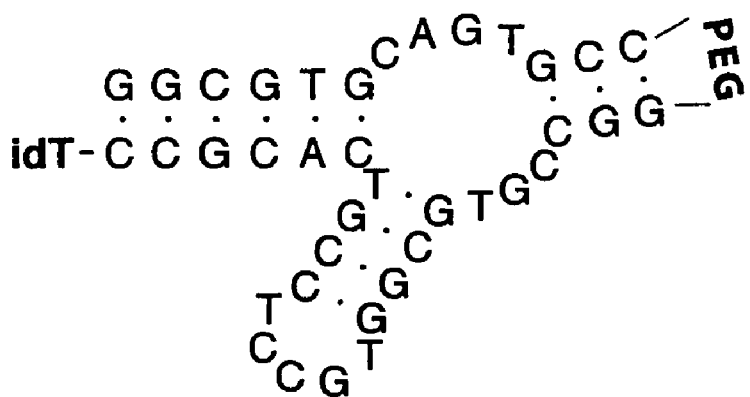
FIG. 5 is an illustration depicting the proposed secondary structure of ARC1029 (SEQ ID NO 214).

Of the initial series, SEQ ID NO 208 to SEQ ID NO 211, only SEQ ID NO 208 demonstrated activity in the cellular assays (see Example 3, below). Comparison of the sequences of aptamers AMX237.B11 (SEQ ID NO 109) and AMX237.G6 (SEQ ID NO 114), AMX238.E9 (SEQ ID NO 115), and AMX238.H5 (SEQ ID NO 118) revealed them to be closely related and to support the predicted secondary structure of the minimized aptamer (SEQ ID NO 208) (see FIGS. 14 and 15). These molecules, ARC1027-1031 (SEQ ID NOS 212-216) further tested our hypothesis about the folding and secondary structure of aptamers AMX237.G6 (SEQ ID NO 114), AMX238.E9 (SEQ ID NO 115), and AMX238.H5 (SEQ ID NO 118) (see FIGS. 5, 14 and 15).

Figure 6:
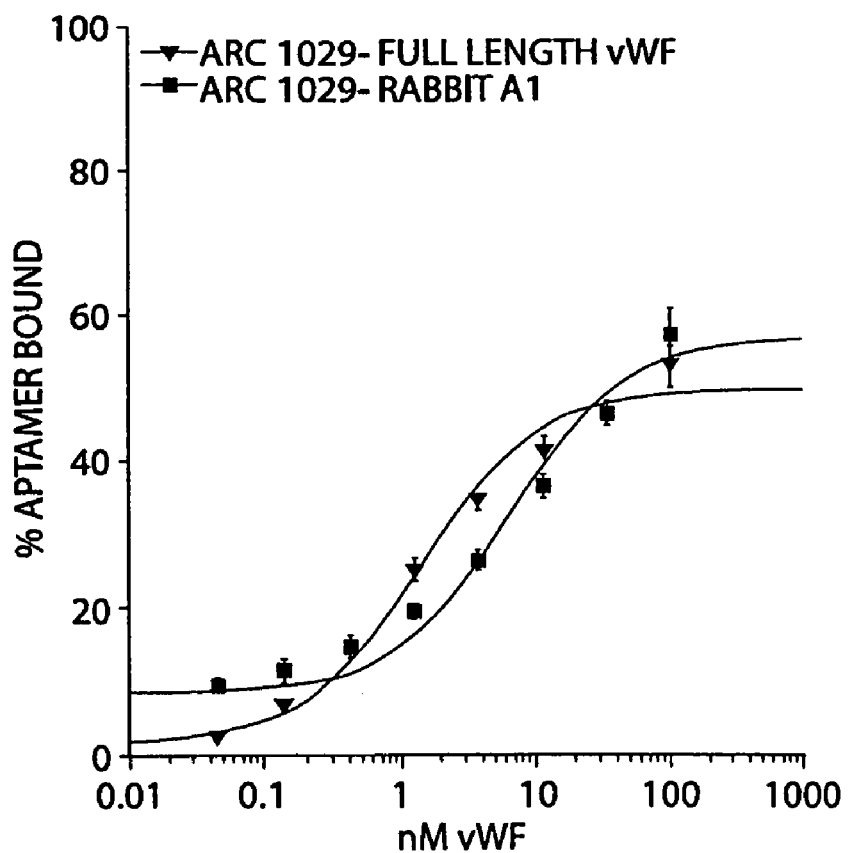
FIG. 6 is a graph of the dot blot binding curves for ARC1029 (SEQ ID NO 214) to full length vWF and rabbit vWF domain A1. A black box in this table indicates a deletion.

For $K_D$ determination, the minimized sequences that showed potent activity in the cellular assays as described in Example 3 below were 5-$^{32}$P end-labeled with γ-32P ATP, and then desalted using two Centri-Spin 10 columns (Princeton Separations Cat. #CS-101, Adelphia, N.J.). Minimers were tested for direct binding to full length human vWF (SEQ ID NO 7), and rabbit vWF A1 domain (SEQ ID NO 6) using a 9 point protein titration (100 nM, 30 nM, 10 nM, 3 nM, 1 nM, 300 pM, 100 pM, 30 pM, 0 pM) (see FIG. 6) in 1× Dulbecco's PBS containing 0.1 mg/mL BSA (final volume of 50 uL) for 30 minutes at room temperature and then applied to a nitrocellulose and nylon filter sandwich in a dot blot apparatus (Schleicher and Schuell, Keene, N.H.). $K_D$ values were calculated by fitting the equation y=(max/(1+K/protein))+yint using KaleidaGraph (KaleidaGraph v. 3.51, Synergy Software). Results of protein binding characterization are tabulated in Table 20.

TABLE 20

DNA 2 aptamer minimer binding data, only aptamer minimers that showed potent activity in cellular assays had their binding affinity measured (see Example 3 below) ('ND' = not done)

| # | Minimer | Full length human vWF $K_D$ (nM) | Human vWF A1 domain $K_D$ (nM) | Rabbit vWF A1 domain $K_D$ (nM) |
|---|---|---|---|---|
| 1 | SEQ ID NO 208 | ND | ND | ND |
| 2 | SEQ ID NO 209 | ND | ND | ND |
| 3 | SEQ ID NO 210 | ND | ND | ND |
| 4 | SEQ ID NO 211 | ND | ND | ND |
| 5 | ARC 1027 (SEQ ID NO 212) | 0.8 | ND | 4.6 |
| 6 | ARC1028 (SEQ ID NO 213) | 1.1 | ND | 3.8 |
| 7 | ARC1029 (SEQ ID NO 214) | 1.4 ± 0.2 | ND | 6.5 ± 1.5 |
| 8 | ARC1030 (SEQ ID NO 215) | No binding | ND | No binding |

TABLE 20-continued

DNA 2 aptamer minimer binding data, only aptamer minimers that showed potent activity in cellular assays had their binding affinity measured (see Example 3 below) ('ND' = not done)

| # | Minimer | Full length human vWF $K_D$ (nM) | Human vWF A1 domain $K_D$ (nM) | Rabbit vWF A1 domain $K_D$ (nM) |
|---|---|---|---|---|
| 9 | ARC1031 (SEQ ID NO 216) | No binding | ND | No binding |

Example 2E

Optimization of ARC1029 Through Aptamer Medicinal Chemistry

Figure 16:
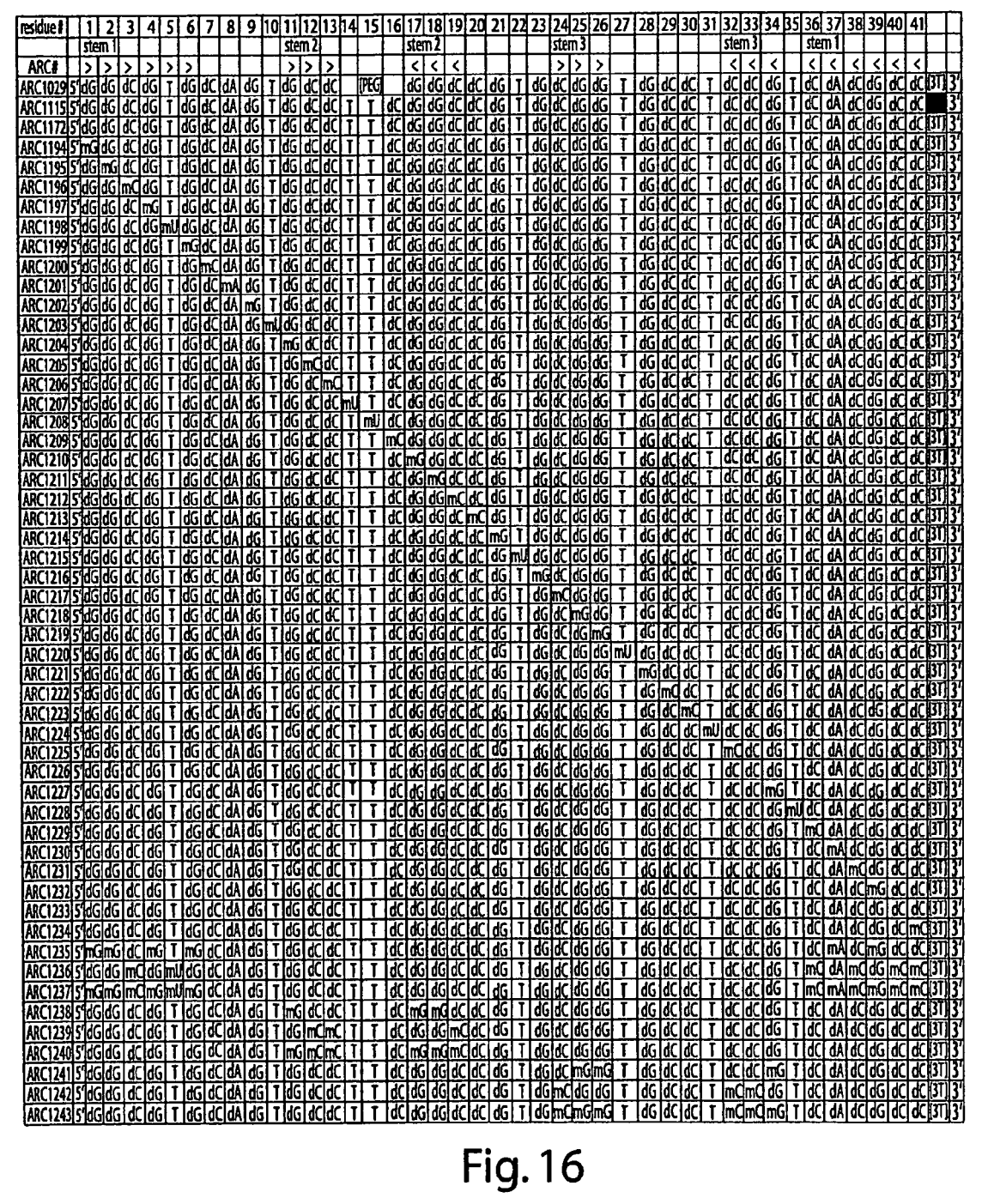

Highly stable and potent variants of ARC1029 (SEQ ID NO 214) were identified through a systematic synthetic modification approach involving 5 phases of aptamer synthesis, purification and assay for binding activity. To facilitate the ease of chemical synthesis during aptamer modification, the PEG spacer of ARC1029 (SEQ ID NO 214 was replaced with a short oligonucleotide sequence, dTdTdC, resulting in ARC1115 (SEQ ID NO 221) as seen in FIG. 16 and Table 21 below. A highly stabilizing 3'-inverted dT was synthesized on the three prime end of ARC1115 (SEQ ID NO 221) resulting in ARC1172 (SEQ ID NO 222) (SEQ ID NO 222) also as seen in FIG. 16 and Table 21 below. Once both ARC1115 (SEQ ID NO 221) and ARC1172 (SEQ ID NO 222) (SEQ ID NO 222) had been shown to bind to human vWF, ARC1172 (SEQ ID NO 222) (SEQ ID NO 222) was used as the basic template for modification as described in the Examples below.

In phase 1 of the modification process, each individual residue in ARC1172 (SEQ ID NO 222) was replaced by the corresponding 2'-O methyl containing residue (with dT being replaced by mU unless otherwise specified) resulting in ARC1194 (SEQ ID NO 223)-ARC1234 as shown in Table 21 below and FIG. 16. Additionally in phase 1, a set of composite replacements were made in the stem regions of ARC1172 (SEQ ID NO 222) resulting in ARC1235 to 1243 also as shown in Table 21 and in FIG. 16.

As described herein, see e.g., in Examples 1, 2, and 3, during the processes of clone screening and truncation that led to ARC1029 (SEQ ID NO 214, there was excellent agreement among the relative potency of aptamers in binding (dot-blot), FACS and BIPA assays. Accordingly, affinity for full length human vWF measured as measured in dot-blot assay binding assays was used to characterize relative affinity of the majority of the aptamer test variants synthesized.

For $K_D$ determination, chemically synthesized aptamers were purified using denaturing polyacrylamide gel electrophoresis, 5' end labeled with γ-$^{32}$P ATP and were tested for direct binding to full length human vWF (Calbiochem Cat. #681300, La Jolla, Calif.). An 8 point protein titration was used in the dot blot binding assay (100n M, 30 nM, 10 nM, 3 nM, 1 nM, 300 pM, 100 pM, 0 pM)) in 1× Dulbecco's PBS containing 0.1 BSA (final volume of 50 uL) for 30 minutes at room temperature. $K_D$ values were calculated by fitting the equation y=(max/(1+K/protein))+yint using KaleidaGraph (KaleidaGraph v. 3.51, Synergy Software). Sequences of the ARC1029 (SEQ ID NO 214) derivatives synthesized, purified and assayed for binding to full length human vWF as well as the results of the protein binding characterization are tabulated Table 21 below, Binding affinity ($K_D$) is presented in the fourth column and extent of aptamer binding at 100 nM vWF is presented in the final column of Table 21.

TABLE 21

Phase 1 Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 221 | ARC1115 | dGdGdCdGTdGdCdAdGTdGdCd CTTdCdGdGdCdCdGTdGdCdGd GTdGdCdCTdCdCdGTdCdAdCd GdCdC | 2 | 36 |
| 222 | ARC1172 | dGdGdCdGTdGdCdAdGTdGdCd CTTdCdGdGdCdCdGTdGdCdGd GTdGdCdCTdCdCdGTdCdAdCd GdCdC-3T | 2 | 37 |
| 223 | ARC1194 | mGdGdCdGTdGdCdAdGTdGdCd CTTdCdGdGdCdCdGTdGdCdGd GTdGdCdCTdCdCdGTdCdAdCd GdCdC-3T | 3 | 46 |
| 224 | ARC1195 | dGmGdCdGTdGdCdAdGTdGdCd CTTdCdGdGdCdCdGTdGdCdGd GTdGdCdCTdCdCdGTdCdAdCd GdCdC-3T | 1 | 55 |
| 225 | ARC1196 | dGdGmCdGTdGdCdAdGTdGdCd CTTdCdGdGdCdCdGTdGdCdGd GTdGdCdCTdCdCdGTdCdAdCd GdCdC-3T | 2 | 46 |
| 226 | ARC1197 | dGdGdCmGTdGdCdAdGTdGdCd CTTdCdGdGdCdCdGTdGdCdGd GTdGdCdCTdCdCdGTdCdAdCd GdCdC-3T | 2 | 46 |
| 227 | ARC1198 | dGdGdCdGmUdGdCdAdGTdGdC dCTTdCdGdGdCdCdGTdGdCdGd GTdGdCdCTdCdCdGTdCdAdCd GdCdC-3T | 0.9 | 50 |
| 228 | ARC1199 | dGdGdCdGTmGdCdAdGTdGdCd CTTdCdGdGdCdCdGTdGdCdGd GTdGdCdCTdCdCdGTdCdAdCd GdCdC-3T | 19 | 28 |
| 229 | ARC1200 | dGdGdCdGTdGmCdAdGTdGdCd CTTdCdGdGdCdCdGTdGdCdGd GTdGdCdCTdCdCdGTdCdAdCd GdCdC-3T | 5 | 25 |
| 230 | ARC1201 | dGdGdCdGTdGdCmAdGTdGdCd CTTdCdGdGdCdCdGTdGdCdGd GTdGdCdCTdCdCdGTdCdAdCd GdCdC-3T | 0.9 | 6 |
| 231 | ARC1202 | dGdGdCdGTdGdCdAmGTdGdCd CTTdCdGdGdCdCdGTdGdCdGd GTdGdCdCTdCdCdGTdCdAdCd GdCdC-3T | 0.4 | 56 |
| 232 | ARC1203 | dGdGdCdGTdGdCdAdGmUdGdC dCTTdCdGdGdCdCdGTdGdCdGd GTdGdCdCTdCdCdGTdCdAdCd GdCdC-3T | 3 | 40 |
| 233 | ARC1204 | dGdGdCdGTdGdCdAdGTmGdCd CTTdCdGdGdCdCdGTdGdCdGd GTdGdCdCTdCdCdGTdCdAdCd GdCdC-3T | 2 | 45 |
| 234 | ARC1205 | dGdGdCdGTdGdCdAdGTdGmCd CTTdCdGdGdCdCdGTdGdCdGd GTdGdCdCTdCdCdGTdCdAdCd GdCdC-3T | 1 | 50 |

TABLE 21-continued

Phase 1 Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 235 | ARC1206 | dGdGdCdGTdGdCdAdGTdGdCm CTTdCdGdGdCdCdGTdGdCdGd GTdGdCdCTdCdCdGTdCdAdCd GdCdC-3T | 2 | 50 |
| 236 | ARC1207 | dGdGdCdGTdGdCdAdGTdGdCd CmUTdCdGdGdCdCdGTdGdCdG dGTdGdCdCTdCdCdGTdCdAdCd GdCdC-3T | 2 | 54 |
| 237 | ARC1208 | dGdGdCdGTdGdCdAdGTdGdCd CTmUdCdGdGdCdCdGTdGdCdG dGTdGdCdCTdCdCdGTdCdAdCd GdCdC-3T | 2 | 45 |
| 238 | ARC1209 | dGdGdCdGTdGdCdAdGTdGdCd CTTmCdGdGdCdCdGTdGdCdGd GTdGdCdCTdCdCdGTdCdAdCd GdCdC-3T | 2 | 44 |
| 239 | ARC1210 | dGdGdCdGTdGdCdAdGTdGdCd CTTdCmGdGdCdCdGTdGdCdGd GTdGdCdCTdCdCdGTdCdAdCd GdCdC-3T | 2 | 49 |
| 240 | ARC1211 | dGdGdCdGTdGdCdAdGTdGdCd CTTdCdGmGdCdCdGTdGdCdGd GTdGdCdCTdCdCdGTdCdAdCd GdCdC-3T | 2 | 47 |
| 241 | ARC1212 | dGdGdCdGTdGdCdAdGTdGdCd CTTdCdGdGmCdCdGTdGdCdGd GTdGdCdCTdCdCdGTdCdAdCd GdCdC-3T | 2 | 49 |
| 242 | ARC1213 | dGdGdCdGTdGdCdAdGTdGdCd CTTdCdGdGdCmCdGTdGdCdGd GTdGdCdCTdCdCdGTdCdAdCd GdCdC-3T | 6 | 43 |
| 243 | ARC1214 | dGdGdCdGTdGdCdAdGTdGdCd CTTdCdGdGdCdCmGTdGdCdGd GTdGdCdCTdCdCdGTdCdAdCd GdCdC-3T | 3 | 39 |
| 244 | ARC1215 | dGdGdCdGTdGdCdAdGTdGdCd CTTdCdGdGdCdCdGmUdGdCdG dGTdGdCdCTdCdCdGTdCdAdCd GdCdC-3T | 3 | 2 |
| 245 | ARC1216 | dGdGdCdGTdGdCdAdGTdGdCd CTTdCdGdGdCdCdGTmGdCdGd GTdGdCdCTdCdCdGTdCdAdCd GdCdC-3T | 0.6 | 40 |
| 246 | ARC1217 | dGdGdCdGTdGdCdAdGTdGdCd CTTdCdGdGdCdCdGTdGmCdGd GTdGdCdCTdCdCdGTdCdAdCd GdCdC-3T | 14 | 18 |
| 247 | ARC1218 | dGdGdCdGTdGdCdAdGTdGdCd CTTdCdGdGdCdCdGTdGdCmGd GTdGdCdCTdCdCdGTdCdAdCd GdCdC-3T | 32 | 2 |
| 248 | ARC1219 | dGdGdCdGTdGdCdAdGTdGdCd CTTdCdGdGdCdCdGTdGdCdGm GTdGdCdCTdCdCdGTdCdAdCd GdCdC-3T | 3 | 33 |

TABLE 21-continued

Phase 1 Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 249 | ARC1220 | dGdGdCdGTdGdCdAdGTdGdCd CTTdCdGdGdCdCdGTdGdCdGd GmUdGdCdCTdCdCdGTdCdAdC dGdCdC-3T | 11 | 17 |
| 250 | ARC1221 | dGdGdCdGTdGdCdAdGTdGdCd CTTdCdGdGdCdCdGTdGdCdGd GTmGdCdCTdCdCdGTdCdAdCd GdCdC-3T | 1 | 43 |
| 251 | ARC1222 | dGdGdCdGTdGdCdAdGTdGdCd CTTdCdGdGdCdCdGTdGdCdGd GTdGmCdCTdCdCdGTdCdAdCd GdCdC-3T | 0.9 | 40 |
| 252 | ARC1223 | dGdGdCdGTdGdCdAdGTdGdCd CTTdCdGdGdCdCdGTdGdCdGd GTdGdCmCTdCdCdGTdCdAdCd GdCdC-3T | 36 | 26 |
| 253 | ARC1224 | dGdGdCdGTdGdCdAdGTdGdCd CTTdCdGdGdCdCdGTdGdCdGd GTdGdCdCmUdCdCdGTdCdAdC dGdCdC-3T | 0.5 | 47 |
| 254 | ARC1225 | dGdGdCdGTdGdCdAdGTdGdCd CTTdCdGdGdCdCdGTdGdCdGd GTdGdCdCTmCdCdGTdCdAdCd GdCdC-3T | 11 | 16 |
| 255 | ARC1226 | dGdGdCdGTdGdCdAdGTdGdCd CTTdCdGdGdCdCdGTdGdCdGd GTdGdCdCTdCmCdGTdCdAdCd GdCdC-3T | 12 | 25 |
| 256 | ARC1227 | dGdGdCdGTdGdCdAdGTdGdCd CTTdCdGdGdCdCdGTdGdCdGd GTdGdCdCTdCdCmGTdCdAdCd GdCdC-3T | 3 | 40 |
| 257 | ARC1228 | dGdGdCdGTdGdCdAdGTdGdCd CTTdCdGdGdCdCdGTdGdCdGd GTdGdCdCTdCdCdGmUdCdAdC dGdCdC-3T | 2 | 43 |
| 258 | ARC1229 | dGdGdCdGTdGdCdAdGTdGdCd CTTdCdGdGdCdCdGTdGdCdGd GTdGdCdCTdCdCdGTmCdAdCd GdCdC-3T | 5 | 37 |
| 259 | ARC1230 | dGdGdCdGTdGdCdAdGTdGdCd CTTdCdGdGdCdCdGTdGdCdGd GTdGdCdCTdCdCdGTdCmAdCd GdCdC-3T | 3 | 46 |
| 260 | ARC1231 | dGdGdCdGTdGdCdAdGTdGdCd CTTdCdGdGdCdCdGTdGdCdGd GTdGdCdCTdCdCdGTdCdAmCd GdCdC-3T | 1 | 50 |
| 261 | ARC1232 | dGdGdCdGTdGdCdAdGTdGdCd CTTdCdGdGdCdCdGTdGdCdGd GTdGdCdCTdCdCdGTdCdAdCm GdCdC-3T | 1 | 51 |
| 262 | ARC1233 | dGdGdCdGTdGdCdAdGTdGdCd CTTdCdGdGdCdCdGTdGdCdGd GTdGdCdCTdCdCdGTdCdAdCd GmCdC-3T | 2 | 39 |

TABLE 21-continued

Phase 1 Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 263 | ARC1234 | dGdGdCdGTdGdCdAdGTdGdCd CTTdCdGdGdCdCdGTdGdCdGd GTdGdCdCTdCdCdGTdCdAdCd GdCmC-3T | 2 | 42 |
| 264 | ARC1235 | mGmGdCmGTmGdCdAdGTdGd CdCTTdCdGdGdCdCdGTdGdCd GdGTdGdCdCTdCdCdGTdCmAd CmGdCdC-3T | 13 | 23 |
| 265 | ARC1236 | dGdGmCdGmUdGdCdAdGTdGd CdCTTdCdGdGdCdCdGTdGdCd GdGTdGdCdCTdCdCdGTmCdA mCdGmCmC-3T | 3 | 32 |
| 266 | ARC1237 | mGmGmCmGmUmGdCdAdGTd GdCdCTTdCdGdGdCdCdGTdGd CdGdGTdGdCdCTdCdCdGTmCm AmCmGmCmC-3T | 41 | 9 |
| 267 | ARC1238 | dGdGdCdGTdGdCdAdGTmGdCd CTTdCmGmCdCdCdGTdGdCdCdG dGTdGdCdCTdCdCdGTdCdAdCd GdCdC-3T | 2 | 43 |
| 268 | ARC1239 | dGdGdCdGTdGdCdAdGTdGmC mCTTdCdGdGmCdCdGTdGdCd GdGTdGdCdCTdCdCdGTdCdAd CdGdCdC-3T | 5 | 37 |
| 269 | ARC1240 | dGdGdCdGTdGdCdAdGTmGmC mCTTdCmGmGmCdCdGTdGdCd GdGTdGdCdCTdCdCdGTdCdAd CdGdCdC-3T | 4 | 40 |
| 270 | ARC1241 | dGdGdCdGTdGdCdAdGTdGdCd CTTdCdGdGdCdCdGTdGdCmG mGTdGdCdCTdCdCmGTdCdAdC dGdCdC-3T | no binding | no binding |
| 271 | ARC1242 | dGdGdCdGTdGdCdAdGTdGdCd CTTdCdGdGdCdCdGTdGmCdGd GTdGdCdCTmCmCdGTdCdAdCd GdCdC-3T | no binding | no binding |
| 272 | ARC1243 | dGdGdCdGTdGdCdAdGTdGdCd CTTdCdGdGdCdCdGTdGmCmG mGTdGdCdCTmCmCmGTdCdAd CdGdCdC-3T | no binding | no binding |

Figure 15B:
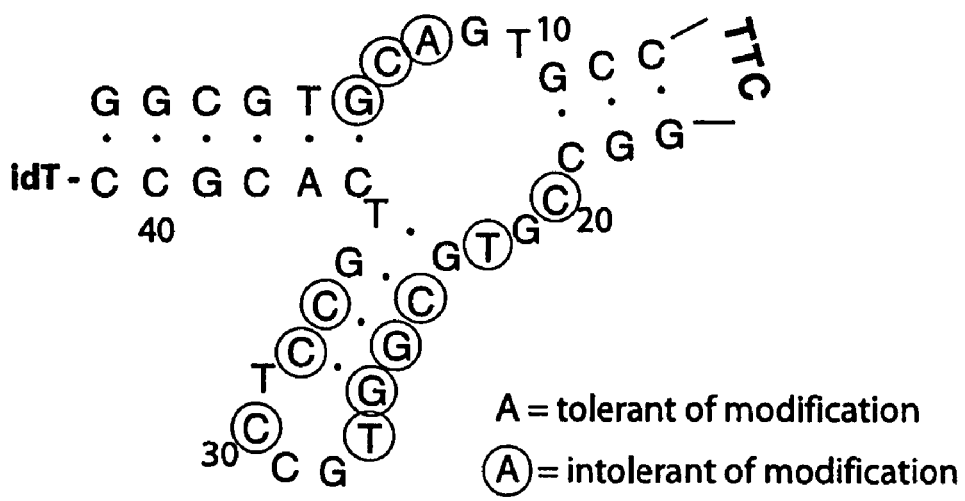
FIG. 15B is an illustration depicting the secondary structure of ARC1172 (SEQ ID NO 222) and which residues are tolerant of 2'-OMe substitution.

As can be seen from the binding data in Table 21, the positions that most readily tolerate substitution of a deoxy residue for a 2'-O methyl residue correlate well with the sequence conservation mapped onto the secondary structure of ARC1029 (SEQ ID NO 214 shown in FIG. 15 thus providing further, independent support for the proposed structure of the aptamer. The positions of ARC1172 (SEQ ID NO 222) that do not tolerate 2'-O-Me modifications as well as the positions that do are shown in FIG. 15B.

Figure 17:
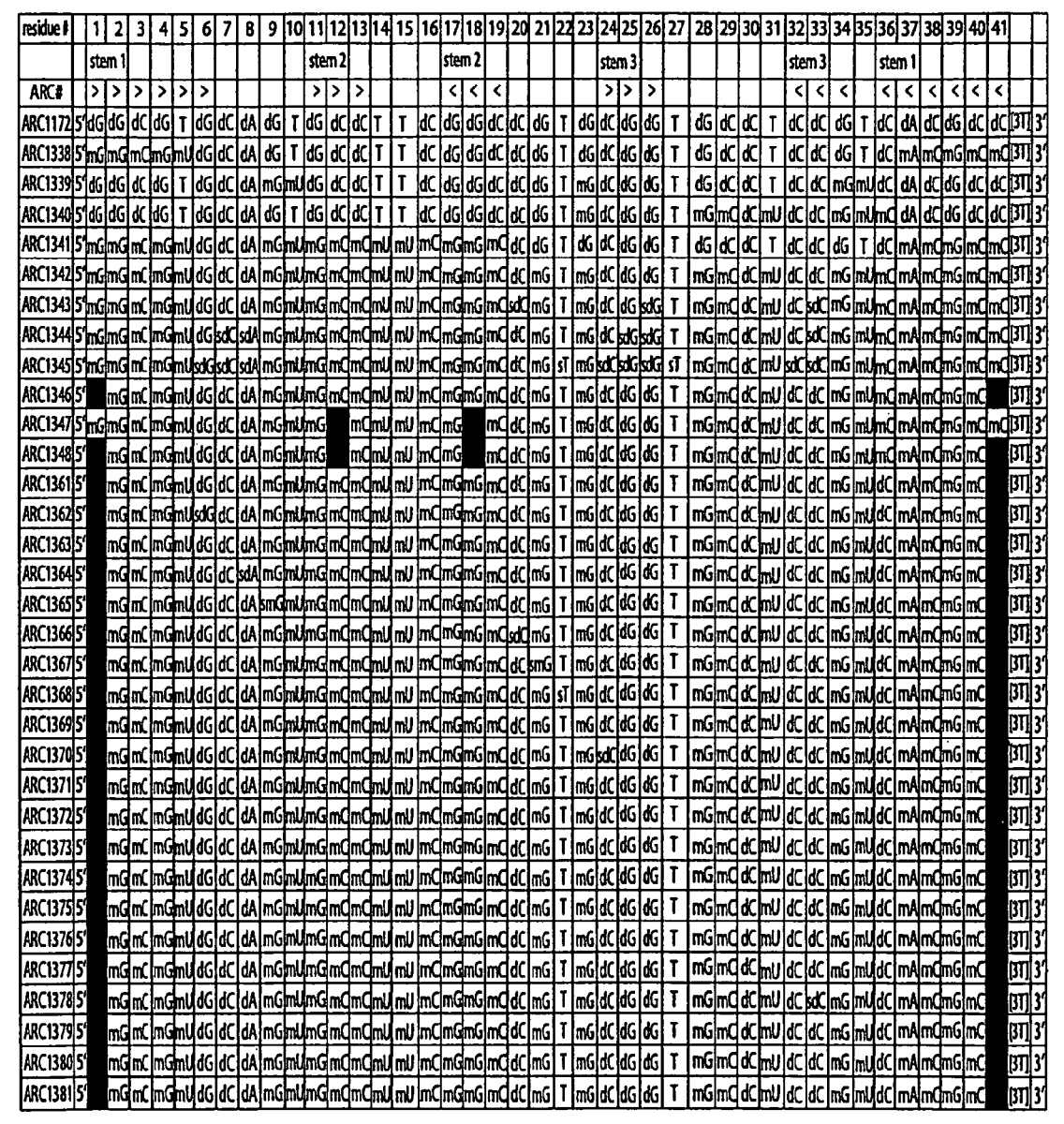

Based upon the structure activity relationship (SAR) results of the individual and composite deoxy to methoxy aptamers described immediately above in the phase 1 modification process, a second series of aptamers was designed, synthesized, purified and tested for binding to vWF. For these and all subsequent aptamers, molecules that retained an affinity ($K_D$) of ~10 nM or better as well as an extent of binding at 100 nM vWF of at least 35% were the goal. ARC1338 (SEQ ID NO 273)-ARC1348 (SEQ ID NO 283), as shown in FIG. 17 and Table 21, were synthesized during phase 2 of the modification process. ARC1338 (SEQ ID NO 273) to 1342 were synthesized with block modifications based on the tolerated individual substitutions from phase 1 modification. ARC1343 (SEQ ID NO 278)-ARC1345 were synthesized each with a different phosphorothioate phosphate backbone modification (see FIG. 17 and Table 22 below) Lastly, ARC1346 (SEQ ID NO 281)-ARC1348 (SEQ ID NO 283) were synthesized to test removing a single base pair from stem 1, stem 2 and from both stems of ARC1342 as shown in FIG. 17 and Table 22 below.

TABLE 22

Phase 2 Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 273 | ARC1338 | mGmGmCmGmUdGdCdAdGTdGdCdCTTdCdGdGdCdCdGTdGdCdGdGTdGdCdCTdCdCdGTdCmAmCmGmCmC-3T | 7.4 | 21 |
| 274 | ARC1339 | dGdGdCdGTdGdCdAmGmUdGdCdCTTdCdGdGdCdCdCmGTmGdCdGdGTdGdCdCTdCdCmGmUmCdAdCdGdCdC-3T | 2.4 | 39 |
| 275 | ARC1340 | dGdGdCdGTdGdCdAdGTdGdCdCTTdCdGdGdCdCdGTmGdCdGdGTmGmCdCmUdCdCmGmUmCdAdCdGdCdC-3T | 7.4 | 43 |
| 276 | ARC1341 | mGmCmCmGmUdGdCdAmGmUmGmCmCmUmUmCmGmGmCdCdGTdGdCdGdGTdGdCdCTdCdCdGTdCmAmCmGmCmC-3T | 22.5 | 26 |
| 277 | ARC1342 | mGmCmCmGmUdGdCdAmGmUmGmCmCmUmUmCmGmGmCdCmGTmGdCdGdGTmGmCdCmUdCdCmGmUmCmAmCmGmCmC-3T | 15.6 | 33 |
| 278 | ARC1343 | mGmCmCmGmUdG-s-dCdAmGmUmGmCmCmUmUmCmGmGmC-s-dCmGTmGdCdG-s-dGTmGmCdCmUdC-s-dCmGmUmCmAmCmGmCmC-3T | 23.9 | 21 |
| 279 | ARC1344 | mGmCmCmGmUdG-s-dC-s-dAmGmUmGmCmCmUmUmCmGmGmC-s-dCmGTmGdC-s-dG-s-dGTmGmCdCmUdC-s-dCmGmUmCmAmCmGmCmC-3T | 4.8 | 17 |
| 280 | ARC1345 | mGmCmCmGmU-s-dG-s-dC-s-dAmGmUmGmCmCmUmUmCmGmGmC-s-dCmG-s-TmG-s-dC-s-dG-s-dG-s-TmGmC-s-dCmU-s-dC-s-dCmGmUmCmAmCmGmCmC-3T | 12.1 | 29 |
| 281 | ARC1346 | mGmCmCmGmUdGdCdAmGmUmGmCmCmUmUmCmGmGmCdCmGTmGdCdGdGTmGmCdCmUdCdCmGmUmCmAmCmGmC-3T | 11 | 51 |
| 282 | ARC1347 | mGmCmCmGmUdGdCdAmGmUmGmCmCmUmUmCmGmCdCmGTmGdCdGdGTmGmCdCmUdCdCmGmUmCmAmCmGmCmC-3T | no binding | no binding |
| 283 | ARC1348 | mGmCmCmGmUdGdCdAmGmUmGmCmUmUmCmGmCdCmGTmGdCdGdGTmGmCdCmUdCdCmGmUmCmAmCmGmC-3T | no binding | no binding |

As seen in Table 22, the results from phase 2 of aptamer modification revealed ARC1346 (SEQ ID NO 281) to be the most potent of the highly substituted ARC1029 (SEQ ID NO 214 derivative aptamers generated thus far. Interestingly as shown by the results with ARC1347 (SEQ ID NO 282) and ARC1348 (SEQ ID NO 283), removal of a base pair from stem 2 is not tolerated in this highly modified context.

ARC1361 (SEQ ID NO 284) to ARC1381 (SEQ ID NO 304), shown in Table 23 and FIG. 17, were synthesized during phase 3 of the aptamer modification process. As the dG to mG substitution at position 6 was poorly tolerated in test variants in phase 1 aptamer modification and guanosine at position 6 pairs with the cytidine at position 36, ARC1346 (SEQ ID NO 281) was synthesized with a mC to dC modification at position 36 resulting in ARC1361 (SEQ ID NO 284) as shown in Table 23 below. ARC1361 (SEQ ID NO 284) served as the base sequence for introduction of single phosphorothioate phosphate backbone modifications that resulted in ARC1362 to ARC1381 (SEQ ID NO 304) also shown in Table 23 below.

TABLE 23

Phase 3 Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 222 | ARC1172 | dGdGdCdGTdGdCdAdGTdGdCdCTTdCdGdGdCdCdGTdGdCdGdGTdGdCdCTdCdCdGTdCdAdCdGdCdC-3T | 2 | 37 |
| 284 | ARC1361 | mGmCmGmUdGdCdAmGmUmGmCmCmUmUmCmGmGmCdCmGTmGdCdGdGTmGmCdCmUdCdCmGmUdCmAmCmGmC-3T | 7.9 | 38.5 |
| 285 | ARC1362 | mGmCmGmU-s-dGdCdAmGmUmGmCmCmUmUmCmGmGmCdCmGTmGdCdGdGTmGmCdCmUdCdCmGmUdCmAmCmGmC-3T | 9.9 | 34.3 |
| 286 | ARC1363 | mGmCmGmUdG-s-dCdAmGmUmGmCmCmUmUmCmGmGmCdCmGTmGdCdGdGTmGmCdCmUdCdCmGmUdCmAmCmGmC-3T | 12.7 | 32.7 |
| 287 | ARC1364 | mGmCmGmUdGdC-s-dAmGmUmGmCmCmUmUmCmGmGmCdCmGTmGdCdGdGTmGmCdCmUdCdCmGmUdCmAmCmGmC-3T | 8.2 | 36.9 |
| 288 | ARC1365 | mGmCmGmUdGdCdA-s-mGmUmGmCmCmUmUmCmGmGmCdCmGTmGdCdGdGTmGmCdCmUdCdCmGmUdCmAmCmGmC-3T | 10.8 | 35.4 |
| 289 | ARC1366 | mGmCmGmUdGdCdAmGmUmGmCmCmUmUmCmGmGmC-s-dCmGTmGdCdGdGTmGmCdCmUdCdCmGmUdCmAmCmGmC-3T | 15.5 | 28.9 |
| 290 | ARC1367 | mGmCmGmUdGdCdAmGmUmGmCmCmUmUmCmGmGmCdC-s-mGTmGdCdGdGTmGmCdCmUdCdCmGmUdCmAmCmGmC-3T | 13.9 | 30.4 |
| 291 | ARC1368 | mGmCmGmUdGdCdAmGmUmGmCmCmUmUmCmGmGmCdCmG-s-TmGdCdGdGTmGmCdCmUdCdCmGmUdCmAmCmGmC-3T | 1.8 | 38.2 |
| 292 | ARC1369 | mGmCmGmUdGdCdAmGmUmGmCmCmUmUmCmGmGmCdCmGT-s-mGdCdGdGTmGmCdCmUdCdCmGmUdCmAmCmGmC-3T | 16.3 | 26.2 |
| 293 | ARC1370 | mGmCmGmUdGdCdAmGmUmGmCmCmUmUmCmGmGmCdCmGTmG-s-dCdGdGTmGmCdCmUdCdCmGmUdCmAmCmGmC-3T | 10.1 | 22.5 |
| 294 | ARC1371 | mGmCmGmUdGdCdAmGmUmGmCmCmUmUmCmGmGmCdCmGTmGdC-s-dGdGTmGmCdCmUdCdCmGmUdCmAmCmGmC-3T | 8.4 | 32.1 |

TABLE 23-continued

Phase 3 Modification Binding Results

Sequence (5' -> 3'),
(NH2 = 5'-hexylamine linker phosphoramidite), (3T = inv dT),
(T = dT), (s = phosphorothioate),
(mN = 2'-O Methyl containing residue), (PEG = polyethylene glycol), (dN = deoxy residue)

| SEQ ID NO: | ARC # | Sequence | $K_D$ (nM) | % binding @ 100 nM vWF |
|---|---|---|---|---|
| 295 | ARC1372 | mGmCmGmUdGdCdAmGmUmGmCmCmUmUmCmGmGmCdCmGTmGdCdG-s-dGTmGmCdCmUdCdCmGmUdCmAmCmGmC-3T | 23.5 | 35.2 |
| 296 | ARC1373 | mGmCmGmUdGdCdAmGmUmGmCmCmUmUmCmGmGmCdCmGTmGdCdGdG-s-TmGmCdCmUdCdCmGmUdCmAmCmGmC-3T | 7.1 | 33.0 |
| 297 | ARC1374 | mGmCmGmUdGdCdAmGmUmGmCmCmUmUmCmGmGmCdCmGTmGdCdGdGT-s-mGmCdCmUdCdCmGmUdCmAmCmGmC-3T | 9.5 | 27.2 |
| 298 | ARC1375 | mGmCmGmUdGdCdAmGmUmGmCmCmUmUmCmGmGmCdCmGTmGdCdGdGTmGmC-s-dCmUdCdCmGmUdCmAmCmGmC-3T | 8.8 | 25.5 |
| 299 | ARC1376 | mGmCmGmUdGdCdAmGmUmGmCmCmUmUmCmGmGmCdCmGTmGdCdGdGTmGmCdC-s-mUdCdCmGmUdCmAmCmGmC-3T | 4.4 | 31.3 |
| 300 | ARC1377 | mGmCmGmUdGdCdAmGmUmGmCmCmUmUmCmGmGmCdCmGTmGdCdGdGTmGmCdCmU-s-dCdCmGmUdCmAmCmGmC-3T | 7.4 | 30.9 |
| 301 | ARC1378 | mGmCmGmUdGdCdAmGmUmGmCmCmUmUmCmGmGmCdCmGTmGdCdGdGTmGmCdCmUdC-s-dCmGmUdCmAmCmGmC-3T | 9.1 | 31.1 |
| 302 | ARC1379 | mGmCmGmUdGdCdAmGmUmGmCmCmUmUmCmGmGmCdCmGTmGdCdGdGTmGmCdCmUdCdC-s-mGmUdCmAmCmGmC-3T | 10.4 | 31.3 |
| 303 | ARC1380 | mGmCmGmUdGdCdAmGmUmGmCmCmUmUmCmGmGmCdCmGTmGdCdGdGTmGmCdCmUdCdCmGmU-s-dCmAmCmGmC-3T | 12.0 | 32.5 |
| 304 | ARC1381 | mGmCmGmUdGdCdAmGmUmGmCmCmUmUmCmGmGmCdCmGTmGdCdGdGTmGmCdCmUdCdCmGmUdC-s-mAmCmGmC-3T | 8.7 | 35.8 |

As shown in Table 23 above, while the majority of the modifications tested in phase 3 had little or no beneficial effect, ARC1368 (SEQ ID NO 291), which contains a single phosphorothioate modification between mG-20 and dT-21 binds to human vWF with an affinity identical (within experimental error) to that of the parent compound, ARC1172 (SEQ ID NO 222).

Figure 18:
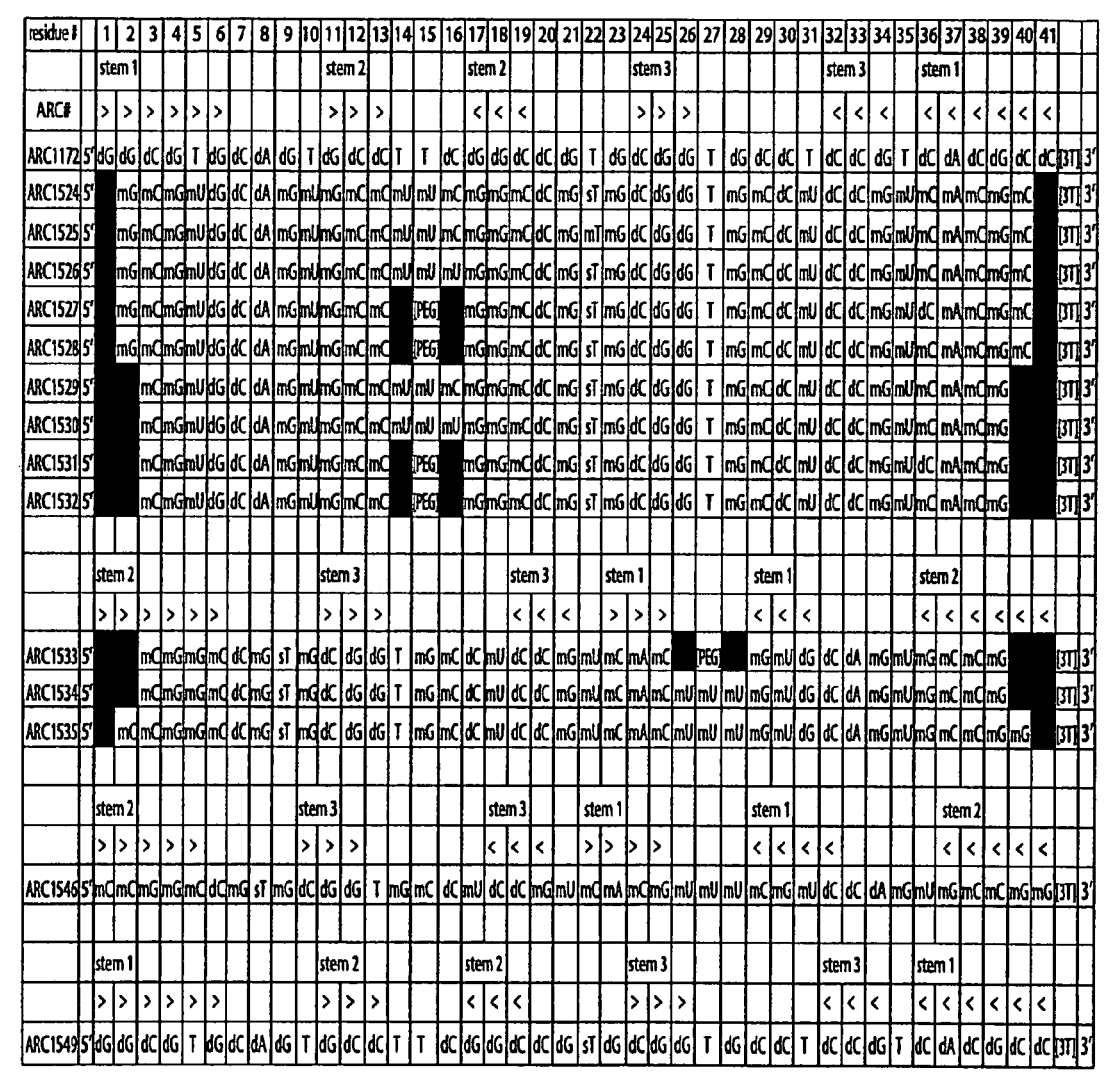
Figure 19:
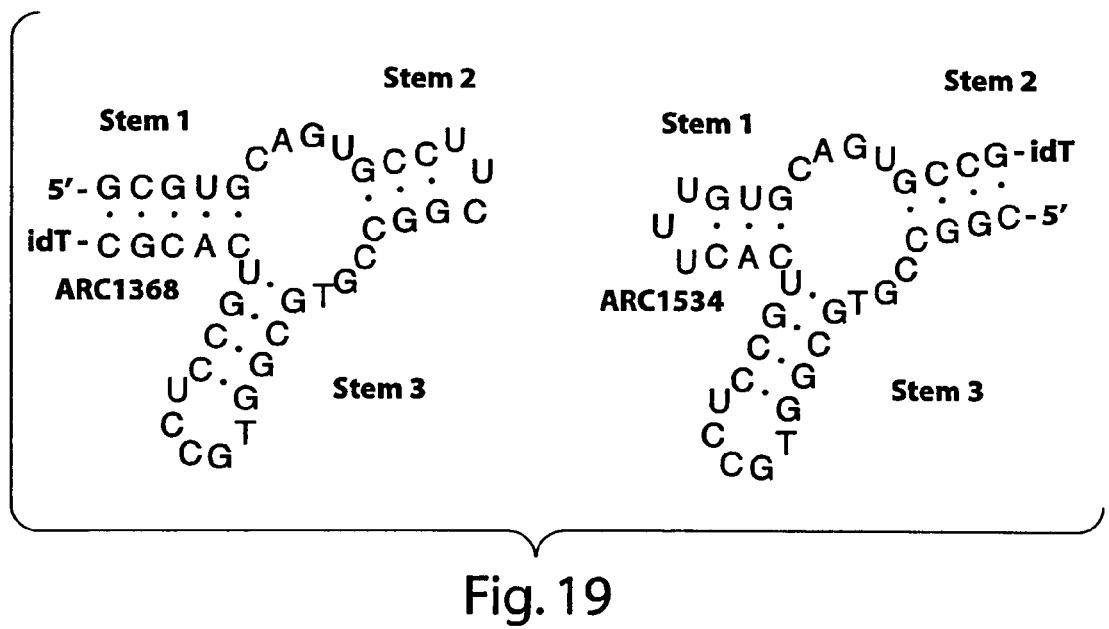
FIG. 19 is an illustration of the secondary structures of ARC1368 (SEQ ID NO 291) and ARC1534 (SEQ ID NO 315).

During phase 4 and phase 5 aptamer modification, ARC1524 (SEQ ID NO 305) to ARC1535 (SEQ ID NO 316), ARC1546 (SEQ ID NO 317) and ARC1759 (SEQ ID NO 318), shown in FIG. 18, were synthesized. A circular permutation of the sequence that closed stem 1 and opened stem 2 as illustrated in FIG. 19 was synthesized.

As shown in Table 24 below, many of these aptamers bound to vWF, however, none were as potent as ARC1368 (SEQ ID NO 291). Interestingly, though consistent with the SAR generated in Phase 1 of aptamer modification, ARC1525, containing only a single change from dT to mT at position 27, showed no binding at all to vWF. ARC1525 was used as a negative control in many of the biological assays in which ARC1368 (SEQ ID NO 291) was subsequently tested. Again, consistent with the SAR data from Phase 3 of aptamer modification, ARC1759 (SEQ ID ARC1172 (SEQ ID NO 222) except that it has single phosphorothioate substitution between the G at position 21 and the T at position 22 showed measurable improvement in affinity relative to ARC1172 (SEQ ID NO 222).

TABLE 24

Phase 4 and 5 Aptamer Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 222 | ARC1172 | dGdGdCdGTdGdCdAdGTdGdCdC TTdCdGdGdCdCdGTdGdCdGdGT dGdCdCTdCdCdGTdCdAdCdGdCd C-3T | 2 | 37 |
| 291 | ARC1368 | mGmCmGmUdGdCdAmGmUmGm CmCmUmUmCmGmGmCdCmG-s- TmGdCdGdGTmGmCdCmUdCdC mGmUdCmAmCmGmC-3T | 1.8 | 38.2 |
| 305 | ARC1524 | mGmCmGmUdGdCdAmGmUmGm CmCmUmUmCmGmGmCdCmG-s- TmGdCdGdGTmGmCdCmUdCdC mGmUmCmAmCmGmC-3T | 5.7 | 26.5 |
| 306 | ARC1525 | mGmCmGmUdGdCdAmGmUmGm CmCmUmUmCmGmGmCdCmGm TmGdCdGdGTmGmCdCmUdCdC mGmUmCmAmCmGmC-3T | No binding | No binding |
| 307 | ARC1526 | mGmCmGmUdGdCdAmGmUmGm CmCmUmUmUmGmGmCdCmG-s- TmGdCdGdGTmGmCdCmUdCdC mGmUmCmAmCmGmC-3T | 4.7 | 29.0 |
| 308 | ARC1527 | mGmCmGmUdGdCdAmGmUmGm CmCPEGmGmGmCdCmG-s- TmGdCdGdGTmGmCdCmUdCdC mGmUdCmAmCmGmC-3T | 3.4 | 14.1 |
| 309 | ARC1528 | mGmCmGmUdGdCdAmGmUmGm CmCPEGmGmGmCdCmG-s- TmGdCdGdGTmGmCdCmUdCdC mGmUmCmAmCmGmC-3T | 4.2 | 10.2 |
| 310 | ARC1529 | mCmGmUdGdCdAmGmUmGmCm CmUmUmCmGmGmCdCmG-s- TmGdCdGdGTmGmCdCmUdCdC mGmUmCmAmCmG-3T | 12.3 | 22.6 |
| 311 | ARC1530 | mCmGmUdGdCdAmGmUmGmCm CmUmUmUmGmGmCdCmG-s- TmGdCdGdGTmGmCdCmUdCdC mGmUmCmAmCmG-3T | 15.0 | 19.2 |
| 312 | ARC1531 | mCmGmUdGdCdAmGmUmGmCm CPEGmGmCdCmG-s- TmGdCdGdGTmGmCdCmUdCdC mGmUdCmAmCmG-3T | 1.5 | 20.0 |
| 313 | ARC1532 | mCmGmUdGdCdAmGmUmGmCm CPEGmGmCdCmG-s- TmGdCdGdGTmGmCdCmUdCdC mGmUmCmAmCmG-3T | 2.6 | 19.3 |
| 314 | ARC1533 | mCmGmGmCdCmG-s- TmGdCdGdGTmGmCdCmUdCdC mGmUmCmAmCPEGmGmUdGdC dAmGmUmGmCmCmG-3T | 4.0 | 31.7 |
| 315 | ARC1534 | mCmGmGmCdCmG-s- TmGdCdGdGTmGmCdCmUdCdC mGmUmCmAmCmUmUmGm UdGdCdAmGmUmGmCmCmG-3T | 62.8 | 25.6 |

TABLE 24-continued

Phase 4 and 5 Aptamer Modification Binding Results

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) | $K_D$ (nM) | % binding @ 100 nM vWF |
|---|---|---|---|---|
| 316 | ARC1535 | mCmCmGmGmCdCmG-s-TmGdCdGdGTmGmCdCmUdCdC mGmUmCmAmCmUmUmUmGm UdGdCdAmGmUmGmCmCmGmG-3T | 27.1 | 48.3 |
| 317 | ARC1546 | mCmCmGmGmCdCmG-s-TmGdCdGdGTmGmCdCmUdCdC mGmUdCmAmCmGmUmUmCmC mGmUdGdCdAmGmUmGmCmCm GmG-3T | 24 | 26 |
| 318 | ARC1759 | dGdGdCdGTdGdCdAdGTdGdCdC TTdCdGdGdCdCdG-s-TdGdCdGdGTdGdCdCTdCdCdGT dCdAdCdGdCdC-3T | 0.7 | 46 |

Example 2F

Conjugation of PEG Moieties to Modified Aptamers

Polyethylene glycol moieties were conjugated to the 5' terminus of ARC1368 (SEQ ID NO 291) and ARC1172 (SEQ ID NO 222) via amine reactive chemistries. The NH2-mGm-CmGmUdGdCdAmGmUmGmCmCmUmUmC-mGmGmCdCmG-s-dTmGdCdGdGTmGmCdCmUdCdC-mGmUdCmAmCmGmC-3T (ARC1368 (SEQ ID NO 291) with a 5' hexylamine modification) and ARC1884 (SEQ ID NO 322) NH2-dGdGdCdGdTdGdCdAdGdTdGdCdCT-dTdCdGdGdCdCdCdGTdGdCdGdGdTdGdCdCTdCdCdGT dCdAdCdGdCdC-3T (ARC1172 (SEQ ID NO 222) with a 5' hexylamine modification) were chemically synthesized.

The amine-modified aptamers were conjugated to different PEG moieties, as indicated in Table 25 below, post-synthetically.

TABLE 25

Hexylamine modified or PEG conjugated aptamers

| SEQ ID NO: | ARC # | Sequence (5' -> 3'), (NH2 = 5'-hexylamine linker phosphoramidite), (3T = inv dT), (T = dT), (s = phosphorothioate), (mN = 2'-O Methyl containing residue), (PEG = polyethylene glycol), (dN = deoxy residue) |
|---|---|---|
| 319 | ARC1635 | NH2-mGmCmGmUdGdCdAmGmUmGm CmCmUmUmCmGmGmCdCmG-s-TmGdCdGdGTmGmCdCmUdCdC mGmUdCmAmCmGmC-3T |
| 320 | ARC1779 | PEG20K-NH2-mGmCmGmUdGdCdAmGmUmGm CmCmUmUmCmGmGmCdCmG-s-TmGdCdGdGTmGmCdCmUdCdC mGmUdCmAmCmGmC-3T |
| 321 | ARC1780 | PEG40K-NH2-mGmCmGmUdGdCdAmGmUmGm CmCmUmUmCmGmGmCdCmG-s-TmGdCdGdGTmGmCdCmUdCdC mGmUdCmAmCmGmC-3T |
| 322 | ARC1884 | NH2-dGdGdCdGdTdGdCdAdGdTdGdCdC TTdCdGdGdCdCdCdGTdGdCdGdGdT dGdCdCTdCdCdGTdCdAdCdGdCd C-3T |
| 323 | ARC1885 | PEG20K-NH2-dGdGdCdGdTdGdCdAdGdTdGdCdC TTdCdGdGdCdCdCdGTdGdCdGdGdT dGdCdCTdCdCdGTdCdAdCdGdCd C-3T |

Example 3

Functional Cell Assays Biological vWF Dependent Assays

The effectiveness of various aptamers in blocking vWF function in several biological assays is described in this Example.

In one assay botrocetin is used. Botrocetin, a protein isolated from snake venom, is known to induce von Willebrand Factor binding to the gpib receptor on live and fixed platelets. This reaction causes agglutination of suspensions of fixed platelets via vWF multimerization. In preparations of platelet rich plasma (hereinafter "PRP"), vWF/botrocetin induction of agglutination is followed by a second phase of platelet aggregation caused by metabolic activation of the platelets.

These two reactions: vWF binding to fixed platelets and vWF mediated platelet aggregation, can be used to measure the activity of aptamers of the invention.

The amount of vWF bound to fixed platelets can be measured with an antibody to vWF. The fluorescence signal from bound antibody incubated with a fluorescein conjugated secondary antibody is then detected and quantified by flow cytometry. The ability of an aptamer of the invention to block vWF binding to platelets is correlated with a reduction in fluorescence signal.

Botrocetin induces the binding of the A1 domain of vWF to platelets, as well as the full length protein. It was determined by the inventors that 6-Histidine-tagged rabbit A1 domain vWF purified protein could be induced to bind to human lyophilized platelets with botrocetin. Rabbit A1 binding to platelets is measured with an anti-poly-His antibody followed by incubation with a phycoerythrin conjugated secondary antibody. The degree of binding can be quantified by flow cytometric analysis. The ability of aptamers to block the binding of rabbit A1 to human fixed platelets was correlated with decreased fluorescence signal.

In platelet rich plasma isolated from fresh human blood, botrocetin induces platelet aggregation via vWF. Platelet aggregate formation can be measured optically as an increase in % light transmittance on a Chronolog Model 490-4D Aggregometer because aggregation of platelets clarifies the plasma. Aptamers of the invention were analyzed for their ability to inhibit botrocetin induced platelet aggregation ("BIPA") in human blood. An aptamer of the invention was considered to be active if it could prevent aggregate formation for six minutes post botrocetin addition.

Another assay of this Example, using the PFA-100 instrument, is an agonist independent but vWF dependent assay that uses the PFA-100 instrument (Harrison et al., Clin. Lab. Haem., v24, p 225-32 (2002)). The PFA-100 simulates the formation of a hemostatic plug under conditions of high shear force in vivo by recording the time required for a platelets to aggregate and block the flow of citrated whole blood through a microscopic aperture in a membrane coated with collagen and either epinephrine or ADP. This activity is von Willebrand factor dependent as high MW vWF multimers bind to immobilized collagen on the membrane and then bind to and activate platelets because of the shear force induced by drawing the blood through the microscopic aperture. Thus this assay is complimentary to the BIPA and FACS assays in that it is vWF dependent, however it has some advantages in that it does not require the addition of the vWF agonist botrocetin and uses whole blood instead of platelet rich plasma.

Another assay of this Example used ADP to induce platelet aggregation. Aggregation of platelet rich plasma (PRP) can be in induced in multiple ways. The snake venom protein botrocetin acts on vWF as described above, stabilizing its interaction with the platelet receptor gpIb thereby inducing platelet aggregation. Binding of vWF to gpIb is an early step in platelet aggregation, thus there is an expectation that inhibitors that block downstream components of the aggregation process (i.e., the IIbIIIa antagonists Integrelin™ and ReoPro™) would also prevent botrocetin induced platelet aggregation. However, in the case of agonists that act directly on platelets and induce aggregation (ADP for example), one would expect that antagonists upstream of the agonist would be ineffective (an anti-vWF aptamer for example), while antagonists that act directly on platelets (IIbIIIa antagonists) would remain potent. The specificity of a vWF antagonist relative to a IIbIIIa antagonist will increase the safety of the anti-vWF antagonist by decreasing the bleeding time associated with treatment. For patients with atherosclerotic plaques in stenosed arteries, platelet aggregation occurs as platelets bind to collagen immobilized vWF on the surface of the plaque. Thus both inhibiting the vWF/gpIb interaction as well as blocking the IIbIIIa receptor binding to fibrin will prevent platelet aggregation. The biological specificity conferred by targeting vWF insures that unlike anti-IIbIIIa treatment, platelets themselves are not targeted directly insuring they can still be activated by other means, thus reducing potential bleeding complications associated with anti-platelet therapy.

The following materials were used in Examples 3A-3D described below: human von Willebrand Factor (vWF) (SEQ ID NO 7), and bovine serum albumin were purchased from Calbiochem (Cat#681300 and #126593, respectively) (La Jolla, Calif.); domain A1 rabbit vWF (SEQ ID NO 6) was expressed and purified using standard methods and conditions. Lyophilized human platelets (P/N 299-2), cuvettes (P/N 312), stir bars (P/N 311), platelet aggregometer (model 490-4D), and AGGRO/LINK Software were purchased from Chronolog (Haverton, Pa.). Botrocetin (12201-100U-B) was manufactured by Pentapharm (Basel, Switzerland). Fresh blood was obtained from apparently healthy, nonsteroidal anti-inflammatory drug ("NSAID") free donors and was drawn into 5 mL 0.105 M Sodium Citrate Vacutainer tubes (Cat#369714) (Becton Dickinson—Franklin Lakes, N.J.). Physiological saline was manufactured by Aldon (Cat #9420306) (Avon, N.Y.) and phosphate buffered saline (Cat #21-040-CV) was purchased from Cellgro (Herndon, Va.). Flow cytometric experiments were performed on a BD Biosciences FACSCAN machine and analyzed with CellQuest Software (San Jose, Calif.). Anti-von Willebrand Factor mouse monoclonal antibody (Cat#GTI-V1A) was purchased from GTI (Waukesha, Wis.). Penta-HIS-biotin conjugate monoclonal antibody (Cat #34440) was purchased from Qiagen (Germany). Anti-mouse IgG2a—FITC conjugate (Cat #553390) was purchased from BD Biosciences (San Diego, Calif.). Anti-mouse IgG-PE conjugate antibody (Cat #715-116-150) was purchased from Jackson ImmunoResearch Laboratories (West Grove, Pa.).

Example 3A

Full Length Human von Willebrand Factor Platelet Binding Assay

Figure 7:
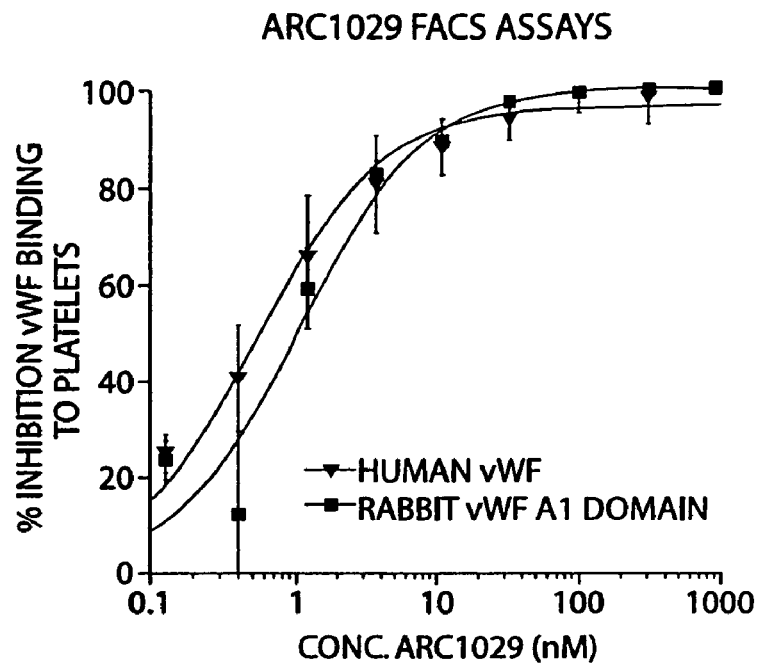
FIG. 7 is a graph of FACS data showing that ARC1029 (SEQ ID NO 214) inhibits binding of human vWF and rabbit vWF A1 domain to lyophilized human platelets.

Aptamer potency to block human vWF binding to lyophilized platelets was assessed by flow cytometric analysis. Titrations of aptamers (0 nM, 0.1 nM to 1000 nM) were pre-incubated briefly with 5 nM of full length human vWF in FACS buffer (PBS plus 0.5% bovine serum albumin) at room temperature in a volume of 50 uL. Another 50 uL containing 5 uL of lyophilized platelets plus 1 uL of 0.1 U/uL of botrocetin in FACS buffer was added to aptamer/vWF. This reaction was allowed to proceed for 15 minutes at 37 degrees C. after which 200 uL of FACS buffer was added. Platelets were collected by a 6 minute spin at 1470 RCF and the supernatant was discarded. The pellets were resuspended in 100 uL of FACS buffer containing a 1:100 dilution of anti-vWF antibody and were incubated at room temperature for 30 minutes. After dilution with 200 uL of FACS buffer, the platelets were spun at 1470 RCF for 6 minutes and the supernatant was discarded. The pellets were resuspended in a 1:100 solution of anti-IgG2a-FITC antibody and were incubated in the dark for 30 minutes at room temperature. The entire 100 uL was diluted into 200 uL of FACS buffer and analyzed immediately by flow cytometric analysis in the FACSCAN. Artifactual data from contaminating debris was eliminated from the analysis by drawing a gate around the population of single and aggregated platelets. Mean fluorescent intensity ("MFI") readings were quantified for each sample analyzed by flow cytometry. Background MFI was subtracted from all data points. Percent inhibition was reported by calculating the percent value of binding of full length human vWF to platelets in the presence of aptamer at a given concentration relative to binding in the absence of any aptamer (see FIG. 7). $IC_{50}$ values were determined by fitting the percent inhibition of vWF binding to platelets as a function of aptamer concentration to the equation:

% inhibition=% inhibition$_{max}$/(1+$IC_{50}$/aptamer conc.)

Results of botrocetin induced vWF binding characterization are tabulated in Table 26 below.

Example 3B

Rabbit von Willebrand Factor Domain A1 Platelet Binding Assay

The ability of aptamers of the invention to block rabbit vWF domain A1 binding to lyophilized platelets was also assessed by flow cytometric analysis. Titrations of aptamers (zero, 0.1 nM to 1000 nM) were preincubated briefly with 4 nM of rabbit A1 vWF in FACS buffer (PBS plus 0.5% bovine serum albumin) at room temperature in a volume of 50 uL. Another 50 uL containing 5 uL of lyophilized platelets plus 1 uL of 0.1 U/uL of botrocetin in FACS buffer was added to aptamer/vWF. This reaction was allowed to proceed for 15 minutes at 37 degrees C. after which 200 uL of FACS buffer was added. Platelets were collected by a 6 minute spin at 1470 RCF and the supernatant was discarded. The pellets were resuspended in 100 uL of FACS buffer containing a 1:200 dilution of anti-Penta-HIS-biotin conjugate antibody and were incubated at room temperature for 30 minutes. After the dilution with 200 uL of FACS buffer, the platelets were spun at 1470 RCF for 6 minutes, and the supernatant was discarded. The pellets were resuspended in a 1:100 solution of anti-IgG-PE antibody and were incubated in the dark for 30 minutes at room temperature. The entire 100 uL was diluted into 200 uL of FACS buffer and analyzed immediately by flow cytometric analysis in the FACSCAN. Contaminating debris was eliminated from the analysis by drawing a gate around the population of single and aggregated platelets and collecting data from 10000 events. Median fluorescent intensity ("MedFI") readings (which are generally equivalent to the MFI readings, described in Example 3a above, for comparative purposes) were quantified for each sample analyzed by flow cytometry. Background MedFI was subtracted from all data points. Percent inhibition was reported by calculating the percent value of binding of full length human VWF to platelets in the presence of aptamer at a given concentration relative to binding in the absence of any aptamer (see FIG. 7). $IC_{50}$ values were determined by fitting the percent inhibition of vWF binding to platelets as a function of aptamer concentration to the equation:

% inhibition=% inhibition$_{max}$/(1+$IC_{50}$/aptamer conc.)

Results of botrocetin induced rabbit A1 vWF binding characterization are tabulated below in Table 26.

TABLE 26

Results of FACS and BIPA Assays ('ND' = not done)

| Aptamer ID | Inhibition of full length hVWF binding in FACS assay | | Inhibition of rabbit VWF A1 domain binding in FACS assay | | ≦200 nM aptamer gives >90% blocking in BIPA at 6 minutes |
|---|---|---|---|---|---|
| | $IC_{50}$ range | Average $IC_{50}$ | $IC_{50}$ range | Average $IC_{50}$ | |
| rRdY aptamer aptamers | | | | | |
| (AMX203.D6) SEQ ID NO 31 | no activity | | ND | | ND |
| (AMX205.H8) SEQ ID NO 32 | no activity | | ND | | ND |
| (AMX205.H11) SEQ ID NO 33 | no activity | | ND | | ND |
| (AMX205.D11) SEQ ID NO 35 | no activity | | ND | | ND |
| (AMX206.F9) SEQ ID NO 36 | no activity | | ND | | ND |
| (AMX206.H9) SEQ ID NO 37 | no activity | | ND | | ND |
| (AMX206.A10) SEQ ID NO 38 | no activity | | ND | | ND |
| (AMX205.F9) SEQ ID NO 39 | no activity | | ND | | ND |
| (AMX206.E7) SEQ ID NO 40 | no activity | | ND | | ND |
| (AMX206.D7) SEQ ID NO 41 | no activity | | ND | | ND |
| (AMX203.A1) SEQ ID NO 43 | no activity | | ND | | ND |
| (AMX203.G9) SEQ ID NO 44 = ARC 842 | 1.2 nM to 8.5 nM | 4.7 nM | 152 pM to 1.6 nM | 592 pM | yes |
| (AMX205.H9) SEQ ID NO 45 | no activity | | ND | | ND |

TABLE 26-continued

Results of FACS and BIPA Assays ('ND' = not done)

| Aptamer ID | Inhibition of full length hVWF binding in FACS assay | | Inhibition of rabbit VWF A1 domain binding in FACS assay | | ≦200 nM aptamer gives >90% blocking in BIPA at 6 minutes |
|---|---|---|---|---|---|
| | $IC_{50}$ range | Average $IC_{50}$ | $IC_{50}$ range | Average $IC_{50}$ | |
| (AMX206.D8) SEQ ID NO 46 | no activity | | no activity | | ND |
| (AMX205.F7) SEQ ID NO 49 = ARC 841 | 321 pM to 1.6 nM | 818 pM | 1.5 nM to 7.1 nM | 4.7 nM | yes |
| (AMX205.H10) SEQ ID NO 50 | no activity | | no activity | | ND |
| rRdY aptamer minimers | | | | | |
| SEQ ID NO 177 | 1.6 nM to 5.4 nM | 3 nM | ND | | ND |
| SEQ ID NO 180 | 731 pM to 3.8 nM | 2 nM | 8.2 nM to 10.5 nM | 9.3 nM | yes |
| SEQ ID NO 183 | 6.6 nM to 99 nM | 26.5 nM | ND | | ND |
| SEQ ID NO 186 | 971 pM to 2.2 nM | 1.3 nM | ND | | ND |
| SEQ ID NO 189 | 564 pM to 1.6 nM | 1.1 nM | ND | | ND |
| SEQ ID NO 192 | 1.1 nM to 5.3 nM | 2.6 nM | 2 nM to 2.3 nM | 2.2 nM | yes |
| SEQ ID NO 194 | no activity | | ND | | ND |
| SEQ ID NO 196 | no activity | | ND | | ND |
| SEQ ID NO 198 | 14 nM to 25 nM | 20.6 nM | 8.5 nM to 16.8 nM | 12.6 nM | ND |
| SEQ ID NO 201 | 1.3 nM to 370 nM | 150 nM | ND | | no activity |
| rRfY aptamer aptamers | | | | | |
| (AMX201.B1) SEQ ID NO 11 | no activity | | ND | | yes |
| (AMX198.G1) SEQ ID NO 12 | no activity | | ND | | ND |
| (AMX201.H3) SEQ ID NO 13 | no activity | | ND | | yes |
| (AMX201.G1) SEQ ID NO 15 | no activity | | ND | | ND |
| (AMX201.C8) SEQ ID NO 23 = ARC 840 | 24 pM to 1.8 nM | 528 pM | 141 pM to 704 pM | 682 pM | yes |
| rRfY aptamer minimers | | | | | |
| SEQ ID NO 165 | 562 pM to 14.4 nM | 6.4 nM | ND | | ND |
| SEQ ID NO 169 | 103 pM to 17 nM | 6.9 nM | ND | | ND |
| SEQ ID NO 172 | 1.8 nM to 7.4 nM | 4.3 nM | ND | | ND |
| SEQ ID NO 174 | 1.3 nM to 12.7 nM | 6.6 nM | 4.9 nM to 5 nM | 6.8 nM | yes |
| DNA SELEX 1, minimer | | | | | |
| ARC845 SEQ ID NO 205 DNA SELEX 2 aptamer aptamers | no activity | no activity | no activity | no activity | no activity |
| AMX237.E10 SEQ ID NO 138 | no activity | | ND | | ND |
| AMX237.G7 SEQ ID NO 134 | 2.3 nM to 14 nM | 6.5 nM | 12.3 nM | | ND |
| AMX.236.G1 SEQ ID NO 164 | 8.6 nM to 72 nM | 46 nM | | | ND |
| AMX237.A11 SEQ ID NO 98 | 466 pM to 5.6 nM | 2.2 nM | 4.7 nM | | ND |
| AMX237.A2 SEQ ID NO 99 | 815 pM to 7.3 nM | 3.5 nM | 7 nM | | ND |
| AMX238.D12 SEQ ID NO 100 | 684 pM to 3.4 nM | 2 nM | 7.2 nM | | ND |
| AMX238.G5 SEQ ID NO 106 | 273 pM to 2.6 nM | 1.1 nM | 5.5 nM | | ND |
| AMX238.E9 SEQ ID NO 115 | 772 pM to 6.5 nM | 3.4 nM | ND | | ND |
| AMX238.H5 SEQ ID NO 118 | 514 pM to 860 pM | 658 pM | ND | | ND |
| AMX237.G6 SEQ ID NO 114 | 1.5 nM to 2.5 nM | 1.9 nM | ND | | yes |

TABLE 26-continued

Results of FACS and BIPA Assays ('ND' = not done)

| Aptamer ID | Inhibition of full length hVWF binding in FACS assay | | Inhibition of rabbit VWF A1 domain binding in FACS assay | | ≤200 nM aptamer gives >90% blocking in BIPA at 6 minutes |
|---|---|---|---|---|---|
| | $IC_{50}$ range | Average $IC_{50}$ | $IC_{50}$ range | Average $IC_{50}$ | |
| AMX237.B11 SEQ ID NO 109 | 151 pM to 4.8 nM | 2.5 nM | 5.7 nM | | ND |
| AMX236.A12 SEQ ID NO 127 | 1.2 nM to 17 nM | 10.7 nM | 14.5 nM | | ND |
| DNA SELEX 2 aptamer minimers | | | | | |
| SEQ ID NO 208 | 1.6 nM to 10.2 nM | 4.3 nM | ND | | ND |
| SEQ ID NO 209 | no activity | | ND | | ND |
| SEQ ID NO 210 | no activity | | ND | | ND |
| SEQ ID NO 211 | no activity | | ND | | ND |
| ARC1027 SEQ ID NO 212 | 208 pM to 4.2 nM | 1.5 nM | 462 pM to 4.2 nM | 2 nM | yes |
| ARC1028 SEQ ID NO 213 | 473 pM to 2.7 nM | 1.2 nM | 526 pM to 2.7 nM | 1.5 nM | yes |
| ARC1029 SEQ ID NO 214 | 333 pM to 1.1 nM | 609 pM | 490 pM to 979 pM | 754 pM | yes |
| ARC1030 SEQ ID NO 215 | no activity | | ND | | ND |
| ARC1031 SEQ ID NO 216 | no activity | | ND | | ND |

Example 3C

Inhibition of Botrocetin Induced Platelet Aggregation (BIPA Assay)

Figure 8:
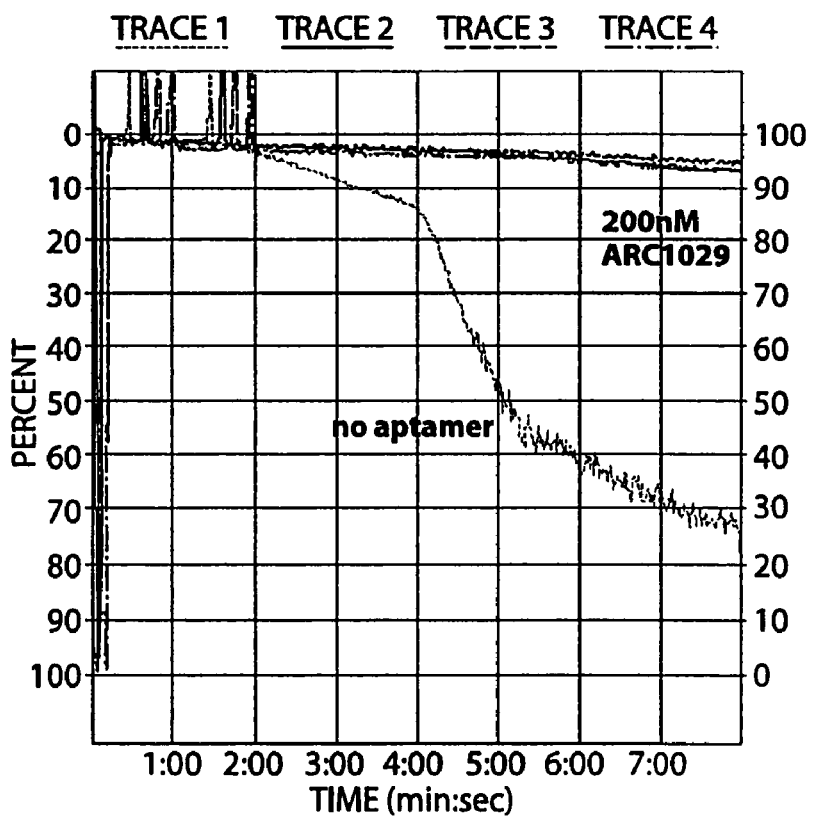
FIG. 8 is a graph of an aggregometer trace showing ARC1029 (SEQ ID NO 214) inhibiting botrocetin induced platelet aggregation over time.
Figure 9:
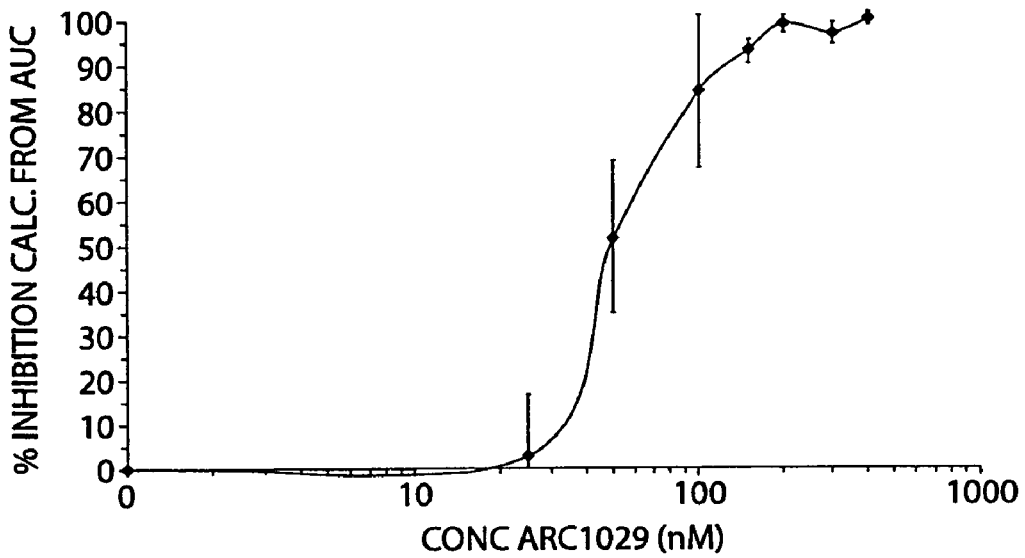
FIG. 9 is a graphical representation of ARC1029 (SEQ ID NO 214) inhibiting botrocetin induced platelet aggregation.

In order to determine the activity of aptamers on live human platelets, BIPA assays were done using freshly prepared platelet rich plasma. Blood was obtained from healthy human donors who had not taken NSAIDS for at least five days. 21¾ gauge butterfly needles (Cat# 367287) from Becton Dickinson were used to draw blood into 0.105 M sodium citrate vacutainer tubes. Collected blood was pooled into 15 mL conical tubes and was spun at 200 g for 20 minutes. The turbid, yellow layer of platelet rich plasma ("PRP") was withdrawn from the tubes, pooled, and set aside at room temperature. The remaining blood was spun at 2500 g for ten minutes. The clarified layer of plasma, known as platelet poor plasma ("PPP"), was withdrawn and set aside at room temperature. PRP was aliquoted into cuvettes containing stir bars at a volume of 470 uL. A sample of 500 uL of PPP was aliquoted into a cuvette and placed in the PPP reference cell of the platelet aggregometer. Samples of PRP were prewarmed at 37 degrees C. in the platelet aggregometer for 3-5 minutes before being used in BIPA assays. First, the concentration of botrocetin needed to induce platelet aggregation for each individual donor was determined by titration. This concentration of botrocetin was used for the remainder of the experiment. Next, aptamer was assayed by adding titrations of aptamer (zero, 1 nM to 1000 nM) to prewarmed PRP for one minute, followed by addition of botrocetin. With platelet aggregation, an increase in amplitude of light transmission is seen (FIG. 8). The concentration at which platelet aggregation is blocked at 90% or greater after 6 minutes is reported in the final column of Table 26. Using the Aggro/LINK Software, area under the curve ("AUC") can be generated from the aggregometer trace and used to calculate percent inhibition of aptamer at any given concentration on botrocetin induced platelet aggregation as seen in FIG. 9 for Aptamer ARC1029 (SEQ ID NO 214).

Example 3D

Biological Activity of Selected Modified Aptamers in a Series of Biological Assays ARC1172 (SEQ ID NO 222), ARC1346 (SEQ ID NO 281), ARC1368 (SEQ ID NO 291), ARC1525 (negative control), ARC1779 (SEQ ID NO 320), ARC1780 (SEQ ID NO 321), and ARC1885 (SEQ ID NO 323) identified in the medchem modification process described in Example 2 above, were tested in a series of biological assays. These assays included the FACS (as described in Example 3A and 3B) and BIPA assays (as described in Example 3C), as well as the platelet PFA-100 assay described below.

Materials:

The following materials were used in the platelet function analyzer (PFA) assay:

Fresh whole blood was collected from healthy non-steroidal anti-inflammatory drug (NSAID) free donors into 5 ml 0.105M sodium citrate tubes (Cat#369714, Becton Dickenson) using 21¼ gauge butterfly needles (Cat#367287, Becton Dickenson). Fresh whole blood was collected from healthy non-steroidal anti-inflammatory drug (NSAID) free cynomolgus macaques. Aptamers were diluted with physiological saline from Aldon (Cat#9420306) in no-additive vacutainer tubes (Cat#366434, Becton Dickenson). Samples were loaded onto collagen/epinephrine test cartridges (Cat#B4170-20A, Dade Behring) which were used in the PFA-100 machine (Dade Behring). Trigger solution (Cat#B4170-50, Dade Behring) was used in the self-test and to pre-wet the test cartridges. O-ring cleaning pads (Cat#B4170-73, Dade Behring) were used in the self-test and in the O-ring cleaning process.

PFA Assay:

A self-test, which included an O-ring cleaning process, was always run on the PFA-100 machine before running any samples to ensure proper function of the machine.

Fresh whole blood was collected from healthy donors or cynomolgus macaques, as indicated in Table 27 below, who/ that had not taken NSAIDs for at least three days. Blood from human donors was collected into 5 ml 0.105M sodium citrate tubes using a 21¾ gauge butterfly needle, and the tubes were gently inverted three times to ensure mixture of blood with sodium citrate. During the entire experiment, the tubes of whole blood were gently inverted every five minutes to prevent settling.

In order to assay the titration of aptamer in whole blood, the aptamer was added to no-additive vacutainer tubes and diluted to the desired concentrations (ex: 0 nM, 1 nM to 1000 nM) using physiological saline such that the final volume was 60l. When the PFA-100 was ready to run the next set of samples, 1940 µl of whole blood was added to the tube containing a concentration of aptamer. This tube was gently inverted three times to thoroughly mix the aptamer and blood. Samples were always run in duplicate on the PFA-100 machine. 800 µl of this blood mixture was loaded into the collagen/epinephrine test cartridges. The test cartridges were loaded onto the PFA-100 machine. The time of occlusion of the aperture was measured by the PFA-100, with a maximal time of 300 seconds. We estimate the $IC_{95}$ in this assay to be the minimum concentration of aptamer that extends the closing time to 300 seconds.

Figure 20:
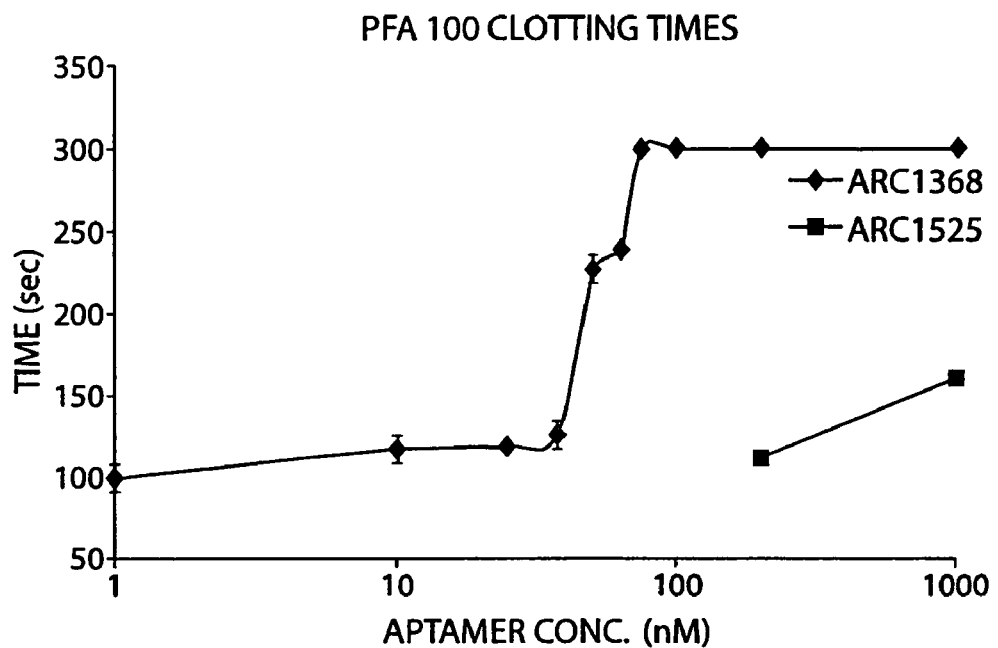
FIG. 20 is a graph depicting the clotting time, in the PFA-100 assay, for human whole blood treated with ARC1368 (SEQ ID NO 291) or ARC1525 (SEQ ID NO 306) as a function of aptamer concentration.

FIG. 20 depicts clotting time in human whole blood as a function of aptamer concentration in the PFA-100 assay for ARC1368 (SEQ ID NO 291) and the negative control ARC1525. Additional results of the FACS, BIPA and PFA-100 assays are tabulated in Table 27 below.

TABLE 27

FACS, BIPA and PFA-100 results

| ARC # | FACS $IC_{50}$ vs human full length vWF (nM) | FACS $IC_{50}$ vs rabbit A1 domain (nM) | ~$IC_{90}$ BIPA (nM) with human platelet rich plasma | ~$IC_{95}$ PFA-100 (nM) with citrated human whole blood | ~$IC_{95}$ PFA-100 (nM) with citrated C. macaque whole blood |
|---|---|---|---|---|---|
| ARC1172 (SEQ ID NO 222) | 2 | 2 | ~200 | ~100 | ND |
| ARC1346 | 50 | 180 | >1000 | ND | ND |
| ARC1368 | 2 | 4.0 | ~200 | ~100 | ~100 |
| ARC1525 | ND | ND | no inhibition | no inhibition | ND |
| ARC1779 | ND | ND | ~100 | ~100 | ND |
| ARC1780 | ND | ND | ~100 | ~100 | ND |
| ARC1885 | ND | ND | ~50 | ~100 | ND |

Figure 21:
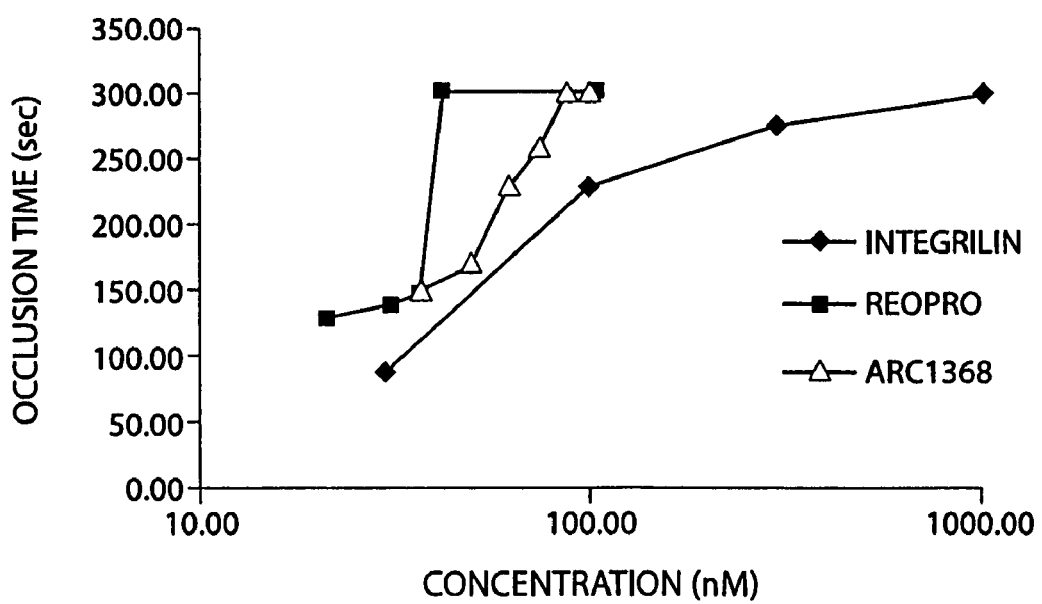
FIG. 21 is a graph depicting occlusion time, in a PFA-100 assay, of human whole blood treated with Integrilin™, ReoPro™ or ARC1368 (SEQ ID NO 291), as a function of drug concentration.
Figure 22:
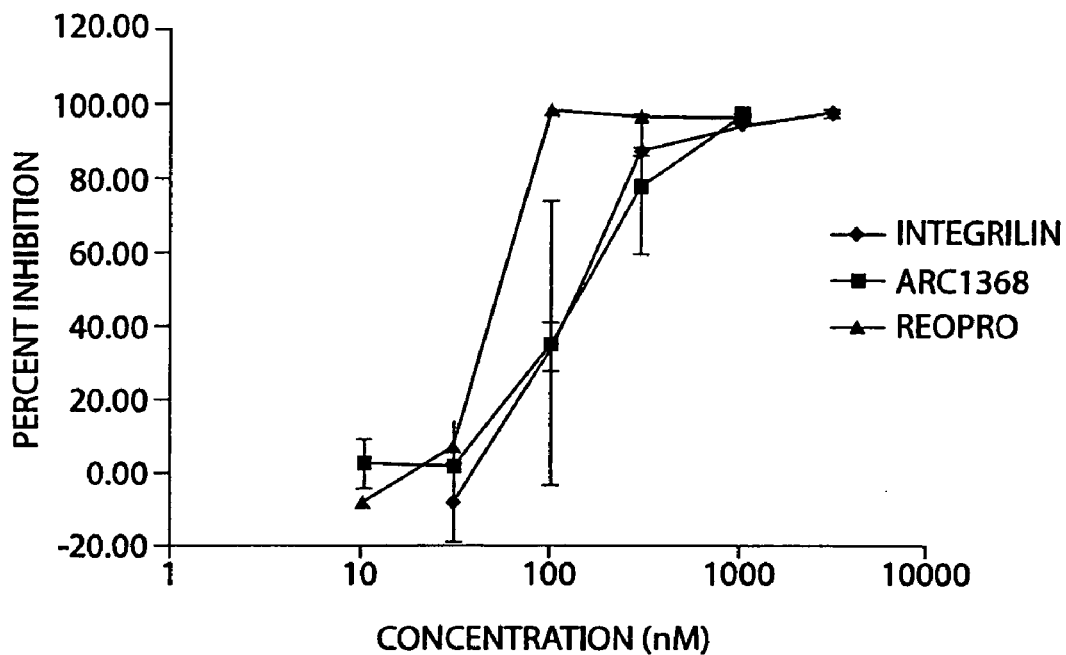
FIG. 22 is a graph depicting percent inhibition, in BIPA, of human PRP, treated with Integrilin™, ReoPro™ or ARC1368 (SEQ ID NO 291), as a function of drug concentration.
Figure 23:
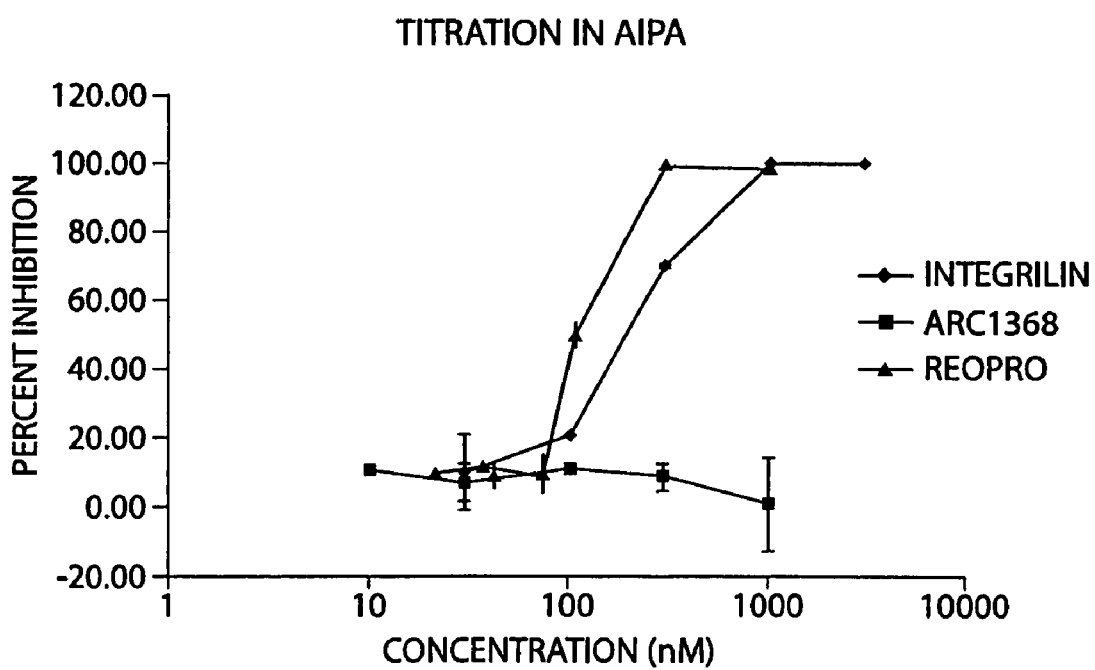
FIG. 23 is a graph depicting percent inhibition, in AIPA, of human PRP, treated with Integrilin™, ReoPro™ or ARC1368 (SEQ ID NO 291), as a function of drug concentration.

As expected, there was a strong correlation among the observed affinities of aptamers for vWF in the binding assay described in Example 2 above and their relative potency in the biological assays. The non-binding negative control ARC1525 did not display activity in any assay in which it was tested Example 3E ARC1368, Integrilin™ and ReoPrO™ in BIPA, PFA-100 and AIPA assays The potency of ARC1368 (SEQ ID NO 291), Integrillin™ and ReoPrO™ were evaluated in human whole blood in PFA-100, in human PRP in BIPA (as described above in Examples 3D and 3C respectively) and ADP Induced Platelet Aggregation (AIPA) assays. AIPA was performed with human PRP exactly as was done for BIPA described above in Example 3C with the exception that instead of adding botrocetin, 10 micromolar ADP (Chronolog, Haverton, Pa.) was added to induce platelet aggregation. The PFA-100 results are shown in FIG. 21. The BIPA results are shown in FIG. 22. The AIPA results are shown in FIG. 23. As can be seen in FIGS. 21 and 22, ARC1368 (SEQ ID NO 291) shows potency comparable to ReoPrO™ in PFA-100 and BIPA assays. Consistent with the vWF dependent mechanism described above, the anti-vWF aptamer shows no ability to block AIPA while the IIbIIIa antagonists remain potent in that assay as shown in FIG. 23.

Example 4

Pharmacokinetic Studies

In Examples 4 and 5, all mass based concentration data refers only to the molecular weight of the oligonucleotide portion of the aptamer, irrespective of the mass conferred by PEG conjugation.

Example 4A

Stability of Anti-vWF Aptamers in Human and Rat Plasma

ARC1172 (SEQ ID NO 222), ARC1346 (SEQ ID NO 281), ARC1368 (SEQ ID NO 291) and ARC1533 were assayed for nuclease stability in both human and rat plasma. Plasma nuclease degradation was measured on denaturing polyacrylamide gel electrophoresis as described below. Briefly, for plasma stability determination, chemically synthesized aptamers were purified using denaturing polyacrylamide gel electrophoresis, 5' end labeled with γ-$^{32}$P ATP and then gel purified again. Trace 32-P labeled aptamer was incubated in the presence of 100 nM unlabeled aptamer in 95% human or rat plasma in a 200 microliter binding reaction. The reaction for the time zero point was made separately with the same components except that the plasma was replaced with PBS. This insured that the amount or radioactivity loaded on gels was consistent across an experiment. Reactions were incubated at 37° C. in a thermocycler for the 1, 3, 10, 30 and 100 hours unless otherwise specified. At each time point, 20 microliters of the reaction was removed, combined with 200 microliters of formamide loading dye and flash frozen in liquid nitrogen and stored at −20° C. After the last time point was taken, frozen samples were thawed and 20 microliters was removed from each time point. SDS was then added to the small samples to a final concentration of 0.1%. The samples were then incubated at 90° C. for 10-15 minutes and loaded directly onto a 15% denaturing PAGE gel and run at 12 W for 35 minutes. Radioactivity on the gels was quantified using a Storm 860 phosphoroimager system. The percentage of full length aptamer at each time point was determined by quantifying the full length aptamer band and dividing by the total counts in the lane. The fraction of full length aptamer at each time-point was then normalized to the percentage full length aptamer of the 0 hour time-point. The fraction of full length aptamer as a function of time was fit to the equation:

$$m1*e^{(-m2*m0)}$$

where m1 is the maximum % full length aptamer (m1=100); and m2 is the rate of degradation. The half-life of the aptamer ($T_{1/2}$) is equal to the (ln 2)/m2.

Figure 24:
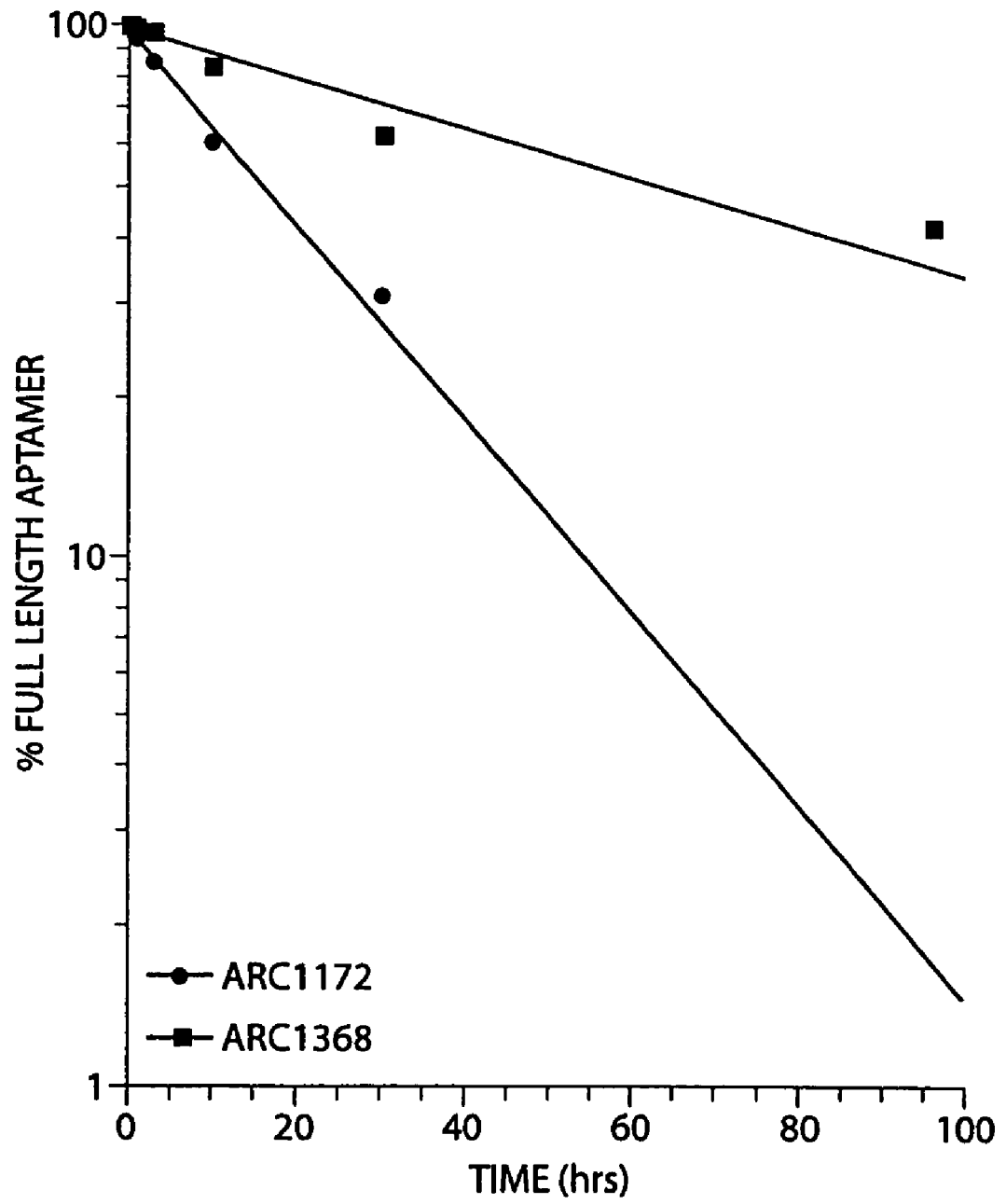
FIG. 24 is a graph depicting percentage of full length ARC1172 (SEQ ID NO 222) or ARC1368 (SEQ ID NO 291), detected in human plasma, as a function of time.

Sample data for human plasma is shown in FIG. 24 and the results for the aptamers tested are summarized in Table 28. Consistent with our expectations, aptamers are more stable in human plasma than in rat plasma and increasing the number of 2'-OMe modifications correlates with increasing plasma stability.

TABLE 28

Aptamer Plasma Stability half-life

| ARC # | T½ Human plasma (hrs) | T½ Rat plasma (hrs) |
|---|---|---|
| ARC1172 (SEQ ID NO 222) | 17 | 3 |
| ARC1346 | not done | 19 |
| ARC1368 | 63 | 21 |
| ARC1533 | 93 | not done |

Example 4B

PK/PD of PEGylated derivatives of ARC1368 in Cynomolgus Macaques

ARC1368 (SEQ ID NO 291), 1779 (SEQ ID NO 320) and 1780 (SEQ ID NO 321) (as described in Example 2 above) were injected intravenously into cynomolgus macaques (n=3/group) at a dosage of 3 mg/kg which was expected to yield an instantaneous plasma concentration of 3 uM, approximately 30-fold higher than the putative effective dose. Subsequently, citrated blood samples were collected at regular intervals and processed for plasma.

To demonstrate that the aptamers were pharmacologically active in vivo, Botracetin-induced platelet aggregation (BIPA) was performed 5 minutes post-dosing, at the presumed plasma $C_{max}$. All animals had complete inhibition of BIPA at this point demonstrating that the aptamers were functional in vivo.

Subsequently, plasma aptamer concentrations were determined using the Oligreen assay (Gray et al., Antisense and Nucleic Acid Drug Development 7 (3):133-140 (1997). The data were subsequently analyzed using the program WinNonlin to yield the pharmacokinetic parameters listed in Tables 29 to 31 below.

Figure 25:
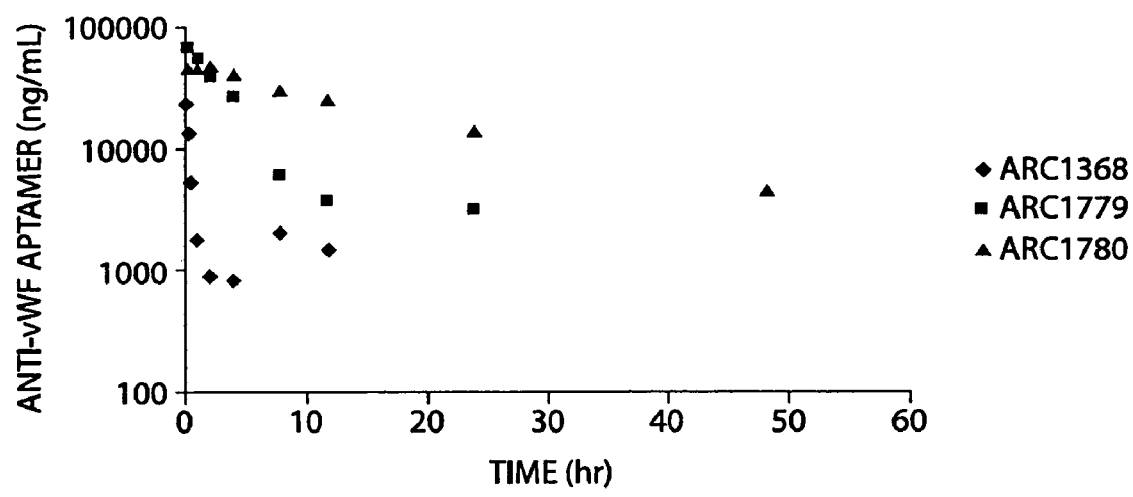
FIG. 25 is a graph depicting primate plasma aptamer concentration (determined using Oligreen analysis) plotted as a function of time following administration of ARC1368 (SEQ ID NO 291), ARC1779 (SEQ ID NO 320) or ARC1780 (SEQ ID NO 321).

Additionally, the primate plasma aptamer concentration plotted as a function of time is depicted in the graph of FIG. 25. The mean concentration-times profiles based on the OliGreen™ assay showed that the pharmacokinetic profiles of ARC1368 (SEQ ID NO 291), ARC1780 (SEQ ID NO 321) and ARC1779 (SEQ ID NO 320) were mainly monophasic. The unPEGylated aptamer (ARC1368 (SEQ ID NO 291)) displayed a rapid distribution phase compared to ARC1779 (SEQ ID NO 320) and ARC1780 (SEQ ID NO 321). Unlike ARC1368 (SEQ ID NO 291), the 40 kDa PEG conjugate ARC1780 (SEQ ID NO 321) displayed prolonged distribution phase compared to ARC1779 (SEQ ID NO 320). ARC1779 (20 kDa PEG) displayed a distribution phase with α-half-life of ~2 hr.

TABLE 29

NonCompartmental Pharmacokinetic Parameter Estimates for ARC1368 After 3 mg/kg IV Administration in Monkeys Based on Oligreen Assay Data

| PK Parameter | Unit | 1101 | 1102 | 1103 | Mean | StdDev |
|---|---|---|---|---|---|---|
| Tmax | hr | 0.08 | 0.08 | 0.08 | 0.08 | 0.00 |
| Cmax | ng/mL | 26409 | 19170 | 23301 | 22960 | 3632 |
| AUC0-last | hr * ng/mL | 23096 | 31926 | 20650 | 25224 | 5932 |
| MRTlast | hr | 4.50 | 5.46 | 3.48 | 4.48 | 0.99 |

TABLE 30

NonCompartmental Pharmacokinetic Parameter Estimates for ARC1779 After 3 mg/kg IV Administration in Monkeys Based on Oligreen Assay Data

| PK Parameter | Unit | 2101 | 2103 | 2104 | Mean | StdDev |
|---|---|---|---|---|---|---|
| Tmax | hr | 0.25 | 0.50 | 0.25 | 0.33 | 0.14 |
| Cmax | ng/mL | 69065 | 65717 | 70344 | 68375 | 2389 |
| AUClast | hr * ng/mL | 309245 | 336590 | 235503 | 293779 | 52288 |
| MRTlast | hr | 5.27 | 4.66 | 2.69 | 4.21 | 1.35 |

TABLE 31

NonCompartmental Pharmacokinetic Parameter Estimates for ARC1780 After 3 mg/kg IV Administration in Monkeys Based on Oligreen Assay Data

| PK Parameter | Unit | 3101 | 3102 | 3103 | Mean | StdDev |
|---|---|---|---|---|---|---|
| Tmax | hr | 2.00 | 2.00 | 0.25 | 1.42 | 1.01 |
| Cmax | ng/mL | 55965 | 37320 | 50690 | 47992 | 9611 |
| AUClast | hr * ng/mL | 740559 | 613180 | 899455 | 751065 | 143426 |
| AUCall | hr * ng/mL | 740559 | 613180 | 899455 | 751065 | 143426 |
| MRTlast | hr | 8.69 | 9.54 | 14.11 | 10.78 | 2.91 |

Following the Oligreen assay analysis, plasma aptamer concentrations were determined for the animals dosed with ARC1779 (SEQ ID NO 320) using a validated HPLC-based assay. The HPLC data were analyzed via noncompartmental and 2-compartment analysis using the program WinNonlin. Reanalysis of the monkey samples with a more sensitive HPLC method generated a concentration-times profile of ARC1779 (SEQ ID NO 320) to be biphasic showing both distribution and elimination phase Consistent with the results observed using the OliGreen assay, the HPLC-based results indicated the distribution half-life ($t_{1/2\alpha}$) was 1.4 h and a elimination half-life was 12.9 ($t_{1/2\beta}$) for ARC1779 (SEQ ID NO 320).

Example 4C

PK/PD of ARC1779 in Cynomolgus Macagues

-PK/PD correlation of ARC1779 was evaluated in three cynomolgus macaques after a single intravenous (IV) bolus dose at 0.5 mg/kg. ARC1779 levels in the plasma were correlated to PD effects of ARC1779 in inhibition of platelet function or prolongation of cutaneous bleeding time (CBT).

Following IV administration, blood was collected percutaneously at various time points post-dose for PK and PD analysis. PD effect of ARC1779 on platelet function was determined by PFA-100 assays and effect of ARC1779 on bleeding was measured by CBT time. In addition, plasma samples were analyzed by HPLC for quantitation of ARC1779 levels. PK parameter estimates were determined by 2-compartment analysis. The results are presented in FIG. 26.

The concentration-time profiles generated for individual monkeys showed predominantly the distribution phase of ARC1779 pharmacokinetics The distribution half-life was determined to be approximately 1.0 hour ($t_{1/2\alpha}$). The elimination half-life ($t_{1/2}\beta$), was not well-determined from the available data.

Figure 26:
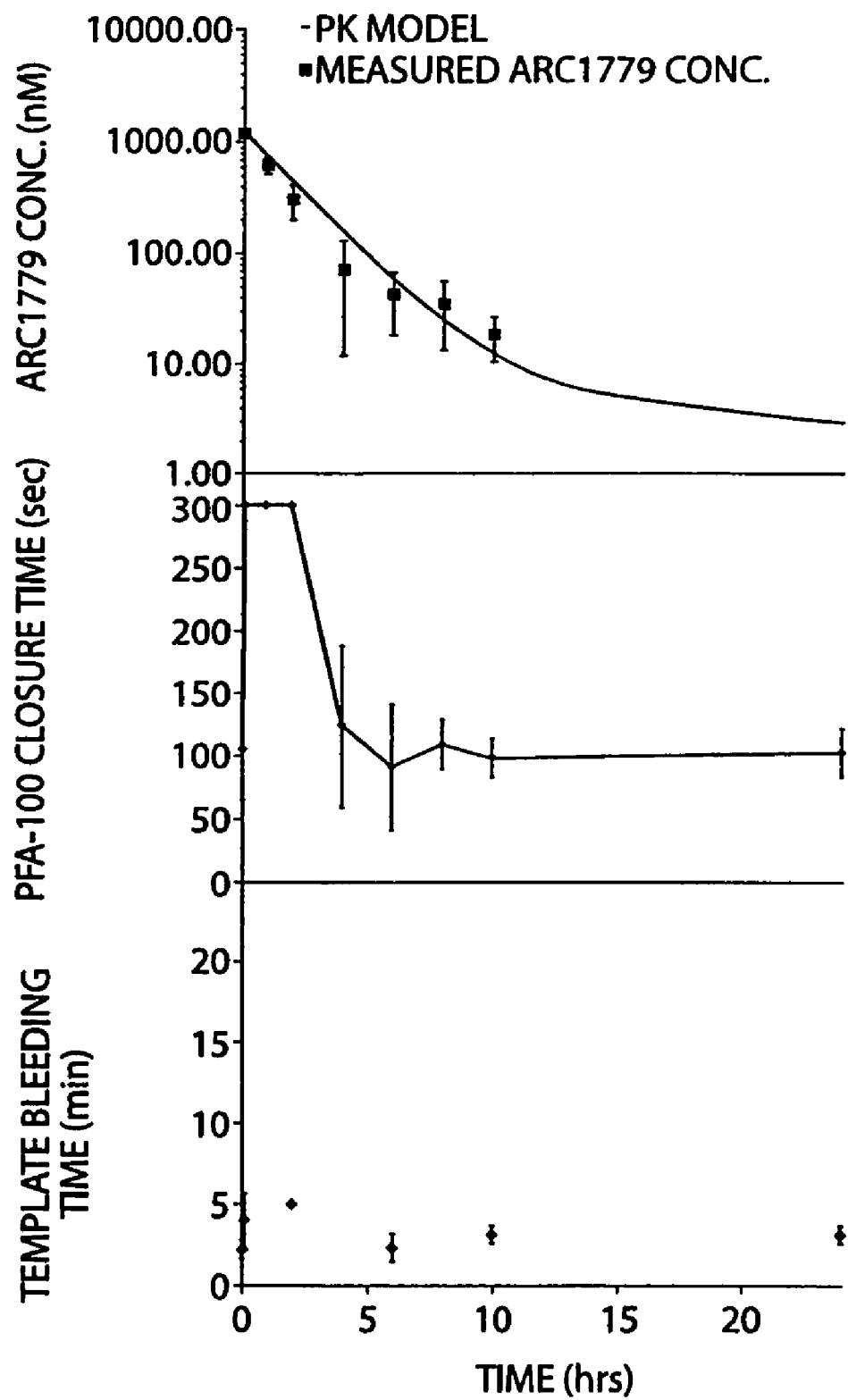
FIG. 26 is a graph showing the time points on the horizontal axis at which blood for testing was drawn from three cynomolgus macaques, ARC1779 (SEQ ID NO 320) plasma concentration (in nM) along the top third of the vertical axis, PFA-100 closure time (in seconds) on the middle third of the vertical axis, and the template or cutaneous bleeding time (in minutes) on the bottom third of the vertical axis. The average from all three animals for plasma aptamer concentration, PFA-100 closure time and cutaneous bleeding time is plotted on the top third, middle third and bottom third of the graph, respectively.

The PD effect of ARC1779 on platelet aggregation measured by the PFA-100 assay is shown in FIG. 26. When the plasma concentrations of ARC1779 were in excess of 300 nM, platelet function was inhibited as assessed by the PFA-100 instrument. However, when plasma aptamer concentrations decreased to approximately 77 nM, platelet function returned to normal.

As also seen in FIG. 26, the PD effect of ARC1779 on bleeding time prolongation was found to be minimal in these studies.

In summary, ARC1779 inhibited platelet function in vivo at a plasma concentration of approximately 300 nM. This in vivo concentration was approximately 3-fold higher than the observed concentration of aptamer necessary to inhibit platelet function in vitro. In contrast, even at high plasma concentrations (1000 nM), ARC1779 showed minimal effect on cutaneous bleeding time following single bolus dosing.

Example 5

Functional Animal Assays

In Examples 4 and 5 described herein, all mass based concentration data refers only to the molecular weight of the oligonucleotide portion of the aptamer, irrespective of the mass conferred by PEG conjugation.

Example 5A

Pharmacodynamics of ARC1779 in Cynomolgus Macaques

C. macaques were dosed at 0.5 mg/kg IV bolus with ARC1779 (SEQ ID NO 320). PFA-100 closure time, BIPA and cutaneous bleeding time ("CBT") were all measured as a function of time throughout the studies. BIPA and PFA-100 closure times were measured as described in previously in Example 3. Cutaneous bleeding times were measured using standard protocols described as follows.

A blood pressure cuff was applied to the biceps region of the forearm to be tested and inflated to maintain a constant pressure of 40 mmHg. Using a Surgicutt® Automated Incision Device (ITC, Edison, N.J.), a longitudinal incision was made over the lateral aspect of the volar surface of the forearm distal to the antecubital crease. A stopwatch was started at the time of incision. At 15-30 seconds post incision, the blood was wicked with Surgicutt® Bleeding Time Blotting Paper (ITC, Edison, N.J.) while avoiding direct contact with the incision. Every 15-30 seconds the blotting paper was rotated and re-blotted at a fresh site on the paper. The blotting was repeated until blood was no longer wicked onto the paper or for 30 minutes whichever came first. Bleeding time is determined to within 30 seconds of the time when blood is no longer wicked onto the paper.

Figures 27, 28:
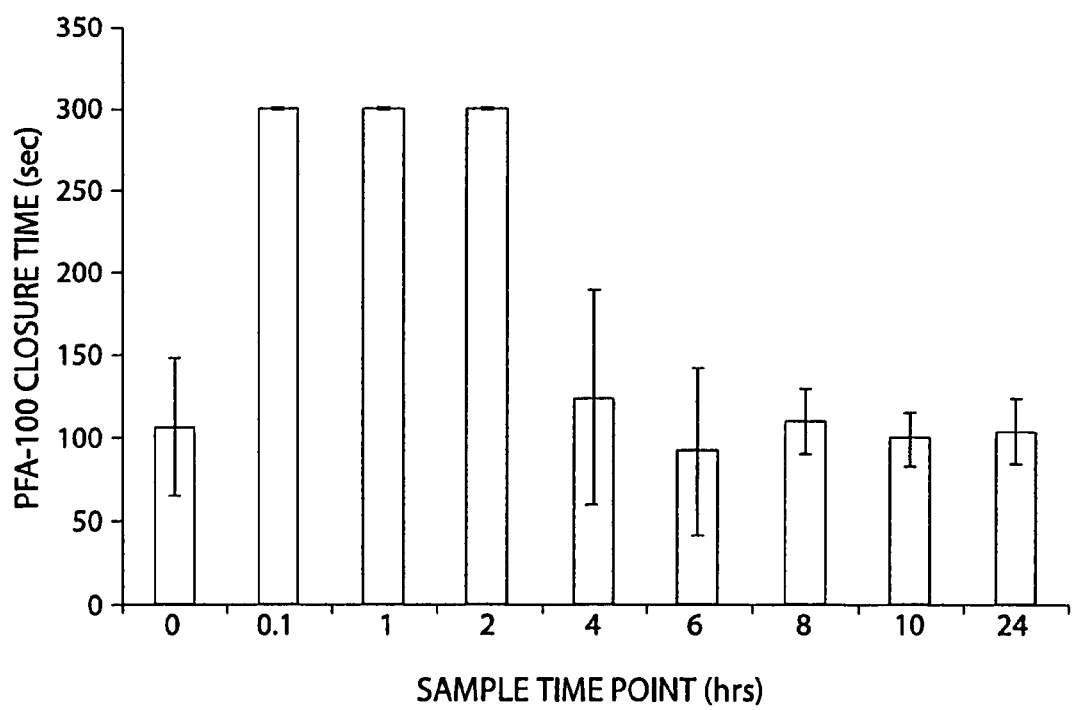
FIG. 27 is a table showing the cutaneous bleeding time (CBT) in minutes, raw BIPA data and PFA-100 closure time (sec) at various time points, shown in column 1, relative to ARC1779 (SEQ ID NO 320) dosing in three different cynomolgus macaques.
FIG. 28 is a graph showing the average PFA-100 closure time at various time points following ARC1779 (SEQ ID NO 320) dosing of C. macaques.
Figure 29:
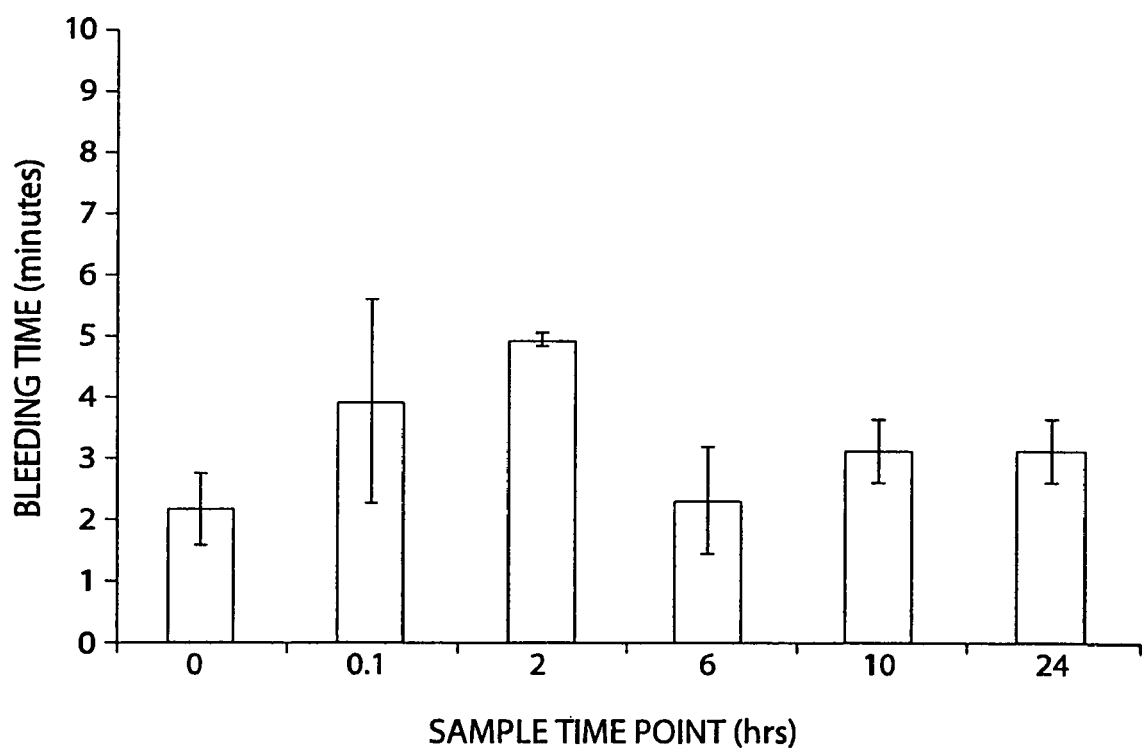
FIG. 29 is a graph showing the average bleeding time of the three ARC1779 (SEQ ID NO 320) treated macaques taken at various time points following dosing.
Figure 30:
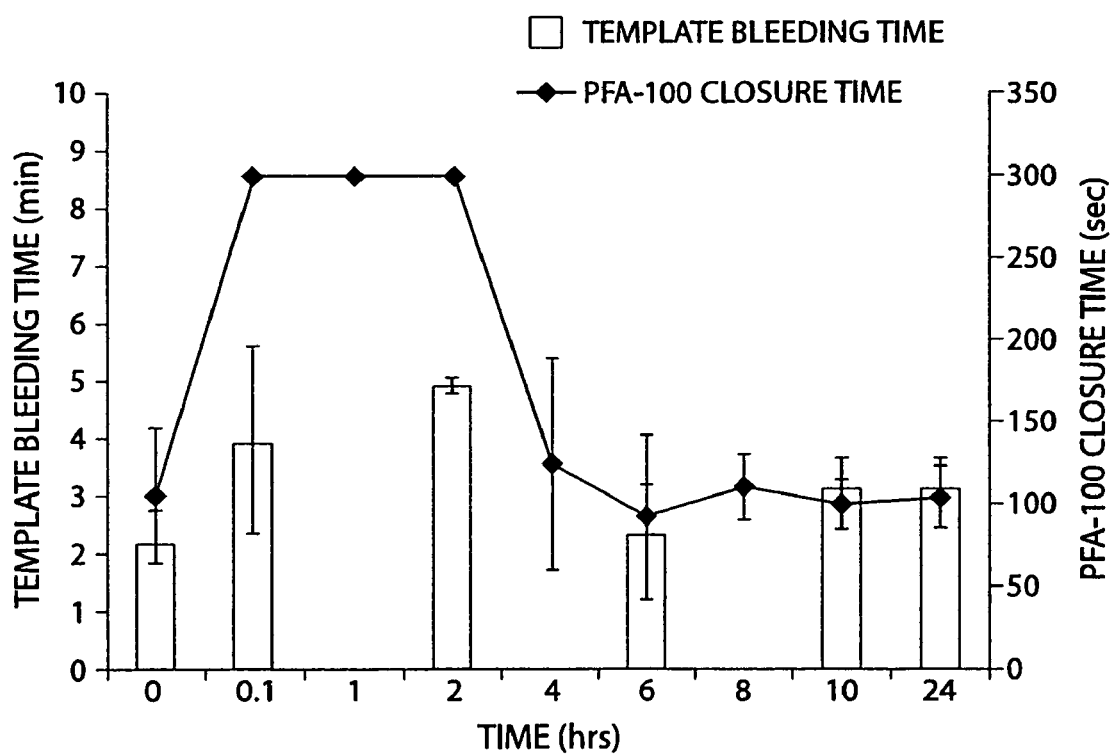
FIG. 30 is a graph correlating the average bleeding time in ARC1779 (SEQ ID NO 320) treated C. macaques (left vertical axis) to the PFA-100 closure time.

The table of FIG. 27 shows the cutaneous bleeding time in minutes, BIPA $IC_{90}$ in nM and PFA $IC_{95}$ in nM at various time points, shown in column 1, relative to ARC1779 (SEQ ID NO 320) dosing for three different animals. FIG. 28 shows a graph of the average PFA-100 closure time from the blood of three ARC1779 (SEQ ID NO 320) treated macaques taken at various time points following dosing. FIG. 29 shows the cutaneous bleeding time of the three ARC1779 (SEQ ID NO 320) treated macaques taken at various time points following dosing. FIG. 30 correlates the average cutaneous bleeding time in ARC1779 (SEQ ID NO 320) treated C. macaques (left vertical axis) to the PFA-100 closure time (right vertical axis). As shown FIGS. 27 to 30, at time points up to and including 2 hours, where BIPA and PFA-100 closure time were maximally inhibited, there is very little increase in cutaneous bleeding times. At concentrations of the anti-gpIIbIIIa antagonist Integrilin™ that yield similar inhibition of platelet aggregation ex vivo, template or cutaneous bleeding times are between 20 and 30 minutes. See, e.g. Phillips, D. R. and Scarborough, R. M., Am J Cardiol, 80(4A): 11B-20B (1997). While not wishing to be bound by any particular theory, these data are consistent with and supportive of our hypothesis that an anti-vWF A1 domain aptamer antagonist will block platelet activity in vivo by blocking platelets from binding to vWF immobilized at sites of vascular damage without inhibiting platelet function and thus without increasing cutaneous bleeding times.

Example 5B

Assessment of ARC1779 in a Cynomolgus Macaque Electrolytic Thrombosis Model

A study was performed to test the efficacy of ARC1779 (SEQ ID NO 320) in inhibiting intra-arterial thrombosis in a well documented non-human primate electrolytic thrombosis model. See, e.g., Rote et al., Stroke, 1994: 25, 1223-1233. Thirteen cynomolgus monkeys were divided into four groups and assigned to a treatment regimen as indicated in table 30 below.

TABLE 32

Electrolytic Thrombosis Study Design

| Group Number | Number of Animals | Test Article | Dose (mg/kg) | Dose Regime | Dose Volume | Necropsy Day |
|---|---|---|---|---|---|---|
| 1 | 3 | Vehicle (saline) | DVE to Group 3 | IV bolus, ~15 minutes prior to initiation of electrical injury followed by continuous infusion on Day 0 | ≦10 mL | Day 0 |
| 2 | 1 | ReoPro ™ (chimeric 7E3) | 0.25 mg/kg | IV bolus, once on Day 0, ~15 minutes prior to initiation of electrical injury | | |
| 3 | 5 | ARC1779 | 0.61 mg/kg bolus + 0.0037 mg/kg/min infusion | IV bolus,, ~15 minutes prior to initiation of electrical injury, followed by continuous infusion on Day 0 | | |
| 4 | 4 | ReoPro ™ (chimeric 7E3) | 0.25 mg/kg bolus + 0.125 µg/kg/min infusion | IV bolus,, ~15 minutes prior to initiation of electrical injury, followed by continuous infusion on Day 0 | | |

DVE = Dose Volume Equivalent,
IV = Intravenous

Each animal was anesthetized prior to surgical preparation, intubated and maintained in anesthesia with isoflurane inhalant anesthetic to effect delivered through a volume-regulated respirator. An intravenous catheter was also placed in a peripheral vein for administration of lactated Ringer's solution during the procedure.

A catheter was placed in the femoral artery of each animal for continuous monitoring of arterial blood pressure. Similarly a catheter was placed in the femoral vein for blood sample collection. Each carotid artery was instrumented with a Doppler flow probe connected to a flow meter. The flow probes were placed around the artery at a point proximal to the insertion of the intra-arterial electrode and stenosis. The stenosis was placed around each carotid artery so that the blood flow was reduced by approximately 50% to 60% without altering the mean blood flow. Blood flow in the carotid arteries was monitored and recorded continuously throughout the observation periods.

Electrolytic injury to the intimal surface of each carotid artery was accomplished via placement of an intravascular electrode. Each electrode was connected to the positive pole of a constant current device and cathode connected to a distant subcutaneous site. Continuous current was delivered to each vessel for a period of 3 hours or for 30 minutes after complete occlusion, whichever was shorter.

Figure 31:
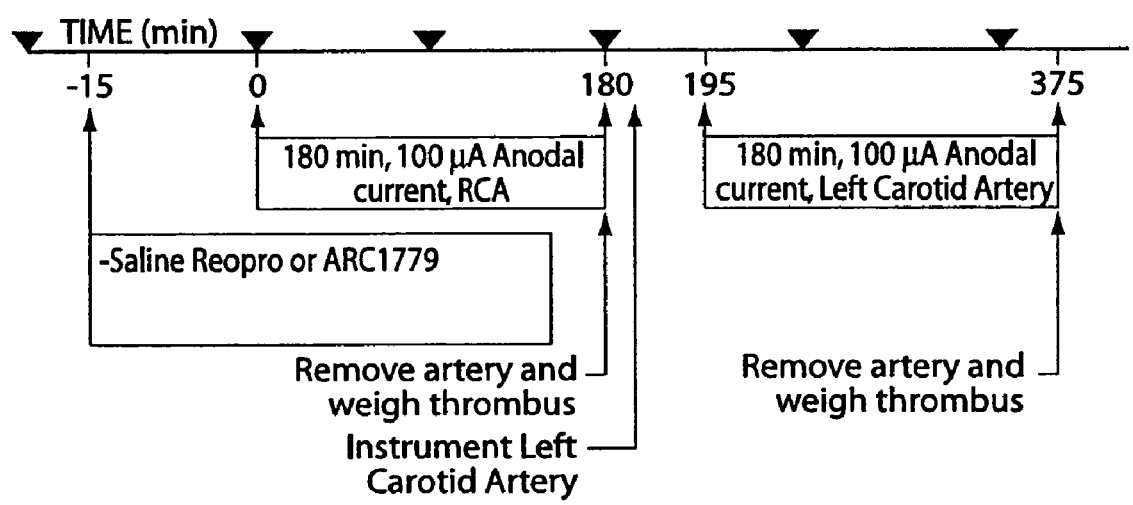
FIG. 31 is a schematic depicting the blood sample collection schedule used in the assessment of ARC1779 (SEQ ID NO 320) in the cynomolgus monkey electrolytic thrombosis model.

Once the electrodes were placed on the right carotid artery ("RCA") the animal was administered the test article as indicated in Table 32 above. Approximately 15 minutes after test article administration, the electrical current was applied at 100 µA. Blood samples and CBT measurements were collected at the time points specified in Blood Sample Collection Schedule as indicated in FIG. 31. The current was terminated ~30 minutes after the blood flow signal remained stable at zero flow (which indicates an occlusive thrombus had been formed at the site) or after 180 minutes of electrical stimulation. Approximately 195 minutes after the test article was administered, the left carotid artery ("LCA") had electrical current administered in a similar fashion as previously described for the RCA. After termination of all surgical procedures and sample collection each animal was euthanized.

Figure 32:
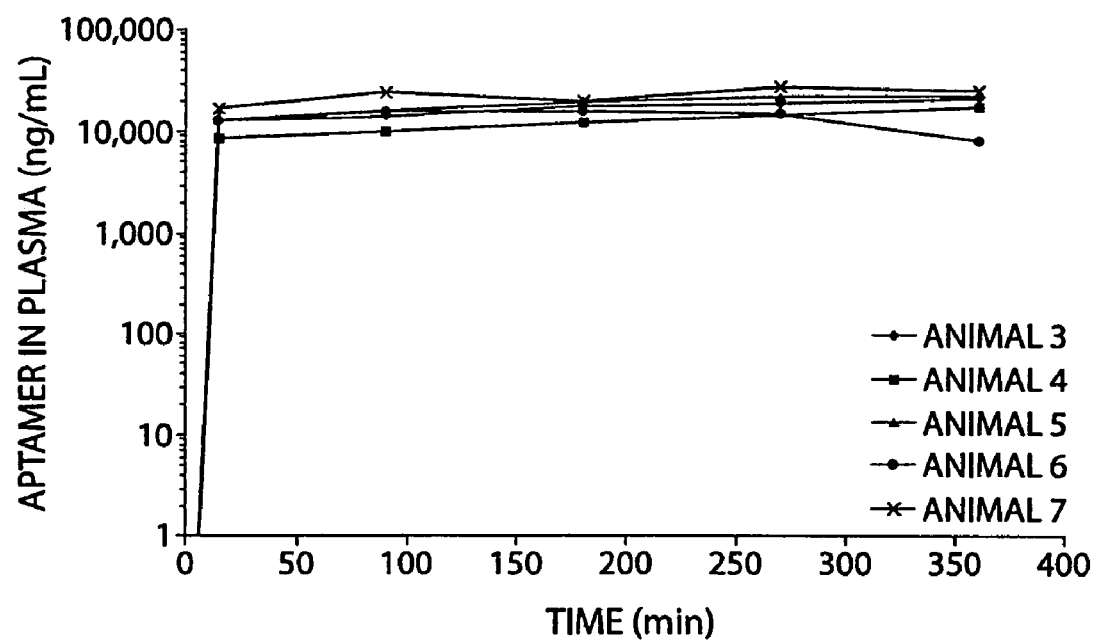
FIG. 32 is graph of ARC1779 (SEQ ID NO 320) plasma concentration (vertical axis) as a function of time in each cynomolgus monkey of treatment group 3 tested in the electrolytic thrombosis model.
Figure 33:
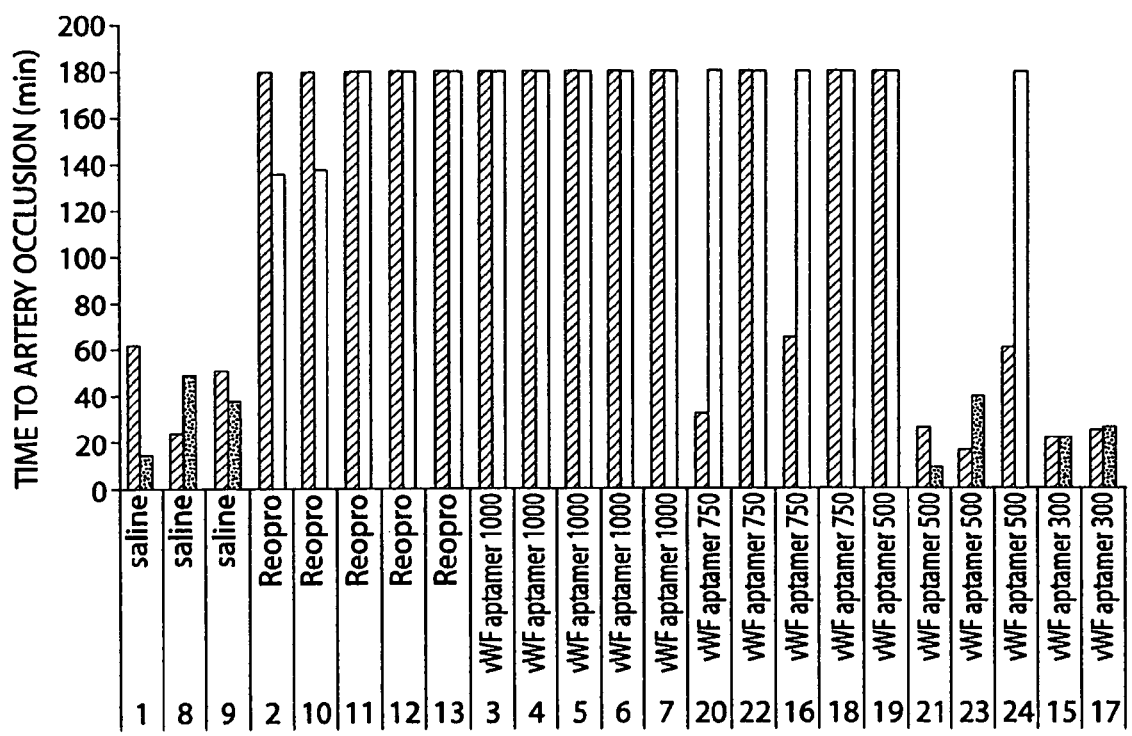
FIG. 33 is a graph of the time to occlusion of the right (hatched bar) or left carotid artery (indicated by a solid bar) in each cynomolgus macaque from each treatment group tested in the cynomolgus monkey electrolytic thrombosis model. Bar pairs 1, 8 and 9 indicate treatment group 1 (vehicle only) Bar pairs 2, 10, 11, 12 and 13 indicates treatment groups 2 and 4 (ReoPro). Bar pairs 3 to 7 indicate treatment group 3 (1000 nM aptamer plasma concentration target group). Bar pairs 20, 22, 16, and 18 indicate treatment group 7 (750 nM plasma aptamer concentration target group). Bar pairs 19, 21, 23 and 24 indicate treatment group 6 (500 nM plasma aptamer concentration target group). Bar pairs 15 and 17 indicate treatment group 5 (300 nM plasma aptamer concentration target group)

The ARC1779 (SEQ ID NO 320) plasma concentration (as measured by HPLC) over time for each animal in treatment group 3 is depicted in FIG. 32. The time to occlusion measured via Doppler flow for each treatment group is indicated in FIG. 33. As can be determined from FIG. 33, ARC1779 (SEQ ID NO 320) inhibited thrombus formation during sequential 180-minute electrical injuries to the carotid arteries of the cynomolgus monkeys in this animal thrombosis model.

Example 5C

Assessment of ARC1779 at Various Doses in a Cynomolgus Macague Electrolytic Thrombosis Model The study described in Example 5B above was extended to test the efficacy of ARC1779 (SEQ ID NO 320) in inhibiting intra-arterial thrombosis in the non-human primate electrolytic thrombosis model at lower aptamer dosage levels.

An additional 10 cynomolgus monkeys (2.5 to 3.5 kg) were divided into treatment groups 5 to 7 and were treated according the regimen indicated in Table 33 below.

TABLE 33

Study Design

| Group Number | No. of Animals | Test Article | Dosage Level | Dose Volume | Dosing Regimen | Necropsy Day |
|---|---|---|---|---|---|---|
| 1 | 3 | Vehicle (Saline) | DVE to Group 3 | ≦10 mL | IV bolus, ~15 minutes prior to initiation of electrical injury, followed by continuous infusion on Day 0 | Day 0 |
| 2 | 1 | Abciximab (ReoPro) | 0.25 mg/kg | | IV bolus, once on Day 0 ~15 minutes prior to initiation of electrical injury | |
| 4 | 5 | Abciximab (ReoPro) | 0.25 mg/kg bolus and 0.125 µg/kg/min | | IV bolus, ~15 minutes prior to initiation of electrical injury, followed by continuous infusion on Day 0 | |

TABLE 33-continued

Study Design

| Group Number | No. of Animals | Test Article | Dosage Level | Dose Volume | Dosing Regimen | Necropsy Day |
|---|---|---|---|---|---|---|
| 3 | 5 | ARC1779 | 0.61 mg/kg bolus and 0.0037 mg/kg/min infusion (1000 nM) | ≦10 mL | IV bolus, ~15 minutes prior to initiation of electrical injury, followed by continuous infusion on Day 0 | Day 0 |
| 5 | 2 | ARC1779 | 0.123 mg/kg bolus and 0.001 mg/kg/min infusion (300 nM) | ≦10 mL | IV bolus, ~15 minutes prior to initiation of electrical injury, followed by continuous infusion on Day 0 | Day 0 |
| 6 | 4 | ARC1779 | 0.2 mg/kg bolus and 0.00165 mg/kg/min infusion (500 nM) | ≦10 mL | IV bolus, ~15 minutes prior to initiation of electrical injury, followed by continuous infusion on Day 0 | Day 0 |
| 7 | 4 | ARC1779 | 0.298 mg/kg bolus and 0.00248 mg/kg/min infusion (750 nM) | ≦10 mL | IV bolus, ~15 minutes prior to initiation of electrical injury, followed by continuous infusion on Day 0 | Day 0 |

The animal procedure for each treatment group in Table 33 was conducted as reported for the animals in Example 5B. The time to occlusion measured via Doppler flow for each treatment group is indicated in FIG. 33.

Figure 34:
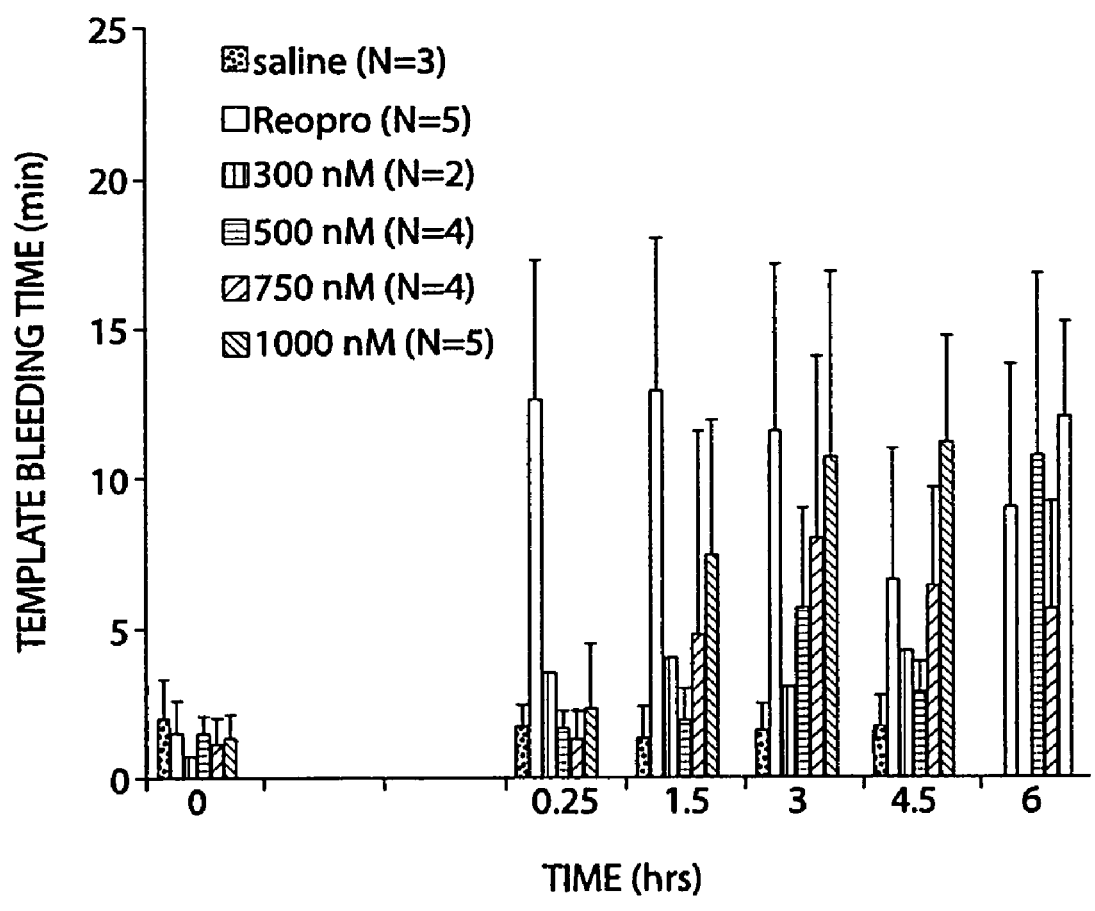
FIG. 34 is a graph showing the cutaneous bleed time in minutes (vertical axis) of the various cynomolgous treatment groups in the electrical injury model taken at the time points shown on the horizontal axis.

Without any platelet antagonist therapy (control animals) 100% of carotid arteries develop occlusive thrombi within 60 minutes. In contrast, only 20% or arteries developed occlusive thrombi in animals treated with Reopro. In the ARC1779 treatment groups at infusion rates targeted to reach constant plasma levels of 1000 nM, 750 nM, 500 nM and 300 nM, 0%, 25%, 63% and 100% of carotid arteries developed occlusive thrombi. In addition to occlusive thrombus formation, we also assessed the effect of ARC1779 on cutaneous bleeding times which is shown in FIG. 34. As can be seen in FIG. 34, at some doses and/or time points in this animal model prolonged CBT was observed, while at other doses and time points CBT was not prolonged.

The invention having now been described by way of written description and example, those of skill in the art will recognize that the invention can be practiced in a variety of embodiments and that the description and examples above are for purposes of illustration and not limitation of the following claims.

What is claimed is:

1. An aptamer comprising SEQ ID NO: 320.
2. The aptamer of claim 1, wherein the aptamer binds to von Willebrand Factor.
3. The aptamer of claim 2, wherein the von Willebrand Factor is human von Willebrand Factor.
4. The aptamer of claim 2, wherein the aptamer inhibits the function of von Willebrand Factor.
5. The aptamer of claim 2, wherein the aptamer modulates von Willebrand Factor-mediated platelet adhesion, activation and/or aggregation.
6. An aptamer that binds to von Willebrand Factor comprising the nucleic acid sequence of SEQ ID NO: 320.
7. The aptamer of claim 6, wherein the von Willebrand Factor is human von Willebrand Factor.
8. The aptamer of claim 6, wherein the aptamer inhibits the function of von Willebrand Factor.
9. The aptamer of claim 6, wherein the aptamer modulates von Willebrand Factor-mediated platelet adhesion, activation and/or aggregation.
10. An aptamer that binds to von Willebrand Factor, wherein the aptamer modulates von Willebrand Factor-mediated platelet adhesion, activation and/or aggregation, wherein the aptamer comprises the nucleic acid sequence of SEQ ID NO: 320.
11. The aptamer of claim 10, wherein the von Willebrand Factor is human von Willebrand Factor.
12. The aptamer of claim 10, wherein the aptamer inhibits the function of von Willebrand Factor.
13. An aptamer comprising:
N-(methoxy-polyethyleneglycol)-6-aminohexylyl-(1→5')-2'-OMe-guanylyl-(3'→5')-2'-OMe-cytidylyl-(3'→5')-2-OMe-guanylyl-(3'→5')-2'-OMe-uracylyl-(3'→5')-2'-deoxyguanylyl-(3'→5')-2'-deoxycytidylyl-(3'→5')-2'-deoxyadenylyl-(3'→5')-2'-OMe-guanylyl-(3'→5')-2'-OMe-uracylyl-(3'→5')-2'-OMe-guanylyl-(3'→5')-2'-OMe-cytidylyl-(3'→5')-2'-OMe-cytidylyl-(3'→5')-2'-OMe-uracylyl-(3'→5')-2'-OMe-uracylyl-(3' 5')-2'-OMe-cytidylyl-(3'→5')-2'-OMe-guanylyl-(3'→5')-2'-OMe-guanylyl-(3'→5')-2'-OMe-cytidylyl-(3'→5')-2'-deoxycytidylyl-(3'→5')-2'-OMe-P-thioguanylyl-(3'→5')-2'-deoxythymidylyl-(3'→5')-2'-OMe-guanylyl-(3'→5')-2'-deoxycytidylyl-(3'→5')-2'-deoxyguanylyl-(3'→5')-2'-deoxyguanylyl-(3'→5')-2'-deoxythymidylyl-(3'→5')-2'-OMe-guanylyl-(3'→5')-2'-OMe-cytidylyl-(3'→5')-2'-deoxycytidylyl-(3'→5')-2'-OMe-uracylyl-(3'→5')-2'-deoxycytidylyl-(3'→5')-2'-deoxycytidylyl-(3'→5')-2'-OMe-guanylyl-(3'→5')-2'-OMe-uracylyl-(3'→5')-2'-deoxycytidylyl-(3'→5')-2'-OMe-adenylyl-(3'→5')-2'-OMe-cytidylyl-(3'→5')-2'-OMe-guanylyl-(3'→5')-2'-OMe-cytidylyl-(3'→5')-(3'→3')-2'-deoxythymidine, 40-sodium salt, wherein the methoxy polyethyleneglycol comprises a molecular weight of 20 kDa.
14. The aptamer of claim 13, wherein the aptamer binds to von Willebrand Factor.
15. The aptamer of claim 14, wherein the von Willebrand Factor is human von Willebrand Factor.
16. The aptamer of claim 14, wherein the aptamer inhibits the function of von Willebrand Factor.
17. The aptamer of claim 14, wherein the aptamer modulates von Willebrand Factor-mediated platelet adhesion, activation and/or aggregation.
18. An aptamer that binds to and inhibits the function of von Willebrand Factor, wherein the aptamer modulates von Willebrand Factor-mediated platelet adhesion, activation and/or aggregation, wherein the aptamer comprises the nucleic acid sequence of SEQ ID NO: 320.
19. The aptamer of claim 18, wherein the von Willebrand Factor is human von Willebrand Factor.

* * * * *

SEQUENCE LISTING

```
<160> NUMBER OF SEQ ID NOS: 327

<210> SEQ ID NO 1
<211> LENGTH: 93
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (25)..(53)
<223> OTHER INFORMATION: n may be any nucleotide (A, T, C or G)
<220> FEATURE:
<221> NAME/KEY: misc_feature
<222> LOCATION: (54)..(54)
<223> OTHER INFORMATION: n is a, c, g, or t

<400> SEQUENCE: 1
catcgatgct agtcgtaacg atccnnnnnn nnnnnnnnnn nnnnnnnnnn nnnncgagaa       60
cgttctctcc tctccctata gtgagtcgta tta                                   93

<210> SEQ ID NO 2
<211> LENGTH: 92
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (24)..(53)
<223> OTHER INFORMATION: n may be any nucleotide (A, T, C or G)
```

<400> SEQUENCE: 2

```
catgcatcgc gactgactag ccgnnnnnnn nnnnnnnnnn nnnnnnnnnn nnngtagaac    60
gttctctcct ctccctatag tgagtcgtat ta                                  92
```

<210> SEQ ID NO 3
<211> LENGTH: 92
<212> TYPE: DNA
<213> ORGANISM: Artificial Sequence
<220> FEATURE:
<223> OTHER INFORMATION: Description of Artificial Sequence: chemically synthesized
<220> FEATURE:
<221> NAME/KEY: misc_feature
<222> LOCATION: (24)..(53)
<223> OTHER INFORMATION: n may be any nucleotide (A, T, C or G)

<400> SEQUENCE: 3

```
catcgatcga tcgatcgaca gcgnnnnnnn nnnnnnnnnn nnnnnnnnnn nnngtagaac    60
gttctctcct ctccctatag tgagtcgtat ta                                  92
```

<210> SEQ ID NO 4
<211> LENGTH: 213
<212> TYPE: PRT
<213> ORGANISM: Artificial Sequence
<220> FEATURE:
<223> OTHER INFORMATION: chemically synthesized

<400> SEQUENCE: 4

```
Met Gly His His His His His His Glu Pro Pro Leu His Asp Phe Tyr
1               5                   10                  15

Cys Ser Arg Leu Leu Asp Leu Val Phe Leu Leu Asp Gly Ser Ser Arg
            20                  25                  30

Leu Ser Glu Ala Glu Phe Glu Val Leu Lys Ala Phe Val Val Asp Met
        35                  40                  45

Met Glu Gln Leu Arg Ile Ser Gln Lys Trp Val Arg Val Ala Val Val
    50                  55                  60

Glu Tyr His Asp Gly Ser His Ala Tyr Ile Gly Leu Lys Asp Arg Lys
65                  70                  75                  80

Arg Pro Ser Glu Leu Arg Arg Ile Ala Ser Gln Val Lys Tyr Ala Gly
                85                  90                  95

Ser Gln Val Ala Ser Thr Ser Glu Val Leu Lys Tyr Thr Leu Phe Gln
            100                 105                 110

Ile Phe Ser Lys Ile Asp Arg Pro Glu Ala Ser Arg Ile Ala Leu Leu
        115                 120                 125

Leu Met Ala Ser Gln Glu Pro Gln Arg Met Ser Arg Asn Phe Val Arg
    130                 135                 140

Tyr Val Gln Gly Leu Lys Lys Lys Val Ile Val Ile Pro Val Gly
145                 150                 155                 160

Ile Gly Pro His Ala Asn Leu Lys Gln Ile Arg Leu Ile Glu Lys Gln
                165                 170                 175

Ala Pro Glu Asn Lys Ala Phe Val Leu Ser Ser Val Asp Glu Leu Glu
            180                 185                 190

Gln Gln Arg Asp Glu Ile Val Ser Tyr Leu Cys Asp Leu Ala Pro Glu
        195                 200                 205

Ala Pro Pro Pro Thr
    210
```

<210> SEQ ID NO 5

```
<211> LENGTH: 246
<212> TYPE: PRT
<213> ORGANISM: Artificial Sequence
<220> FEATURE:
<223> OTHER INFORMATION: chemically synthesized

<400> SEQUENCE: 5

Met Arg Gly Ser His His His His His Gly Ser Gln Glu Pro Gly
1               5                   10                  15

Gly Leu Val Val Pro Pro Thr Asp Ala Pro Val Ser Pro Thr Thr Leu
                20                  25                  30

Tyr Val Glu Asp Ile Ser Glu Pro Pro Leu His Asp Phe Tyr Cys Ser
                35                  40                  45

Arg Leu Leu Asp Leu Val Phe Leu Leu Asp Gly Ser Ser Arg Leu Ser
        50                  55                  60

Glu Ala Glu Phe Glu Val Leu Lys Ala Phe Val Val Asp Met Met Glu
65                  70                  75                  80

Arg Leu Arg Ile Ser Gln Lys Trp Val Arg Val Ala Val Val Glu Tyr
                85                  90                  95

His Asp Gly Ser His Ala Tyr Ile Gly Leu Lys Asp Arg Lys Arg Pro
                100                 105                 110

Ser Glu Leu Arg Arg Ile Ala Ser Gln Val Lys Tyr Ala Gly Ser Gln
                115                 120                 125

Val Ala Ser Thr Ser Glu Val Leu Lys Tyr Thr Leu Phe Gln Ile Phe
        130                 135                 140

Ser Lys Ile Asp Arg Pro Glu Ala Ser Arg Ile Ala Leu Leu Leu Met
145                 150                 155                 160

Ala Ser Gln Glu Pro Gln Arg Met Ser Arg Asn Phe Val Arg Tyr Val
                165                 170                 175

Gln Gly Leu Lys Lys Lys Lys Val Ile Val Ile Pro Val Gly Ile Gly
                180                 185                 190

Pro His Ala Asn Leu Lys Gln Ile Arg Leu Ile Glu Lys Gln Ala Pro
        195                 200                 205

Glu Asn Lys Ala Phe Val Leu Ser Ser Val Asp Glu Leu Glu Gln Gln
    210                 215                 220

Arg Asp Glu Ile Val Ser Tyr Leu Cys Asp Leu Ala Pro Glu Ala Pro
225                 230                 235                 240

Pro Pro Thr Leu Pro Pro
                245

<210> SEQ ID NO 6
<211> LENGTH: 213
<212> TYPE: PRT
<213> ORGANISM: Artificial Sequence
<220> FEATURE:
<223> OTHER INFORMATION: chemically synthesized

<400> SEQUENCE: 6

Met Gly His His His His His Glu Pro Pro Leu His Asp Phe Tyr
1               5                   10                  15

Trp Ser Asn Leu Met Asp Leu Val Phe Leu Leu Asp Gly Ser Ala Gln
                20                  25                  30

Leu Ser Glu Ala Glu Phe Gly Val Leu Lys Ala Phe Val Val Ser Val
        35                  40                  45

Met Glu Arg Leu His Ile Ser Gln Lys Arg Ile Arg Val Ala Val Val
        50                  55                  60

Glu Tyr His Asp Gly Ser His Ser Tyr Ile Ser Leu Lys Asp Arg Lys
65                  70                  75                  80
```

```
Arg Pro Ser Glu Leu Arg Arg Ile Ala Ser Gln Val Lys Tyr Ala Gly
                85                  90                  95

Gly Pro Val Ala Ser Thr Ser Glu Val Leu Lys Tyr Thr Leu Phe His
            100                 105                 110

Ile Phe Ser Asn Val Asp Arg Pro Glu Ala Ser Arg Ile Ala Leu Leu
            115                 120                 125

Leu Ser Ala Ser Gln Glu Thr Pro Arg Met Val Arg Asn Leu Val Arg
130                 135                 140

Tyr Ala Gln Gly Leu Lys Lys Glu Lys Val Ile Val Ile Pro Val Gly
145                 150                 155                 160

Ile Gly Pro His Val Ser Leu Arg Gln Ile His Leu Ile Glu Lys Gln
                165                 170                 175

Ala Pro Glu Asn Lys Ala Phe Val Leu Ser Gly Val Asp Glu Leu Glu
            180                 185                 190

Gln Arg Arg Asp Glu Ile Ile Ser Tyr Leu Cys Asp Leu Gly Pro Glu
            195                 200                 205

Ala Pro Val Pro Thr
            210

<210> SEQ ID NO 7
<211> LENGTH: 2813
<212> TYPE: PRT
<213> ORGANISM: Artificial Sequence
<220> FEATURE:
<223> OTHER INFORMATION: chemically synthesized

<400> SEQUENCE: 7

Met Ile Pro Ala Arg Phe Ala Gly Val Leu Leu Ala Leu Ala Leu Ile
1               5                   10                  15

Leu Pro Gly Thr Leu Cys Ala Glu Gly Thr Arg Gly Arg Ser Ser Thr
                20                  25                  30

Ala Arg Cys Ser Leu Phe Gly Ser Asp Phe Val Asn Thr Phe Asp Gly
            35                  40                  45

Ser Met Tyr Ser Phe Ala Gly Tyr Cys Ser Tyr Leu Leu Ala Gly Gly
50                  55                  60

Cys Gln Lys Arg Ser Phe Ser Ile Ile Gly Asp Phe Gln Asn Gly Lys
65                  70                  75                  80

Arg Val Ser Leu Ser Val Tyr Leu Gly Glu Phe Phe Asp Ile His Leu
                85                  90                  95

Phe Val Asn Gly Thr Val Thr Gln Gly Asp Gln Arg Val Ser Met Pro
            100                 105                 110

Tyr Ala Ser Lys Gly Leu Tyr Leu Glu Thr Glu Ala Gly Tyr Tyr Lys
            115                 120                 125

Leu Ser Gly Glu Ala Tyr Gly Phe Val Ala Arg Ile Asp Gly Ser Gly
130                 135                 140

Asn Phe Gln Val Leu Leu Ser Asp Arg Tyr Phe Asn Lys Thr Cys Gly
145                 150                 155                 160

Leu Cys Gly Asn Phe Asn Ile Phe Ala Glu Asp Asp Phe Met Thr Gln
                165                 170                 175

Glu Gly Thr Leu Thr Ser Asp Pro Tyr Asp Phe Ala Asn Ser Trp Ala
            180                 185                 190

Leu Ser Ser Gly Glu Gln Trp Cys Glu Arg Ala Ser Pro Pro Ser Ser
            195                 200                 205

Ser Cys Asn Ile Ser Ser Gly Glu Met Gln Lys Gly Leu Trp Glu Gln
            210                 215                 220
```

```
Cys Gln Leu Leu Lys Ser Thr Ser Val Phe Ala Arg Cys His Pro Leu
225                 230                 235                 240

Val Asp Pro Glu Pro Phe Val Ala Leu Cys Glu Lys Thr Leu Cys Glu
            245                 250                 255

Cys Ala Gly Gly Leu Glu Cys Ala Cys Pro Ala Leu Leu Glu Tyr Ala
        260                 265                 270

Arg Thr Cys Ala Gln Glu Gly Met Val Leu Tyr Gly Trp Thr Asp His
    275                 280                 285

Ser Ala Cys Ser Pro Val Cys Pro Ala Gly Met Glu Tyr Arg Gln Cys
290                 295                 300

Val Ser Pro Cys Ala Arg Thr Cys Gln Ser Leu His Ile Asn Glu Met
305                 310                 315                 320

Cys Gln Glu Arg Cys Val Asp Gly Cys Ser Cys Pro Glu Gly Gln Leu
            325                 330                 335

Leu Asp Glu Gly Leu Cys Val Glu Ser Thr Glu Cys Pro Cys Val His
        340                 345                 350

Ser Gly Lys Arg Tyr Pro Pro Gly Thr Ser Leu Ser Arg Asp Cys Asn
    355                 360                 365

Thr Cys Ile Cys Arg Asn Ser Gln Trp Ile Cys Ser Asn Glu Glu Cys
370                 375                 380

Pro Gly Glu Cys Leu Val Thr Gly Gln Ser His Phe Lys Ser Phe Asp
385                 390                 395                 400

Asn Arg Tyr Phe Thr Phe Ser Gly Ile Cys Gln Tyr Leu Leu Ala Arg
            405                 410                 415

Asp Cys Gln Asp His Ser Phe Ser Ile Val Ile Glu Thr Val Gln Cys
        420                 425                 430

Ala Asp Asp Arg Asp Ala Val Cys Thr Arg Ser Val Thr Val Arg Leu
    435                 440                 445

Pro Gly Leu His Asn Ser Leu Val Lys Leu Lys His Gly Ala Gly Val
450                 455                 460

Ala Met Asp Gly Gln Asp Ile Gln Leu Pro Leu Leu Lys Gly Asp Leu
465                 470                 475                 480

Arg Ile Gln His Thr Val Thr Ala Ser Val Arg Leu Ser Tyr Gly Glu
            485                 490                 495

Asp Leu Gln Met Asp Trp Asp Gly Arg Gly Arg Leu Leu Val Lys Leu
        500                 505                 510

Ser Pro Val Tyr Ala Gly Lys Thr Cys Gly Leu Cys Gly Asn Tyr Asn
    515                 520                 525

Gly Asn Gln Gly Asp Asp Phe Leu Thr Pro Ser Gly Leu Ala Glu Pro
530                 535                 540

Arg Val Glu Asp Phe Gly Asn Ala Trp Lys Leu His Gly Asp Cys Gln
545                 550                 555                 560

Asp Leu Gln Lys Gln His Ser Asp Pro Cys Ala Leu Asn Pro Arg Met
            565                 570                 575

Thr Arg Phe Ser Glu Glu Ala Cys Ala Val Leu Thr Ser Pro Thr Phe
        580                 585                 590

Glu Ala Cys His Arg Ala Val Ser Pro Leu Pro Tyr Leu Arg Asn Cys
    595                 600                 605

Arg Tyr Asp Val Cys Ser Cys Ser Asp Gly Arg Glu Cys Leu Cys Gly
610                 615                 620

Ala Leu Ala Ser Tyr Ala Ala Ala Cys Ala Gly Arg Gly Val Arg Val
625                 630                 635                 640

Ala Trp Arg Glu Pro Gly Arg Cys Glu Leu Asn Cys Pro Lys Gly Gln
            645                 650                 655
```

```
Val Tyr Leu Gln Cys Gly Thr Pro Cys Asn Leu Thr Cys Arg Ser Leu
            660                 665                 670

Ser Tyr Pro Asp Glu Glu Cys Asn Glu Ala Cys Leu Glu Gly Cys Phe
            675                 680                 685

Cys Pro Pro Gly Leu Tyr Met Asp Glu Arg Gly Asp Cys Val Pro Lys
690                 695                 700

Ala Gln Cys Pro Cys Tyr Tyr Asp Gly Glu Ile Phe Gln Pro Glu Asp
705                 710                 715                 720

Ile Phe Ser Asp His His Thr Met Cys Tyr Cys Glu Asp Gly Phe Met
                725                 730                 735

His Cys Thr Met Ser Gly Val Pro Gly Ser Leu Leu Pro Asp Ala Val
            740                 745                 750

Leu Ser Ser Pro Leu Ser His Arg Ser Lys Arg Ser Leu Ser Cys Arg
            755                 760                 765

Pro Pro Met Val Lys Leu Val Cys Pro Ala Asp Asn Leu Arg Ala Glu
770                 775                 780

Gly Leu Glu Cys Thr Lys Thr Cys Gln Asn Tyr Asp Leu Glu Cys Met
785                 790                 795                 800

Ser Met Gly Cys Val Ser Gly Cys Leu Cys Pro Pro Gly Met Val Arg
                805                 810                 815

His Glu Asn Arg Cys Val Ala Leu Glu Arg Cys Pro Cys Phe His Gln
            820                 825                 830

Gly Lys Glu Tyr Ala Pro Gly Glu Thr Val Lys Ile Gly Cys Asn Thr
            835                 840                 845

Cys Val Cys Arg Asp Arg Lys Trp Asn Cys Thr Asp His Val Cys Asp
850                 855                 860

Ala Thr Cys Ser Thr Ile Gly Met Ala His Tyr Leu Thr Phe Asp Gly
865                 870                 875                 880

Leu Lys Tyr Leu Phe Pro Gly Glu Cys Gln Tyr Val Leu Val Gln Asp
                885                 890                 895

Tyr Cys Gly Ser Asn Pro Gly Thr Phe Arg Ile Leu Val Gly Asn Lys
            900                 905                 910

Gly Cys Ser His Pro Ser Val Lys Cys Lys Arg Val Thr Ile Leu
            915                 920                 925

Val Glu Gly Gly Glu Ile Glu Leu Phe Asp Gly Glu Val Asn Val Lys
930                 935                 940

Arg Pro Met Lys Asp Glu Thr His Phe Glu Val Val Glu Ser Gly Arg
945                 950                 955                 960

Tyr Ile Ile Leu Leu Leu Gly Lys Ala Leu Ser Val Val Trp Asp Arg
                965                 970                 975

His Leu Ser Ile Ser Val Val Leu Lys Gln Thr Tyr Gln Glu Lys Val
            980                 985                 990

Cys Gly Leu Cys Gly Asn Phe Asp  Gly Ile Gln Asn Asn  Asp Leu Thr
            995                 1000                1005

Ser Ser  Asn Leu Gln Val Glu  Glu Asp Pro Val Asp  Phe Gly Asn
    1010                1015                1020

Ser Trp  Lys Val Ser Ser Gln  Cys Ala Asp Thr Arg  Lys Val Pro
    1025                1030                1035

Leu Asp  Ser Ser Pro Ala Thr  Cys His Asn Asn Ile  Met Lys Gln
    1040                1045                1050

Thr Met  Val Asp Ser Ser Cys  Arg Ile Leu Thr Ser  Asp Val Phe
    1055                1060                1065

Gln Asp  Cys Asn Lys Leu Val  Asp Pro Glu Pro Tyr  Leu Asp Val
```

```
                 1070                1075                1080
Cys Ile Tyr Asp Thr Cys Ser Cys Glu Ser Ile Gly Asp Cys Ala
    1085                1090                1095

Cys Phe Cys Asp Thr Ile Ala Ala Tyr Ala His Val Cys Ala Gln
    1100                1105                1110

His Gly Lys Val Val Thr Trp Arg Thr Ala Thr Leu Cys Pro Gln
    1115                1120                1125

Ser Cys Glu Glu Arg Asn Leu Arg Glu Asn Gly Tyr Glu Cys Glu
    1130                1135                1140

Trp Arg Tyr Asn Ser Cys Ala Pro Ala Cys Gln Val Thr Cys Gln
    1145                1150                1155

His Pro Glu Pro Leu Ala Cys Pro Val Gln Cys Val Glu Gly Cys
    1160                1165                1170

His Ala His Cys Pro Pro Gly Lys Ile Leu Asp Glu Leu Leu Gln
    1175                1180                1185

Thr Cys Val Asp Pro Glu Asp Cys Pro Val Cys Glu Val Ala Gly
    1190                1195                1200

Arg Arg Phe Ala Ser Gly Lys Lys Val Thr Leu Asn Pro Ser Asp
    1205                1210                1215

Pro Glu His Cys Gln Ile Cys His Cys Asp Val Val Asn Leu Thr
    1220                1225                1230

Cys Glu Ala Cys Gln Glu Pro Gly Gly Leu Val Val Pro Pro Thr
    1235                1240                1245

Asp Ala Pro Val Ser Pro Thr Thr Leu Tyr Val Glu Asp Ile Ser
    1250                1255                1260

Glu Pro Pro Leu His Asp Phe Tyr Cys Ser Arg Leu Leu Asp Leu
    1265                1270                1275

Val Phe Leu Leu Asp Gly Ser Ser Arg Leu Ser Glu Ala Glu Phe
    1280                1285                1290

Glu Val Leu Lys Ala Phe Val Val Asp Met Met Glu Arg Leu Arg
    1295                1300                1305

Ile Ser Gln Lys Trp Val Arg Val Ala Val Val Glu Tyr His Asp
    1310                1315                1320

Gly Ser His Ala Tyr Ile Gly Leu Lys Asp Arg Lys Arg Pro Ser
    1325                1330                1335

Glu Leu Arg Arg Ile Ala Ser Gln Val Lys Tyr Ala Gly Ser Gln
    1340                1345                1350

Val Ala Ser Thr Ser Glu Val Leu Lys Tyr Thr Leu Phe Gln Ile
    1355                1360                1365

Phe Ser Lys Ile Asp Arg Pro Glu Ala Ser Arg Ile Ala Leu Leu
    1370                1375                1380

Leu Met Ala Ser Gln Glu Pro Gln Arg Met Ser Arg Asn Phe Val
    1385                1390                1395

Arg Tyr Val Gln Gly Leu Lys Lys Lys Lys Val Ile Val Ile Pro
    1400                1405                1410

Val Gly Ile Gly Pro His Ala Asn Leu Lys Gln Ile Arg Leu Ile
    1415                1420                1425

Glu Lys Gln Ala Pro Glu Asn Lys Ala Phe Val Leu Ser Ser Val
    1430                1435                1440

Asp Glu Leu Glu Gln Gln Arg Asp Glu Ile Val Ser Tyr Leu Cys
    1445                1450                1455

Asp Leu Ala Pro Glu Ala Pro Pro Pro Thr Leu Pro Pro His Met
    1460                1465                1470
```

```
Ala Gln Val Thr Val Gly Pro Gly Leu Leu Val Ser Thr Leu
1475                1480                1485

Gly Pro Lys Arg Asn Ser Met Val Leu Asp Val Ala Phe Val Leu
1490                1495                1500

Glu Gly Ser Asp Lys Ile Gly Glu Ala Asp Phe Asn Arg Ser Lys
1505                1510                1515

Glu Phe Met Glu Glu Val Ile Gln Arg Met Asp Val Gly Gln Asp
1520                1525                1530

Ser Ile His Val Thr Val Leu Gln Tyr Ser Tyr Met Val Thr Val
1535                1540                1545

Glu Tyr Pro Phe Ser Glu Ala Gln Ser Lys Gly Asp Ile Leu Gln
1550                1555                1560

Arg Val Arg Glu Ile Arg Tyr Gln Gly Gly Asn Arg Thr Asn Thr
1565                1570                1575

Gly Leu Ala Leu Arg Tyr Leu Ser Asp His Ser Phe Leu Val Ser
1580                1585                1590

Gln Gly Asp Arg Glu Gln Ala Pro Asn Leu Val Tyr Met Val Thr
1595                1600                1605

Gly Asn Pro Ala Ser Asp Glu Ile Lys Arg Leu Pro Gly Asp Ile
1610                1615                1620

Gln Val Val Pro Ile Gly Val Gly Pro Asn Ala Asn Val Gln Glu
1625                1630                1635

Leu Glu Arg Ile Gly Trp Pro Asn Ala Pro Ile Leu Ile Gln Asp
1640                1645                1650

Phe Glu Thr Leu Pro Arg Glu Ala Pro Asp Leu Val Leu Gln Arg
1655                1660                1665

Cys Cys Ser Gly Glu Gly Leu Gln Ile Pro Thr Leu Ser Pro Ala
1670                1675                1680

Pro Asp Cys Ser Gln Pro Leu Asp Val Ile Leu Leu Leu Asp Gly
1685                1690                1695

Ser Ser Ser Phe Pro Ala Ser Tyr Phe Asp Glu Met Lys Ser Phe
1700                1705                1710

Ala Lys Ala Phe Ile Ser Lys Ala Asn Ile Gly Pro Arg Leu Thr
1715                1720                1725

Gln Val Ser Val Leu Gln Tyr Gly Ser Ile Thr Thr Ile Asp Val
1730                1735                1740

Pro Trp Asn Val Val Pro Glu Lys Ala His Leu Leu Ser Leu Val
1745                1750                1755

Asp Val Met Gln Arg Glu Gly Gly Pro Ser Gln Ile Gly Asp Ala
1760                1765                1770

Leu Gly Phe Ala Val Arg Tyr Leu Thr Ser Glu Met His Gly Ala
1775                1780                1785

Arg Pro Gly Ala Ser Lys Ala Val Val Ile Leu Val Thr Asp Val
1790                1795                1800

Ser Val Asp Ser Val Asp Ala Ala Ala Asp Ala Ala Arg Ser Asn
1805                1810                1815

Arg Val Thr Val Phe Pro Ile Gly Ile Gly Asp Arg Tyr Asp Ala
1820                1825                1830

Ala Gln Leu Arg Ile Leu Ala Gly Pro Ala Gly Asp Ser Asn Val
1835                1840                1845

Val Lys Leu Gln Arg Ile Glu Asp Leu Pro Thr Met Val Thr Leu
1850                1855                1860

Gly Asn Ser Phe Leu His Lys Leu Cys Ser Gly Phe Val Arg Ile
1865                1870                1875
```

```
Cys Met Asp Glu Asp Gly Asn Glu Lys Arg Pro Gly Asp Val Trp
    1880            1885                1890
Thr Leu Pro Asp Gln Cys His Thr Val Thr Cys Gln Pro Asp Gly
    1895            1900                1905
Gln Thr Leu Leu Lys Ser His Arg Val Asn Cys Asp Arg Gly Leu
    1910            1915                1920
Arg Pro Ser Cys Pro Asn Ser Gln Ser Pro Val Lys Val Glu Glu
    1925            1930                1935
Thr Cys Gly Cys Arg Trp Thr Cys Pro Cys Val Cys Thr Gly Ser
    1940            1945                1950
Ser Thr Arg His Ile Val Thr Phe Asp Gly Gln Asn Phe Lys Leu
    1955            1960                1965
Thr Gly Ser Cys Ser Tyr Val Leu Phe Gln Asn Lys Glu Gln Asp
    1970            1975                1980
Leu Glu Val Ile Leu His Asn Gly Ala Cys Ser Pro Gly Ala Arg
    1985            1990                1995
Gln Gly Cys Met Lys Ser Ile Glu Val Lys His Ser Ala Leu Ser
    2000            2005                2010
Val Glu Leu His Ser Asp Met Glu Val Thr Val Asn Gly Arg Leu
    2015            2020                2025
Val Ser Val Pro Tyr Val Gly Gly Asn Met Glu Val Asn Val Tyr
    2030            2035                2040
Gly Ala Ile Met His Glu Val Arg Phe Asn His Leu Gly His Ile
    2045            2050                2055
Phe Thr Phe Thr Pro Gln Asn Asn Glu Phe Gln Leu Gln Leu Ser
    2060            2065                2070
Pro Lys Thr Phe Ala Ser Lys Thr Tyr Gly Leu Cys Gly Ile Cys
    2075            2080                2085
Asp Glu Asn Gly Ala Asn Asp Phe Met Leu Arg Asp Gly Thr Val
    2090            2095                2100
Thr Thr Asp Trp Lys Thr Leu Val Gln Glu Trp Thr Val Gln Arg
    2105            2110                2115
Pro Gly Gln Thr Cys Gln Pro Ile Leu Glu Glu Gln Cys Leu Val
    2120            2125                2130
Pro Asp Ser Ser His Cys Gln Val Leu Leu Leu Pro Leu Phe Ala
    2135            2140                2145
Glu Cys His Lys Val Leu Ala Pro Ala Thr Phe Tyr Ala Ile Cys
    2150            2155                2160
Gln Gln Asp Ser Cys His Gln Glu Gln Val Cys Glu Val Ile Ala
    2165            2170                2175
Ser Tyr Ala His Leu Cys Arg Thr Asn Gly Val Cys Val Asp Trp
    2180            2185                2190
Arg Thr Pro Asp Phe Cys Ala Met Ser Cys Pro Pro Ser Leu Val
    2195            2200                2205
Tyr Asn His Cys Glu His Gly Cys Pro Arg His Cys Asp Gly Asn
    2210            2215                2220
Val Ser Ser Cys Gly Asp His Pro Ser Glu Gly Cys Phe Cys Pro
    2225            2230                2235
Pro Asp Lys Val Met Leu Glu Gly Ser Cys Val Pro Glu Glu Ala
    2240            2245                2250
Cys Thr Gln Cys Ile Gly Glu Asp Gly Val Gln His Gln Phe Leu
    2255            2260                2265
Glu Ala Trp Val Pro Asp His Gln Pro Cys Gln Ile Cys Thr Cys
```

```
                     2270              2275              2280

Leu Ser Gly Arg Lys Val Asn Cys Thr Thr Gln Pro Cys Pro Thr
    2285              2290              2295

Ala Lys Ala Pro Thr Cys Gly Leu Cys Glu Val Ala Arg Leu Arg
    2300              2305              2310

Gln Asn Ala Asp Gln Cys Cys Pro Glu Tyr Glu Cys Val Cys Asp
    2315              2320              2325

Pro Val Ser Cys Asp Leu Pro Pro Val Pro His Cys Glu Arg Gly
    2330              2335              2340

Leu Gln Pro Thr Leu Thr Asn Pro Gly Glu Cys Arg Pro Asn Phe
    2345              2350              2355

Thr Cys Ala Cys Arg Lys Glu Glu Cys Lys Arg Val Ser Pro Pro
    2360              2365              2370

Ser Cys Pro Pro His Arg Leu Pro Thr Leu Arg Lys Thr Gln Cys
    2375              2380              2385

Cys Asp Glu Tyr Glu Cys Ala Cys Asn Cys Val Asn Ser Thr Val
    2390              2395              2400

Ser Cys Pro Leu Gly Tyr Leu Ala Ser Thr Ala Thr Asn Asp Cys
    2405              2410              2415

Gly Cys Thr Thr Thr Thr Cys Leu Pro Asp Lys Val Cys Val His
    2420              2425              2430

Arg Ser Thr Ile Tyr Pro Val Gly Gln Phe Trp Glu Glu Gly Cys
    2435              2440              2445

Asp Val Cys Thr Cys Thr Asp Met Glu Asp Ala Val Met Gly Leu
    2450              2455              2460

Arg Val Ala Gln Cys Ser Gln Lys Pro Cys Glu Asp Ser Cys Arg
    2465              2470              2475

Ser Gly Phe Thr Tyr Val Leu His Glu Gly Glu Cys Cys Gly Arg
    2480              2485              2490

Cys Leu Pro Ser Ala Cys Glu Val Val Thr Gly Ser Pro Arg Gly
    2495              2500              2505

Asp Ser Gln Ser Ser Trp Lys Ser Val Gly Ser Gln Trp Ala Ser
    2510              2515              2520

Pro Glu Asn Pro Cys Leu Ile Asn Glu Cys Val Arg Val Lys Glu
    2525              2530              2535

Glu Val Phe Ile Gln Gln Arg Asn Val Ser Cys Pro Gln Leu Glu
    2540              2545              2550

Val Pro Val Cys Pro Ser Gly Phe Gln Leu Ser Cys Lys Thr Ser
    2555              2560              2565

Ala Cys Cys Pro Ser Cys Arg Cys Glu Arg Met Glu Ala Cys Met
    2570              2575              2580

Leu Asn Gly Thr Val Ile Gly Pro Gly Lys Thr Val Met Ile Asp
    2585              2590              2595

Val Cys Thr Thr Cys Arg Cys Met Val Gln Val Gly Val Ile Ser
    2600              2605              2610

Gly Phe Lys Leu Glu Cys Arg Lys Thr Thr Cys Asn Pro Cys Pro
    2615              2620              2625

Leu Gly Tyr Lys Glu Glu Asn Asn Thr Gly Glu Cys Cys Gly Arg
    2630              2635              2640

Cys Leu Pro Thr Ala Cys Thr Ile Gln Leu Arg Gly Gly Gln Ile
    2645              2650              2655

Met Thr Leu Lys Arg Asp Glu Thr Leu Gln Asp Gly Cys Asp Thr
    2660              2665              2670
```

His Phe Cys Lys Val Asn Glu Arg Gly Glu Tyr Phe Trp Glu Lys
2675                2680                2685

Arg Val Thr Gly Cys Pro Pro Phe Asp Glu His Lys Cys Leu Ala
2690                2695                2700

Glu Gly Gly Lys Ile Met Lys Ile Pro Gly Thr Cys Cys Asp Thr
2705                2710                2715

Cys Glu Glu Pro Glu Cys Asn Asp Ile Thr Ala Arg Leu Gln Tyr
2720                2725                2730

Val Lys Val Gly Ser Cys Lys Ser Glu Val Glu Val Asp Ile His
2735                2740                2745

Tyr Cys Gln Gly Lys Cys Ala Ser Lys Ala Met Tyr Ser Ile Asp
2750                2755                2760

Ile Asn Asp Val Gln Asp Gln Cys Ser Cys Cys Ser Pro Thr Arg
2765                2770                2775

Thr Glu Pro Met Gln Val Ala Leu His Cys Thr Asn Gly Ser Val
2780                2785                2790

Val Tyr His Glu Val Leu Asn Ala Met Glu Cys Lys Cys Ser Pro
2795                2800                2805

Arg Lys Cys Ser Lys
2810

<210> SEQ ID NO 8
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (18)..(57)
<223> OTHER INFORMATION: n may be any nucleotide (A, T, C or G)

<400> SEQUENCE: 8
ggagcgcact cagccacnnn nnnnnnnnnn nnnnnnnnnn nnnnnnnttt         60
cgacctctct gctagc                                              76

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 9
taatacgact cactatagga gcgcactcag ccac                          34

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 10
gctagcagag aggtcgaaa                                           19

<210> SEQ ID NO 11
<211> LENGTH: 76
<212> TYPE: DNA
<213> ORGANISM: Artificial Sequence

```
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 11
ggagcgcacu cagccacaga gcccugagug uaugaucgcc uagaucuauc gaugcuuuuu      60
cgaccucucu gcuagc                                                     76

<210> SEQ ID NO 12
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'OH (ribo); all
      pyrimidines (U and C) are 2'-fluoro

<400> SEQUENCE: 12
ggagcgcacu cagccacaac acuaaugggg aaaguucaag gauucuugac cggugcguuu      60
cgaccucucu gcuagc                                                     76

<210> SEQ ID NO 13
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 13
ggagcgcacu cagccacuaa cgguugaucu caggacuaaa uagucaacaa ggaugcguuu      60
cgaccucucu gcuagc                                                     76

<210> SEQ ID NO 14
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 14
ggagcgcacu cagccacaga gcccugagug uaugaucgcc gagaucuauc gaugcuuuuu      60
cgaccucucu gcuagc                                                     76

<210> SEQ ID NO 15
<211> LENGTH: 76
<212> TYPE: DNA
<213> ORGANISM: Artificial Sequence
```

```
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 15
ggagcgcacu cagccacgcu cgguggggaa auuuuagccu aauuggcuac uugugcguuu    60
cgaccucucu gcuagc                                                   76

<210> SEQ ID NO 16
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 16
ggagcgcacu cagccacggu ggucagucag ugauaugauu aaguucagcu guggcuguuu    60
cgaccucucu gcuagc                                                   76

<210> SEQ ID NO 17
<211> LENGTH: 75
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 17
ggagcgcacu cagccacacc gaggcuggau aucuacgaga ggaagugcug cuugaauuuc    60
gaccucucug cuagc                                                    75

<210> SEQ ID NO 18
<211> LENGTH: 75
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 18
ggagcgcacu cagccacacu gaggcuggau aucuacgaga ggaagugcug cuuggauuuc    60
gaccucucug cuagc                                                    75

<210> SEQ ID NO 19
<211> LENGTH: 75
<212> TYPE: DNA
<213> ORGANISM: Artificial Sequence
```

```
<220> FEATURE:
<223> OTHER INFORMATION: Description of Artificial Sequence: chemically
      synthesized
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 19
ggagcgcacu cagccacugg uccuuagcua guuguacuag cgacgcguuc aggugguuuc    60
gaccucucug cuagc                                                    75

<210> SEQ ID NO 20
<211> LENGTH: 75
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 20
ggagcgcacu cagccacuaa cgguugaucu caggacuaau agucaacaag gaugcguuuc    60
gaccucucug cuagc                                                    75

<210> SEQ ID NO 21
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 21
ggagcgcacu cagccacuaa cggcugaucu caggacuaaa uagucaacaa ggaugcguuu    60
cgaccucucu gcuagc                                                   76

<210> SEQ ID NO 22
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 22
ggagcgcacu cagccacccu gucgucuuuu gguagucagc caaaagcuag uugguuguuu    60
cgaccucucu gcuagc                                                   76

<210> SEQ ID NO 23
<211> LENGTH: 76
<212> TYPE: DNA
<213> ORGANISM: Artificial Sequence
```

```
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 23
ggagcgcacu cagccacccu cgcaagcauu uuaagaauga cuugugccgc uggcuguuuu      60
cgaccucucu gcuagc                                                      76

<210> SEQ ID NO 24
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 24
ggagcgcacu cagccacuuu acggugaaag ucucucgggg uuccgaguua cggugcguuu      60
cgaccucucu gcuagc                                                      76

<210> SEQ ID NO 25
<211> LENGTH: 76
<212> TYPE: DNA
<213> ORGANISM: Artificial Sequence
<220> FEATURE:
<223> OTHER INFORMATION: all purines (A and G) are 2'-OH (ribo); all
      pyrimidines (U and C) are 2'-fluoro
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 25
ggagcgcacu cagccacggu aacauuguuu ccggcgauuc uuugaacgcc gucgugguuu      60
cgaccucucu gcuagc                                                      76

<210> SEQ ID NO 26
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 26
ggagcgcacu cagccaccag uuaugcuggc uuuggucuuu gacugucuga guguucguuu      60
cgaccucucu gcuagc                                                      76

<210> SEQ ID NO 27
<211> LENGTH: 76
<212> TYPE: DNA
<213> ORGANISM: Artificial Sequence
```

```
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all pyrines (A and G) are 2'-OH; all
      pyrimidines (U and C) are 2'-fluoro

<400> SEQUENCE: 27
ggagcgcacu cagccacugg ggcugaucuc gcacgauagu ucgugucaag gaugcguuuu    60
cgaccucucu gcuagc                                                   76

<210> SEQ ID NO 28
<211> LENGTH: 75
<212> TYPE: DNA
<213> ORGANISM: Artificial Sequence
<220> FEATURE:
<223> OTHER INFORMATION: all purines (A and G) are 2'-OH (ribo); all
      pyrimidines (U and C) are 2'-fluoro
<220> FEATURE:
<221> NAME/KEY: modified_base
<222> LOCATION: (1)..(75)
<223> OTHER INFORMATION: all purines (A and G) are 2'-OH (ribo); all
      pyrimidines (U and C) are 2'-fluoro

<400> SEQUENCE: 28
ggagcgcacu cagccacgcc cacgucaaau uauagucuac uuugaugugc ccgugguuuc    60
gaccucucug cuagc                                                    75

<210> SEQ ID NO 29
<211> LENGTH: 73
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(73)
<223> OTHER INFORMATION: all purines (A and G) are 2'-OH (ribo); all
      pyrimidines (U and C) are 2'-fluoro

<400> SEQUENCE: 29
ggagcgcacu cagccacgcu guacacugau guuguaacau guaccccug gcuguuucga     60 ccucucugcu agc                                                      73

<210> SEQ ID NO 30
<211> LENGTH: 76
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(76)
<223> OTHER INFORMATION: all purines (A and G) are 2'-OH (ribo); all
      pyrimidines (U and C) are 2'-fluoro

<400> SEQUENCE: 30
ggagcgcacu cagccacuuc gacuuucaug ucugaagucc cugcagugcg agagacguuu    60
cgaccucucu gcuagc                                                   76

<210> SEQ ID NO 31
<211> LENGTH: 76
<212> TYPE: DNA
<213> ORGANISM: Artificial Sequence
```

<220> FEATURE:
<223> OTHER INFORMATION: Description of Artificial Sequence: chemically
     synthesized

<400> SEQUENCE: 31
ggagcgcact cagccacagt tctgtcggtg atgaattagc gcgagagctg tgggacgttt    60
cgacctctct gctagc                                                   76

<210> SEQ ID NO 32
<211> LENGTH: 75
<212> TYPE: DNA
<213> ORGANISM: Artificial Sequence
<220> FEATURE:
<223> OTHER INFORMATION: Description of Artificial Sequence: chemically
     synthesized

<400> SEQUENCE: 32
ggagcgcact cagccacaaa cggacggtga tggattaacg cgggtttatg gcaaggtttc    60
gacctctctg ctagc                                                    75

<210> SEQ ID NO 33
<211> LENGTH: 76
<212> TYPE: DNA
<213> ORGANISM: Artificial Sequence
<220> FEATURE:
<223> OTHER INFORMATION: Description of Artificial Sequence: chemically
     synthesized

<400> SEQUENCE: 33
ggagcgcact cagccacggc acgacggtga tggattagcg cggtgtcggt ggtgtcattt    60
cgacctctct gctagc                                                   76

<210> SEQ ID NO 34
<211> LENGTH: 76
<212> TYPE: DNA
<213> ORGANISM: Artificial Sequence
<220> FEATURE:
<223> OTHER INFORMATION: Description of Artificial Sequence: chemically
     synthesized

<400> SEQUENCE: 34
ggagcgcact cagccactca aggggtcgc gtggggacga agggttgcag tgtgtcgttt    60
cgacctctct gctagc                                                   76

<210> SEQ ID NO 35
<211> LENGTH: 76
<212> TYPE: DNA
<213> ORGANISM: Artificial Sequence
<220> FEATURE:
<223> OTHER INFORMATION: Description of Artificial Sequence: chemically
     synthesized

<400> SEQUENCE: 35
ggagcgcact cagccacggc acgacggtga tgaattagcg cggtgtcggt ggtgtcattt    60
cgacctctct gctagc                                                   76

<210> SEQ ID NO 36
<211> LENGTH: 76
<212> TYPE: DNA
<213> ORGANISM: Artificial Sequence
<220> FEATURE:
<223> OTHER INFORMATION: Description of Artificial Sequence: chemically
     synthesized

<400> SEQUENCE: 36
ggagcgcact cagccacgga gcgtcggtga tggattagcg cggctccgtg gtacacattt    60
cgacctctct gctagc                                                    76

<210> SEQ ID NO 37
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 37
ggagcgcact cagccacgga gcgtcggtga tggattagcg cggttccgtg gtacaccttt    60
cgacctctct gctagc                                                    76

<210> SEQ ID NO 38
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 38
ggagcgcact cagccacggc atgacggtga tgaattagcg cggtgtcggt ggtgtcattt    60
cgacctctct gctagc                                                    76

<210> SEQ ID NO 39
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 39
ggagcgcact cagccacgga gcgtcggtga tggattagcg cggctccgtg gtacgccttt    60
cgacctctct gctagc                                                    76

<210> SEQ ID NO 40
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 40
ggagcgcact cagccacgga gcgtcggtga tggattagcg cggctccgtg gtacaccttt    60
cgacctctct gctagc                                                    76

<210> SEQ ID NO 41
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 41
ggagcgcact cagccacggc acgacggtga tgaattagcg cggtgtcggt ggtgttattt    60
cgacctctct gctagc                                                    76

-continued

<210> SEQ ID NO 42
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 42
ggagcgcact cagccaccac ggggacgggt agggcgggcg aggtggtggc attagcgttt      60
cgacctctct gctagc                                                     76

<210> SEQ ID NO 43
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 43
ggagcgcact cagccacagt tctgtcggtg atgaattagc gcgggagctg tgggacgttt      60
cgacctctct gctagc                                                     76

<210> SEQ ID NO 44
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 44
ggagcgcact cagccacggg gtgggtagac ggcgggtatg tggctggtgt cgaagggttt      60
cgacctctct gctagc                                                     76

<210> SEQ ID NO 45
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 45
ggagcgcact cagccacgac ggtgatggat tagcgcggtg gagaagatgc gctgttgttt      60
cgacctctct gctagc                                                     76

<210> SEQ ID NO 46
<211> LENGTH: 75
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 46
ggagcgcact cagccacgac ggtgatggat tagcgcggtg gatcttaacg tgcgagtttc      60
gacctctctg ctagc                                                      75

<210> SEQ ID NO 47
<211> LENGTH: 77
<212> TYPE: DNA
<213> ORGANISM: Artificial Sequence

```
<220> FEATURE:
<223> OTHER INFORMATION: Description of Artificial Sequence: chemically
      synthesized

<400> SEQUENCE: 47
ggagcgcact cagccactga agggtaagga cgaggagggt atacagtgtg cgcgtgtatt      60
tcgacctctc tgctagc                                                    77

<210> SEQ ID NO 48
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 48
ggagcgcact cagccacaac tggttgtcgg tgatggcatt aacgcggacc aggcatgttt      60
cgacctctct gctagc                                                     76

<210> SEQ ID NO 49
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 49
ggagcgcact cagccacacg acattggcgg gttgtaatta ccacgcatgg ctgtttgttt      60
cgacctctct gctagc                                                     76

<210> SEQ ID NO 50
<211> LENGTH: 76
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 50
ggagcgcact cagccactgt tgccgacggt gatgtattaa cgcgggcaac gttggtgttt      60
cgacctctct gctagc                                                     76

<210> SEQ ID NO 51
<211> LENGTH: 80
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (21)..(60)
<223> OTHER INFORMATION: n may be any nucleotide (A, T, G, or C)

<400> SEQUENCE: 51
ctacctacga tctgactagc nnnnnnnnnn nnnnnnnnnn nnnnnnnnnn nnnnnnnnnn      60
gcttactctc atgtagttcc                                                 80

<210> SEQ ID NO 52
<211> LENGTH: 20
<212> TYPE: DNA
<213> ORGANISM: Artificial Sequence
<220> FEATURE:
```

```
<223> OTHER INFORMATION: Description of Artificial Sequence: chemically
      synthesized primer

<400> SEQUENCE: 52
ctacctacga tctgactagc                                                      20

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 53
aggaactaca tgagagtaag c                                                    21

<210> SEQ ID NO 54
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 54
ctacctacga tctgactagc ggaatgagaa tgctgatgga ttgctcaggt ctgctggctg          60
cttactctca tgtagttcc                                                       79

<210> SEQ ID NO 55
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 55
ctacctacga tctgactagc ggaatgagaa tgctggtgga ttgctcaggt ctgctggctg          60
cttactctca tgtagttcc                                                       79

<210> SEQ ID NO 56
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 56
ctacctacga tctgactagc ggaacgagaa tgctgatgga ttgctcaggt ctgctggctg          60
cttactctca tgtagttcc                                                       79

<210> SEQ ID NO 57
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 57
ctacctacga tctgactagc ggaataagaa tgctgatgga ttgctcaggt ctgctggctg          60
cttactctca tgtagttcc                                                       79
```

<210> SEQ ID NO 58
<211> LENGTH: 79
<212> TYPE: DNA
<213> ORGANISM: Artificial Sequence
<220> FEATURE:
<223> OTHER INFORMATION: Description of Artificial Sequence: chemically
synthesized

<400> SEQUENCE: 58
ctacctacga tctgactagc ggaatgagaa tgttgatgga ttgctcaggt ctgctggctg      60
cttactctca tgtagttcc                                                   79

<210> SEQ ID NO 59
<211> LENGTH: 79
<212> TYPE: DNA
<213> ORGANISM: Artificial Sequence
<220> FEATURE:
<223> OTHER INFORMATION: Description of Artificial Sequence: chemically
synthesized

<400> SEQUENCE: 59
ctacctacga tctgactagc ggaatgagag tgctgatgga ttgctcaggt ctgctggctg      60
cttactctca tgtagttcc                                                   79

<210> SEQ ID NO 60
<211> LENGTH: 79
<212> TYPE: DNA
<213> ORGANISM: Artificial Sequence
<220> FEATURE:
<223> OTHER INFORMATION: Description of Artificial Sequence: chemically
synthesized

<400> SEQUENCE: 60
ctacctacga tctgactagc ggaatgagaa tgttggtgga ttgctcaggt ctgctggctg      60
cttactctca tgtagttcc                                                   79

<210> SEQ ID NO 61
<211> LENGTH: 79
<212> TYPE: DNA
<213> ORGANISM: Artificial Sequence
<220> FEATURE:
<223> OTHER INFORMATION: Description of Artificial Sequence: chemically
synthesized

<400> SEQUENCE: 61
ctacctacga tctgactagc ggaatgagag tgctggtgga ttgctcaggt ctgctggctg      60
cttactctca tgtagttcc                                                   79

<210> SEQ ID NO 62
<211> LENGTH: 79
<212> TYPE: DNA
<213> ORGANISM: Artificial Sequence
<220> FEATURE:
<223> OTHER INFORMATION: Description of Artificial Sequence: chemically
synthesized

<400> SEQUENCE: 62
ctacctacga tctgactagc ggaatgagaa tgctgatgga ttgttcaggt ctgctggctg      60
cttactctca tgtagttcc                                                   79

<210> SEQ ID NO 63
<211> LENGTH: 79
<212> TYPE: DNA
<213> ORGANISM: Artificial Sequence

```
<220> FEATURE:
<223> OTHER INFORMATION: Description of Artificial Sequence: chemically
      synthesized

<400> SEQUENCE: 63
ctacctacga tctgactagc ggaatgagaa tgctgatgga ttgctcaggt ctgctgactg      60
cttactctca tgtagttcc                                                  79

<210> SEQ ID NO 64
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 64
ctacctacga tctgactagc ggaatgagaa tgctgatgga ttgcccaggt ctgctggctg      60
cttactctca tgtagttcc                                                  79

<210> SEQ ID NO 65
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 65
ctacctacga tctgactagc ggaatgagaa tgctggtgga ttgcccaggt ctgctggctg      60
cttactctca tgtagttcc                                                  79

<210> SEQ ID NO 66
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 66
ctacctacga tctgactagc ggaatgagaa tgttggtgga ttgctcaggt ctgctggctg      60
cttactctca tgtagttcc                                                  79

<210> SEQ ID NO 67
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 67
ctacctacga tctgactagc ggaatgagga tgctggtgga ttgctcaggt ctgctggctg      60
cttactctca tgtagttcc                                                  79

<210> SEQ ID NO 68
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 68
```

```
ctacctacga tctgactagc ggaatgagag tgctgatgga ttgctcaggt ctactggctg    60
cttactctca tgtagttcc                                                 79
```

<210> SEQ ID NO 69
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 69

```
ctacctacga tctgactagc ggaatgagga tgctgatgga ttggtcaggt ctgctggctg    60
cttactctca tgtagttcc                                                 79
```

<210> SEQ ID NO 70
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 70

```
ctacctacga tctgactagc gggatgagag tgctggtgga ttgctcaggt ctgctggctg    60
cttactctca tgtagttcc                                                 79
```

<210> SEQ ID NO 71
<211> LENGTH: 79
<212> TYPE: DNA
<213> ORGANISM: Artificial Sequence
<220> FEATURE:
<223> OTHER INFORMATION: Description of Artificial Sequence: chemcially
      synthesized

<400> SEQUENCE: 71

```
ctacctacga tctgactagc gcaatgagga tgctgatgga ttgctcaggt ctgctggctg    60
cttactctca tgtagttcc                                                 79
```

<210> SEQ ID NO 72
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 72

```
ctacctacga tctgactagc ggaatgagga tgctgatgga ttgcacaggt ctgctggctg    60
cttactctca tgtagttcc                                                 79
```

<210> SEQ ID NO 73
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 73

```
ctacctacga tctgactagc ggaatgagga tgctggtgga ttgctcaggt ctgttggctg    60
cttactctca tgtagttcc                                                 79
```

```
<210> SEQ ID NO 74
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 74
ctacctacga tctgactagc gaaacactag gttggttagg attggtgtgt ttccgttctg      60
cttactctca tgtagttcc                                                  79

<210> SEQ ID NO 75
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 75
ctacctacga tctgactagc gaaacactag gttggttagg attggtgtgt tcccgctctg      60
cttactctca tgtagttcc                                                  79

<210> SEQ ID NO 76
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 76
ctacctacga tctgactagc gaaacactag gttggttagg attggtgtgt tcccgccctg      60
cttactctca tgtagttcc                                                  79

<210> SEQ ID NO 77
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 77
ctacctacga tctgactagc gaaacactag gttggttagg attggtgtgt ttctgctctg      60
cttactctca tgtagttcc                                                  79

<210> SEQ ID NO 78
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 78
ctacctacga tctgactagc gaaacactag gttggttagg attggtgtgt ttccgctttg      60
cttactctca tgtagttcc                                                  79

<210> SEQ ID NO 79
<211> LENGTH: 79
<212> TYPE: DNA
<213> ORGANISM: Artificial Sequence
```

-continued

<220> FEATURE:
<223> OTHER INFORMATION: Description of Artificial Sequence: chemically
    synthesized

<400> SEQUENCE: 79
ctacctacga tctgactagc ggaacactag gttggttagg attggtgtgt tcccgttttg    60
cttactctca tgtagttcc                                                 79

<210> SEQ ID NO 80
<211> LENGTH: 79
<212> TYPE: DNA
<213> ORGANISM: Artificial Sequence
<220> FEATURE:
<223> OTHER INFORMATION: Description of Artificial Sequence: chemically
    synthesized

<400> SEQUENCE: 80
ctacctacga tctgactagc gaaacactag gttggttagg attggtgtgt tcccgctttg    60
cttactctca tgtagttcc                                                 79

<210> SEQ ID NO 81
<211> LENGTH: 79
<212> TYPE: DNA
<213> ORGANISM: Artificial Sequence
<220> FEATURE:
<223> OTHER INFORMATION: Description of Artificial Sequence: chemically
    synthesized

<400> SEQUENCE: 81
ctacctacga tctgactagc gaaacactag gttggttagg attggtgtgt tcccgctatg    60
cttactctca tgtagttcc                                                 79

<210> SEQ ID NO 82
<211> LENGTH: 79
<212> TYPE: DNA
<213> ORGANISM: Artificial Sequence
<220> FEATURE:
<223> OTHER INFORMATION: Description of Artificial Sequence: chemically
    synthesized

<400> SEQUENCE: 82
ctacctacga tctgactagc gaaacactag gttggttagg attggtgtgt tcccgctatg    60
cttactctca tgtagttcc                                                 79

<210> SEQ ID NO 83
<211> LENGTH: 80
<212> TYPE: DNA
<213> ORGANISM: Artificial Sequence
<220> FEATURE:
<223> OTHER INFORMATION: Description of Artificial Sequence: chemically
    synthesized

<400> SEQUENCE: 83
ctacctacga tctgactagc tgagtagtta gtaactttt attatggttt ggtgggtctg     60
gcttactctc atgtagttcc                                                80

<210> SEQ ID NO 84
<211> LENGTH: 80
<212> TYPE: DNA
<213> ORGANISM: Artificial Sequence
<220> FEATURE:
<223> OTHER INFORMATION: Description of Artificial Sequence: chemically
    synthesized

<400> SEQUENCE: 84

```
ctacctacga tctgactagc tgagtagtca gtaattttt attatggttt ggtgggcctg    60
gcttactctc atgtagttcc                                              80
```

<210> SEQ ID NO 85
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 85

```
ctacctacga tctgactagc aaggggattg gctccgggtc tggcgtgctt ggcacctctg    60
gcttactctc atgtagttcc                                               80
```

<210> SEQ ID NO 86
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 86

```
ctacctacga tctgactagc aaggggattg gctccgggtc tggcgtgctt ggtacctccg    60
gcttactctc atgtagttcc                                               80
```

<210> SEQ ID NO 87
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 87

```
ctacctacga tctgactagc aaggggattg gctccgggtc tggcgtgctt ggcatcttcg    60
gcttactctc atgtagttcc                                               80
```

<210> SEQ ID NO 88
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 88

```
ctacctacga tctgactagc aaggggattg gctccgggtc tggcgtgctc ggcacctttg    60
gcttactctc atgtagttcc                                               80
```

<210> SEQ ID NO 89
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 89

```
ctacctacga tctgactagc ggaatgagaa ggctggtgga ttgctcaggt ctgctggctg    60
cttactctca tgtagttcc                                                79
```

```
<210> SEQ ID NO 90
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 90
ctacctacga tctgactagc ggaatgagta tgctgatgga ttgctcaggt ctgctggctg      60
cttactctca tgtagttcc                                                  79

<210> SEQ ID NO 91
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 91
ctacctacga tctgactagc ggaatgagaa ggctgatgga ttgctcaggt ctgctggctg      60
cttactctca tgtagttcc                                                  79

<210> SEQ ID NO 92
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 92
ctacctacga tctgactagc ggaatgagag cgctgatgga ttgctcaggt ctgctggctg      60
cttactctca tgtagttcc                                                  79

<210> SEQ ID NO 93
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 93
ctacctacga tctgactagc aaggggattg gctccgggtc tggcgtgctc ggcacttccg      60
gcttactctc atgtagttcc                                                 80

<210> SEQ ID NO 94
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 94
ctacctacga tctgactagc aaggggattg gctccgggtc tggcgtgctc ggcaccttcg      60
gcttactctc atgtagttcc                                                 80

<210> SEQ ID NO 95
<211> LENGTH: 79
<212> TYPE: DNA
<213> ORGANISM: Artificial Sequence
```

```
<220> FEATURE:
<223> OTHER INFORMATION: Description of Artificial Sequence: chemically
      synthesized
<220> FEATURE:
<221> NAME/KEY: misc_feature
<222> LOCATION: (29)..(57)
<223> OTHER INFORMATION: where Y is C or T; R is A or G; H is A, C, or T.

<400> SEQUENCE: 95
ctacctacga tctgactagc ggaatgagra tgytgrtgga ttgchcaggt ctrytgrctg    60
cttactctca tgtagttcc                                                 79

<210> SEQ ID NO 96
<211> LENGTH: 78
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (22)..(58)
<223> OTHER INFORMATION: where Y is C or T; R is A or G; H is A, C,
      or T.

<400> SEQUENCE: 96
ctacctacga tctgactagc graacactag gttggttagg rttggtgtgt tycygyyhgc    60
ttactctcat gtagttcc                                                  78

<210> SEQ ID NO 97
<211> LENGTH: 80
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (49)..(59)
<223> OTHER INFORMATION: Where Y is C or T; R is A or G; H is A, C,
      or T.

<400> SEQUENCE: 97
ctacctacga tctgactagc aaggggattg gctccgggtc tggcgtgcty ggyayyyyyg    60
gcttactctc atgtagttcc                                                80

<210> SEQ ID NO 98
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 98
ctacctacga tctgactagc tccagtgttt tatccaataa ccgtgcggtg cctccgtgag    60
cttactctca tgtagttcc                                                 79

<210> SEQ ID NO 99
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 99
```

```
ctacctacga tctgactagc tccagtgttt catccaataa ccgtgcggtg cctccgtgag    60
cttactctca tgtagttcc                                                 79

<210> SEQ ID NO 100
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 100
ctacctacga tctgactagc tccagtgttt cattcaataa ccgtgcggtg cctccgtgag    60
cttactctca tgtagttcc                                                 79

<210> SEQ ID NO 101
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 101
ctacctacga tctgactagc tccagtgttt catttaataa ccgtgcggtg cctccgtgag    60
cttactctca tgtagttcc                                                 79

<210> SEQ ID NO 102
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 102
ctacctacga tctgactagc tccagtgttt catctaataa ccgtgcggtg cctccgtgag    60
cttactctca tgtagttcc                                                 79

<210> SEQ ID NO 103
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 103
ctacctacga tctgactagc tccagtgttt catccaataa ccgtgcggtg cttccgtgag    60
cttactctca tgtagttcc                                                 79

<210> SEQ ID NO 104
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 104
ctacctacga tctgactagc tccagtgttt tgtctaataa ccgtgcggtg cctccgtgag    60
cttactctca tgtagttcc                                                 79
```

```
<210> SEQ ID NO 105
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 105
ctacctacga tctgactagc tccagtgttt tatataataa ccgtgcggtg cctccgtgat      60
gcttactctc atgtagttcc                                                 80

<210> SEQ ID NO 106
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 106
ctacctacga tctgactagc tccagtgttt tattcaataa ccgtgcggtg cctccgtgag      60
cttactctca tgtagttcc                                                  79

<210> SEQ ID NO 107
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 107
ctacctacga tctgactagc tccagtgttt tattcaataa ccgtgcggtg cctccgtgat      60
gcttactctc atgtagttcc                                                 80

<210> SEQ ID NO 108
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 108
ctacctacga tctgactagc tccagtgttt tattcaataa ccgtgcggtg tctccgtgag      60
cttactctca tgtagttcc                                                  79

<210> SEQ ID NO 109
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 109
ctacctacga tctgactagc tccagtgttt tatctaataa ccgtgcggtg cctccgtgag      60
cttactctca tgtagttcc                                                  79

<210> SEQ ID NO 110
<211> LENGTH: 80
<212> TYPE: DNA
<213> ORGANISM: Artificial Sequence
<220> FEATURE:
```

-continued

<223> OTHER INFORMATION: Description of Artificial Sequence: chemically
      synthesized

<400> SEQUENCE: 110
ctacctacga tctgactagc tccagtgttt tatctaataa ccgtgcggtg cctccgtgat    60
gcttactctc atgtagttcc                                               80

<210> SEQ ID NO 111
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 111
ctacctacga tctgactagc tccagtgttt tatccaacaa ccgtgcggtg cctccgtgag    60
cttactctca tgtagttcc                                                79

<210> SEQ ID NO 112
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 112
ctacctacga tctgactagc tccagtgttt tatccaataa ccgtgcgggg cctccgtgat    60
gcttactctc atgtagttcc                                               80

<210> SEQ ID NO 113
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 113
ctacctacga tctgactagc tccagtgttt tatccaataa ccgtgcggtg cctccgtgat    60
gcttactctc atgtagttcc                                               80

<210> SEQ ID NO 114
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 114
ctacctacga tctgactagc gtgcagtgcc tattccaggc cgtgcggtgc ctccgtcacg    60
cttactctca tgtagttcc                                                79

<210> SEQ ID NO 115
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 115

```
ctacctacga tctgactagc gtgcagtgcc catcttaggc cgtgcggtgc ctccgtcacg      60
cttactctca tgtagttcc                                                   79

<210> SEQ ID NO 116
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 116
ctacctacga tctgactagc gtgcagtgcc tattttaggc cgtgcggtgc ctccgtcacg      60
cttactctca tgtagttcc                                                   79

<210> SEQ ID NO 117
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 117
ctacctacga tctgactagc gtgcagtgcc tattttaggt cgtgcggggc ctccgtcacg      60
cttactctca tgtagttcc                                                   79

<210> SEQ ID NO 118
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 118
ctacctacga tctgactagc gtgcagtgcc tattctaggc cgtgcggtgc ctccgtcacg      60
cttactctca tgtagttcc                                                   79

<210> SEQ ID NO 119
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 119
ctacctacga tctgactagc gtgcagtgcc tattctaggc cgtgcggtgc ctccgtcatg      60
cttactctca tgtagttcc                                                   79

<210> SEQ ID NO 120
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 120
ctacctacga tctgactagc atgcagtgcc cattctaggc cgtgcggtgc ctccgtcatg      60
cttactctca tgtagttcc                                                   79
```

<210> SEQ ID NO 121
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 121
ctacctacga tctgactagc ttggtagcga ttctgtggag ctgcggtttg gtcgacgtca    60
gcttactctc atgtagttcc                                                80

<210> SEQ ID NO 122
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 122
ctacctacga tctgactagc ttggtagcga ttttgtggag ctgcggtttg gtcgacgtca    60
gcttactctc atgtagttcc                                                80

<210> SEQ ID NO 123
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 123
ctacctacga tctgactagc ttggtagtga ctttgtggag ctgcggtttg gtcgacgtca    60
gcttactctc atgtagttcc                                                80

<210> SEQ ID NO 124
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 124
ctacctacga tctgactagc gtgcagtgcc cattccaggc cgtgcggtat cctccgtcac    60
gcttactctc atgtagttcc                                                80

<210> SEQ ID NO 125
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 125
ctacctacga tctgactagc gtgcagtgcc tatcccaggc cgtgcggtag cctccgtcac    60
gcttactctc atgtagttcc                                                80

<210> SEQ ID NO 126
<211> LENGTH: 80
<212> TYPE: DNA
<213> ORGANISM: Artificial Sequence
<220> FEATURE:

<223> OTHER INFORMATION: Description of Artificial Sequence: chemically
      synthesized

<400> SEQUENCE: 126
ctacctacga tctgactagc gtgcagtgcc tatctcaggc cgtgcggtat cctccgtcac    60
gcttactctc atgtagttcc                                                80

<210> SEQ ID NO 127
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 127
ctacctacga tctgactagc ttggtagcga ctctgtggag ctgcggtttg gtcgacgtca    60
gcttactctc atgtagttcc                                                80

<210> SEQ ID NO 128
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 128
ctacctacga tctgactagc ttggtagcga ctctgtggag ctgcggtctg gtcgacgtca    60
gcttactctc atgtagttcc                                                80

<210> SEQ ID NO 129
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 129
ctacctacga tctgactagc ttggtagcga ctctgtggag ctgcggtctg gccgacgtca    60
gcttactctc atgtagttcc                                                80

<210> SEQ ID NO 130
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 130
ctacctacga tctgactagc ttggtagcga cactgtggag ctgcggtttg gttgacgtca    60
gcttactctc atgtagttcc                                                80

<210> SEQ ID NO 131
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 131

```
ctacctacga tctgactagc ttggtagcga ccctgtggag ctgcggtttg gtcgacgtca    60
gcttactctc atgtagttcc                                                80

<210> SEQ ID NO 132
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 132
ctacctacga tctgactagc ttggtagcga ctccgtggag ctgcggtttg gtcgacgtca    60
gcttactctc atgtagttcc                                                80

<210> SEQ ID NO 133
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 133
ctacctacga tctgactagc ttggtagcga ctcagaggag ctgcggtttg gtcgacgtca    60
gcttactctc atgtagttcc                                                80

<210> SEQ ID NO 134
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 134
ctacctacga tctgactagc ttggtagcga ctttgtggag ctgcggtttg gtcgacgtca    60
gcttactctc atgtagttcc                                                80

<210> SEQ ID NO 135
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 135
ctacctacga tctgactagc ttggtagcga ctttgtggag ctgcggtttg gtcgacatca    60
gcttactctc atgtagttcc                                                80

<210> SEQ ID NO 136
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 136
ctacctacga tctgactagc ttggtagcga ctttgtggag atgcggtttg gttgacgtca    60
gcttactctc atgtagttcc                                                80
```

```
<210> SEQ ID NO 137
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 137
ctacctacga tctgactagc ggaatgagaa tgttggtgga ttgctcaggt ctgctggctg      60
cttactctca tgtagttcc                                                  79

<210> SEQ ID NO 138
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 138
ctacctacga tctgactagc ggaatgagaa tgctggtgga ttgctcaggt ctgctggctg      60
cttactctca tgtagttcc                                                  79

<210> SEQ ID NO 139
<211> LENGTH: 78
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 139
ctacctacga tctgactagc ggaatgagaa gctggtggat tgctcaggtc tgctggctgc      60
ttactctcat gtagttcc                                                   78

<210> SEQ ID NO 140
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 140
ctacctacga tctgactagc ggaatgagga tgctggtgga ttgctcaggt ctgctggctg      60
cttactctca tgtagttcc                                                  79

<210> SEQ ID NO 141
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 141
ctacctacga tctgactagc ggaatgagaa tgcaggtgga ttgctcaggt ctgctggctg      60
cttactctca tgtagttcc                                                  79

<210> SEQ ID NO 142
<211> LENGTH: 79
<212> TYPE: DNA
<213> ORGANISM: Artificial Sequence
<220> FEATURE:
```

```
<223> OTHER INFORMATION: Description of Artificial Sequence: chemically
      synthesized

<400> SEQUENCE: 142
ctacctacga tctgactagc ggaatgagaa tgcagatgga ttgctcaggt ctgctggctg    60
cttactctca tgtagttcc                                                 79

<210> SEQ ID NO 143
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 143
ctacctacga tctgactagc ggaatgagag tgttggtgga ttgctcaggt ctgctggctg    60
cttactctca tgtagttcc                                                 79

<210> SEQ ID NO 144
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 144
ctacctacga tctgactagc ggaatgagag tgctggtgga ttgctcaggt ctgctggctg    60
cttactctca tgtagttcc                                                 79

<210> SEQ ID NO 145
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 145
ctacctacga tctgactagc ggaatgagta tgctggtgga ttgctcaggt ctgctggctg    60
cttactctca tgtagttcc                                                 79

<210> SEQ ID NO 146
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 146
ctacctacga tctgactagc ggaatgagta tgctgatgga ttgctcaggt ctgctggctg    60
cttactctca tgtagttcc                                                 79

<210> SEQ ID NO 147
<211> LENGTH: 78
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 147
```

-continued ctacctacga tctgactagc ttgtcgcact tttggttggt ctggttggtt ctaagtgcgc    60
ttactctcat gtagttcc                                                 78

<210> SEQ ID NO 148
<211> LENGTH: 78
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 148
ctacctacga tctgactagc ttgtcgcact tttggttggt ctggttggtt ttaagtgcgc    60
ttactctcat gtagttcc                                                 78

<210> SEQ ID NO 149
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 149
ctacctacga tctgactagc ttggtagcga cacagtggag ctgcggtttg gtcgacgtca    60
gcttactctc atgtagttcc                                               80

<210> SEQ ID NO 150
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 150
ctacctacga tctgactagc tcaaagtatt acttattggc aataagtcgt ttactctata    60
gcttactctc atgtagttcc                                               80

<210> SEQ ID NO 151
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 151
ctacctacga tctgactagc tttcagtctt ccacatttat agggtttggc attgggtctg    60
gcttactctc atgtagttcc                                               80

<210> SEQ ID NO 152
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 152
ctacctacga tctgactagc tttcagtctt ctacatttat agggtttggc attgggtctg    60
gcttactctc atgtagttcc                                               80

```
<210> SEQ ID NO 153
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 153
ctacctacga tctgactagc tttcagtctt ccacgtttat agggtttggc attgggtctg    60
gcttactctc atgtagttcc                                                80

<210> SEQ ID NO 154
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 154
ctacctacga tctgactagc ttttagtctt ccacatttat agggtttggc attgggtctg    60
gcttactctc atgtagttcc                                                80

<210> SEQ ID NO 155
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 155
ctacctacga tctgactagc tttcagtctt tcacatttat agggtttggc attgggtctg    60
gcttactctc atgtagttcc                                                80

<210> SEQ ID NO 156
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 156
ctacctacga tctgactagc tttcagtctt tcatatttat agggtttggc attgggtctg    60
gcttactctc atgtagttcc                                                80

<210> SEQ ID NO 157
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 157
ctacctacga tctgactagc cagttctggg aaaaattatt tttttatttc gatcgtatat    60
gcttactctc atgtagttcc                                                80

<210> SEQ ID NO 158
<211> LENGTH: 80
<212> TYPE: DNA
<213> ORGANISM: Artificial Sequence
<220> FEATURE:
```

<223> OTHER INFORMATION: Description of Artificial Sequence: chemically
      synthesized

<400> SEQUENCE: 158
ctacctacga tctgactagc cagttctggg aaaaattatt tttttatttc gatcgtattt    60
gcttactctc atgtagttcc                                               80

<210> SEQ ID NO 159
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 159
ctacctacga tctgactagc ctcagattga ctccggccga cttgttttaa tcttctgagt    60
gcttactctc atgtagttcc                                               80

<210> SEQ ID NO 160
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 160
ctacctacga tctgactagc ccccacttat cgtgtacctt atgatatgtc gaatactctt    60
gcttactctc atgtagttcc                                               80

<210> SEQ ID NO 161
<211> LENGTH: 78
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 161
ctacctacga tctgactagc cttacctatt cccttctgcg gaatacgtcg agtactatgc    60
ttactctcat gtagttcc                                                 78

<210> SEQ ID NO 162
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 162
ctacctacga tctgactagc cagttctggg aaaaatcatt ttttatttcg atcgtatttg    60
cttactctca tgtagttcc                                                79

<210> SEQ ID NO 163
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 163

```
ctacctacga tctgactagc aagggqattg gctccgggtc tggcgtgctt ggcatctttg      60
gcttactctc atgtagttcc                                                  80

<210> SEQ ID NO 164
<211> LENGTH: 80
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 164
ctacctacga tctgactagc ctcagattga ctccggctga cttgttttaa tcttctgagt      60
gcttactctc atgtagttcc                                                  80

<210> SEQ ID NO 165
<211> LENGTH: 56
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 165
ggagcgcact cagccaccct cgcaagcatt ttaagaatga cttgtgccgc tggctg          56

<210> SEQ ID NO 166
<211> LENGTH: 25
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 166
gatcgatcta atacgactca ctata                                            25

<210> SEQ ID NO 167
<211> LENGTH: 18
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 167
cagccagcgg cacaagtc                                                    18

<210> SEQ ID NO 168
<211> LENGTH: 79
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 168
tcgatctaat acgactcact ataggagcgc actcagccac cctcgcaagc attttaagaa      60
tgacttgtgc cgctggctg                                                   79

<210> SEQ ID NO 169
<211> LENGTH: 46
<212> TYPE: DNA
<213> ORGANISM: Artificial Sequence
<220> FEATURE:
<223> OTHER INFORMATION: Description of Artificial Sequence: chemically
```

```
                                  synthesized

<400> SEQUENCE: 169
ggaccaccct cgcaagcatt ttaagaatga cttgtgccgc tggtcc                46

<210> SEQ ID NO 170
<211> LENGTH: 18
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 170
ggaccagcgg cacaagtc                                               18

<210> SEQ ID NO 171
<211> LENGTH: 71
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 171
gatcgatcta atacgactca ctataggacc accctcgcaa gcattttaag aatgacttgt   60
gccgctggtc c                                                      71

<210> SEQ ID NO 172
<211> LENGTH: 45
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 172
ggaccaccct cgcaagcatt gagaaatgac ttgtgccgct ggtcc                  45

<210> SEQ ID NO 173
<211> LENGTH: 70
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 173
gatcgatcta atacgactca ctataggacc accctcgcaa gcattgagaa atgacttgtg   60
ccgctggtcc                                                        70

<210> SEQ ID NO 174
<211> LENGTH: 36
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 174
ggaccaccct cgcaacgaga gttgtgccgc tggtcc                           36

<210> SEQ ID NO 175
<211> LENGTH: 18
<212> TYPE: DNA
<213> ORGANISM: Artificial Sequence
```

<220> FEATURE:
<223> OTHER INFORMATION: Description of Artificial Sequence: chemically
      synthesized primer

<400> SEQUENCE: 175
ggaccagcgg cacaactc                                                   18

<210> SEQ ID NO 176
<211> LENGTH: 61
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 176
gatcgatcta atacgactca ctataggacc accctcgcaa cgagagttgt gccgctggtc     60
c                                                                     61

<210> SEQ ID NO 177
<211> LENGTH: 45
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 177
ggagcgcact cagccacggg gtgggtagac ggcgggtatg tggct                     45

<210> SEQ ID NO 178
<211> LENGTH: 18
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 178
agccacatac ccgccgtc                                                   18

<210> SEQ ID NO 179
<211> LENGTH: 70
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 179
gatcgatcta atacgactca ctataggagc gcactcagcc acggggtggg tagacggcgg     60
gtatgtggct                                                            70

<210> SEQ ID NO 180
<211> LENGTH: 38
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 180
ggagccacgg ggtgggtaga cggcgggtat gtggctcc                             38

<210> SEQ ID NO 181
<211> LENGTH: 18

<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 181
ggagccacat acccgccg                                                   18

<210> SEQ ID NO 182
<211> LENGTH: 63
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 182
gatcgatcta atacgactca ctataggagc cacggggtgg gtagacggcg ggtatgtggc     60
tcc                                                                   63

<210> SEQ ID NO 183
<211> LENGTH: 32
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 183
gggacggggt gggtagacgg cgggtatgtc cc                                   32

<210> SEQ ID NO 184
<211> LENGTH: 15
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 184
gggacatacc cgccg                                                      15

<210> SEQ ID NO 185
<211> LENGTH: 57
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 185
gatcgatcta atacgactca ctatagggac ggggtgggta gacggcgggt atgtccc        57

<210> SEQ ID NO 186
<211> LENGTH: 53
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 186
ggagcgcact cagccacacg acattggcgg gttgtaatta ccacgcatgg ctg            53

<210> SEQ ID NO 187
<211> LENGTH: 18

```
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 187
cagccatgcg tggtaatt                                                       18

<210> SEQ ID NO 188
<211> LENGTH: 78
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 188
gatcgatcta atacgactca ctataggagc gcactcagcc acacgacatt ggcgggttgt         60
aattaccacg catggctg                                                       78

<210> SEQ ID NO 189
<211> LENGTH: 45
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 189
ggagccacac gacattggcg ggttgtaatt accacgcatg gctcc                         45

<210> SEQ ID NO 190
<211> LENGTH: 14
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 190
ggagccatgc gtgg                                                           14

<210> SEQ ID NO 191
<211> LENGTH: 70
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 191
gatcgatcta atacgactca ctataggagc cacacgacat tggcgggttg taattaccac         60
gcatggctcc                                                                70

<210> SEQ ID NO 192
<211> LENGTH: 42
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 192
ggagccacac gacattggcg ggcgagagcc acgcatggct cc                            42
```

```
<210> SEQ ID NO 193
<211> LENGTH: 67
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 193
gatcgatcta atacgactca ctataggagc cacacgacat tggcgggcga gagccacgca    60
tggctcc                                                              67

<210> SEQ ID NO 194
<211> LENGTH: 38
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 194
ggagccacac gacattggcg agagccacgc atggctcc                            38

<210> SEQ ID NO 195
<211> LENGTH: 63
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 195
gatcgatcta atacgactca ctataggagc cacacgacat tggcgagagc cacgcatggc    60
tcc                                                                  63

<210> SEQ ID NO 196
<211> LENGTH: 45
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 196
ggagccacac gagagtggcg ggttgtaatt accacgcatg gctcc                    45

<210> SEQ ID NO 197
<211> LENGTH: 70
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 197
gatcgatcta atacgactca ctataggagc cacacgagag tggcgggttg taattaccac    60
gcatggctcc                                                           70

<210> SEQ ID NO 198
<211> LENGTH: 38
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 198
```

```
ggccacacga cattggcggg cgagagccac gcatggcc                             38
```

<210> SEQ ID NO 199
<211> LENGTH: 17
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 199

```
ggccatgcgt ggctctc                                                    17
```

<210> SEQ ID NO 200
<211> LENGTH: 63
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 200

```
gatcgatcta atacgactca ctataggcca cacgacattg cgggcgaga gccacgcatg      60 gcc                                                                   63
```

<210> SEQ ID NO 201
<211> LENGTH: 37
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 201

```
ggagccacac gacattggcg cgagagcgca tggctcc                              37
```

<210> SEQ ID NO 202
<211> LENGTH: 17
<212> TYPE: DNA
<213> ORGANISM: Artificial Sequence
<220> FEATURE:
<223> OTHER INFORMATION: Description of Artificial Sequence: chemically
      synthesized primer

<400> SEQUENCE: 202

```
ggagccatgc gctctcg                                                    17
```

<210> SEQ ID NO 203
<211> LENGTH: 62
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 203

```
gatcgatcta atacgactca ctataggagc cacacgacat tggcgcgaga gcgcatggct    60
cc                                                                   62
```

<210> SEQ ID NO 204
<211> LENGTH: 42
<212> TYPE: DNA
<213> ORGANISM: Artificial Sequence
<220> FEATURE:
<223> OTHER INFORMATION: Description of Artificial Sequence: chemically
      synthesized

```
<400> SEQUENCE: 204
ccagcggaat gagaatgctg atggattgct caggtctgct gg                               42

<210> SEQ ID NO 205
<211> LENGTH: 48
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 205
atgagagtgc tggtggattg ctcaggtctg ctggctgctt actctcat                         48

<210> SEQ ID NO 206
<211> LENGTH: 36
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 206
cgatctgact agcggaatga gaatgctggt ggatcg                                      36

<210> SEQ ID NO 207
<211> LENGTH: 44
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 207
gatctgacta gcgcaatgag gatgcdtgat ggattgctca ggtc                             44

<210> SEQ ID NO 208
<211> LENGTH: 42
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 208
ggacgatctg actagctcca gtgttttatc taataaccgt cc                               42

<210> SEQ ID NO 209
<211> LENGTH: 49
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 209
ggagctccag tgttttatct aataaccgtg cggtgcctcc gtgagctcc                        49

<210> SEQ ID NO 210
<211> LENGTH: 29
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 210
```

```
ggagctgcgg tttggtcgac gtcagctcc                                      29
```

<210> SEQ ID NO 211
<211> LENGTH: 29
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 211

```
ggtagcgact ctgtggagct gcggtttgg                                      29
```

<210> SEQ ID NO 212
<211> LENGTH: 46
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (46)..(46)
<223> OTHER INFORMATION: thymidine at position 46 is a 3' inverted
      deoxythymidine (3' to 3' linked)

<400> SEQUENCE: 212

```
ggcgtgcagt gcctattcta ggccgtgcgg tgcctccgtc acgcct                   46
```

<210> SEQ ID NO 213
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (13)..(14)
<223> OTHER INFORMATION: thymidine at position 13 is modified by a PEG
      and attached to the adenosine at position 14
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 213

```
gcgtgcagtg cctaggccgt gcggtgcctc cgtcacgcct                          40
```

<210> SEQ ID NO 214
<211> LENGTH: 39
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (13)..(14)
<223> OTHER INFORMATION: cytidine at position 13 is modified by a PEG
      and attached to the the guanosine at position 14
<220> FEATURE:
<221> NAME/KEY: misc_feature
<222> LOCATION: (39)..(39)
<223> OTHER INFORMATION: thymidine at position 39 is a 3' inverted
      deoxythymidine (3' to 3' linked)

<400> SEQUENCE: 214

```
ggcgtgcagt gccggccgtg cggtgcctcc gtcacgcct                           39
```

<210> SEQ ID NO 215
<211> LENGTH: 41
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (30)..(31)
<223> OTHER INFORMATION: guanosine at position 30 is modified by a PEG
      and attached to the cytidine at position 31
<220> FEATURE:
<221> NAME/KEY: misc_feature
<222> LOCATION: (41)..(41)
<223> OTHER INFORMATION: thymidine at position 41 is a 3' inverted
      deoxythymidine (3' to 3' linked)

<400> SEQUENCE: 215
ggcgtgcagt gcctattcta ggccgtgcgg ccgtcacgcc t                          41

<210> SEQ ID NO 216
<211> LENGTH: 36
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (14)..(15)
<223> OTHER INFORMATION: thymidine at position 14 is modified by a PEG
      and attached to the adenosine at position 15
<220> FEATURE:
<221> NAME/KEY: misc_feature
<222> LOCATION: (25)..(26)
<223> OTHER INFORMATION: guanosine at position 25 is modified by a PEG
      and attached to the cytidine at position 26
<220> FEATURE:
<221> NAME/KEY: misc_feature
<222> LOCATION: (36)..(36)
<223> OTHER INFORMATION: thymidine at position 36 is a 3' inverted
      deoxythymidine (3' to 3' linked)

<400> SEQUENCE: 216
ggcgtgcagt gcctaggccg tgcggccgtc acgcct                               36

<210> SEQ ID NO 217
<211> LENGTH: 36
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(4)
<223> OTHER INFORMATION: n is a, t, c or g
<220> FEATURE:
<221> NAME/KEY: misc_feature
<222> LOCATION: (15)..(16)
<223> OTHER INFORMATION: n is a, t, c or g
<220> FEATURE:
<221> NAME/KEY: misc_feature
<222> LOCATION: (17)..(20)
<223> OTHER INFORMATION: n is a, t, c or g and represents 1 to 4
      nucleotides
<220> FEATURE:
<221> NAME/KEY: misc_feature
<222> LOCATION: (21)..(22)
<223> OTHER INFORMATION: n is a, t, c or g
<220> FEATURE:
<221> NAME/KEY: misc_feature
<222> LOCATION: (33)..(36)
<223> OTHER INFORMATION: n is a, t, c or g

```
<400> SEQUENCE: 217
nnnncaccct cgcannnnnn nntgtgccgc tgnnnn                                36

<210> SEQ ID NO 218
<211> LENGTH: 32
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(5)
<223> OTHER INFORMATION: n is a, t, c or g
<220> FEATURE:
<221> NAME/KEY: misc_feature
<222> LOCATION: (28)..(32)
<223> OTHER INFORMATION: n is a, t, c or g

<400> SEQUENCE: 218
nnnnnrggry rggtagacgg cgggyrtnnn nn                                    32

<210> SEQ ID NO 219
<211> LENGTH: 38
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(2)
<223> OTHER INFORMATION: n is a, t, c or g
<220> FEATURE:
<221> NAME/KEY: misc_feature
<222> LOCATION: (21)..(26)
<223> OTHER INFORMATION: n is a, t, c or g
<220> FEATURE:
<221> NAME/KEY: misc_feature
<222> LOCATION: (37)..(38)
<223> OTHER INFORMATION: n is a, t, c or g

<400> SEQUENCE: 219
nnccacacga cattggcggg nnnnnnccac gcatggnn                              38

<210> SEQ ID NO 220
<211> LENGTH: 37
<212> TYPE: DNA
<213> ORGANISM: Artificial Sequence
<220> FEATURE:
<223> OTHER INFORMATION: chemically synthesized
<220> FEATURE:
<221> NAME/KEY: misc_feature
<222> LOCATION: (1)..(5)
<223> OTHER INFORMATION: n is t, c, g or a
<220> FEATURE:
<221> NAME/KEY: misc_feature
<222> LOCATION: (11)..(12)
<223> OTHER INFORMATION: n is t, c, g or a
<220> FEATURE:
<221> NAME/KEY: misc_feature
<222> LOCATION: (13)..(13)
<223> OTHER INFORMATION: n is t, c, g or a and represents 3 to 10
      nucleotides
<220> FEATURE:
<221> NAME/KEY: misc_feature
<222> LOCATION: (14)..(15)
<223> OTHER INFORMATION: n is t, c, g or a
<220> FEATURE:
<221> NAME/KEY: misc_feature
<222> LOCATION: (33)..(37)
<223> OTHER INFORMATION: n is t, c, g or a

<400> SEQUENCE: 220
nnnnncagtg nnnnnycgtg cggkryytcc gtnnnnn                               37
```

<210> SEQ ID NO 221
<211> LENGTH: 41
<212> TYPE: DNA
<213> ORGANISM: Artificial Sequence
<220> FEATURE:
<223> OTHER INFORMATION: Description of Artificial Sequence: chemically
      synthesized

<400> SEQUENCE: 221
ggcgtgcagt gccttcggcc gtgcggtgcc tccgtcacgc c                            41

<210> SEQ ID NO 222
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 222
ggcgtgcagt gccttcggcc gtgcggtgcc tccgtcacgc ct                           42

<210> SEQ ID NO 223
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(1)
<223> OTHER INFORMATION: guanosine at position 1 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 223
ggcgtgcagt gccttcggcc gtgcggtgcc tccgtcacgc ct                           42

<210> SEQ ID NO 224
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (2)..(2)
<223> OTHER INFORMATION: guanosine at position 2 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 224
ggcgtgcagt gccttcggcc gtgcggtgcc tccgtcacgc ct                           42

<210> SEQ ID NO 225
<211> LENGTH: 42
<212> TYPE: DNA

```
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (3)..(3)
<223> OTHER INFORMATION: cytidine at position 3 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 225
ggcgtgcagt gccttcggcc gtgcggtgcc tccgtcacgc ct                              42

<210> SEQ ID NO 226
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (4)..(4)
<223> OTHER INFORMATION: guanosine at position 4 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 226
ggcgtgcagt gccttcggcc gtgcggtgcc tccgtcacgc ct                              42

<210> SEQ ID NO 227
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (5)..(5)
<223> OTHER INFORMATION: uracil at position 5 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 227
ggcgugcagt gccttcggcc gtgcggtgcc tccgtcacgc ct                              42

<210> SEQ ID NO 228
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (6)..(6)
<223> OTHER INFORMATION: guanosine at position 6 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)
```

<400> SEQUENCE: 228
ggcgtgcagt gccttcggcc gtgcggtgcc tccgtcacgc ct        42

<210> SEQ ID NO 229
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (7)..(7)
<223> OTHER INFORMATION: cytidine at position 7 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 229
ggcgtgcagt gccttcggcc gtgcggtgcc tccgtcacgc ct        42

<210> SEQ ID NO 230
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (8)..(8)
<223> OTHER INFORMATION: adenosine at position 8 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 230
ggcgtgcagt gccttcggcc gtgcggtgcc tccgtcacgc ct        42

<210> SEQ ID NO 231
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (9)..(9)
<223> OTHER INFORMATION: guanosine at position 9 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 231
ggcgtgcagt gccttcggcc gtgcggtgcc tccgtcacgc ct        42

<210> SEQ ID NO 232
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base

```
<222> LOCATION: (10)..(10)
<223> OTHER INFORMATION: Uracil at position 10 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 232
ggcgtgcagu gccttcggcc gtgcggtgcc tccgtcacgc ct                         42

<210> SEQ ID NO 233
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (11)..(11)
<223> OTHER INFORMATION: guanosine at position 11 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 233
ggcgtgcagt gccttcggcc gtgcggtgcc tccgtcacgc ct                         42

<210> SEQ ID NO 234
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (12)..(12)
<223> OTHER INFORMATION: cytidine at position 12 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 234
ggcgtgcagt gccttcggcc gtgcggtgcc tccgtcacgc ct                         42

<210> SEQ ID NO 235
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (13)..(13)
<223> OTHER INFORMATION: cytidine at position 13 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 235
ggcgtgcagt gccttcggcc gtgcggtgcc tccgtcacgc ct                         42

<210> SEQ ID NO 236
```

```
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (14)..(14)
<223> OTHER INFORMATION: uracil at position 14 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 236
ggcgtgcagt gccutcggcc gtgcggtgcc tccgtcacgc ct                          42

<210> SEQ ID NO 237
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (15)..(15)
<223> OTHER INFORMATION: uracil at position 15 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 237
ggcgtgcagt gcctucggcc gtgcggtgcc tccgtcacgc ct                          42

<210> SEQ ID NO 238
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (16)..(16)
<223> OTHER INFORMATION: cytidine at position 16 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 238
ggcgtgcagt gccttcggcc gtgcggtgcc tccgtcacgc ct                          42

<210> SEQ ID NO 239
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (17)..(17)
<223> OTHER INFORMATION: guanosine at position 17 is 2'-O-Methyl
<220> FEATURE:
<221> NAME/KEY: misc_feature
<222> LOCATION: (42)..(42)
<223> OTHER INFORMATION: thymidine at position 42 is a 3' inverted
``` deoxythymidine (3' to 3' linked)

<400> SEQUENCE: 239
ggcgtgcagt gccttcggcc gtgcggtgcc tccgtcacgc ct        42

<210> SEQ ID NO 240
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (18)..(18)
<223> OTHER INFORMATION: guanosine at position 18 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 240
ggcgtgcagt gccttcggcc gtgcggtgcc tccgtcacgc ct        42

<210> SEQ ID NO 241
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (19)..(19)
<223> OTHER INFORMATION: Cytidine at position 19 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 241
ggcgtgcagt gccttcggcc gtgcggtgcc tccgtcacgc ct        42

<210> SEQ ID NO 242
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (20)..(20)
<223> OTHER INFORMATION: cyidine at position 20 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 242
ggcgtgcagt gccttcggcc gtgcggtgcc tccgtcacgc ct        42

<210> SEQ ID NO 243
<211> LENGTH: 42
<212> TYPE: DNA
<213> ORGANISM: Artificial Sequence
<220> FEATURE:
<223> OTHER INFORMATION: Description of Artificial Sequence: chemically
      synthesized

```
<220> FEATURE:
<221> NAME/KEY: modified_base
<222> LOCATION: (21)..(21)
<223> OTHER INFORMATION: guanosine at position 21 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 243
ggcgtgcagt gccttcggcc gtgcggtgcc tccgtcacgc ct                          42

<210> SEQ ID NO 244
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (22)..(22)
<223> OTHER INFORMATION: uracil at position 22 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 244
ggcgtgcagt gccttcggcc gugcggtgcc tccgtcacgc ct                          42

<210> SEQ ID NO 245
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (23)..(23)
<223> OTHER INFORMATION: guanosine at position 23 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 245
ggcgtgcagt gccttcggcc gtgcggtgcc tccgtcacgc ct                          42

<210> SEQ ID NO 246
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (24)..(24)
<223> OTHER INFORMATION: cytidine at position 24 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 246
ggcgtgcagt gccttcggcc gtgcggtgcc tccgtcacgc ct                          42
```

```
<210> SEQ ID NO 247
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (25)..(25)
<223> OTHER INFORMATION: guanosine at position 25 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 247
ggcgtgcagt gccttcggcc gtgcggtgcc tccgtcacgc ct                         42

<210> SEQ ID NO 248
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (26)..(26)
<223> OTHER INFORMATION: guanosine at position 26 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' tp 3' linked)

<400> SEQUENCE: 248
ggcgtgcagt gccttcggcc gtgcggtgcc tccgtcacgc ct                         42

<210> SEQ ID NO 249
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (27)..(27)
<223> OTHER INFORMATION: uracil at position 27 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 249
ggcgtgcagt gccttcggcc gtgcggugcc tccgtcacgc ct                         42

<210> SEQ ID NO 250
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (28)..(28)
<223> OTHER INFORMATION: guanosine at position 28 is 2'-O-Methyl
<220> FEATURE:
<221> NAME/KEY: misc_feature
```

<222> LOCATION: (42)..(42)
       <223> OTHER INFORMATION: thymidine at position 42 is a 3' inverted
             deoxythymidine (3' to 3' linked)

<400> SEQUENCE: 250
ggcgtgcagt gccttcggcc gtgcggtgcc tccgtcacgc ct                              42

<210> SEQ ID NO 251
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (29)..(29)
<223> OTHER INFORMATION: cytidine at position 29 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 251
ggcgtgcagt gccttcggcc gtgcggtgcc tccgtcacgc ct                              42

<210> SEQ ID NO 252
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (30)..(30)
<223> OTHER INFORMATION: cytidine at position 30 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine

<400> SEQUENCE: 252
ggcgtgcagt gccttcggcc gtgcggtgcc tccgtcacgc ct                              42

<210> SEQ ID NO 253
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (31)..(31)
<223> OTHER INFORMATION: uracil at position 31 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 253
ggcgtgcagt gccttcggcc gtgcggtgcc uccgtcacgc ct                              42

<210> SEQ ID NO 254
<211> LENGTH: 42
<212> TYPE: DNA
<213> ORGANISM: Artificial Sequence
<220> FEATURE:

-continued

```
<223> OTHER INFORMATION: Description of Artificial Sequence: chemically
      synthesized
<220> FEATURE:
<221> NAME/KEY: modified_base
<222> LOCATION: (32)..(32)
<223> OTHER INFORMATION: cytidine at position 32 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 254
ggcgtgcagt gccttcggcc gtgcggtgcc tccgtcacgc ct                          42

<210> SEQ ID NO 255
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (33)..(33)
<223> OTHER INFORMATION: Cytidine at position 33 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 255
ggcgtgcagt gccttcggcc gtgcggtgcc tccgtcacgc ct                          42

<210> SEQ ID NO 256
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (34)..(34)
<223> OTHER INFORMATION: guanosine at position 34 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 256
ggcgtgcagt gccttcggcc gtgcggtgcc tccgtcacgc ct                          42

<210> SEQ ID NO 257
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (35)..(35)
<223> OTHER INFORMATION: uracil at position 35 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 257
```
ggcgtgcagt gccttcggcc gtgcggtgcc tccgucacgc ct    42

<210> SEQ ID NO 258
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (36)..(36)
<223> OTHER INFORMATION: cytidine at position 36 is 2'-OMethyl
<220> FEATURE:
<221> NAME/KEY: misc_feature
<222> LOCATION: (42)..(42)
<223> OTHER INFORMATION: thymidine at position 42 is a 3' inverted
      deoxythymidine

<400> SEQUENCE: 258
ggcgtgcagt gccttcggcc gtgcggtgcc tccgtcacgc ct    42

<210> SEQ ID NO 259
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (37)..(37)
<223> OTHER INFORMATION: adenosine at position 37 is 2'-OMethyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 259
ggcgtgcagt gccttcggcc gtgcggtgcc tccgtcacgc ct    42

<210> SEQ ID NO 260
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (38)..(38)
<223> OTHER INFORMATION: cytidine at position 38 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 260
ggcgtgcagt gccttcggcc gtgcggtgcc tccgtcacgc ct    42

<210> SEQ ID NO 261
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (39)..(39)
<223> OTHER INFORMATION: guanosine at position 39 is 2'-O-Methyl

```
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 261
ggcgtgcagt gccttcggcc gtgcggtgcc tccgtcacgc ct                         42

<210> SEQ ID NO 262
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (40)..(40)
<223> OTHER INFORMATION: cytidine at position 40 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 262
ggcgtgcagt gccttcggcc gtgcggtgcc tccgtcacgc ct                         42

<210> SEQ ID NO 263
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (41)..(41)
<223> OTHER INFORMATION: cytidine at position 41 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 263
ggcgtgcagt gccttcggcc gtgcggtgcc tccgtcacgc ct                         42

<210> SEQ ID NO 264
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(2)
<223> OTHER INFORMATION: guanosines at positions 1 and 2 are 2'-O-Methyl
<220> FEATURE:
<221> NAME/KEY: modified_base
<222> LOCATION: (4)..(4)
<223> OTHER INFORMATION: guanosine at position 4 is 2'-O-Methyl
<220> FEATURE:
<221> NAME/KEY: modified_base
<222> LOCATION: (6)..(6)
<223> OTHER INFORMATION: guanosine at position 6 is 2'-O-Methyl
<220> FEATURE:
<221> NAME/KEY: modified_base
<222> LOCATION: (37)..(37)
<223> OTHER INFORMATION: adenosine at position 37 is 2'-O-Methyl
<220> FEATURE:
<221> NAME/KEY: modified_base
```

```
<222> LOCATION: (39)..(39)
<223> OTHER INFORMATION: guanosine at position 37 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 264
ggcgtgcagt gccttcggcc gtgcggtgcc tccgtcacgc ct                          42

<210> SEQ ID NO 265
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (3)..(3)
<223> OTHER INFORMATION: cytidine at position 3 is 2'-O-Methyl
<220> FEATURE:
<221> NAME/KEY: modified_base
<222> LOCATION: (5)..(5)
<223> OTHER INFORMATION: uracil at position 5 is 2'-O-Methyl
<220> FEATURE:
<221> NAME/KEY: modified_base
<222> LOCATION: (36)..(36)
<223> OTHER INFORMATION: cytidine at position 36 is 2'-O-Methyl
<220> FEATURE:
<221> NAME/KEY: modified_base
<222> LOCATION: (38)..(38)
<223> OTHER INFORMATION: cytidine at position 3 is 2'-O-Methyl
<220> FEATURE:
<221> NAME/KEY: modified_base
<222> LOCATION: (40)..(40)
<223> OTHER INFORMATION: cytidine at position 36 is 2'-O-Methyl
<220> FEATURE:
<221> NAME/KEY: modified_base
<222> LOCATION: (41)..(41)
<223> OTHER INFORMATION: cytidine at position 36 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 265
ggcgugcagt gccttcggcc gtgcggtgcc tccgtcacgc ct                          42

<210> SEQ ID NO 266
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(2)
<223> OTHER INFORMATION: guanosines at positions 1 and 2 are 2'-O-Methyl
<220> FEATURE:
<221> NAME/KEY: modified_base
<222> LOCATION: (3)..(3)
<223> OTHER INFORMATION: cytidine at position 3 is 2'-O-Methyl
<220> FEATURE:
<221> NAME/KEY: modified_base
<222> LOCATION: (4)..(4)
<223> OTHER INFORMATION: guanosine at position 4 is 2'-O-Methyl
<220> FEATURE:
<221> NAME/KEY: modified_base
<222> LOCATION: (5)..(5)
<223> OTHER INFORMATION: uracil at position 5 is 2'-O-Methyl
<220> FEATURE:
<221> NAME/KEY: modified_base
```

```
<222> LOCATION: (6)..(6)
<223> OTHER INFORMATION: guanosine at position 6 is 2'-O-Methyl
<220> FEATURE:
<221> NAME/KEY: modified_base
<222> LOCATION: (36)..(36)
<223> OTHER INFORMATION: cytidine at position 36 is 2'-O-Methyl
<220> FEATURE:
<221> NAME/KEY: modified_base
<222> LOCATION: (37)..(37)
<223> OTHER INFORMATION: adenosine at position 37 is 2'-O-Methyl
<220> FEATURE:
<221> NAME/KEY: modified_base
<222> LOCATION: (38)..(38)
<223> OTHER INFORMATION: cytidine at position 38 is 2'-O-Methyl
<220> FEATURE:
<221> NAME/KEY: modified_base
<222> LOCATION: (39)..(39)
<223> OTHER INFORMATION: guanosine at position 39 is 2'-O-Methyl
<220> FEATURE:
<221> NAME/KEY: modified_base
<222> LOCATION: (40)..(41)
<223> OTHER INFORMATION: cytidines at positions 40 and 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 266
ggcgugcagt gccttcggcc gtgcggtgcc tccgtcacgc ct                         42

<210> SEQ ID NO 267
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (11)..(11)
<223> OTHER INFORMATION: guanosine at position 11 is 2'-O-Methyl
<220> FEATURE:
<221> NAME/KEY: modified_base
<222> LOCATION: (17)..(18)
<223> OTHER INFORMATION: guanosines at positions 17 and 18 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 267
ggcgtgcagt gccttcggcc gtgcggtgcc tccgtcacgc ct                         42

<210> SEQ ID NO 268
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (12)..(13)
<223> OTHER INFORMATION: cytidines at positions 12 and 13 are 2'-O-
      Methyl
<220> FEATURE:
<221> NAME/KEY: modified_base
<222> LOCATION: (19)..(19)
<223> OTHER INFORMATION: cytidine at position 19 is 2'-O-Methyl
<220> FEATURE:
<221> NAME/KEY: misc_feature
<222> LOCATION: (42)..(42)
```

```
<223> OTHER INFORMATION: thymidine at position 42 is a 3' inverted
      deoxythymidine (3' to 3' linked)

<400> SEQUENCE: 268
ggcgtgcagt gccttcggcc gtgcggtgcc tccgtcacgc ct                              42

<210> SEQ ID NO 269
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (11)..(11)
<223> OTHER INFORMATION: guanosine at position 11 is 2'-O-Methyl
<220> FEATURE:
<221> NAME/KEY: modified_base
<222> LOCATION: (12)..(13)
<223> OTHER INFORMATION: cytidines at positions 12 and 13 are 2'-O-
      Methyl
<220> FEATURE:
<221> NAME/KEY: modified_base
<222> LOCATION: (17)..(18)
<223> OTHER INFORMATION: guanosines at positions 17 and 18 are 2'-O-
      Methyl
<220> FEATURE:
<221> NAME/KEY: modified_base
<222> LOCATION: (19)..(19)
<223> OTHER INFORMATION: cytidine at position 19 is 2'-O-Methyl
<220> FEATURE:
<221> NAME/KEY: modified_base
<222> LOCATION: (42)..(42)
<223> OTHER INFORMATION: thymidine at position 42 is a 3' inverted
      deoxythymidine (3' to 3' linked)

<400> SEQUENCE: 269
ggcgtgcagt gccttcggcc gtgcggtgcc tccgtcacgc ct                              42

<210> SEQ ID NO 270
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (25)..(26)
<223> OTHER INFORMATION: guanosines at positions 25 and 26 are 2'-O-
      Methyl
<220> FEATURE:
<221> NAME/KEY: modified_base
<222> LOCATION: (34)..(34)
<223> OTHER INFORMATION: guanosine at position 34 is 2'-O-Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 270
ggcgtgcagt gccttcggcc gtgcggtgcc tccgtcacgc ct                              42

<210> SEQ ID NO 271
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
```

```
<222> LOCATION: (24)..(24)
<223> OTHER INFORMATION: cytidine at position 24 is 2'-O-Methyl
<220> FEATURE:
<221> NAME/KEY: modified_base
<222> LOCATION: (32)..(33)
<223> OTHER INFORMATION: cytidines at positions 32 and 33 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 271
ggcgtgcagt gccttcggcc gtgcggtgcc tccgtcacgc ct                          42

<210> SEQ ID NO 272
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (24)..(24)
<223> OTHER INFORMATION: cytidine at position 24 is 2'-O-Methyl
<220> FEATURE:
<221> NAME/KEY: modified_base
<222> LOCATION: (25)..(26)
<223> OTHER INFORMATION: guanosines at positions 25 and 26 are 2'-O-
      Methyl
<220> FEATURE:
<221> NAME/KEY: modified_base
<222> LOCATION: (32)..(33)
<223> OTHER INFORMATION: cytidines at positions 32 and 33 are 2'-O-
      Methyl
<220> FEATURE:
<221> NAME/KEY: modified_base
<222> LOCATION: (34)..(34)
<223> OTHER INFORMATION: guanosine at position 34 is 2'-O-Methyl
<220> FEATURE:
<221> NAME/KEY: modified_base
<222> LOCATION: (42)..(42)
<223> OTHER INFORMATION: thymidine at position 42 is a 3' inverted
      deoxythymidine (3' to 3' linked)

<400> SEQUENCE: 272
ggcgtgcagt gccttcggcc gtgcggtgcc tccgtcacgc ct                          42

<210> SEQ ID NO 273
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O
      Methyl
<220> FEATURE:
<221> NAME/KEY: modified_base
<222> LOCATION: (37)..(41)
<223> OTHER INFORMATION: all residues at positions 37 to 41 are 2'-O
      Methyl
<220> FEATURE:
<221> NAME/KEY: modified_base
<222> LOCATION: (42)..(42)
<223> OTHER INFORMATION: thymidine at position 42 is a 3' inverted
      deoxythymidine (3' to 3' linked)

<400> SEQUENCE: 273
ggcgugcagt gccttcggcc gtgcggtgcc tccgtcacgc ct                          42
```

<210> SEQ ID NO 274
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (9)..(10)
<223> OTHER INFORMATION: all residues at positions 9 to 10 are 2'-O-
      Methyl
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (23)..(23)
<223> OTHER INFORMATION: the residue at position 23 is 2'-O-Methyl
<220> FEATURE:
<221> NAME/KEY: modified_base
<222> LOCATION: (34)..(36)
<223> OTHER INFORMATION: all residues at positions 34 to 36 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 274
ggcgtgcagu gccttcggcc gtgcggtgcc tccgucacgc ct                        42

<210> SEQ ID NO 275
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (23)..(23)
<223> OTHER INFORMATION: the residue at position 23 is 2'-O-Methyl
<220> FEATURE:
<221> NAME/KEY: modified_base
<222> LOCATION: (28)..(29)
<223> OTHER INFORMATION: all residues at positions 28 to 29 are 2'-O-
      Methyl
<220> FEATURE:
<221> NAME/KEY: modified_base
<222> LOCATION: (31)..(31)
<223> OTHER INFORMATION: the  residue at position 31 is 2'-O-Methyl
<220> FEATURE:
<221> NAME/KEY: modified_base
<222> LOCATION: (34)..(36)
<223> OTHER INFORMATION: all residues at positions 34 to 36 are 2'-O-
      Methyl
<220> FEATURE:
<221> NAME/KEY: modified_base
<222> LOCATION: (42)..(42)
<223> OTHER INFORMATION: thymidine at position 42 is a 3' inverted
      deoxythymidine (3' to 3' linked)

<400> SEQUENCE: 275
ggcgtgcagt gccttcggcc gtgcggtgcc uccgucacgc ct                        42

<210> SEQ ID NO 276
<211> LENGTH: 42
<212> TYPE: DNA
<213> ORGANISM: Artificial Sequence
<220> FEATURE:
<223> OTHER INFORMATION: Description of Artificial Sequence: chemically -continued

```
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
<221> NAME/KEY: modified_base
<222> LOCATION: (9)..(19)
<223> OTHER INFORMATION: all residues at positions 9 to 19 are 2'-O-
      Methyl
<220> FEATURE:
<221> NAME/KEY: modified_base
<222> LOCATION: (37)..(41)
<223> OTHER INFORMATION: all residues at positions 37 to 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 276
ggcgugcagu gccuucggcc gtgcggtgcc tccgtcacgc ct                          42

<210> SEQ ID NO 277
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
<221> NAME/KEY: modified_base
<222> LOCATION: (9)..(19)
<223> OTHER INFORMATION: all residues at positions 9 to 19 are 2'-O-
      Methyl
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (23)..(23)
<223> OTHER INFORMATION: the residue at position 23 is 2'-O-Methyl
<220> FEATURE:
<221> NAME/KEY: modified_base
<222> LOCATION: (28)..(29)
<223> OTHER INFORMATION: all residues at positions 28 to 29 are 2'-O-
      Methyl
<220> FEATURE:
<221> NAME/KEY: modified_base
<222> LOCATION: (31)..(31)
<223> OTHER INFORMATION: the residue at position 31 is 2'-O-Methyl
<220> FEATURE:
<221> NAME/KEY: modified_base
<222> LOCATION: (34)..(41)
<223> OTHER INFORMATION: all residues at positions 34 to 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 277
ggcgugcagu gccuucggcc gtgcggtgcc uccgucacgc ct                          42

<210> SEQ ID NO 278
<211> LENGTH: 42
<212> TYPE: DNA
```

```
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
<221> NAME/KEY: misc_feature
<222> LOCATION: (6)..(7)
<223> OTHER INFORMATION: guanosine at position 6 is modified by a
      phosphorothioate and attached to the cytidine at position 7
<220> FEATURE:
<221> NAME/KEY: modified_base
<222> LOCATION: (9)..(19)
<223> OTHER INFORMATION: all residues at positions 9 to 19 are 2'-O-
      Methyl
<220> FEATURE:
<221> NAME/KEY: misc_feature
<222> LOCATION: (19)..(20)
<223> OTHER INFORMATION: cytidine at position 19 is modified by a
      phosphorothioate and attached to the cytidine at position 20
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (23)..(23)
<223> OTHER INFORMATION: the residue at position 23 is 2'-O-Methyl
<220> FEATURE:
<221> NAME/KEY: misc_feature
<222> LOCATION: (25)..(26)
<223> OTHER INFORMATION: guanosine at position 25 is modified by a
      phosphorothioate and attached to the guanosine at position 26
<220> FEATURE:
<221> NAME/KEY: modified_base
<222> LOCATION: (28)..(29)
<223> OTHER INFORMATION: all residues at positions 28 to 29 are 2'-O-
      Methyl
<220> FEATURE:
<221> NAME/KEY: modified_base
<222> LOCATION: (31)..(31)
<223> OTHER INFORMATION: the residue at position 31 is 2'-O-Methyl
<220> FEATURE:
<221> NAME/KEY: misc_feature
<222> LOCATION: (32)..(33)
<223> OTHER INFORMATION: cytidine at position 32 is modified by a
      phophorothioate and attached to the cytidine at position 33
<220> FEATURE:
<221> NAME/KEY: modified_base
<222> LOCATION: (34)..(41)
<223> OTHER INFORMATION: all residues at positions 34 to 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 278
ggcgugcagu gccuucggcc gtgcggtgcc uccgucacgc ct                        42

<210> SEQ ID NO 279
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
```

```
<221> NAME/KEY: misc_feature
<222> LOCATION: (6)..(7)
<223> OTHER INFORMATION: guanosine at position 6 is modified by a
      phophorothioate and attached to the cytidine at position 7
<220> FEATURE:
<221> NAME/KEY: misc_feature
<222> LOCATION: (7)..(8)
<223> OTHER INFORMATION: cytidine at position 7 is modified by a
      phosphorothioate and attached to the adenosine at position 8
<220> FEATURE:
<221> NAME/KEY: modified_base
<222> LOCATION: (9)..(19)
<223> OTHER INFORMATION: all residues at positions 9 to 19 are 2'-O-
      Methyl
<220> FEATURE:
<221> NAME/KEY: misc_feature
<222> LOCATION: (19)..(20)
<223> OTHER INFORMATION: cytidine at position 19 is modified by a
      phosphorothioate and attached to the cytidine at position 20
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (23)..(23)
<223> OTHER INFORMATION: the residue at position 23 is 2'-O-Methyl
<220> FEATURE:
<221> NAME/KEY: misc_feature
<222> LOCATION: (24)..(25)
<223> OTHER INFORMATION: cytidine at position 24 is modified by a
      phosphorothioate and attached to the guanosine at position 25
<220> FEATURE:
<221> NAME/KEY: misc_feature
<222> LOCATION: (25)..(26)
<223> OTHER INFORMATION: guanosine at position 25 is modified by a
      phosphorothioate and attached to the guanosine at position 26
<220> FEATURE:
<221> NAME/KEY: modified_base
<222> LOCATION: (28)..(29)
<223> OTHER INFORMATION: all residues at positions 28 to 29 are 2'-O-
      Methyl
<220> FEATURE:
<221> NAME/KEY: modified_base
<222> LOCATION: (31)..(31)
<223> OTHER INFORMATION: the residue at position 31 is 2'-O-Methyl
<220> FEATURE:
<221> NAME/KEY: misc_feature
<222> LOCATION: (32)..(33)
<223> OTHER INFORMATION: cytidine at position 32 is modified by a
      phosphorothioate and attached to the cytidine at position 33
<220> FEATURE:
<221> NAME/KEY: modified_base
<222> LOCATION: (34)..(41)
<223> OTHER INFORMATION: all residues at positions 34 to 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 279
ggcgugcagu gccuucggcc gtgcggtgcc uccgucacgc ct                              42

<210> SEQ ID NO 280
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
```

```
<221> NAME/KEY: misc_feature
<222> LOCATION: (5)..(6)
<223> OTHER INFORMATION: uracil at position 5 is modified by a
      phosphorothioate and attached to the guanosine at position 6
<220> FEATURE:
<221> NAME/KEY: misc_feature
<222> LOCATION: (6)..(7)
<223> OTHER INFORMATION: guanosine at position 6 is modified by a
      phosphorothioate and attached to the cytidine at position 7
<220> FEATURE:
<221> NAME/KEY: misc_feature
<222> LOCATION: (7)..(8)
<223> OTHER INFORMATION: cytidine at position 7 is modified by a
      phosphorothioate and attached to the adenosine at position 8
<220> FEATURE:
<221> NAME/KEY: modified_base
<222> LOCATION: (9)..(19)
<223> OTHER INFORMATION: all residues at positions 9 to 19 are 2'-O-
      Methyl
<220> FEATURE:
<221> NAME/KEY: misc_feature
<222> LOCATION: (19)..(20)
<223> OTHER INFORMATION: cytidine at position 19 is modified by a
      phosphorothioate and attached to the cytidine at position 20
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: misc_feature
<222> LOCATION: (21)..(22)
<223> OTHER INFORMATION: guanosine at position 21 is modified with a
      phosphorothioate and attached to the thymidine at position 22
<220> FEATURE:
<221> NAME/KEY: modified_base
<222> LOCATION: (23)..(23)
<223> OTHER INFORMATION: the residue at position 23 is 2'-O-Methyl
<220> FEATURE:
<221> NAME/KEY: misc_feature
<222> LOCATION: (23)..(24)
<223> OTHER INFORMATION: guanosine at position 23 is modified by a
      phosphorothioate and attached to the cytidine at position 24
<220> FEATURE:
<221> NAME/KEY: misc_feature
<222> LOCATION: (24)..(25)
<223> OTHER INFORMATION: cytidine at position 24 is modified by a
      phosphorothiate and attached to the guanosine at position 25
<220> FEATURE:
<221> NAME/KEY: misc_feature
<222> LOCATION: (25)..(26)
<223> OTHER INFORMATION: guanosine at position 25 is modified by a
      phosphorothioate and attached to the guanosine at position 26
<220> FEATURE:
<221> NAME/KEY: misc_feature
<222> LOCATION: (26)..(27)
<223> OTHER INFORMATION: guanosine at position 26 is modified by a
      phosphorothioate and attached to the thymidine at position 27
<220> FEATURE:
<221> NAME/KEY: modified_base
<222> LOCATION: (28)..(29)
<223> OTHER INFORMATION: all residues at position 28 to 29 are 2'-O-
      Methyl
<220> FEATURE:
<221> NAME/KEY: misc_feature
<222> LOCATION: (29)..(30)
<223> OTHER INFORMATION: cytidine at position 29 is modified by a
      phosphorothioate and attached to the cytidine at position 30
<220> FEATURE:
<221> NAME/KEY: modified_base
<222> LOCATION: (31)..(31)
<223> OTHER INFORMATION: the residue at position 31 is 2'-O-Methyl
<220> FEATURE:
<221> NAME/KEY: misc_feature
<222> LOCATION: (31)..(32)
<223> OTHER INFORMATION: uracil at position 31 is modified by a
      phosphorothioate and attached to the cytidine at position 32
<220> FEATURE:
<221> NAME/KEY: misc_feature
<222> LOCATION: (32)..(33)
<223> OTHER INFORMATION: cytidine at position 32 is modified by a
```

-continued phosphorothioate and attached to the cytidine at position 33
<220> FEATURE:
<221> NAME/KEY: modified_base
<222> LOCATION: (34)..(41)
<223> OTHER INFORMATION: all residues at positions 34 to 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 280
ggcgugcagu gccuucggcc gtgcggtgcc uccgucacgc ct                    42

<210> SEQ ID NO 281
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-methyl
<220> FEATURE:
<221> NAME/KEY: modified_base
<222> LOCATION: (22)..(22)
<223> OTHER INFORMATION: the residue at position 22 is 2'-O-methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(39)
<223> OTHER INFORMATION: all residues at positions 33 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 281
gcgugcagug ccuucggccg tgcggtgccu ccgucacgct                       40

<210> SEQ ID NO 282
<211> LENGTH: 40
<212> TYPE: DNA
<213> ORGANISM: Artificial Sequence
<220> FEATURE:
<223> OTHER INFORMATION: Desciption of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:

```
<221> NAME/KEY: modified_base
<222> LOCATION: (9)..(17)
<223> OTHER INFORMATION: all residues at positions 9 to 17 are 2'-O-
      Methyl
<220> FEATURE:
<221> NAME/KEY: modified_base
<222> LOCATION: (19)..(19)
<223> OTHER INFORMATION: the residue at position 19 is 2'-O-Methyl
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (26)..(27)
<223> OTHER INFORMATION: all residues at positions 26 to 27 are 2'-O-
      Methyl
<220> FEATURE:
<221> NAME/KEY: modified_base
<222> LOCATION: (29)..(29)
<223> OTHER INFORMATION: the residue at position 29 is 2'-O-Methyl
<220> FEATURE:
<221> NAME/KEY: modified_base
<222> LOCATION: (32)..(39)
<223> OTHER INFORMATION: all residues at positions 32 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 282
ggcgugcagu gcuucgccgt gcggtgccuc cgucacgcct                           40

<210> SEQ ID NO 283
<211> LENGTH: 38
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(16)
<223> OTHER INFORMATION: all residues at positions 8 to 16 are 2'-O-
      Methyl
<220> FEATURE:
<221> NAME/KEY: modified_base
<222> LOCATION: (18)..(18)
<223> OTHER INFORMATION: the residue at position 18 is 2'-O-Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (25)..(26)
<223> OTHER INFORMATION: all residues at position 25 to 26 are 2'-O-
      Methyl
<220> FEATURE:
<221> NAME/KEY: modified_base
<222> LOCATION: (31)..(37)
<223> OTHER INFORMATION: all residues at positions 31 to 37 are 2'-O-
      Methyl
<220> FEATURE:
<221> NAME/KEY: misc_feature
<222> LOCATION: (38)..(38)
<223> OTHER INFORMATION: thymidine at position 38 is a 3' inverted
      deoxythymidine (3' to 3' linked)

<400> SEQUENCE: 283
```

-continued gcgugcagug cuucgccgtg cggtgccucc gucacgct 38

```
<210> SEQ ID NO 284
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all the residues at postions 27 to 28 are 2'-
      O-Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all the residues at positions 33 to 34 are 2'-
      O-Methyl
<220> FEATURE:
<221> NAME/KEY: modified_base
<222> LOCATION: (36)..(39)
<223> OTHER INFORMATION: all the residues at positions 36 to 39 are 2'-
      O-Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 284
```
gcgugcagug ccuucggccg tgcggtgccu ccgucacgct 40

```
<210> SEQ ID NO 285
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (4)..(5)
<223> OTHER INFORMATION: uracil at position 4 is modified with a
      phosphorothioate and attached to the guanosine at position 5
<220> FEATURE:
<221> NAME/KEY: modified_base
<222> LOCATION: (7)..(18)
<223> OTHER INFORMATION: all residues at positions 7 to 18 are 2'-O-
      Methyl
```

-continued

```
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all the residues at positions 27 to 28 are
      2'-O-Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all of the residues at positions 33 to 34 are
      2'-O-Methyl
<220> FEATURE:
<221> NAME/KEY: modified_base
<222> LOCATION: (36)..(39)
<223> OTHER INFORMATION: all of the residues at positions 36 to 39 are
      2'-O-Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 285
gcgugcagug ccuucggccg tgcggtgccu ccgucacgct                           40

<210> SEQ ID NO 286
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (5)..(6)
<223> OTHER INFORMATION: guanosine at position 5 is modified by a
      phosphorothioate and attached to the cytidine at the 6 position
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all the residues at positions 27-28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
```

```
<223> OTHER INFORMATION: all the residues at positions 33 to 34 are
      2'-O-Methyl
<220> FEATURE:
<221> NAME/KEY: modified_base
<222> LOCATION: (36)..(39)
<223> OTHER INFORMATION: all residues at positions 36 to 39 are 2'-
      O-Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 286
gcgugcagug ccuucggccg tgcggtgccu ccgucacgct                          40

<210> SEQ ID NO 287
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (6)..(7)
<223> OTHER INFORMATION: cytidine at position 6 is modified by a
      phosphorothioate and attached to the adenosine at position 7
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 287
gcgugcagug ccuucggccg tgcggtgccu ccgucacgct                          40

<210> SEQ ID NO 288
<211> LENGTH: 40
<212> TYPE: DNA
<213> ORGANISM: Artificial Sequence
<220> FEATURE:
<223> OTHER INFORMATION: Description of Artificial Sequence: chemically
```

```
          synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (7)..(8)
<223> OTHER INFORMATION: adenosine at position 7 is modified by a
      phosphorothioate and attached to the guanosine at position 8
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-
      O-Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 288
gcgugcagug ccuucggccg tgcggtgccu ccgucacgct                           40

<210> SEQ ID NO 289
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: misc_feature
<222> LOCATION: (18)..(19)
<223> OTHER INFORMATION: cytidine at position 18 is modified by a
      phosphorothioate attached to the cytidine at position 19
<220> FEATURE:
<221> NAME/KEY: modified_base
<222> LOCATION: (20)..(20)
<223> OTHER INFORMATION: the residue at position 20 is 2'-O-Methyl
```

```
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all the residues at positions 33 to 34 are
      2'-O-Methyl
<220> FEATURE:
<221> NAME/KEY: modified_base
<222> LOCATION: (36)..(38)
<223> OTHER INFORMATION: all the residues at positions 36 to 38 are
      2'-O-Methyl
<220> FEATURE:
<221> NAME/KEY: modified_base
<222> LOCATION: (40)..(40)
<223> OTHER INFORMATION: thymidine at position 40 is a 3' inverted
      deoxythymidine (3' to 3' linked)

<400> SEQUENCE: 289
gcgugcagug ccuucggccg tgcggtgccu ccgucacgct                           40

<210> SEQ ID NO 290
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (7)..(18)
<223> OTHER INFORMATION: all residues at positions 7 to 18 are 2'-O-
      Methyl
<220> FEATURE:
<221> NAME/KEY: misc_feature
<222> LOCATION: (19)..(20)
<223> OTHER INFORMATION: cytidine at position 19 is modified by a
      phosphorothioate and attached to the guanosine at the 20 position
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
```

```
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 290
gcgugcagug ccuucggccg tgcggtgccu ccgucacgct                    40

<210> SEQ ID NO 291
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: misc_feature
<222> LOCATION: (20)..(21)
<223> OTHER INFORMATION: guanosine at position 20 is modified by a
      phosphorothioate and attached to the thymidine at position 21
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 291
gcgugcagug ccuucggccg tgcggtgccu ccgucacgct                    40

<210> SEQ ID NO 292
<211> LENGTH: 40
<212> TYPE: DNA
<213> ORGANISM: Artificial Sequence
<220> FEATURE:
<223> OTHER INFORMATION: Description of Artificial Sequence: chemically
```

-continued synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: misc_feature
<222> LOCATION: (21)..(22)
<223> OTHER INFORMATION: Thymidine at position 21 is modified by a
      phosphorothioate and attached to the guanosine at position 22
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 292
gcgugcagug ccuucggccg tgcggtgccu ccgucacgct                    40

<210> SEQ ID NO 293
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:

```
<221> NAME/KEY: misc_feature
<222> LOCATION: (22)..(23)
<223> OTHER INFORMATION: guanosine at position 22 is modified by a
      phosphorothioate and attached to the cytidine at position 23
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 293
gcgugcagug ccuucggccg tgcggtgccu ccgucacgct                          40

<210> SEQ ID NO 294
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: misc_feature
<222> LOCATION: (23)..(24)
<223> OTHER INFORMATION: cytidine at position 23 is modified by a
      phosphorothioate and attached to the guanosine at position 24
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
```

<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 294
gcgugcagug ccuucggccg tgcggtgccu ccgucacgct                              40

<210> SEQ ID NO 295
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: misc_feature
<222> LOCATION: (24)..(25)
<223> OTHER INFORMATION: guanosine at position 24 is modified by a
      phosphorothioate and attached to the guanosine at position 25
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is 3' inverted
      deoxythymidine (3' to 3' linked)

<400> SEQUENCE: 295
gcgugcagug ccuucggccg tgcggtgccu ccgucacgct                              40

<210> SEQ ID NO 296
<211> LENGTH: 40
<212> TYPE: DNA
<213> ORGANISM: Artificial Sequence
<220> FEATURE:
<223> OTHER INFORMATION: Description of Artificial Sequence: chemically

```
              synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: misc_feature
<222> LOCATION: (25)..(26)
<223> OTHER INFORMATION: guanosine at position 25 is modified by
      phosphorothioate and attached to the guanosine at position 26
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 296
gcgugcagug ccuucggccg tgcggtgccu ccgucacgct                           40

<210> SEQ ID NO 297
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
```

```
<221> NAME/KEY: misc_feature
<222> LOCATION: (26)..(27)
<223> OTHER INFORMATION: thymidine at position 26 is modified by
      phosphorothioate and attached to the guanosine at position 27
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 297
gcgugcagug ccuucggccg tgcggtgccu ccgucacgct                          40

<210> SEQ ID NO 298
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: misc_feature
<222> LOCATION: (28)..(29)
<223> OTHER INFORMATION: cytidine at position 28 is modified by a
      phosphorothioate and attached to the cytidine at position 29
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at position 33 to 34 are 2'-O-
      Methyl
<220> FEATURE:
<221> NAME/KEY: modified_base
```

```
<222> LOCATION: (36)..(39)
<223> OTHER INFORMATION: all residues at position 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 298
gcgugcagug ccuucggccg tgcggtgccu ccgucacgct                             40

<210> SEQ ID NO 299
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: misc_feature
<222> LOCATION: (29)..(30)
<223> OTHER INFORMATION: cytidine at position 29 is modified by a
      phosphorothioate and attached to the uracil at position 30
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is 3' inverted
      deoxythymidine (3' to 3' linked)

<400> SEQUENCE: 299
gcgugcagug ccuucggccg tgcggtgccu ccgucacgct                             40

<210> SEQ ID NO 300
<211> LENGTH: 40
<212> TYPE: DNA
<213> ORGANISM: Artificial Sequence
<220> FEATURE:
<223> OTHER INFORMATION: Description of Artificial Sequence: chemically
```

```
          synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: misc_feature
<222> LOCATION: (30)..(31)
<223> OTHER INFORMATION: uracil at position 30 is modified by a
      phosphorothioate and attached to the cytidine at position 31
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is 3' inverted
      deoxythymidine (3' to 3' linked)

<400> SEQUENCE: 300
gcgugcagug ccuucggccg tgcggtgccu ccgucacgct                              40

<210> SEQ ID NO 301
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
```

```
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: misc_feature
<222> LOCATION: (31)..(32)
<223> OTHER INFORMATION: cytidine at position 31 is modified by a
      phosphothioate and attached to the cytidine at position 32
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythumidine (3' to 3' linked)

<400> SEQUENCE: 301
gcgugcagug ccuucggccg tgcggtgccu ccgucacgct                       40

<210> SEQ ID NO 302
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: misc_feature
<222> LOCATION: (32)..(33)
<223> OTHER INFORMATION: cytidine at position 32 is modified by a
      phosphorothioate and attached to the guanosine at position 33
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
```

```
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 302
gcgugcagug ccuucggccg tgcggtgccu ccgucacgct                    40

<210> SEQ ID NO 303
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: misc_feature
<222> LOCATION: (34)..(35)
<223> OTHER INFORMATION: uracil at position 34 is modified by a
      phosphorothioate and attached to the cytidine at position 35
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 303
gcgugcagug ccuucggccg tgcggtgccu ccgucacgct                    40

<210> SEQ ID NO 304
<211> LENGTH: 40
<212> TYPE: DNA
<213> ORGANISM: Artificial Sequence
<220> FEATURE:
<223> OTHER INFORMATION: Description of Artificial Sequence: chemically
```

```
                    synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: misc_feature
<222> LOCATION: (35)..(36)
<223> OTHER INFORMATION: cytidine at position 35 is modified by a
      phosphorothioate and attached to the adenosine at position 36
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 304
gcgugcagug ccuucggccg tgcggtgccu ccgucacgct                              40

<210> SEQ ID NO 305
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: misc_feature
<222> LOCATION: (20)..(21)
<223> OTHER INFORMATION: guanosine at position 20 is modified by a
      phosphorothioate and attached to the thymidine at position 21
```

```
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(39)
<223> OTHER INFORMATION: all residues at positions 33 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 305
gcgugcagug ccuucggccg tgcggtgccu ccgucacgct                              40

<210> SEQ ID NO 306
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(22)
<223> OTHER INFORMATION: all residues at positions 20 to 22 are 2'-O-
      Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(39)
<223> OTHER INFORMATION: all residues at positions 33 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 306
gcgugcagug ccuucggccg tgcggtgccu ccgucacgct                              40

<210> SEQ ID NO 307
<211> LENGTH: 40
<212> TYPE: DNA
<213> ORGANISM: Artificial Sequence
```

```
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: misc_feature
<222> LOCATION: (20)..(21)
<223> OTHER INFORMATION: guanosine at position 20 is modified by a
      phosphorothioate and attached to the thymidine at position 21
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(39)
<223> OTHER INFORMATION: all the residues at positions 33 to 39 are
      2'-O-Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 307
gcgugcagug ccuuuggccg tgcggtgccu ccgucacgct                              40

<210> SEQ ID NO 308
<211> LENGTH: 37
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(12)
<223> OTHER INFORMATION: all residues at positions 8 to 12 are 2'-O-
      Methyl
<220> FEATURE:
<221> NAME/KEY: misc_feature
<222> LOCATION: (12)..(13)
<223> OTHER INFORMATION: cytidine at position 12 is modified by a PEG
      and attached to the guanosine at position 13
<220> FEATURE:
<221> NAME/KEY: modified_base
<222> LOCATION: (13)..(15)
<223> OTHER INFORMATION: all residues at positions 13 to 15 are 2'-O-
      Methyl
<220> FEATURE:
<221> NAME/KEY: modified_base
```

```
<222> LOCATION: (17)..(17)
<223> OTHER INFORMATION: the residue at position 17 is 2'-O-Methyl
<220> FEATURE:
<221> NAME/KEY: misc_feature
<222> LOCATION: (17)..(18)
<223> OTHER INFORMATION: guanosine at position 17 is modified by a
      phosphorothioate and attached to the thymidine at position 18
<220> FEATURE:
<221> NAME/KEY: modified_base
<222> LOCATION: (19)..(19)
<223> OTHER INFORMATION: the residue at position 19 is 2'-O-Methyl
<220> FEATURE:
<221> NAME/KEY: modified_base
<222> LOCATION: (24)..(25)
<223> OTHER INFORMATION: all residues at positions 24 and 25 are
      2'-O-Methyl
<220> FEATURE:
<221> NAME/KEY: modified_base
<222> LOCATION: (27)..(27)
<223> OTHER INFORMATION: the residue at position 27 is 2'-O-Methyl
<220> FEATURE:
<221> NAME/KEY: modified_base
<222> LOCATION: (30)..(31)
<223> OTHER INFORMATION: all residues at positions 30 to 31 are 2'-
      O-Methyl
<220> FEATURE:
<221> NAME/KEY: modified_base
<222> LOCATION: (33)..(36)
<223> OTHER INFORMATION: all residues at positions 33 to 36 are 2'-
      O-Methyl
<220> FEATURE:
<221> NAME/KEY: misc_feature
<222> LOCATION: (37)..(37)
<223> OTHER INFORMATION: thymidine at position 37 is a 3' inverted
      deoxythymidine (3' to 3' linked)

<400> SEQUENCE: 308
gcgugcagug ccggccgtgc ggtgccuccg ucacgct                              37

<210> SEQ ID NO 309
<211> LENGTH: 37
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(12)
<223> OTHER INFORMATION: all residues at positions 8 to 12 are 2'-O-
      Methyl
<220> FEATURE:
<221> NAME/KEY: misc_feature
<222> LOCATION: (12)..(13)
<223> OTHER INFORMATION: cytidine at position 12 is modified by a PEG
      and attached to the guanosine at position 13
<220> FEATURE:
<221> NAME/KEY: modified_base
<222> LOCATION: (13)..(15)
<223> OTHER INFORMATION: all residues at positions 13 to 15 are 2'-O-
      Methyl
<220> FEATURE:
<221> NAME/KEY: modified_base
<222> LOCATION: (17)..(17)
<223> OTHER INFORMATION: the residue at position 17 is 2'-O-Methyl
<220> FEATURE:
<221> NAME/KEY: misc_feature
<222> LOCATION: (17)..(18)
<223> OTHER INFORMATION: guanosine at position 17 is modified with a
      phosphorothioate and attached to the thymidine at position 18
<220> FEATURE:
<221> NAME/KEY: modified_base
<222> LOCATION: (19)..(19)
```

-continued

<223> OTHER INFORMATION: the residue at position 19 is 2'-O-Methyl
<220> FEATURE:
<221> NAME/KEY: modified_base
<222> LOCATION: (24)..(25)
<223> OTHER INFORMATION: all residues at positions 24 and 25 are 2'-
      O-Methyl
<220> FEATURE:
<221> NAME/KEY: modified_base
<222> LOCATION: (27)..(27)
<223> OTHER INFORMATION: the residue at position 27 is 2'-O-Methyl
<220> FEATURE:
<221> NAME/KEY: modified_base
<222> LOCATION: (30)..(36)
<223> OTHER INFORMATION: all residues at positions 30 to 36 are 2'-
      O-Methyl
<220> FEATURE:
<221> NAME/KEY: misc_feature
<222> LOCATION: (37)..(37)
<223> OTHER INFORMATION: thymidine at position 37 is 3' inverted
      deoxythymidine (3' to 3' linked)

<400> SEQUENCE: 309
gcgugcagug ccggccgtgc ggtgccuccg ucacgct                                 37

<210> SEQ ID NO 310
<211> LENGTH: 38
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(3)
<223> OTHER INFORMATION: all residues at positions 1 to 3 are 2'-O-
      Methyl
<220> FEATURE:
<221> NAME/KEY: modified_base
<222> LOCATION: (7)..(17)
<223> OTHER INFORMATION: all residues at positions 7 to 17 are 2'-O-
      Methyl
<220> FEATURE:
<221> NAME/KEY: misc_feature
<222> LOCATION: (19)..(20)
<223> OTHER INFORMATION: guanosine at position 19 is modified by
      phosphorothioate and attached to the thymidine at position 20
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (26)..(27)
<223> OTHER INFORMATION: all residues at positions 26 to 27 are 2'-O-
      Methyl
<220> FEATURE:
<221> NAME/KEY: modified_base
<222> LOCATION: (29)..(29)
<223> OTHER INFORMATION: the residue at position 29 is 2'-O-Methyl
<220> FEATURE:
<221> NAME/KEY: modified_base
<222> LOCATION: (32)..(37)
<223> OTHER INFORMATION: all residues at positions 32 to 37 are  2'-
      O-Methyl
<220> FEATURE:
<221> NAME/KEY: misc_feature
<222> LOCATION: (38)..(38)
<223> OTHER INFORMATION: thymidine at position 38 is a 3' inverted
      deoxythymidine (3' to 3' linked)

<400> SEQUENCE: 310
cgugcagugc cuucggccgt gcggtgccuc cgucacgt                                38

<210> SEQ ID NO 311
<211> LENGTH: 38
<212> TYPE: DNA

```
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(3)
<223> OTHER INFORMATION: all residues at positions 1 to 3 are 2'-O-
      Methyl
<220> FEATURE:
<221> NAME/KEY: modified_base
<222> LOCATION: (7)..(17)
<223> OTHER INFORMATION: all residues at positions 7 to 17 are 2'-O-
      Methyl
<220> FEATURE:
<221> NAME/KEY: modified_base
<222> LOCATION: (19)..(19)
<223> OTHER INFORMATION: the residue at position 19 is 2'-O-Methyl
<220> FEATURE:
<221> NAME/KEY: misc_feature
<222> LOCATION: (19)..(20)
<223> OTHER INFORMATION: guanosine at position 19 is modified by a
      phosphorothioate and attached to the thymidine at position 20
<220> FEATURE:
<221> NAME/KEY: modified_base
<222> LOCATION: (21)..(21)
<223> OTHER INFORMATION: the residue at position 21 is 2'-O-Methyl
<220> FEATURE:
<221> NAME/KEY: modified_base
<222> LOCATION: (26)..(27)
<223> OTHER INFORMATION: all residues at positions 26 to 27 are 2'-O-
      Methyl
<220> FEATURE:
<221> NAME/KEY: modified_base
<222> LOCATION: (29)..(29)
<223> OTHER INFORMATION: the residue at position 29 is 2'-O-Methyl
<220> FEATURE:
<221> NAME/KEY: modified_base
<222> LOCATION: (32)..(37)
<223> OTHER INFORMATION: all residues at positions 32 to 37 are 2'-O-
    Methyl
<220> FEATURE:
<221> NAME/KEY: misc_feature
<222> LOCATION: (38)..(38)
<223> OTHER INFORMATION: thymidine at position 38 is a 3' inverted
      deoxythymidine (3' to 3' linked)

<400> SEQUENCE: 311
cgugcagugc cuuuggccgt gcggtgccuc cgucacgt                           38

<210> SEQ ID NO 312
<211> LENGTH: 35
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(3)
<223> OTHER INFORMATION: all residues at positions 1 to 3 are 2'-O-
      Methyl
<220> FEATURE:
<221> NAME/KEY: modified_base
<222> LOCATION: (7)..(11)
<223> OTHER INFORMATION: all residues at positions 7 to 11are 2'-O-
      Methyl
<220> FEATURE:
<221> NAME/KEY: misc_feature
<222> LOCATION: (11)..(12)
<223> OTHER INFORMATION: cytidine at position 11 is modified by a PEG
      and attached to the guanosine at position 12
<220> FEATURE:
<221> NAME/KEY: modified_base
<222> LOCATION: (12)..(14)
<223> OTHER INFORMATION: all residues at positions 12 to 14 are 2'-O-
      Methyl
<220> FEATURE:
```

```
<221> NAME/KEY: misc_feature
<222> LOCATION: (16)..(17)
<223> OTHER INFORMATION: guanosine at position 16 is modified by a
      phosphorothioate and attached to the thymidine at position 17
<220> FEATURE:
<221> NAME/KEY: modified_base
<222> LOCATION: (16)..(16)
<223> OTHER INFORMATION: the residue at 16 is 2'-O-Methyl
<220> FEATURE:
<221> NAME/KEY: modified_base
<222> LOCATION: (18)..(18)
<223> OTHER INFORMATION: the residue at 16 is 2'-O-Methyl
<220> FEATURE:
<221> NAME/KEY: modified_base
<222> LOCATION: (23)..(24)
<223> OTHER INFORMATION: all residues at positions 23 to 24 are 2'-O-
      Methyl
<220> FEATURE:
<221> NAME/KEY: modified_base
<222> LOCATION: (26)..(26)
<223> OTHER INFORMATION: the residue at position 26 is 2'-O-Methyl
<220> FEATURE:
<221> NAME/KEY: modified_base
<222> LOCATION: (29)..(30)
<223> OTHER INFORMATION: all residues at positions 29 to 30 are 2'-O-
      Methyl
<220> FEATURE:
<221> NAME/KEY: modified_base
<222> LOCATION: (32)..(34)
<223> OTHER INFORMATION: all residues at positions 32 to 34 are 2'-O-
      Methyl
<220> FEATURE:
<221> NAME/KEY: misc_feature
<222> LOCATION: (35)..(35)
<223> OTHER INFORMATION: thymidine at position 35 is a 3' inverted
      deoxythymidine (3' to 3' linked)

<400> SEQUENCE: 312
cgugcagugc cggccgtgcg gtgccuccgu cacgt                              35

<210> SEQ ID NO 313
<211> LENGTH: 35
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(3)
<223> OTHER INFORMATION: all residues at positions 1 to 3 are 2'-O-
      Methyl
<220> FEATURE:
<221> NAME/KEY: modified_base
<222> LOCATION: (7)..(11)
<223> OTHER INFORMATION: all residues at positions 7 to 11 are 2'-O-
      Methyl
<220> FEATURE:
<221> NAME/KEY: misc_feature
<222> LOCATION: (11)..(12)
<223> OTHER INFORMATION: cytidine at position 11 is modified by a PEG
      and attached to the guanosine at position 12
<220> FEATURE:
<221> NAME/KEY: modified_base
<222> LOCATION: (12)..(14)
<223> OTHER INFORMATION: all residues at positions 12 to 14 are 2'-O-
      Methyl
<220> FEATURE:
<221> NAME/KEY: misc_feature
<222> LOCATION: (16)..(17)
<223> OTHER INFORMATION: guanosine at position 16 is modified by a
      phosphorothioate and attached to the thymidine at position 17
<220> FEATURE:
<221> NAME/KEY: modified_base
<222> LOCATION: (16)..(16)
<223> OTHER INFORMATION: the residue at position 16 is 2'-O-Methyl
<220> FEATURE:
<221> NAME/KEY: modified_base
```

```
<222> LOCATION: (18)..(18)
<223> OTHER INFORMATION: the residue at position 18 is 2'-O-Methyl
<220> FEATURE:
<221> NAME/KEY: modified_base
<222> LOCATION: (23)..(24)
<223> OTHER INFORMATION: all residues at positions 23 to 24 are 2'-O-
      Methyl
<220> FEATURE:
<221> NAME/KEY: modified_base
<222> LOCATION: (26)..(26)
<223> OTHER INFORMATION: the residue at position 26 is 2'-O-Methyl
<220> FEATURE:
<221> NAME/KEY: modified_base
<222> LOCATION: (29)..(34)
<223> OTHER INFORMATION: all residues at positions 29 to 34 are 2'-O-
      Methyl
<220> FEATURE:
<221> NAME/KEY: misc_feature
<222> LOCATION: (35)..(35)
<223> OTHER INFORMATION: thymidine at position 35 is 3' inverted
      deoxythymidine (3' to 3' linked)

<400> SEQUENCE: 313
cgugcagugc cggccgtgcg gtgccuccgu cacgt                              35

<210> SEQ ID NO 314
<211> LENGTH: 35
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (6)..(7)
<223> OTHER INFORMATION: guanosine at position 6 is modified by a
      phosphorothioate and attached to the thymidine at position 7
<220> FEATURE:
<221> NAME/KEY: modified_base
<222> LOCATION: (6)..(6)
<223> OTHER INFORMATION: the residue at position 6 is 2'-O-Methyl
<220> FEATURE:
<221> NAME/KEY: modified_base
<222> LOCATION: (13)..(14)
<223> OTHER INFORMATION: all residues at positions 13 to 14 are 2'-O-
      Methyl
<220> FEATURE:
<221> NAME/KEY: modified_base
<222> LOCATION: (16)..(16)
<223> OTHER INFORMATION: the residue at position 16 is 2'-O-Methyl
<220> FEATURE:
<221> NAME/KEY: modified_base
<222> LOCATION: (19)..(23)
<223> OTHER INFORMATION: all residues at positions 19 to 23 are 2'-O-
      Methyl
<220> FEATURE:
<221> NAME/KEY: misc_feature
<222> LOCATION: (23)..(24)
<223> OTHER INFORMATION: cytidine at position 23 is modified by a PEG
      and attached to the guanosine at position 24
<220> FEATURE:
<221> NAME/KEY: modified_base
<222> LOCATION: (24)..(25)
<223> OTHER INFORMATION: all residues at positions 24 to 25 are 2'-O-
      Methyl
<220> FEATURE:
<221> NAME/KEY: modified_base
<222> LOCATION: (29)..(34)
<223> OTHER INFORMATION: all residues at positions 29 to 34 are 2'-O-
      Methyl
<220> FEATURE:
<221> NAME/KEY: misc_feature
<222> LOCATION: (35)..(35)
```

-continued

<223> OTHER INFORMATION: thymidine at position 35 is a 3' inverted
      deoxythymidine (3' to 3' linked)

<400> SEQUENCE: 314
cggccgtgcg gtgccuccgu cacgugcagu gccgt                                    35

<210> SEQ ID NO 315
<211> LENGTH: 38
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (6)..(7)
<223> OTHER INFORMATION: guanosine at position 6 is modified by a
      phosphorothioate and attached to the thymidine at position 7
<220> FEATURE:
<221> NAME/KEY: modified_base
<222> LOCATION: (6)..(6)
<223> OTHER INFORMATION: the residue at position 6 is 2'-O-Methyl
<220> FEATURE:
<221> NAME/KEY: modified_base
<222> LOCATION: (8)..(8)
<223> OTHER INFORMATION: the residue at position 8 is 2'-O-Methyl
<220> FEATURE:
<221> NAME/KEY: modified_base
<222> LOCATION: (13)..(14)
<223> OTHER INFORMATION: all residues at positions 13-14 are 2'-O-
      Methyl
<220> FEATURE:
<221> NAME/KEY: modified_base
<222> LOCATION: (16)..(16)
<223> OTHER INFORMATION: the residue at position 16 is 2'-O-Methyl
<220> FEATURE:
<221> NAME/KEY: modified_base
<222> LOCATION: (19)..(28)
<223> OTHER INFORMATION: all residues at positions 19 to 28 are 2'-O-
      Methyl
<220> FEATURE:
<221> NAME/KEY: modified_base
<222> LOCATION: (32)..(37)
<223> OTHER INFORMATION: all residues at positions 32 to 37 are 2'-O-
      Methyl
<220> FEATURE:
<221> NAME/KEY: modified_base
<222> LOCATION: (38)..(38)
<223> OTHER INFORMATION: the residue at position 38 is 2'-O-Methyl

<400> SEQUENCE: 315
cggccgtgcg gtgccuccgu cacuugugc agugccgt                                  38

<210> SEQ ID NO 316
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
<221> NAME/KEY: misc_feature
<222> LOCATION: (7)..(8)
<223> OTHER INFORMATION: guanosine at position 7 is modified by a
      phosphorothioate and attached to the thymidine at position 8
<220> FEATURE:

```
<221> NAME/KEY: modified_base
<222> LOCATION: (7)..(7)
<223> OTHER INFORMATION: the residue at the 7 position is 2'-O-Methyl
<220> FEATURE:
<221> NAME/KEY: modified_base
<222> LOCATION: (9)..(9)
<223> OTHER INFORMATION: the residue at the 9 position is 2'-O-Methyl
<220> FEATURE:
<221> NAME/KEY: modified_base
<222> LOCATION: (14)..(15)
<223> OTHER INFORMATION: all residues at positions 14 to 15 are 2'-O-
      Methyl
<220> FEATURE:
<221> NAME/KEY: modified_base
<222> LOCATION: (17)..(17)
<223> OTHER INFORMATION: the residue at position 17 is 2'-O-Methyl
<220> FEATURE:
<221> NAME/KEY: modified_base
<222> LOCATION: (20)..(29)
<223> OTHER INFORMATION: all residues at positions 20 to 29 are 2'-O-
      Methyl
<220> FEATURE:
<221> NAME/KEY: modified_base
<222> LOCATION: (33)..(39)
<223> OTHER INFORMATION: all residues at positions 33 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 316
ccggccgtgc ggtgccuccg ucacuuugug cagugccggt                                40

<210> SEQ ID NO 317
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(5)
<223> OTHER INFORMATION: all residues at positions 1 to 5 are 2'-O-
      Methyl
<220> FEATURE:
<221> NAME/KEY: misc_feature
<222> LOCATION: (7)..(8)
<223> OTHER INFORMATION: guanosine at position 7 is modified by a
      phosphorothiolate and attached to the thymidine at position 8
<220> FEATURE:
<221> NAME/KEY: modified_base
<222> LOCATION: (9)..(9)
<223> OTHER INFORMATION: the residue at position 9 is 2'-O-Methyl
<220> FEATURE:
<221> NAME/KEY: modified_base
<222> LOCATION: (14)..(15)
<223> OTHER INFORMATION: all residues at positions 14 to 15 are 2'-O-
      Methyl
<220> FEATURE:
<221> NAME/KEY: modified_base
<222> LOCATION: (17)..(17)
<223> OTHER INFORMATION: the residue at position 17 is  2'-O-Methyl
<220> FEATURE:
<221> NAME/KEY: modified_base
<222> LOCATION: (20)..(21)
<223> OTHER INFORMATION: all residues at positions 20 to 21 are  2'-
      O-Methyl
<220> FEATURE:
<221> NAME/KEY: modified_base
<222> LOCATION: (23)..(31)
<223> OTHER INFORMATION: all residues at positions 23 to 31 are  2'-
      O-Methyl
<220> FEATURE:
<221> NAME/KEY: modified_base
<222> LOCATION: (35)..(41)
```

```
<223> OTHER INFORMATION: all residues at positions 35 to 41 are 2'-O-
      Methyl
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 317
ccggccgtgc ggtgccuccg ucacguuccg ugcagugccg gt                            42

<210> SEQ ID NO 318
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (21)..(22)
<223> OTHER INFORMATION: guanosine at position 21 is modified by a
      phosphorothioate and attached to the thymidine at position 22
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 318
ggcgtgcagt gccttcggcc gtgcggtgcc tccgtcacgc ct                            42

<210> SEQ ID NO 319
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(1)
<223> OTHER INFORMATION: 2'-O-methyl guanosine at position 1 is
      modified by an amine linker
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: misc_feature
<222> LOCATION: (20)..(21)
<223> OTHER INFORMATION: guanosine at position 20 is modified by a
      phosphorothioate and attached to thymidine at position 21
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
```

```
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is 3' inverted
      deoxythymidine (3' to 3' linked)

<400> SEQUENCE: 319
gcgugcagug ccuucggccg tgcggtgccu ccgucacgct                            40

<210> SEQ ID NO 320
<211> LENGTH: 40
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (1)..(1)
<223> OTHER INFORMATION: 2'-O-methyl guanosine at position 1 is
      modified by a 20 kDa PEG and attached to the nucleotide via an
      amine linker
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: misc_feature
<222> LOCATION: (20)..(21)
<223> OTHER INFORMATION: guanosine at position 20 is modified by a
      phosphorothioate and attached to the thymidine at position 21
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: all residues at positions 27 to 28 are 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-O-
      Methyl
<220> FEATURE:
<221> NAME/KEY: modified_base
<222> LOCATION: (36)..(39)
<223> OTHER INFORMATION: all residues at positions 36 to 39 are 2'-O-
      Methyl
<220> FEATURE:
<221> NAME/KEY: misc_feature
<222> LOCATION: (40)..(40)
<223> OTHER INFORMATION: thymidine at position 40 is a 3' inverted
```

-continued deoxythymidine (3' to 3' linked)

<400> SEQUENCE: 320
gcgugcagug ccuucggccg tgcggtgccu ccgucacgct                40

<210> SEQ ID NO 321
<211> LENGTH: 41
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: modified_base
<222> LOCATION: (1)..(4)
<223> OTHER INFORMATION: all residues at positions 1 to 4 are 2'-O-
      Methyl
<220> FEATURE:
<221> NAME/KEY: misc_feature
<222> LOCATION: (1)..(1)
<223> OTHER INFORMATION: 2'-O-methyl guanosine at position 1 is
      modified by a 40 kDa PEG and attached to the nucleotide via an
      amine linker
<220> FEATURE:
<221> NAME/KEY: modified_base
<222> LOCATION: (8)..(18)
<223> OTHER INFORMATION: all residues at positions 8 to 18 are 2'-O-
      Methyl
<220> FEATURE:
<221> NAME/KEY: misc_feature
<222> LOCATION: (20)..(21)
<223> OTHER INFORMATION: guanosine at position 20 is modified by
      phosphothioate and attached to the thymidine at position 21
<220> FEATURE:
<221> NAME/KEY: modified_base
<222> LOCATION: (20)..(20)
<223> OTHER INFORMATION: the residue at position 20 is 2'-O-Methyl
<220> FEATURE:
<221> NAME/KEY: modified_base
<222> LOCATION: (22)..(22)
<223> OTHER INFORMATION: the residue at position 22 is 2'-O-Methyl
<220> FEATURE:
<221> NAME/KEY: modified_base
<222> LOCATION: (27)..(28)
<223> OTHER INFORMATION: the residue at position 27 to 28 is 2'-O-
      Methyl
<220> FEATURE:
<221> NAME/KEY: modified_base
<222> LOCATION: (30)..(30)
<223> OTHER INFORMATION: the residue at position 30 is 2'-O-Methyl
<220> FEATURE:
<221> NAME/KEY: modified_base
<222> LOCATION: (33)..(34)
<223> OTHER INFORMATION: all residues at positions 33 to 34 are 2'-
      O-Methyl
<220> FEATURE:
<221> NAME/KEY: modified_base
<222> LOCATION: (36)..(39)
<223> OTHER INFORMATION: all residues at positions 36 to 39 are 2'-
      O-Methyl
<220> FEATURE:
<221> NAME/KEY: misc_feature
<222> LOCATION: (40)..(40)
<223> OTHER INFORMATION: thymidine at position 40 is a 3' inverted
      deoxythymidine (3' to 3' linked)

<400> SEQUENCE: 321
gcgugcagug ccuucggccg stgcggtgcc uccgucacgc t                41

<210> SEQ ID NO 322
<211> LENGTH: 42
<212> TYPE: DNA
<213> ORGANISM: Artificial Sequence
<220> FEATURE:
<223> OTHER INFORMATION: Description of Artificial Sequence:
      chemically synthesized

```
<220> FEATURE:
<221> NAME/KEY: misc_feature
<222> LOCATION: (1)..(1)
<223> OTHER INFORMATION: deoxyguanosine at position 1 is modified by
      an amine linker
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 322
ggcgtgcagt gccttcggcc gtgcggtgcc tccgtcacgc ct                     42

<210> SEQ ID NO 323
<211> LENGTH: 42
<212> TYPE: DNA
<213> ORGANISM: Artificial Sequence
<220> FEATURE:
<223> OTHER INFORMATION: Description of Artificial Sequence: chemically
      synthesized
<220> FEATURE:
<221> NAME/KEY: misc_feature
<222> LOCATION: (1)..(1)
<223> OTHER INFORMATION: deoxyguanosine at position 1 is modified by a
      20 kDa PEG and attached to the nucleotide via an amine linker
<220> FEATURE:
<221> NAME/KEY: misc_feature
<222> LOCATION: (42)..(42)
<223> OTHER INFORMATION: thymidine at position 42 is a 3' inverted
      deoxythymidine (3' to 3' linked)

<400> SEQUENCE: 323
ggcgtgcagt gccttcggcc gtgcggtgcc tccgtcacgc ct                     42

<210> SEQ ID NO 324

<400> SEQUENCE: 324

000

<210> SEQ ID NO 325
<211> LENGTH: 80
<212> TYPE: DNA
<213> ORGANISM: Artificial Sequence
<220> FEATURE:
<223> OTHER INFORMATION: Description of Artificial Sequence:
      chemically synthesized

<400> SEQUENCE: 325
ctacctacga tctgactagc ttggtagyga yhyhgwggag mtgcggtytg gyygacrtca   60
gcttactctc atgtagttcc                                              80

<210> SEQ ID NO 326
<211> LENGTH: 80
<212> TYPE: DNA
<213> ORGANISM: Artificial Sequence
<220> FEATURE:
<223> OTHER INFORMATION: Description of Artificial Sequence:
      chemically synthesized

<400> SEQUENCE: 326
ctacctacga tctgactagc ctcagattga ctccggcyga cttgttttaa tcttctgagt   60
gcttactctc atgtagttcc                                              80

<210> SEQ ID NO 327
<211> LENGTH: 78
<212> TYPE: DNA
<213> ORGANISM: Artificial Sequence
```

-continued

```
<220> FEATURE:
<223> OTHER INFORMATION: Description of Artificial Sequence:
      chemically synthesized

<400> SEQUENCE: 327
ctacctacga tctgactagc cyyacytaty systwcykyr krataygtcg artactmtgc       60
ttactctcat gtagttcc                                                    78
```